United States Patent
Devasthale et al.

(10) Patent No.: US 10,851,098 B2
(45) Date of Patent: Dec. 1, 2020

(54) AZOLE AMIDES AND AMINES AS ALPHA V INTEGRIN INHIBITORS

(71) Applicant: BRISTOL-MYERS SQUIBB COMPANY, Princeton, NJ (US)

(72) Inventors: Pratik Devasthale, Plainsboro, NJ (US); Wei Wang, Princeton, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 16/347,829

(22) PCT Filed: Nov. 7, 2017

(86) PCT No.: PCT/US2017/060390
§ 371 (c)(1),
(2) Date: May 7, 2019

(87) PCT Pub. No.: WO2018/089358
PCT Pub. Date: May 17, 2018

(65) Prior Publication Data
US 2019/0256513 A1  Aug. 22, 2019

Related U.S. Application Data

(60) Provisional application No. 62/418,838, filed on Nov. 8, 2016.

(51) Int. Cl.
| | |
|---|---|
| *C07D 471/04* | (2006.01) |
| *C07D 401/12* | (2006.01) |
| *C07D 401/14* | (2006.01) |
| *C07D 403/12* | (2006.01) |
| *A61P 35/00* | (2006.01) |

(52) U.S. Cl.
CPC ............ *C07D 471/04* (2013.01); *A61P 35/00* (2018.01); *C07D 401/12* (2013.01); *C07D 401/14* (2013.01); *C07D 403/12* (2013.01)

(58) Field of Classification Search
CPC ..... A61P 35/00; C07D 401/12; C07D 401/14; C07D 403/12; C07D 471/04
See application file for complete search history.

(56) References Cited

U.S. PATENT DOCUMENTS

| | | | |
|---|---|---|---|
| 5,760,029 A | 6/1998 | Jadhav et al. | |
| 6,090,944 A | 7/2000 | Hutchinson | |
| 6,114,328 A * | 9/2000 | Wityak | C07D 261/04 514/227.8 |
| 2008/0045521 A1 | 2/2008 | Arnould et al. | |
| 2008/0255183 A1 | 10/2008 | Arnould et al. | |
| 2016/0264566 A1 | 9/2016 | DeGrado et al. | |
| 2019/0263808 A1* | 8/2019 | Zhao | A61P 19/10 |

FOREIGN PATENT DOCUMENTS

| | | |
|---|---|---|
| WO | WO1999/26945 A1 | 6/1999 |
| WO | WO199930709 A1 | 6/1999 |
| WO | WO2002060438 A1 | 8/2002 |
| WO | WO2006108040 A1 | 10/2006 |
| WO | WO2007141473 A1 | 12/2007 |
| WO | WO2011098603 A1 | 8/2011 |
| WO | WO2014154725 A1 | 10/2014 |
| WO | WO2015091426 A1 | 6/2015 |
| WO | WO2016046225 A1 | 3/2016 |
| WO | WO2016046226 A1 | 3/2016 |
| WO | WO2016046230 A1 | 3/2016 |
| WO | WO2016046241 A1 | 3/2016 |
| WO | WO2016134223 A2 | 8/2016 |

OTHER PUBLICATIONS

International Preliminary Report on Patentability for PCT/US2017/060390, dated May 14, 2019.
Kapp et al., "Integrin Modulators: a patent review", Expert Opinion on Therapeutic Patents, vol. 23(10), pp. 1273-1295 (2013).
Piras, M. et al., High-Affinity "Click" RGD Peptidomimetics as Radiolabeled Probes for Imaging αvβ3 Integrin.
Raboisson, P. et al., "Identification of novel short chain 4-substituted indoles as potent αvβ3 antagonist using structure-based drug design", European Journal of Medicinal Chemistry, vol. 42, pp. 334-343 (2007).

* cited by examiner

*Primary Examiner* — Erich A Leeser
(74) *Attorney, Agent, or Firm* — Gary Greenblatt

(57) ABSTRACT

The present invention provides compounds of Formula (I): (Formula (I)), or stereoisomers, tautomers, or pharmaceutically acceptable salts or solvates thereof, wherein all the variables are as defined herein. These compounds are inhibitors to αv-containing integrins. This invention also relates to pharmaceutical compositions comprising these compounds and methods of treating a disease, disorder, or condition associated with dysregulation of αv-containing integrins, such as pathological fibrosis, transplant rejection, cancer, osteoporosis, and inflammatory disorders, by using the compounds and pharmaceutical compositions.

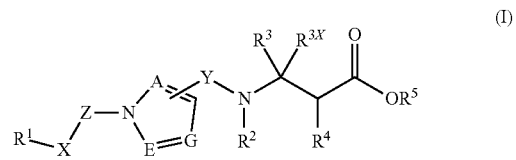

(I)

16 Claims, No Drawings

AZOLE AMIDES AND AMINES AS ALPHA V INTEGRIN INHIBITORS

CROSS REFERENCE TO RELATED APPLICATION

This application is a national phase application under 35 U.S.C. § 371 of International Patent Application No. PCT/US2017/060390, filed Nov. 7, 2017, which claims priority to U.S. Provisional Application Ser. No. 62/418,838 filed Nov. 8, 2016, which are expressly incorporated fully herein by reference.

FIELD OF THE INVENTION

The present invention relates to substituted azole amides and amines as αv integrin inhibitors, pharmaceutical compositions comprising such compounds and to their use in therapy, especially in the treatment or prophylaxis of diseases, disorders, and conditions for which an αv integrin inhibitor is indicated in a human.

BACKGROUND OF THE INVENTION

Integrins belong to a large family of α/β heterodimeric transmembrane proteins that are involved in cell adhesion to a wide variety of extracellular matrix proteins, cell-cell interactions, cell migration, proliferation, survival, and in maintenance of tissue integrity (Barczyk et al. *Cell and Tissue Research* 2010, 339, 269; Srichai, M. B.; Zent, R. in *Cell-Extracellular Matrix Interactions in Cancer,* 2010). In mammals, there are 24 α/β integrin heterodimers known from various combinations of 18 alpha and 8 beta subunits. Transforming Growth Factor-β (TGF-β) has a central role in driving a number of pathological processes underlying fibrosis, cell growth, and autoimmune diseases. Alpha V (αv) Integrins, that include αvβ1, αvβ3, αvβ5, αvβ6, and αvβ8, are involved in a critical pathway that leads to the conversion of latent TGF-β to its active form (Henderson, N. C.; Sheppard, D. *Biochim, Biophys. Acta* 2013, 1832, 891). Thus, antagonism of such αv integrin-mediated activation of latent TGF-β provides a viable therapeutic approach to intervene in TGF-β-driven pathological states (Sheppard, D. *Eur. Resp. Rev.* 2008, 17, 157; Goodman, S. L.; Picard, M. *Trends Pharmacol. Sciences* 2012, 33(7), 405; Hinz, B. *Nature Medicine* 2013, 19(12), 1567; Pozzi, A.; Zent, R. *J. Am. Soc. Nephrol.* 2013, 24(7), 1034). All five αv integrins belong to a small subset (8 out of 24) of integrins that recognize the Arginine-Glycine-Aspartic acid (RGD) motif present in their native ligands such as fibronectin, vitronectin, and Latency-Associated Peptide (LAP).

The expression of αv integrin subtypes varies significantly. For example, αvβ6 is expressed on epithelial cells at very low levels in healthy tissue but is significantly upregulated during inflammation and wound healing. αvβ3 and αvβ5 are expressed on osteoclasts, endothelial, smooth muscle, and solid tumor cells, as well as on pericytes and podocytes, while αvβ1 is expressed on activated fibroblasts and mesangial cells.

Fibrotic conditions that represent major unmet medical needs are Idiopathic Pulmonary Fibrosis (IPF), liver and kidney fibrosis, Non-Alcoholic Fatty Liver Disease (NAFLD), Non-Alcoholic Steato-Hepatitis (NASH), as well as systemic sclerosis. Two drugs, pirfenidone and nintedanib, that act by non-integrin-mediated mechanisms, have recently been approved for treatment of IPF. The present invention relates to compounds that inhibit or antagonize the action of one or more of the αv integrins in the treatment of pathological conditions, such as fibrosis and cancer, mediated by these integrins.

A number of selective or nonselective small molecule, peptidic, and antibody-based inhibitors of αv integrins have been reported in the literature (Kapp, T. G. et al. *Expert Opin. Ther. Patents* 2013, 23(10), 1273; O'Day, S. et al. *Brit. J. Cancer* 2011, 105(3), 346; Pickarski, M. et al. *Oncol. Rep.* 2015, 33, 2737; Wirth, M. et al. *Eur. Urol.* 2014, 897; Henderson, N. C. et al. *Nature Medicine* 2012, 19(12), 1617; Horan, G. S. et al. *Am. J. Resp. Crit. Care Med.* 2008, 177, 56; Puthawala, K. et al. *Am. J. Resp. Crit. Care Med.* 2008, 177, 82; Reed, N. I. et al. *Sci. Transl. Med.* 2015, 7(288), 288ra79; Anderson, N. A. et al. WO 2014/154725 A1, WO 2016/046225 A1, WO 2016/046226 A1, WO 2016/046230 A1, WO 2016/046241 A1).

SUMMARY OF THE INVENTION

In one aspect, the present invention provides compounds of Formula (I), (II), (IIa), (IIb), (IIc), (IId), (IIe), (IIf), and (III) as well as the subgenus and species thereof, including stereoisomers, tautomers, pharmaceutically acceptable salts, or solvates thereof, which are useful as αv integrin inhibitors.

In another aspect, the present invention also provides processes and intermediates for making the compounds of the present invention.

In another aspect, the present invention also provides pharmaceutical compositions comprising a pharmaceutically acceptable carrier and at least one of the compounds of the present invention or stereoisomers, tautomers, pharmaceutically acceptable salts, or solvates thereof.

In another aspect, the compounds of the invention may be used in therapy, either alone or in combination with one or more additional therapeutic agents.

The compounds of the invention may be used in the treatment of a disease, disorder, or condition associated with dysregulation of ax-containing integrins in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used for the manufacture of a medicament for the treatment of a disease, disorder, or condition associated with dysregulation of $\alpha_v$-containing integrins in a patient.

Other features and advantages of the invention will be apparent from the following detailed description and claims.

DETAILED DESCRIPTION OF THE INVENTION

The present application provides compounds, including all stereoisomers, solvates, prodrugs and pharmaceutically acceptable salt and solvate forms thereof, according to Formula I. The present application also provides pharmaceutical compositions containing at least one compound according to Formula I, or a stereoisomer, a tautomer, or a pharmaceutically acceptable salt or a solvate thereof, and optionally at least one additional therapeutic agent. Additionally, the present application provides methods for treating a patient suffering from an αv Integrin-modulated disease or disorder such as for example, Idiopathic Pulmonary Fibrosis (IPF), liver and kidney fibrosis, Non-Alcoholic Fatty Liver Disease (NAFLD), Non-Alcoholic Steato-Hepatitis (NASH), cardiac fibrosis, and systemic sclerosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

I. Compounds of the Invention

In one embodiment, the present invention provides, inter alia, a compound of Formula (I):

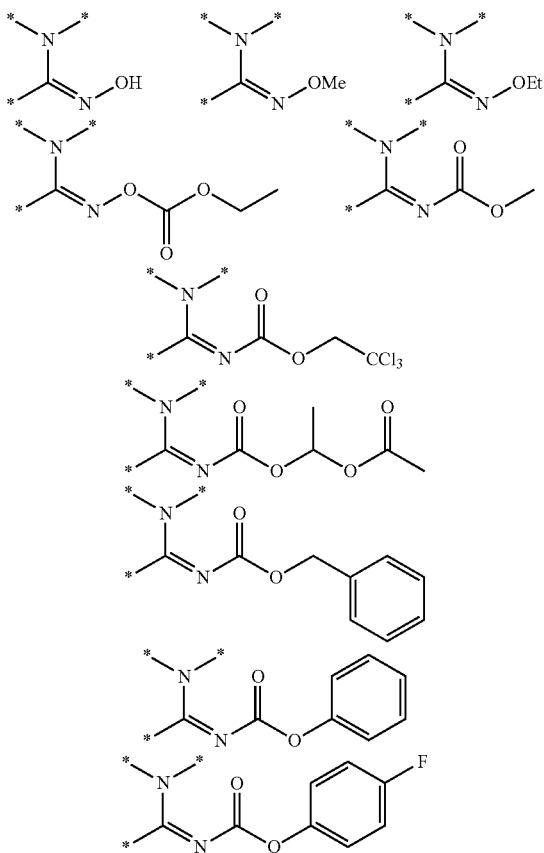

or a stereoisomer, a tautomer, or a pharmaceutically acceptable salt or a solvate thereof,
wherein:

A, E, and G are independently N or $CR^6$;

R is an Arginine mimetic moiety selected from the group consisting of

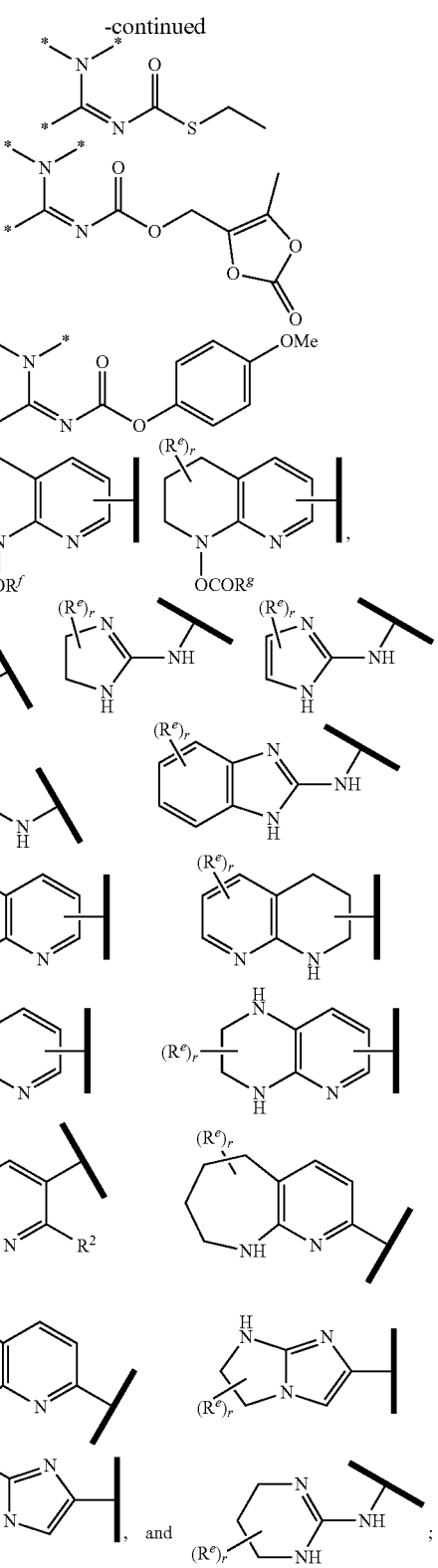

one of the asterisks in each of the arginine mimetics moiety is an attachment point to X, and the other two asterisks are hydrogen;

$R^f$=H, Me, Et, COOEt;

$R^g$=$CH_3$, $CH_2CH_3$, $CH_2CCl_3$, phenyl, 4-fluorophenyl, 4-methoxyphenyl, benzyl,

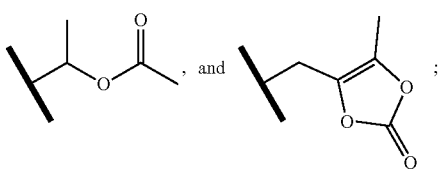

$R^e$ is OH, $C_{1-4}$ alkyl, halo, haloalkyl, or $C_{1-4}$ cycloalkyl;

r is an integer of 0, 1, 2, or 3;

Z is a covalent bond, O, S, NH, —O—($C_{1-3}$ alkylene)-, —S—($C_{1-3}$ alkylene)-, or —NH—($C_{1-3}$ alkylene)-, wherein the $C_{1-3}$ alkylene is each independently substituted with 0, 1, or 2 $R^{7a}$;

X is a $C_{1-6}$ alkylene substituted with 0, 1, or 2 $R^{7b}$;

Y is C(O) or $CH_2$;

$R^2$ is hydrogen or $C_{1-6}$ alkyl;

$R^3$ is hydrogen, 3- to 10-membered carbocyclyl, carbocyclylalkyl, 6- to 10-membered aryl, arylalkyl, 3- to 14-membered heterocyclyl, heterocyclylalkyl, 5- to 14-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^8$;

$R^{3X}$ is hydrogen; or alternatively, $R^3$ and $R^{3X}$, together with the atom to which they are attached, form a carbocyclyl or a heterocyclyl, and the carbocyclyl and heterocyclyl are each independently substituted with 0, 1, 2, or 3 $R^{12}$;

$R^4$ is hydrogen, $C_{1-10}$ alkyl, 3- to 10-membered carbocyclyl, carbocyclylalkyl, 3 to 10-membered heterocyclyl, heterocyclylalkyl, 6- to 10-membered aryl, arylalkyl, 5- to 14-membered heteroaryl, heteroarylalkyl, $NR^aR^b$, OH, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$; wherein the alkyl, carbocyclyl, heterocyclyl, aryl, and heteroaryl, by themselves or as part of another group, are each independently substituted with 0, 1, 2, or 3 $R^{15}$;

n is an integer of 1 or 2;

$R^5$ is H, $R^{5a}$, or a structural moiety selected from

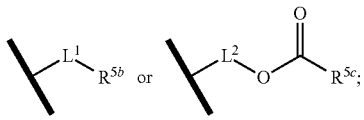

$L^1$ and $L^2$ are each independently $C_{1-4}$ alkylene;

$R^{5a}$ and $R^{5b}$ are each independently $C_{1-6}$ alkyl, phenyl, or 5- to 7-membered heterocyclyl; wherein the alkyl, phenyl, and heterocyclyl are each independently substituted with 0 to 3 $R^{5d}$; $R^{5c}$ is $C_{1-6}$ alkyl or 5- to 7-membered carbocyclyl; wherein the alkyl and carbocyclyl are each independently substituted with 0 to 3 $R^{5d}$;

$R^{5d}$, at each occurrence, is independently halo, OH, alkoxy, oxo, or alkyl; or alternatively, two adjacent $R^{5d}$, together with the atoms to which they are attached, form a carbocyclyl moiety;

$R^6$ is hydrogen, $C_{1-6}$ alkyl, $C_{3-5}$ cycloalkyl, heteroalkyl, cycloheteroalkyl, aryl, or heteroaryl, wherein the alkyl, cycloalkyl, heterocyclyl, cycloheteroalkyl, aryl, and heteroaryl are each independently substituted with 0, 1, 2, or 3 $R^9$;

$R^{7a}$ and $R^{7b}$ are each independently halo, cyano, hydroxyl, oxo, $NR^aR^b$, $C_{1-6}$ alkyl, haloalkyl, hydroxyalkyl, aminoalkyl, alkoxy, haloalkoxy, heteroalkyl, aryl, cycloalkyl, heteroaryl, cycloheteroalkyl, amido, carbamate, or sulfonamide; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the cycloalkyl and cycloheteroalkyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^8$ at each occurrence is independently halo, cyano, nitro, OH, $NR^aR^b$, $C_{1-6}$ alkyl, alkoxy, alkylamino, haloalkyl, haloalkoxy, haloalkylamino, hydroxyalkyl, aminoalkyl, alkylsulfonyl, sulfonamide, 3 to 6 membered carbocyclyl, 3 to 6 membered heterocyclyl, 6- to 10-membered aryl, or 5- to 10-membered heteroaryl; or alternatively, two $R^8$ at adjacent positions, together with the atoms to which they are attached, form a carbocyclyl or heterocyclyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^{12}$ at each occurrence is independently halo, cyano, nitro, OH, alkoxy, $NR^aR^b$, alkyl, heteroalkyl, aryl, cycloalkyl, heteroaryl, or cycloheteroalkyl; or alternatively, two $R^{12}$ at adjacent positions, together with the atoms to which they are attached, form a carbocyclyl or heterocyclyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the cycloalkyl and cycloheteroalkyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^9$ at each occurrence is independently halo, cyano, nitro, OH, alkoxy, $NR^aR^b$, $C_{1-6}$ alkyl, heteroalkyl, aryl, cycloalkyl, heteroaryl, or cycloheteroalkyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the cycloalkyl and cycloheteroalkyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^{10}$ is $C_{1-6}$ alkyl, 3 to 10 membered carbocyclyl, or 3 to 10 membered heterocyclyl, wherein the alkyl, carbocyclyl, heterocyclyl are each independently substituted with 0, 1, 2, or 3 $R^{11}$;

$R^{11}$ is halo, cyano, nitro, OH, alkoxy, $NR^aR^b$, alkyl, aryl, cycloalkyl, heteroaryl, cycloheteroalkyl, or $S(O)_g$(aryl); wherein the aryl, alkyl, cycloalkyl, heteroaryl, and cycloheteroalkyl are each independently substituted with 0, 1, 2, or 3 $R^{13}$;

g is an integer of 1 or 2;

$R^a$ and $R^b$, at each occurrence, are independently hydrogen, $C_{1-10}$ alkyl, 3 to 10 membered carbocyclyl, or 3 to 10 membered heterocyclyl; wherein the alkyl, carbocyclyl, heterocyclyl are each independently substituted with 0, 1, 2, or 3 $R^{14}$;

$R^{13}$ and $R^{14}$, at each occurrence, are independently halo, cyano, nitro, OH, alkoxy, $NR^aR^b$, alkyl, heteroalkyl, aryl, cycloalkyl, heteroaryl, or cycloheteroalkyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the cycloalkyl and cycloheteroalkyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide; and $R^{15}$ at each occurrence is independently halo, cyano, nitro, OH, $NR^aR^b$, $C_{1-6}$ alkyl, alkoxy, alkylamino, haloalkyl, haloalkoxy, haloalkylamino, hydroxyalkyl, aminoalkyl, alkylsulfonyl, sulfonamide, 3 to 6 membered carbocyclyl, 3 to 6 membered heterocyclyl, 6- to 10-membered aryl, or 5- to 10-membered heteroaryl; or alternatively, two $R^9$ at adjacent positions, together with the atoms to which they are attached, form a carbocyclyl or heterocyclyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide.

In one embodiment of Formula (I), Z is a covalent bond.

In one embodiment of Formula (I), $R^a$ and $R^b$, at one or more occurrence, are both hydrogen. In another embodiment, one of $R^a$ and $R^b$, at one or more occurrence, is hydrogen, while the other one is not hydrogen.

In one embodiment of Formula (I), A, E, and G, together with the nitrogen and carbon atoms, form a ring moiety selected from the following structural formula:

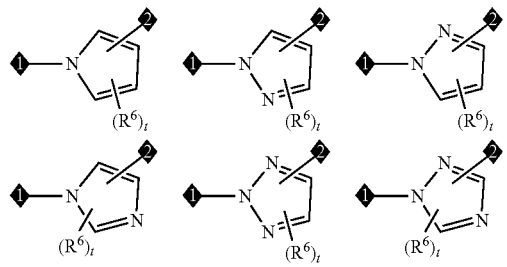

-continued

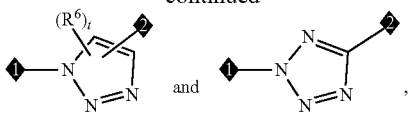

◆ Attachment point for X.
◈ Attachment point for Y.

and t is an integer of 0, 1, 2, or 3.

In one embodiment of Formula (I), A, E, and G, together with the nitrogen and carbon atoms, form a ring moiety selected from a structural formula:

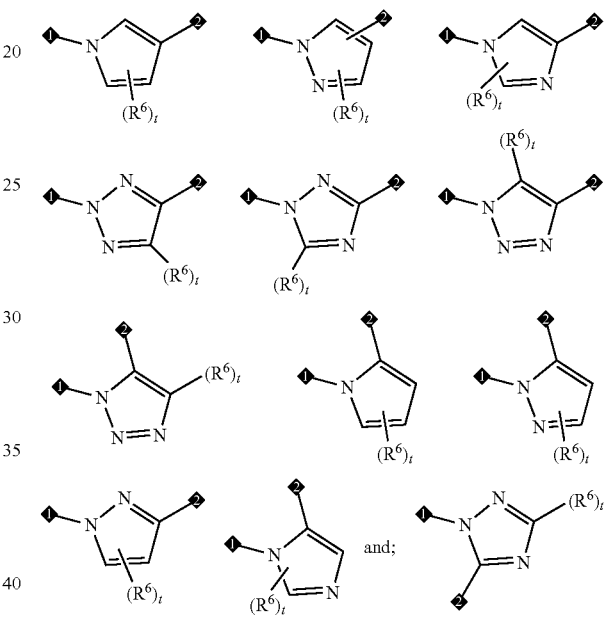

◆ Attachment point for X.
◈ Attachment point for Y.

and $R^6$, at each occurrence, is independently $C_{1-6}$ alkyl, $C_{1-6}$ hydroxyalkyl, $C_{1-6}$ aminoalkyl, $C_{1-6}$ alkoxy, $C_{1-6}$ alkoxyalkyl, $C_{1-6}$ haloalkyl, or phenyl.

In yet one embodiment of Formula (I), A, E, and G, together with the nitrogen and carbon atoms, form a ring moiety selected from the following structural formula:

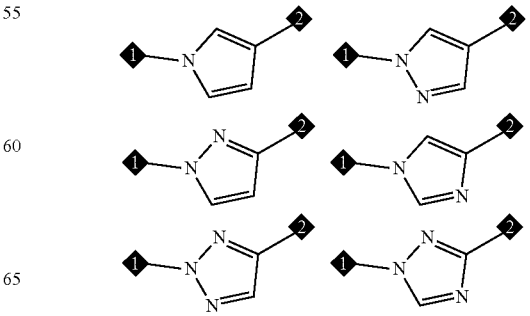

-continued

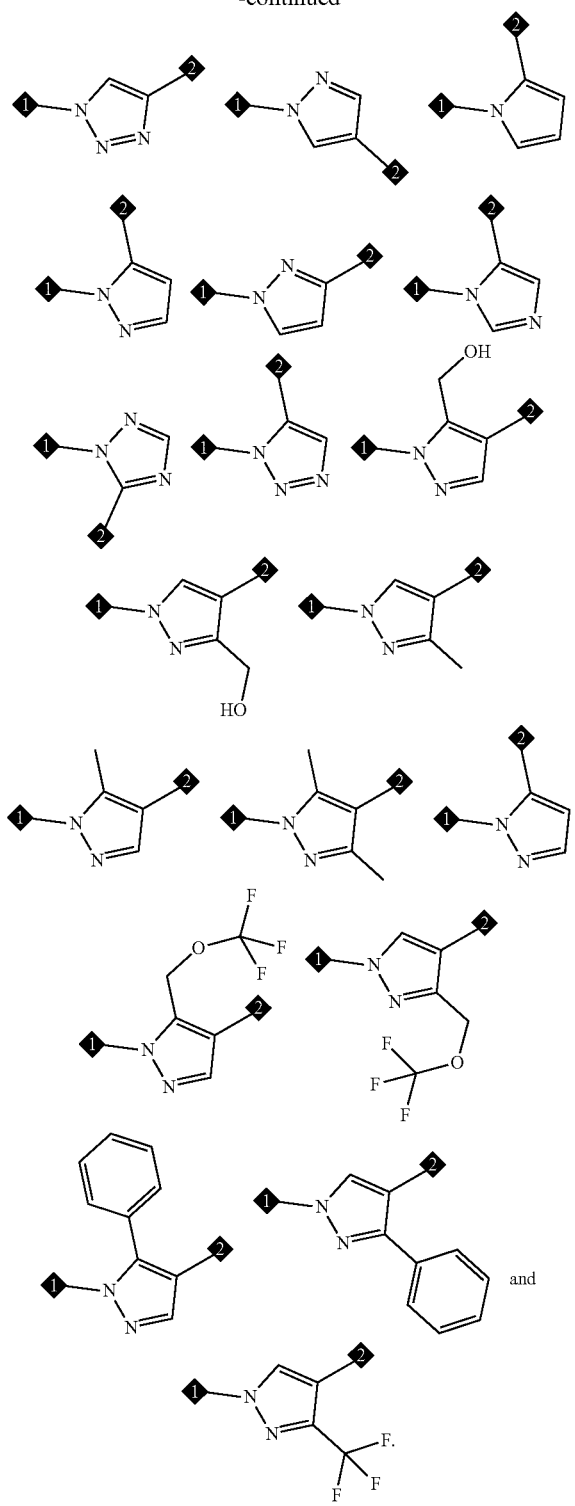

◆ Attachment point for X.
◆ Attachment point for Y.

Examples of the arginine mimetic moiety, i.e., $R^1$ of Formula (I), can be found in Peterlin Masic, Lucija, "Arginine Mimetic Structures in Biologically Active Antagonists and Inhibitors"; Current Medicinal Chemistry, Volume 13, Number 30, December 2006, pp. 3627-3648, Publisher: Bentham Science Publishers. In one embodiment, $R^1$ is an arginine mimetic moiety selected from the group consisting of

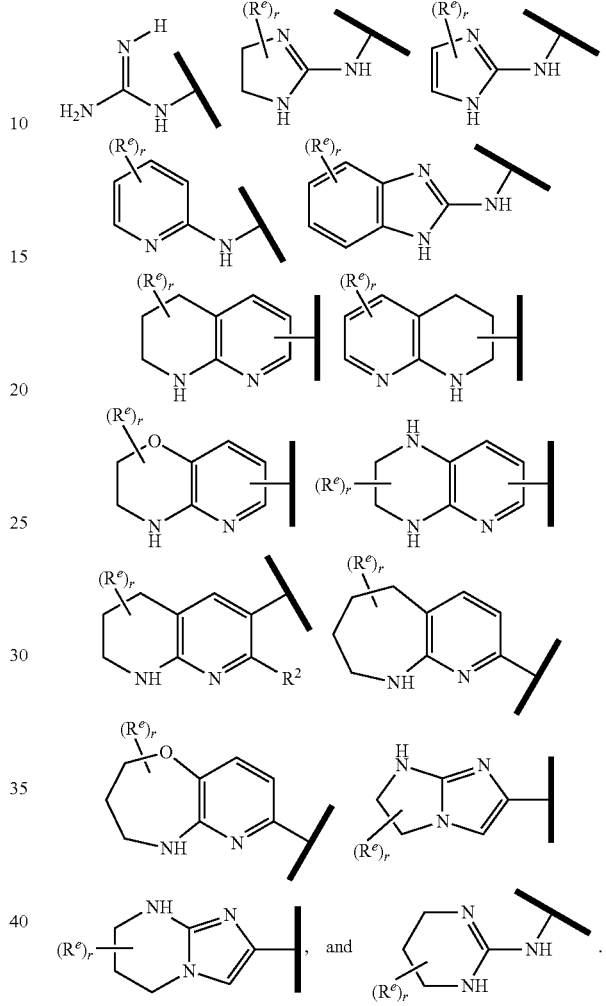

In one embodiment, $R^1$ is an arginine mimetic moiety selected from the group consisting of

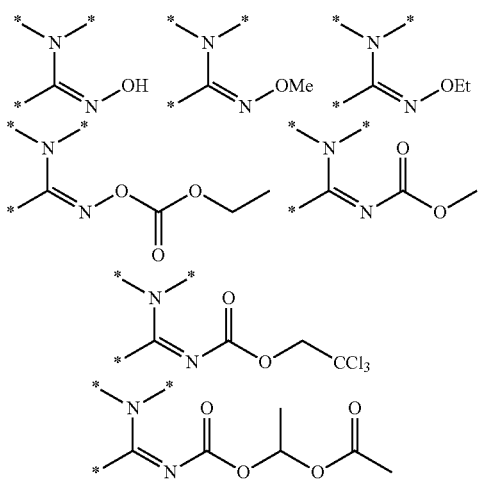

-continued

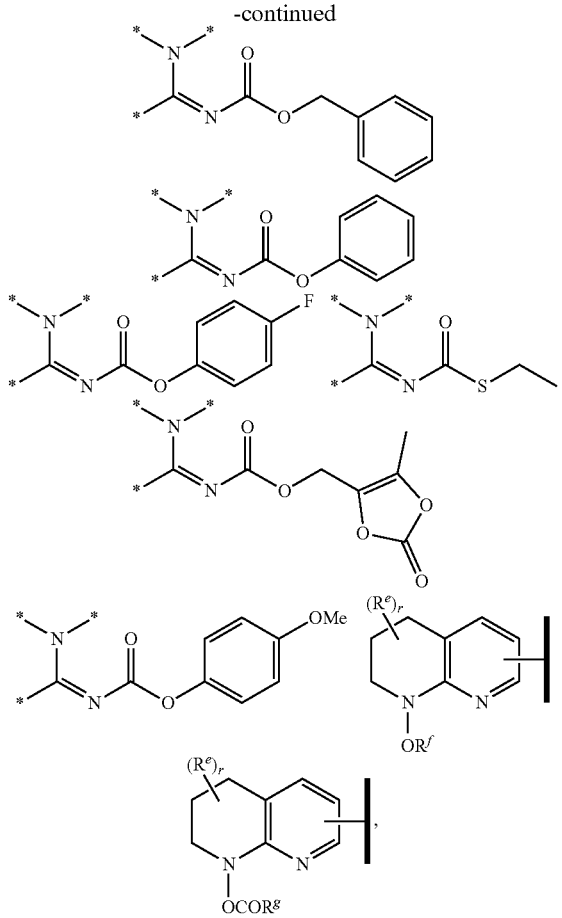

wherein, one of the asterisks in each of the arginine mimetics moiety is an attachment point to X and the other two asterisks are hydrogen;

$R^f$=H, Me, Et, COOEt;

$R^g$=$CH_3$, $CH_2CH_3$, $CH_2CCl_3$, ethyl, phenyl, 4-fluorophenyl, 4-methoxyphenyl, benzyl,

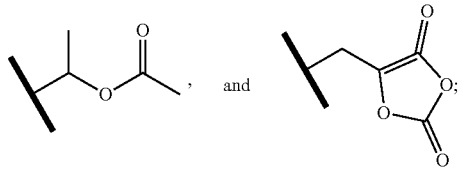

$R^e$ is OH, $C_{1-4}$ alkyl, halo, haloalkyl, or $C_{1-4}$ cycloalkyl; and r is an integer of 0, 1, 2, or 3.

In one embodiment of Formula (I), the compounds are represented by Formula (II) or (III):

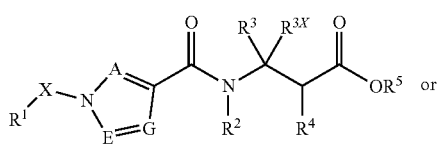

(II)

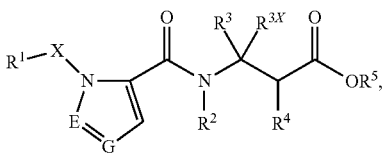

(III)

or a stereoisomer, a tautomer, or a pharmaceutically acceptable salt or a solvate thereof, wherein:

A, E, and G are independently N or $CR^6$;

R is an arginine mimetic moiety selected from the group consisting of

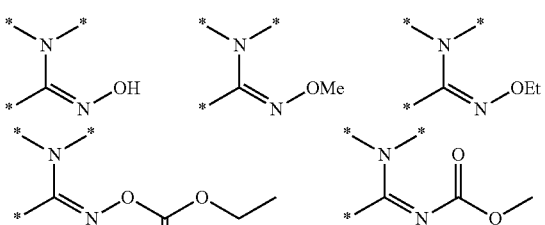

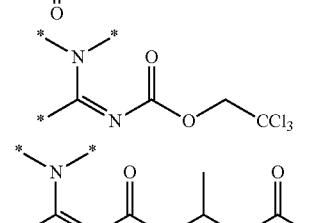

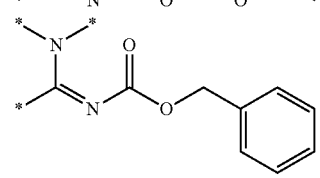

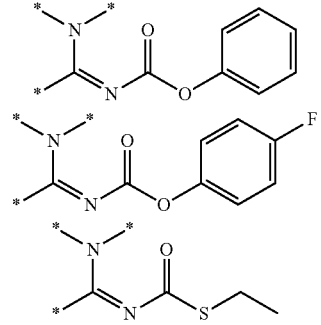

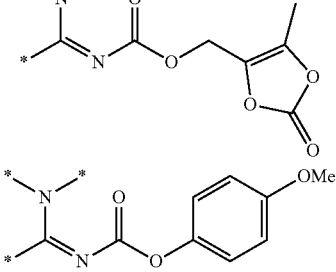

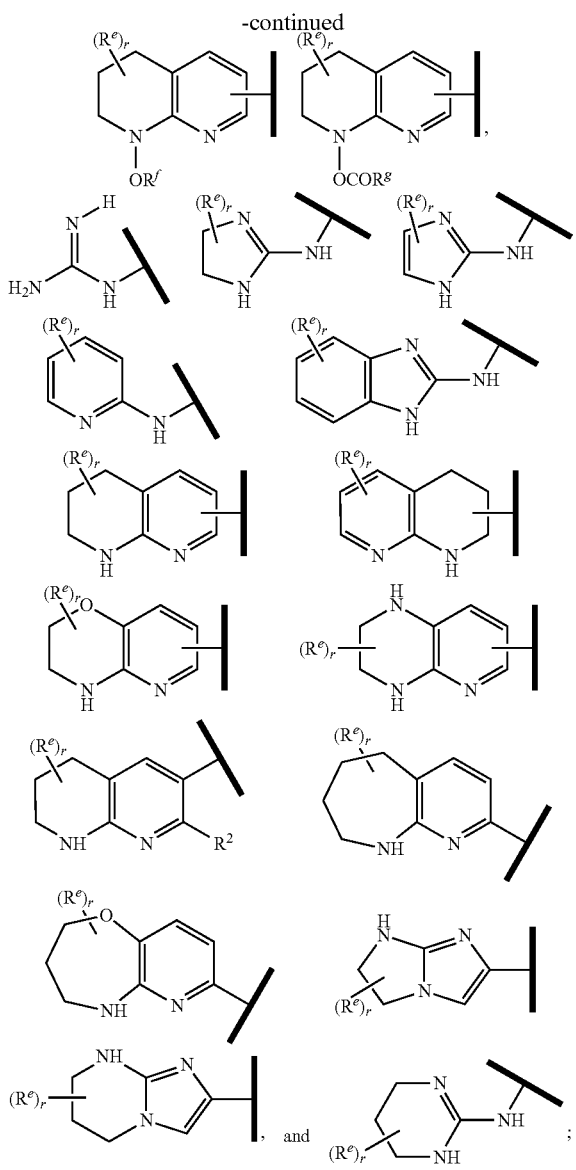

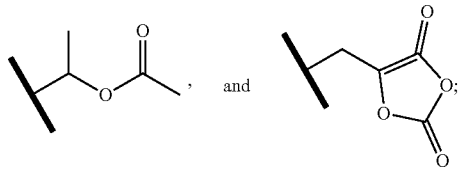

one of the asterisks in each of the arginine mimetics moiety is an attachment point to X, and the other two asterisks are hydrogen;

R$^f$=H, Me, Et, COOEt;
R$^g$=CH$_3$, CH$_2$CCl$_3$, phenyl, 4-fluorophenyl, 4-methoxyphenyl, benzyl,

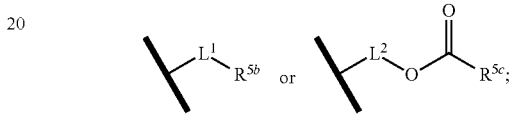

R$^e$ is OH, C$_{1-4}$ alkyl, halo, haloalkyl, or C$_{1-4}$ cycloalkyl;
r is an integer of 0, 1, 2, or 3;
X is a C$_{1-3}$ alkylene substituted with 0, 1, or 2 R$^{7b}$;
Y is C(O) or CH$_2$;
R$^2$ is hydrogen or C$_{1-6}$ alkyl;

R$^3$ is hydrogen, C$_{1-10}$ alkyl, 3 to 10 membered carbocyclyl, or 3 to 10 membered heterocyclyl, wherein the alkyl, carbocyclyl, and heterocyclyl are each independently substituted with 0, 1, 2, or 3 R$^8$;

R$^{3X}$ is hydrogen; or alternatively, R$^3$ and R$^{3X}$, together with the atom to which they are attached, form a carbocyclyl (e.g., cycloalkyl) or a heterocyclyl (e.g., cycloheteroalkyl), and the carbocyclyl and heterocyclyl are each independently substituted with 0, 1, 2, or 3 R$^{12}$;

R$^4$ is hydrogen, C$_{1-10}$ alkyl, 3 to 10 membered carbocyclyl, 3 to 10 membered heterocyclyl, NR$^a$R$^b$, OH, OR$^a$, S(O)$_n$R$^{10}$, C(O)NR$^a$R$^b$, NHC(O)OR$^a$, NHC(O)NR$^a$R$^b$, NHC(O)R$^{10}$, OC(O)NR$^a$R$^b$, OC(O)R$^{10}$, NHS(O)$_n$NR$^a$R$^b$, or NHS(O)$_n$R$^{10}$;

n is an integer of 1 or 2;
R$^5$ is H, R$^{5a}$, or a structural moiety selected from $$\begin{array}{c} \xi\!\!-\!\!\overset{\mid}{\underset{\mid}{C}}\!\!-\!\!L^1\!\!-\!\!R^{5b} \end{array} \quad \text{or} \quad \begin{array}{c} \xi\!\!-\!\!\overset{\mid}{\underset{\mid}{C}}\!\!-\!\!L^2\!\!-\!\!O\!\!-\!\!\underset{\underset{O}{\|}}{C}\!\!-\!\!R^{5c}; \end{array}$$

L$^1$ and L$^2$ are each independently C$_{1-4}$ alkylene;
R$^{5a}$ and R$^{5b}$ are each independently C$_{1-6}$ alkyl, phenyl, or 5- to 7-membered heterocyclyl; wherein the alkyl, phenyl, and heterocyclyl are each independently substituted with 0 to 3 R$^{5d}$;
R$^{5c}$ is C$_{1-6}$ alkyl or 5- to 7-membered carbocyclyl; wherein the alkyl and carbocyclyl are each independently substituted with 0 to 3 R$^{5d}$;
R$^{5d}$, at each occurrence, is independently halo, OH, alkoxy, oxo, or alkyl; or alternatively, two adjacent R$^{5d}$, together with the atoms to which they are attached, form a carbocyclyl moiety;
R$^6$ is hydrogen, C$_{1-6}$ alkyl, C$_{3-5}$ cycloalkyl, heteroalkyl, cycloheteroalkyl, aryl, or heteroaryl, wherein the alkyl, cycloalkyl, heteroalkyl, cycloheteroalkyl, aryl, and heteroaryl are each independently substituted with 0, 1, 2, or 3 R$^9$;
R$^{7b}$ is halo, cyano, nitro, OH, alkoxy, NR$^a$R$^b$, alkyl, heteroalkyl, aryl, cycloalkyl, heteroaryl, or cycloheteroalkyl;
R$^8$ and R$^{12}$, at each occurrence, are independently halo, cyano, nitro, OH, alkoxy, NR$^a$R$^b$, alkyl, heteroalkyl, aryl, cycloalkyl, heteroaryl, or cycloheteroalkyl; or alternatively, two R$^8$ at adjacent positions, together with the atoms to which they are attached, form a carbocyclyl or heterocyclyl; or two R$^{12}$ at adjacent positions, together with the atoms to which they are attached, form a carbocyclyl or heterocyclyl;
R$^9$ at each occurrence is independently halo, cyano, nitro, OH, alkoxy, NR$^a$R$^b$, alkyl, heteroalkyl, aryl, cycloalkyl, heteroaryl, or cycloheteroalkyl;
R$^{10}$ is C$_{1-6}$ alkyl, 3 to 10 membered carbocyclyl, or 3 to 10 membered heterocyclyl, wherein the alkyl, carbocyclyl, heterocyclyl are each independently substituted with 0, 1, 2, or 3 R$^{11}$;
R$^{11}$ is halo, cyano, nitro, OH, alkoxy, NR$^a$R$^b$, alkyl, aryl, cycloalkyl, heteroaryl, cycloheteroalkyl, or S(O)$_g$(aryl); wherein the aryl, alkyl, cycloalkyl, heteroaryl, and cycloheteroalkyl are each independently substituted with 0, 1, 2, or 3 R$^{13}$;
g is an integer of 1 or 2;
R$^a$ and R$^b$, at each occurrence, are independently hydrogen, C$_{1-10}$ alkyl, 3 to 10 membered carbocyclyl, or 3 to 10 membered heterocyclyl; wherein the alkyl, carbocyclyl, heterocyclyl are each independently substituted with 0, 1, 2, or 3 $R^{14}$; and $R^{13}$ and $R^{14}$, at each occurrence, are independently halo, cyano, nitro, OH, alkoxy, $NR^aR^b$, alkyl, heteroalkyl, aryl, cycloalkyl, heteroaryl, or cycloheteroalkyl.

In one embodiment of Formula (I), (II), or (III), $R^6$, at each occurrence, is independently hydrogen, $C_{1-6}$ alkyl, $C_{1-6}$ hydroxyalkyl, $C_{1-6}$ aminoalkyl, $C_{1-6}$ alkoxy, $C_{1-6}$ alkoxyalkyl, $C_{1-6}$ haloalkyl, or phenyl. In another embodiment, $R^6$ is H, $CH_3$, $CH_2OH$, $CH_2OC(CH_3)_3$, $CH_2OC(CF_3)_3$, $CF_3$, or phenyl.

In one embodiment of Formula (I), (II), or (III), X is $C_{1-4}$ alkylene. In another embodiment, X is $CH_2$, $CH_2CH_2$, or $CH_2CH_2CH_2$.

In one embodiment of Formula (I), (II), or (III), $R^2$ is H, methyl, ethyl, or isopropyl.

In one embodiment of Formula (I), (II), or (III), $R^3$ and $R^{3X}$ are not both hydrogen.

In one embodiment of Formula (I), (II), or (III), $R^1$ is selected from a structural formula selected from the group consisting of

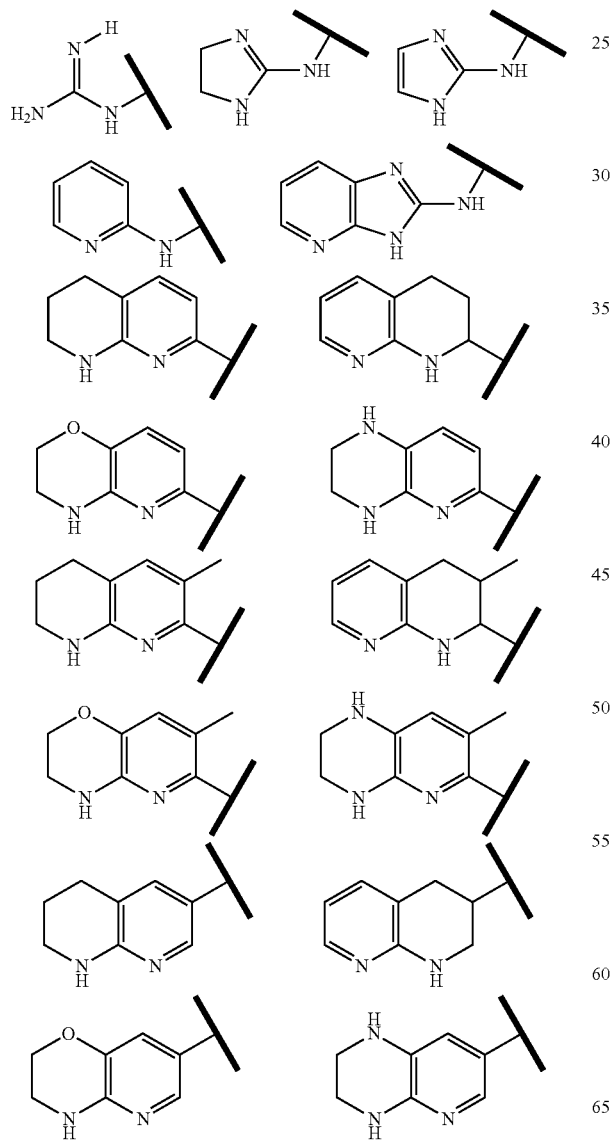

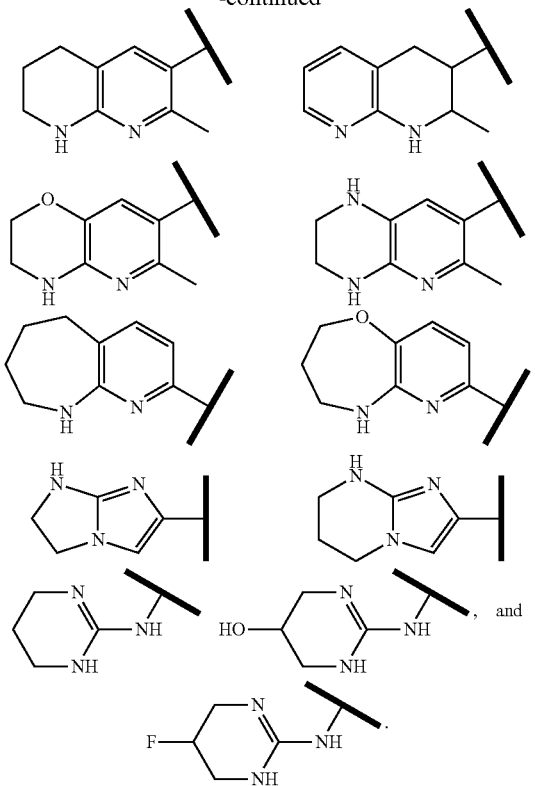

In one embodiment of Formula (I), (II), or (III), $R^1$ is selected from a structural formula selected from the group consisting of

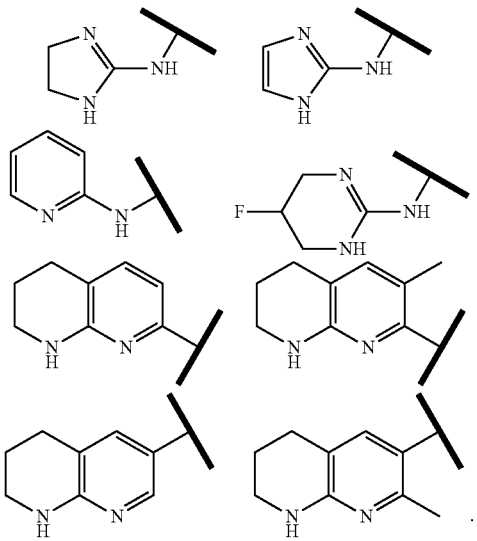

In one embodiment of Formula (I), (II), or (III), $R^3$ is selected from the group consisting of hydrogen, $C_{1-6}$ alkyl, 6 to 10 membered aryl, or 5 to 10 membered heteroaryl, wherein each of the alkyl, aryl, heteroaryl is independently substituted with 0, 1, 2, or 3 $R^8$; $R^{3X}$ is hydrogen; and $R^8$ is halo, cyano, nitro, OH, $NR^aR^b$, alkyl, hydroxyalkyl, alkoxy, alkoxyalkyl, aryl, aryloxy, cycloalkyl, haloalkyl, or haloalkoxy; or alternatively, two $R^8$ at adjacent positions, together with the atoms to which they are attached, form a carbocyclyl or heterocyclyl moiety.

In one embodiment of Formula (I), (II), or (III), $R^3$ is selected from the group consisting of H, methyl,

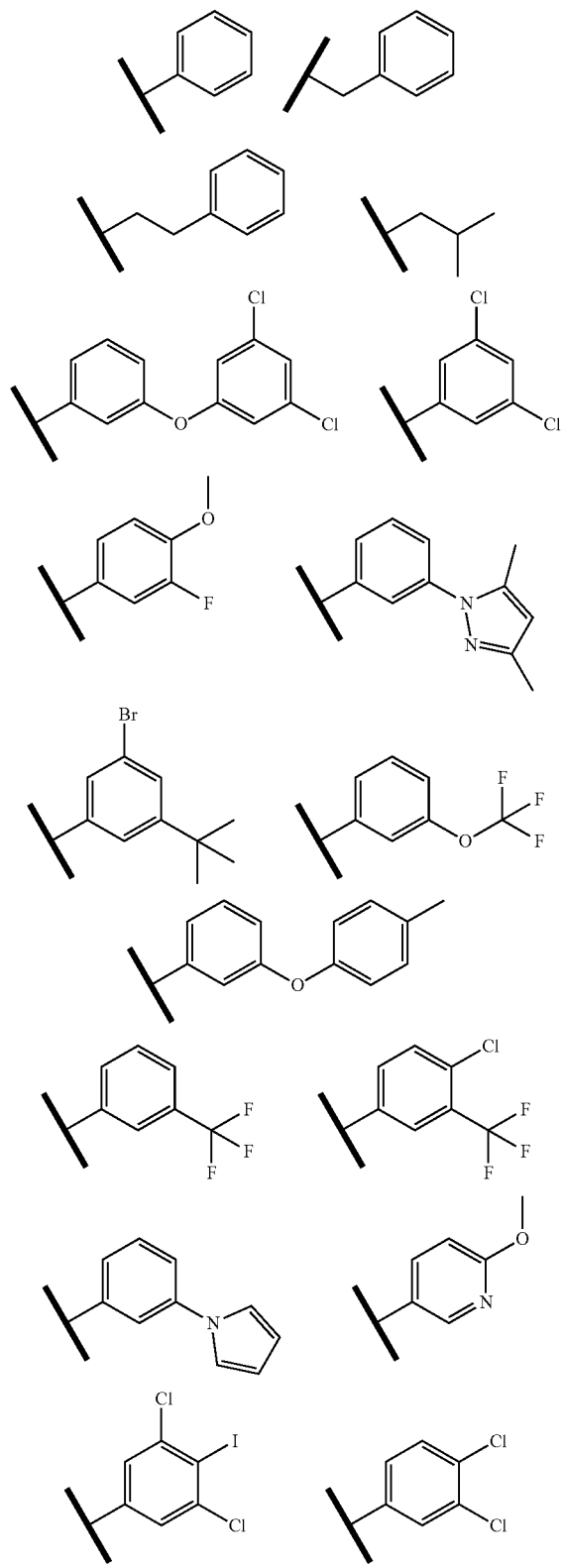

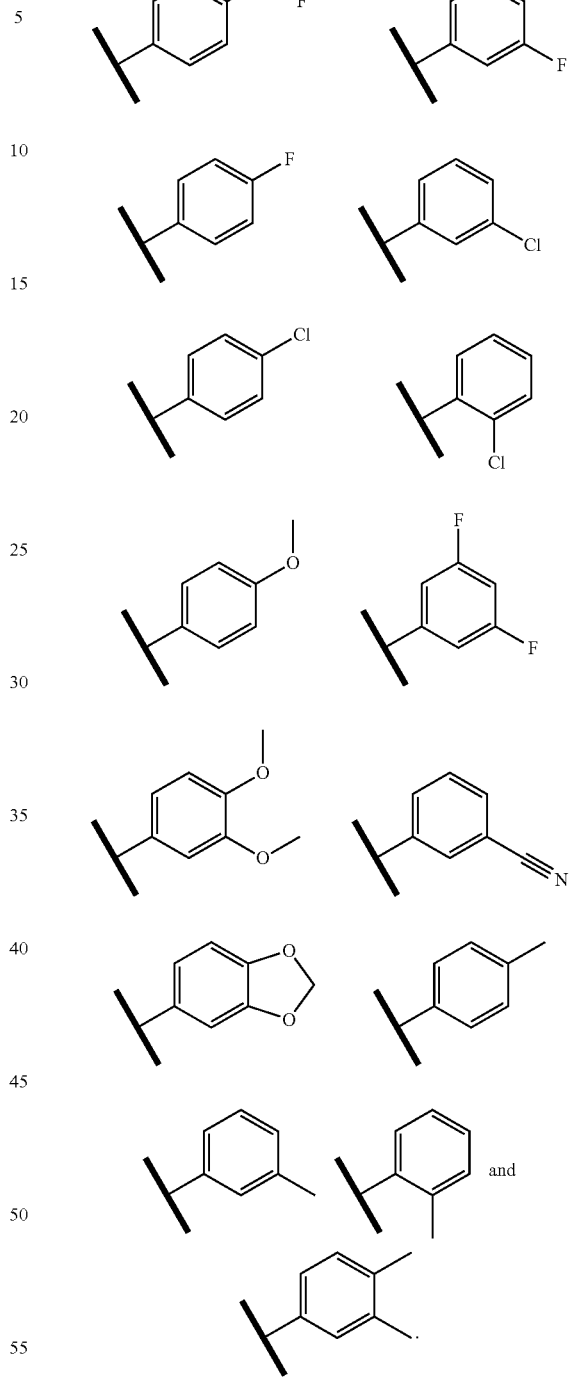

In one embodiment of Formula (I), (II), or (III), $R^3$ and $R^{3X}$, together with the atom to which they are attached, form a carbocyclyl or heterocyclyl, and the carbocyclyl and heterocyclyl are each independently substituted with 0, 1, 2, or 3 $R^{12}$. In another embodiment, $R^3$ and $R^{3X}$, together with the atom to which they are attached, form a cycloalkyl substituted with 0, 1, 2, or 3 $R^{12}$. In yet another embodiment, $R^3$ and $R^{3X}$, together with the atom to which they are attached, form a structural moiety selected from

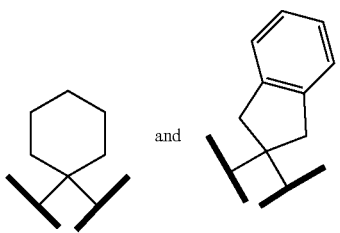

In one embodiment of Formula (I), (II), or (III), $R^4$ is hydrogen.

In one embodiment of Formula (I), (II), or (III), $R^{10}$ is $C_{1-6}$ alkyl, phenyl, benzyl, or 3 to 10 membered heterocycloalkyl, wherein the alkyl, phenyl, benzyl, and heterocycloalkyl are each independently substituted with 0 to 3 $R^{11}$; and $R^{11}$ is halo, alkoxy, alkyl, aryl, cycloalkyl, heteroaryl, heterocycloalkyl, or $S(O)_g$(phenyl). In another embodiment of the compound of Formula (I) (II), or (III), $R^4$ is selected from H, $NR^aR^b$, and the following structural moiety

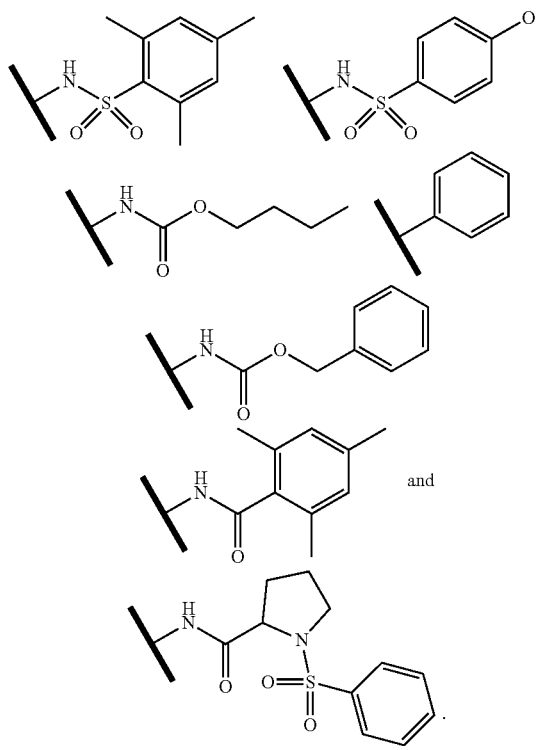

In one embodiment of Formula (I), (II), or (III), $R^3$ is hydrogen or $C_{1-6}$ alkyl; and $R^{3X}$ is hydrogen.

In one embodiment of Formula (I), (II), or (III), $R^5$ is H or $R^{5a}$; and $R^{5a}$ is methyl, ethyl, isopropyl, n-butyl, isopentyl, or a structural moiety selected from

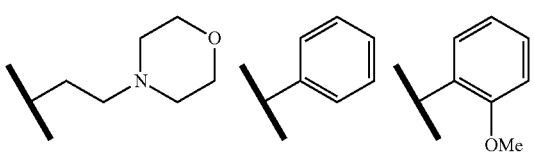

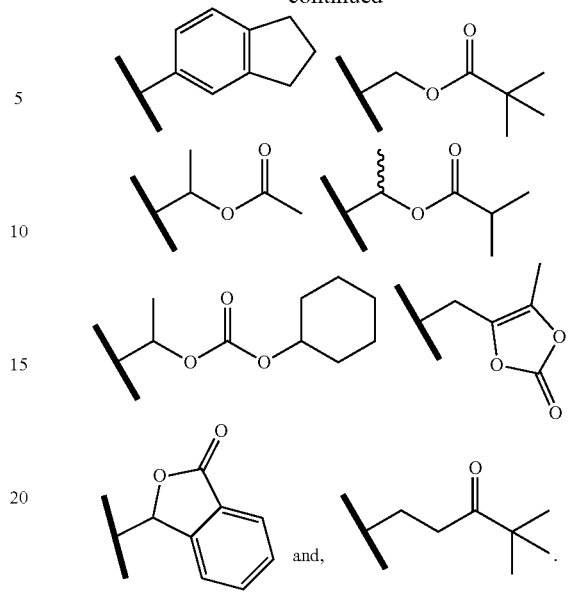

In one embodiment of Formula (I) or (II), the compound is represented by structural Formula (IIa) or (IIb):

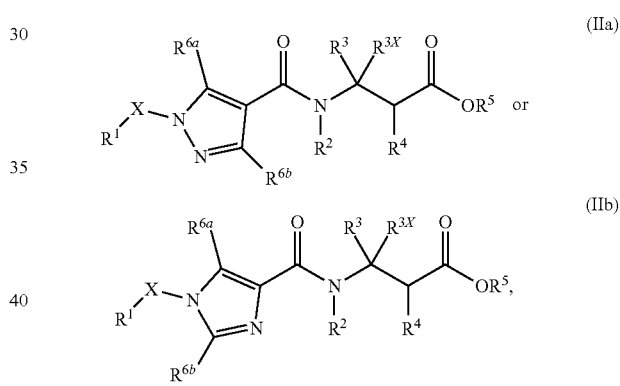

wherein $R^{6a}$ and $R^{6b}$ are each independently hydrogen, $C_{1-6}$ alkyl, $C_{1-6}$ hydroxyalkyl, $C_{1-6}$ aminoalkyl, $C_{1-6}$ alkoxy, $C_{1-6}$ alkoxyalkyl, $C_{1-6}$ haloalkyl, or phenyl.

In one embodiment of Formula (IIa), $R^{6a}$ is hydrogen, $C_{1-6}$ alkyl, $C_{1-6}$ hydroxyalkyl, $C_{1-6}$ aminoalkyl, $C_{1-6}$ alkoxy, $C_{1-6}$ alkoxyalkyl, $C_{1-6}$ haloalkyl, or phenyl; and $R^{6b}$ is hydrogen.

In one embodiment of Formula (IIb), $R^{6a}$ is hydrogen; and $R^{6b}$ is hydrogen, $C_{1-6}$ alkyl, $C_{1-6}$ hydroxyalkyl, $C_{1-6}$ aminoalkyl, $C_{1-6}$ alkoxy, $C_{1-6}$ alkoxyalkyl, $C_{1-6}$ haloalkyl, or phenyl.

In one embodiment of Formula (IIa) or (IIb), $R^{6a}$ and $R^{6b}$ are both hydrogen.

In one embodiment of Formula (IIa) or (IIb), $R^3$ is hydrogen; and $R^4$ is $C_{1-10}$ alkyl, 3 to 10 membered carbocyclyl, 3 to 10 membered heterocyclyl, $NR^aR^b$, OH, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$.

In one embodiment of Formula (IIa) or (IIb), $R^3$ is $C_{1-10}$ alkyl, 3 to 10 membered carbocyclyl, or 3 to 10 membered heterocyclyl, wherein the alkyl, carbocyclyl, heterocyclyl are each independently substituted with 0, 1, 2, or 3 $R^8$; and $R^4$ is hydrogen.

In one embodiment of Formula (I) (II), or (III), the compounds are represented by structural Formula (IIc), (IId) or (IIe):

(IIc)

(IId)

(IIe)

(IIf)

In one embodiment of Formula (IIc), (IId), (IIe), or (IIf), wherein $R^3$ is hydrogen; and $R^4$ is $C_{1-10}$ alkyl, 3 to 10 membered carbocyclyl, 3 to 10 membered heterocyclyl, $NR^aR^b$, OH, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$.

In one embodiment of Formula (IIc), (IId), (IIe), or (IIf), wherein $R^4$ is $C_{1-10}$ alkyl, 6 to 10 membered aryl, 5 to 10 membered heteroaryl, $NR^aR^b$, OH, $OR^a$, $NHC(O)OR^a$, $NHC(O)NR^aR^b$, $NHC(O)R^{10}$, $NHS(O)_nNR^aR^b$, and $NHS(O)_nR^{10}$; $R^{10}$ is $C_{1-6}$ alkyl, 6 to 10 membered aryl, 5 to 10 membered heteroaryl, or 3 to 10 membered heterocycloalkyl, wherein each of the alkyl, aryl, heteroaryl, and heterocycloalkyl is independently substituted with 0, 1, 2, or 3 $R^{11}$; and $R^{11}$ is halo, cyano, OH, alkoxy, $NR^aR^b$, aryl, cycloalkyl, heteroaryl, heterocycloalkyl, or $S(O)_g(aryl)$.

In one embodiment of Formula (IIc), (IIe), or (IIf), wherein $R^4$ is selected from a structural moiety in a group consisting of -continued and In one embodiment of Formula (IIc), (IId), (IIe), or (IIf), wherein $R^3$ is $C_{1-10}$ alkyl, 3 to 10 membered carbocyclyl, or 3 to 10 membered heterocyclyl, wherein the alkyl, carbocyclyl, heterocyclyl are each independently substituted with 0, 1, 2, or 3 $R^8$; and $R^4$ is hydrogen.

In one embodiment of Formula (IIc), (IId), (IIe), or (IIf), wherein $R^2$ is hydrogen.

In certain specific embodiments, the present invention provides a compound selected from any subset list of compounds or a single compound from the exemplified examples, or a stereoisomer, a tautomer, a pharmaceutically acceptable salt, or a solvate thereof.

II. Pharmaceutical Compositions, Therapeutic Utilities, and Combinations

In one embodiment, the present invention provides a composition comprising at least one of the compounds of the present invention, or a stereoisomer, a tautomer, or a pharmaceutically acceptable salt or a solvate thereof.

In one embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

In another embodiment, the present invention provides a method for the treatment of a disease, disorder, or condition associated with dysregulation of αv integrins in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an integrin receptor antagonizing effect in a patient comprising administering a therapeutically effective amount of a compound of the present invention, or a stereoisomer, a tautomer, or a pharmaceutically acceptable salt or solvate thereof, to the patient. In one embodiment, the integrin receptor antagonizing effect is an antagonizing effect to any of αvβ6, αvβ1, αvβ3, αvβ5, and αvβ8; or a combination of one or more of αvβ6, αvβ1, αvβ3, αvβ5, and αvβ8. For example, the integrin receptor antagonizing effect can be an αvβ6, αvβ1, αvβ3, αvβ5, and αvβ8 antagonizing effect.

In some embodiments, the disease, disorder, or condition is associated with fibrosis, including pulmonary, liver, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of αv integrins that can be prevented, modulated, or treated according to the present invention include, but are not limited to, transplant injection, fibrotic disorders (e. g., idiopathic pulmonary fibrosis (IPF), interstitial lung disease, liver fibrosis, kidney fibrosis, skin fibrosis, systemic sclerosis), inflammatory disorders (e.g., acute hepatitis, chronic hepatitis, non-alcoholic steatohepatitis (NASH), psoriasis, irritable bowel syndrome (IBS), inflammatory bowel disease (IBD)), osteoporosis, as well as cell-proliferative disorders (e.g., cancer, myeloma, fibroma, hepatocarcinoma, leukemia, Kaposi's sarcoma, solid tumors).

The fibrotic disorders, inflammatory disorders, as well as cell-proliferative disorders that are suitable to be prevented or treated by the compounds of the present invention include, but are not limited to, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, non-alcoholic fatty liver disease (NAFLD), alcoholic or non-alcoholic steatohepatitis (NASH), acute hepatitis, chronic hepatitis, liver cirrhosis, primary sclerosing cholangitis, drug-induced hepatitis, biliary cirrhosis, portal hypertension, regenerative failure, liver hypofunction, hepatic blood flow disorder, nephropathy, pneumonia, psoriasis, irritable bowel syndrome (IBS), inflammatory bowel disease (IBD), abnormal pancreatic secretion, benign prostatic hyperplasia, neuropathic bladder disease, spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocarcinoma, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-αvβ6 monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol, 3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, Sar$^9$, Met(O$_2$)$^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic (32 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as Idiopathic Pulmonary Fibrosis (IPF), liver and kidney fibrosis, Non-Alcoholic Fatty Liver Disease (NALFD), Non-Alcoholic Steato-Hepatitis (NASH), cardiac fibrosis, and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997), ACC inhibitors (for example, CP-640186 and NDI-010976), FGF21 agonist (for example LY2405319), caspase inhibitors (for example, emricasan), NOX4 inhibitors (for example, GKT137831), MGAT2 inhibitor, and bile acid/fatty acid conjugates (for example aramchol). The αv inhibitors of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as Alemtuzumab, Atezolizumab, Ipilimumab, Nivolumab, Ofatumumab, Pembrolizumab, and Rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day.

Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., FXR agonists or other pharmaceutically active material.

The above other therapeutic agents, when employed in combination with the compounds of the present invention may be used, for example, in those amounts indicated in the Physicians' Desk Reference, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the αv integrins. Such compounds may be provided in a commercial kit, for example, for use in pharmaceutical research involving αv integrins activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof and, (c) a package insert stating that the pharmaceutical composition can be used for the treatment of dyslipidemias and the sequalae thereof. In another embodiment, the package insert states that the pharmaceutical composition can be used in combination (as defined previously) with a second therapeutic agent for the treatment of fibrosis and the sequalae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

III. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. As used herein, "a compound of the invention" or "compounds of the invention" means one or more compounds encompassed by Formula (I), (II), (IIa), (IIb), (IIc), (IId), (IIe), (IIf), or (III), or a stereoisomer, a tautomer, or a pharmaceutically acceptable salt or solvate thereof.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkyl amine (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or $sp^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$. "Benzyl" can also be represented by formula "Bn".

The term "lower alkoxy", "alkoxy" or "alkyloxy", "aryloxy" or "aralkoxy" refers to any of the above alkyl, aralkyl or aryl groups linked to an oxygen atom. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "lower alkylthio", "alkylthio", "thioalkoxy", "arylthio", or "aralkylthio" represents an alkyl, aryl, or aralkyl group as defined above with the indicated number of carbon atoms attached through a sulphur bridge; for example methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "$C_1$ to $C_6$ alkylcarbonyl" (or alkylcarbonyl), is intended to include $C_1$, $C_2$, $C_3$, $C_4$, $C_5$, and $C_6$ alkyl-C(O)— groups.

The term "alkylsulfonyl" or "sulfonamide" as used herein alone or as part of another group refers to alkyl or amino linked to a sulfonyl group. For example, alkylsulfonyl may be represented by —$S(O)_2R'$, while sulfonamide may be represented by —$S(O)_2NR^cR^d$. R' is $C_1$ to $C_6$ alkyl; and $R^c$ and $R^d$ are the same as defined below.

The term "alkylsulfonyl" or "sulfonamide", as used herein alone or as part of another group, refers to alkyl or amino linked to a sulfonyl group. For example, alkylsulfonyl may be represented by —$S(O)_2R'$, while sulfonamide may be represented by —$S(O)_2NR^cR^d$. R' is $C_1$ to $C_6$ alkyl; and $R^c$ and $R^d$ are the same as defined below for "amino".

The term "carbamate" as used herein alone or as part of another group refers to oxygen linked to an amido group. For example, alkylcarbonyl may be represented by $N(R^cR^d)$—C(O)—O—, and $R^c$ and $R^d$ are the same as defined below for "amino".

The term "carbamate" as used herein alone or as part of another group refers to amino linked to a carbonyl group.

The term "amino" is defined as —$NR^cR^d$, wherein $R^c$ and $R^d$ are independently hydrogen or $C_{1-6}$ alkyl; or alternatively, $R^c$ and $R^d$, taken together with the atoms to which they are attached, form a 3- to 8-membered carbocyclic or heterocyclic ring which is optionally substituted with one or more group selected from halo, cyano, hydroxyl, amino, oxo, $C_{1-6}$ alkyl, alkoxy, and aminoalkyl. When $R^c$ or $R^d$ (or both of them) is $C_{1-6}$ alkyl, the amino group can also be referred to as alkylamino. Examples of alkylamino group include, without limitation, —$NH_2$, methylamino, ethylamino, propylamino, isopropylamino and the like.

The term "aminoalkyl" refers to an alkyl group on which one of the hydrogen atoms is replaced by an amino group. For example, aminoalkyl may be represented by $N(R^cR^d)$-alkylene-. "$C_1$ to $C_6$" or "$C_{1-6}$" aminoalkyl" (or aminoalkyl), is intended to include $C_1$, $C_2$, $C_3$, $C_4$, $C_5$, and $C_6$ aminoalkyl groups.

The term "halogen" or "halo" as used herein alone or as part of another group refers to chlorine, bromine, fluorine, and iodine, with chlorine or fluorine being preferred.

"Haloalkyl" is intended to include both branched and straight-chain saturated aliphatic hydrocarbon groups having the specified number of carbon atoms, substituted with one or more halogens. "$C_1$ to $C_6$ haloalkyl" or "$C_{1-6}$ haloalkyl" (or haloalkyl), is intended to include $C_1$, $C_2$, $C_3$, $C_4$, $C_5$, and $C_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or Cl, preferably F, such as polyfluoroalkyl, for example, $CF_3CH_2$, $CF_3$ or $CF_3CF_2CH_2$.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or Cl, preferably F, such as polyfluoroalkoxy, for example, $CF_3CH_2O$, $CF_3O$ or $CF_3CF_2CH_2O$.

"Hydroxyalkyl" are intended to include both branched and straight-chain saturated aliphatic hydrocarbon groups having the specified number of carbon atoms, substituted with 1 or more hydroxyl (OH). "$C_1$ to $C_6$ hydroxyalkyl" (or hydroxyalkyl), is intended to include $C_1$, $C_2$, $C_3$, $C_4$, $C_5$, and $C_6$ hydroxyalkyl groups.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

The term "cycloheteroalkyl" refers to cyclized heteroalkyl groups, including mono-, bi- or poly-cyclic ring systems. "$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, the term "azacyclyl" refers to a cycloheteroalkyl containing one or more nitrogen atoms in the ring. Example azacyclyl groups include, but are not limited to, pyrrolidinyl, piperidinyl, morpholinyl, and piperazinyl.

As used herein, "carbocycle", "carbocyclyl", or "carbocyclic" is intended to mean any stable 3-, 4-, 5-, 6-, 7-, or 8-membered monocyclic or 5-, 6-, 7-, 8-, 9-, 10-, 11-, 12-, or 13-membered polycyclic (including bicyclic or tricyclic) hydrocarbon ring, any of which may be saturated or partially unsaturated. That is, the term "carbocycle", "carbocyclyl", or "carbocyclic" includes, without limitation, cycloalkyl and cycloalkenyl. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, indanyl, adamantyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, indanyl, and tetrahydronaphthyl. A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

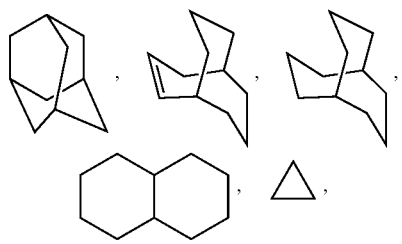

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated or partially unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from the group consisting of N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of hetercyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, dihydrofuro[2,3-b]tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of heteroaryl include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl.

Unless otherwise indicated, "carbocyclyl" or "heterocyclyl" may optionally include one to three additional rings fused to the carbocyclic ring or the heterocyclic ring (such as aryl, cycloalkyl, heteroaryl or cycloheteroalkyl rings, for example,

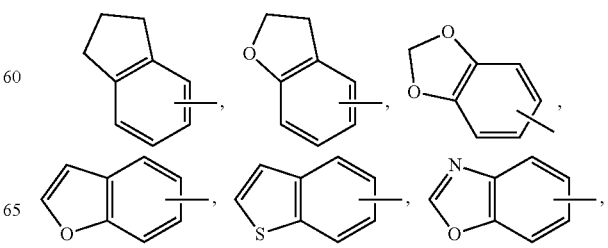

-continued

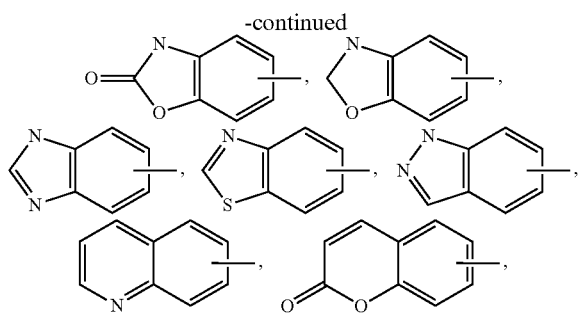

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

In accordance with a convention used in the art, a bond pointing to a bold line, such as

as used in structural formulas herein, depicts the bond that is the point of attachment of the moiety or substituent to the core or backbone structure.

In accordance with a convention used in the art, a wavy bond in a structural formula, such as

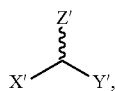

is used to depict a stereogenic center of the carbon atom to which X', Y', and Z' are attached and is intended to represent both enantiomers in a single FIGURE. That is, a structural formula with such as wavy bond denotes each of the enantiomers individually, such as

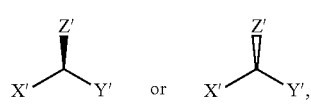

as well as a racemic mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

When a dotted ring is used within a ring structure, this indicates that the ring structure may be saturated, partially saturated or unsaturated.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule For example, one skilled in the art would readily understand that a 1,2,3-triazole exists in two tautomeric forms as defined above:

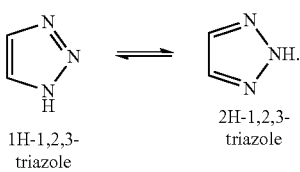 [SMILES: c1c[nH]nn1 ; c1cn[nH]n1]

1H-1,2,3-
triazole 2H-1,2,3-
triazole

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate.

Preferred salts of the compounds of Formula I which contain an acid group include sodium, potassium and magnesium salts and pharmaceutically acceptable organic amines.

In addition, the compounds of the present invention may have prodrug forms. Any compound that will be converted in vivo to provide the bioactive agent is a prodrug within the scope and spirit of the invention. The term "prodrug" as used herein encompasses both the prodrugs based on the carboxylic acid residue, i.e., "prodrug esters", and the prodrugs based on the arginine mimetics moiety, i.e., "prodrugs of arginine mimetics". Such prodrugs are preferably administered orally since hydrolysis in many instances occurs principally under the influence of the digestive enzymes. Parenteral administration may be used where the ester per se is active, or in those instances where hydrolysis occurs in the blood.

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Examples of such prodrug esters include:

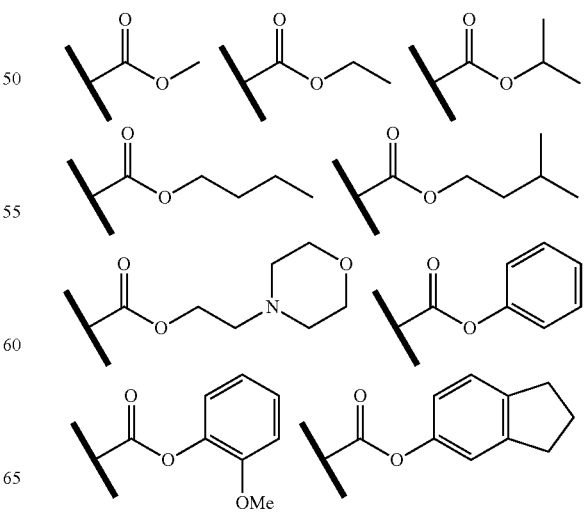

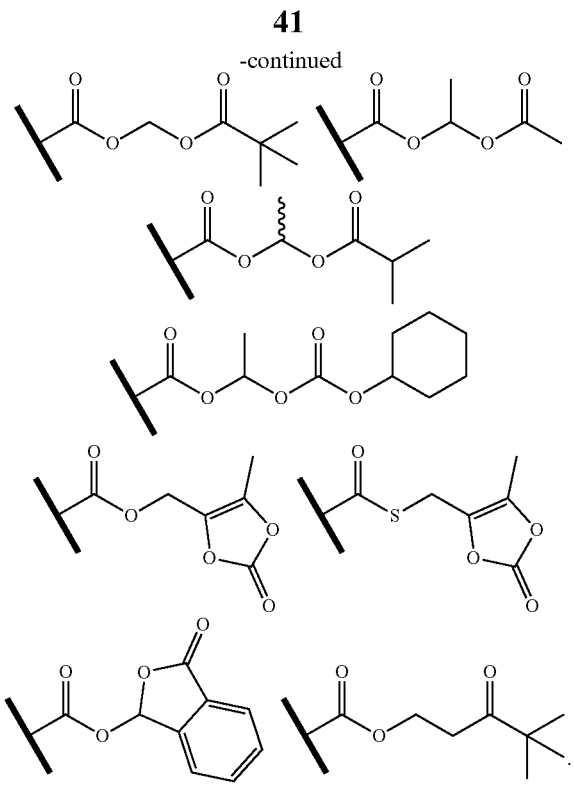

The compounds of the present invention contain an arginine mimetics moiety which can form physiologically hydrolyzable esters that serve as prodrugs, i.e., "prodrugs of arginine mimetics", by being hydrolyzed in the body to yield the compounds of the present invention per se. Representative examples of prodrugs of arginine mimetics include:

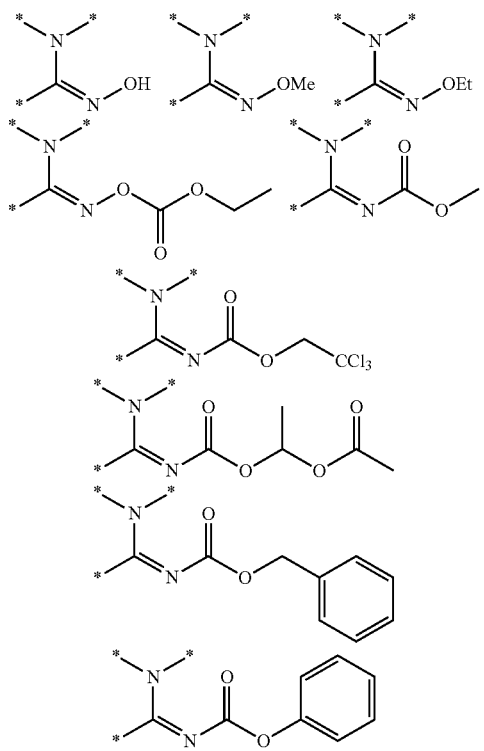

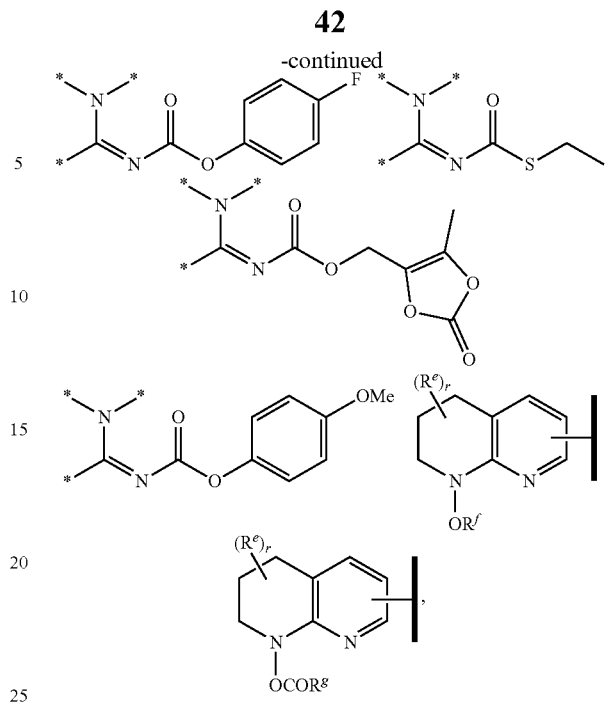

wherein, one of the asterisks in each of the arginine mimetics moiety is an attachment point to the parent molecule and the other two asterisks are hydrogen; $R^f$=H, Me, Et, COOEt; $R^g$=$CH_3$, $CH_2CCl_3$, phenyl, 4-fluorophenyl, 4-methoxyphenyl, benzyl,

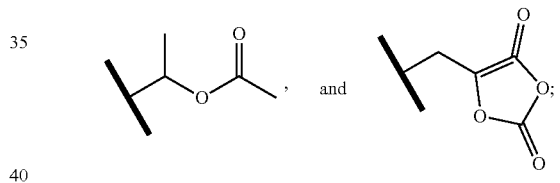

$R^e$ is OH, $C_{1-4}$ alkyl, halo, haloalkyl, or $C_{1-4}$ cycloalkyl; and r is an integer of 0, 1, 2, or 3.

Furthermore, various forms of prodrugs are well known in the art. For examples of such prodrug derivatives, see:

Bundgaard, H., ed., *Design of Prodrugs*, Elsevier (1985), and Widder, K. et al., eds., *Methods in Enzymology*, 112:309-396, Academic Press (1985);

Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

Bundgaard, H., *Adv. Drug Deliv. Rev.*, 8:1-38 (1992);

Bundgaard, H. et al., *J. Pharm. Sci.*, 77:285 (1988); and

Kakeya, N. et al., *Chem. Pharm. Bull.*, 32:692 (1984).

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "a", "13", "R", "S", "E", and "Z" are stereochemical designations familiar to one skilled in the art.

The compounds of the present invention can be prepared as shown in the following reaction schemes and description thereof, as well as relevant published literature procedures that may be used by one skilled in the art. Exemplary reagents and procedures for these reactions appear hereinafter and in the working Examples.

Abbreviations

The following abbreviations are employed herein:
Ph=phenyl
Bn=benzyl
t-Bu=tertiary butyl
Me=methyl
Et=ethyl
TMS=trimethylsilyl
TBS=tert-butyldimethylsilyl
THF=tetrahydrofuran
$Et_2O$=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
$i-Pr_2NEt$ or DIPEA=diisopropylethylamine
$Et_3N$=triethylamine
DMAP=4-dimethylaminopyridine
$NaBH_4$=sodium borohydride
n-BuLi=n-butyllithium
Pd/C=palladium on carbon
KOH=potassium hydroxide
NaOH=sodium hydroxide
LiOH=lithium hydroxide
$K_2CO_3$=potassium carbonate
$NaHCO_3$=sodium bicarbonate
Ar=argon
$N_2$=nitrogen
EDC=3-ethyl-3'-(dimethylamino)propyl-carbodiimide hydrochloride (or 1-[(3-(dimethyl)amino)propyl])-3-ethyl-carbodiimide hydrochloride)
HOBT=1-hydroxybenzotriazole hydrate
DIC=1,3-dipropylcarbodiimide
BOP=(benzotriazol-1-yloxy)tris(dimethylamino)phosphonium hexafluorophosphate
PyBOP=benzotriazol-1-yloxy-tripyrrolidino phosphonium hexafluorophosphate
HATU=1-[bis(dimethylamino)methylene]-1H-1,2,3-triazolo[4,5-b]pyridinium 3-oxid hexafluorophosphate
LiHMDS=lithium bis(trimethylsilyl)amide
LDA=lithium diisopropylamide
DDQ=2,3-dichloro-5,6-dicyano-1,4-benzoquinone
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point
HPLC-1: Sun fire C18 (4.6×150 mm) 3.5 micron, gradient 10 to 100% B:A for 12 min, then 3 min hold at 100% B. Mobile phase A: 0.05% TFA in water:$CH_3CN$ (95:5)
Mobile phase B: 0.05% TFA in $CH_3CN$:water (95:5)
TFA Buffer pH=2.5; Flow rate: 1 mL/min; Wavelength: 254 nm, 220 nm.
HPLC-2: XBridge Phenyl (4.6×150 mm) 3.5 micron, gradient 10 to 100% B:A for 12 min, then 3 min hold at 100% B.
Mobile phase A: 0.05% TFA in water:$CH_3CN$ (95:5)

Mobile phase B: 0.05% TFA in $CH_3CN$:water (95:5)
TFA Buffer pH=2.5; Flow rate: 1 mL/min; Wavelength: 254 nm, 220 nm.

IV. Methods of Preparation

The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds described in this invention. A particularly useful compendium of synthetic methods which may be applicable to the preparation of compounds of the present invention may be found in Larock, R. C., *Comprehensive Organic Transformations*, VCH, New York (1989).

The compounds of the present invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used. A particularly useful compendium of synthetic methods which may be applicable to the preparation of compounds of the present invention may be found in Larock, R. C., *Comprehensive Organic Transformations*, VCH, New York (1989).

Generic Schemes

The azole analogs of Formula (I') can be prepared according to the general routes shown in Schemes 1 to 4 using methods known in the literature. As shown in Scheme 1, azole 1 can be converted to the N-alkylated azole-acid 2 via alkylation with a suitable alkylating agent, functionalization to $R^1$, and deprotection of the ester to yield carboxylic acid 2. At a suitable step in the above synthetic sequence, the carboxylic ester or acid moiety shown in structure 1 or 2, respectively, can be reduced to the alcohol and then converted to a leaving group such as a mesylate, tosylate, or a halide represented by 3.

Scheme 1: General Scheme for preparation of Formula (I', $R^5$ = H)

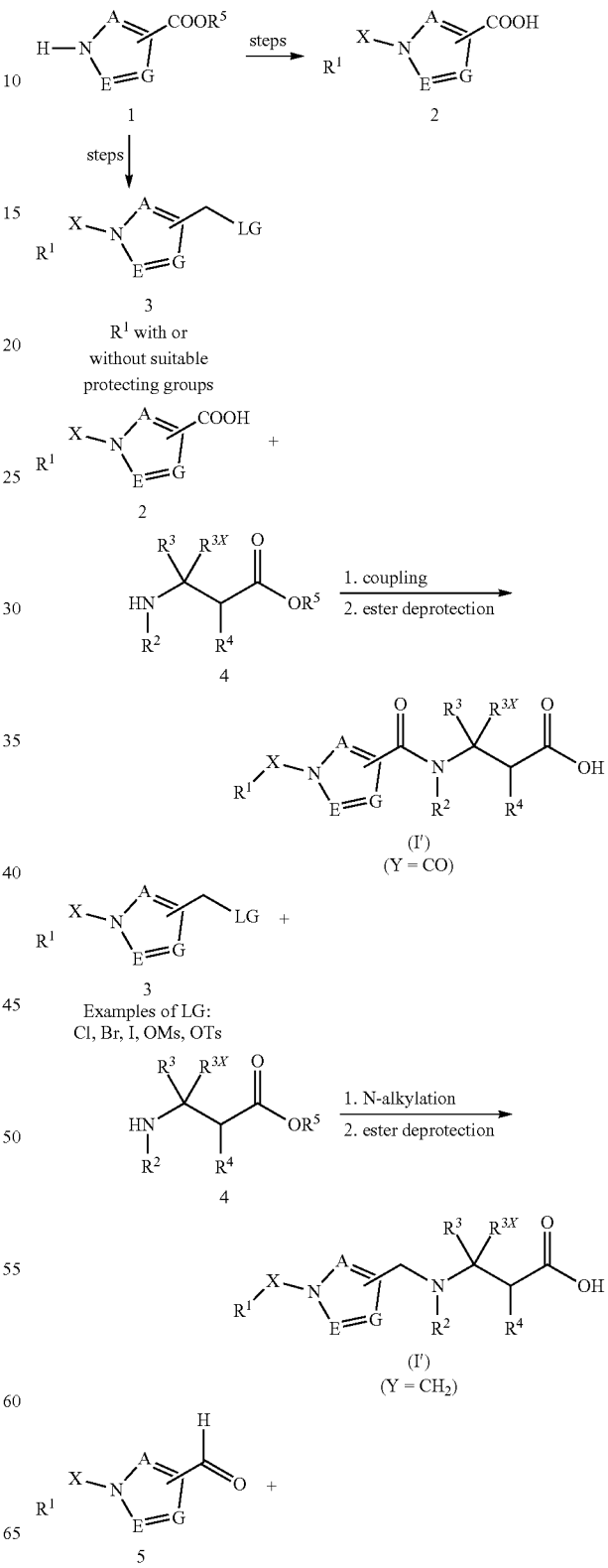

-continued

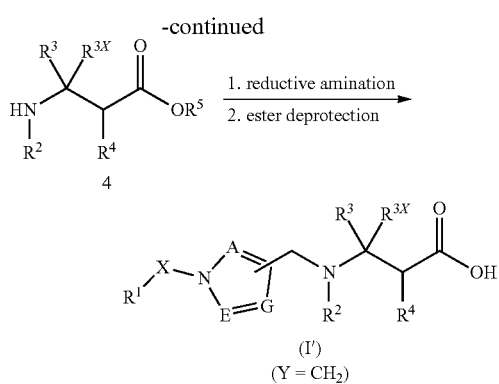

Compounds of Formula (I'), when Y=CO and $R^5$=H, were obtained by first reacting azole-acid 2 with aminoester 4 under standard amide coupling conditions known to those skilled in the art, followed by deprotection of the resulting carboxylic ester. Aminoesters 4 can be prepared using methods known in the literature (for example, Hutchinson, J. H. et al. *J. Med Chem.* 2003, 46, 4790; Henderson, N. C. et al. *Nature Medicine* 2013, 19, 1617). Compounds of formula (I), when Y=$CH_2$ and $R^5$=H, were obtained by alkylating aminoester 4 with azole 3 or via a reduction amination of azole-aldehyde or azole-ketone 5 and aminoester 4, followed by deprotection of the resulting carboxylic ester.

Scheme 2: Example of synthesis of Formula (I') (Y = CO; $R^5$ = H; Formulas 15, 16 and 17) with tetrahydronaphthyridine as Arginine mimetic ($R^1$):

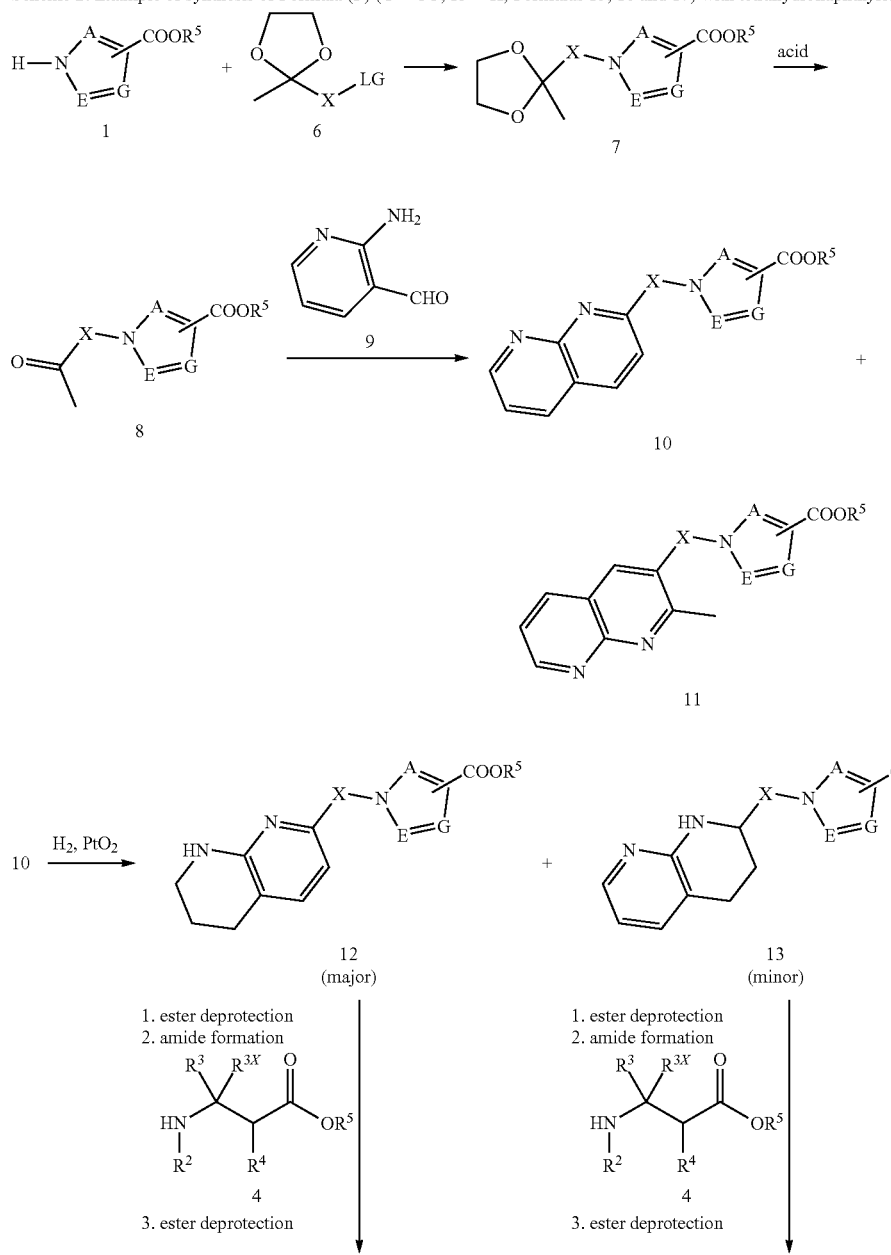

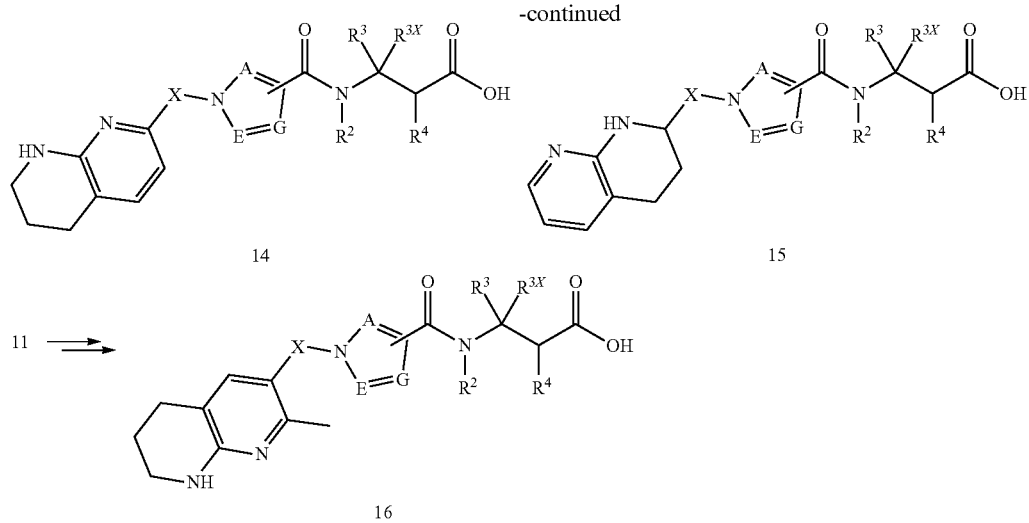

Scheme 2 outlines examples of synthesis of Formula (I') (Y=CO; $R^5$=H; Formulas 15, 16, and 17) that contain tetrahydronaphthyridines as arginine mimetics. Alkylation of azole-ester 1 with ketal-protected electrophile 6 followed by deprotection can afford ketone 8. Isomeric naphthyridines 10 and 11 can be obtained via Friedlander condensations of ketone 8 and 2-aminonicotinaldehyde. Selective ring reduction of 10 in the presence of a catalyst such as $PtO_2$ can afford tetrahydronaphthyridines 12 (major) and 13 (minor). Further transformations of 12 and 13 using methods described earlier can yield compounds 14 and 15, respectively. Compound 11 can be converted to 16 using a protocol similar to the one used for conversion of 10 to 14.

Scheme 3: Example of synthesis of Formula (I') (Y = CO; $R^5$ = H; Formula 22) with 2-aminopyridine as Arginine mimetic ($R^1$):

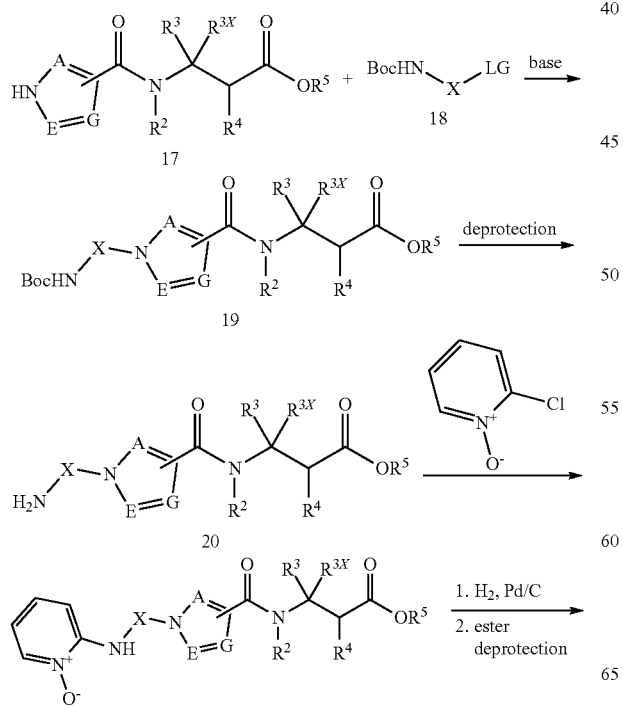

Scheme 3 depicts an example of synthesis of Formula (I') (Y=CO; $R^5$=H; Formula 22) with 2-aminopyridine as an arginine mimetic. Azole-ester 17 can be alkylated with Boc-protected amine 18 to yield ester 19 which after reacting with 2-chloropyridine oxide can afford N-oxide 21. Reduction of 21 to the pyridine in the presence of Pd/C followed ester deprotection can yield compound 22.

Scheme 4: Example of synthesis of Formula (I') (Y = CO; $R^5$ = H; Formula 23) with 2-aminodihydroimidazole as Arginine mimetic ($R^1$):

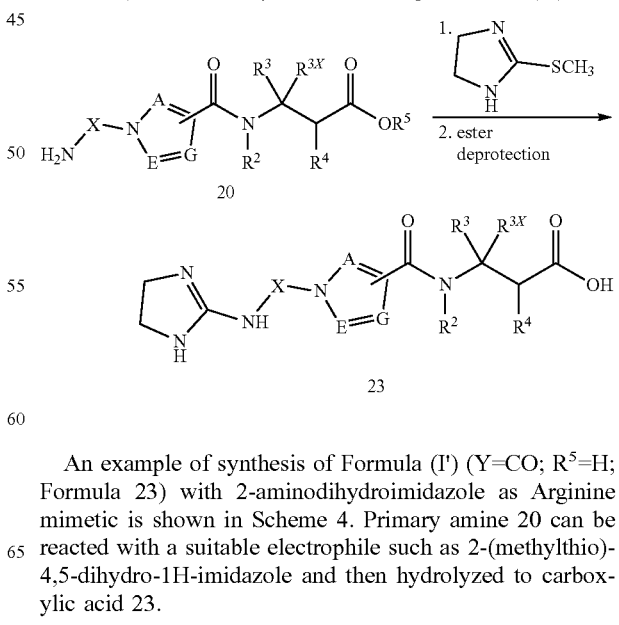

An example of synthesis of Formula (I') (Y=CO; $R^5$=H; Formula 23) with 2-aminodihydroimidazole as Arginine mimetic is shown in Scheme 4. Primary amine 20 can be reacted with a suitable electrophile such as 2-(methylthio)-4,5-dihydro-1H-imidazole and then hydrolyzed to carboxylic acid 23.

EXAMPLES

The following Examples serve to better illustrate, but not limit, some of the preferred embodiments of the application.

Synthesis of Intermediates

Intermediate 1. 1-(2-(5,6,7,8-Tetrahydro-1,8-naph-thyridin-2-yl)ethyl)-1H-pyrazole-4-carboxylic acid

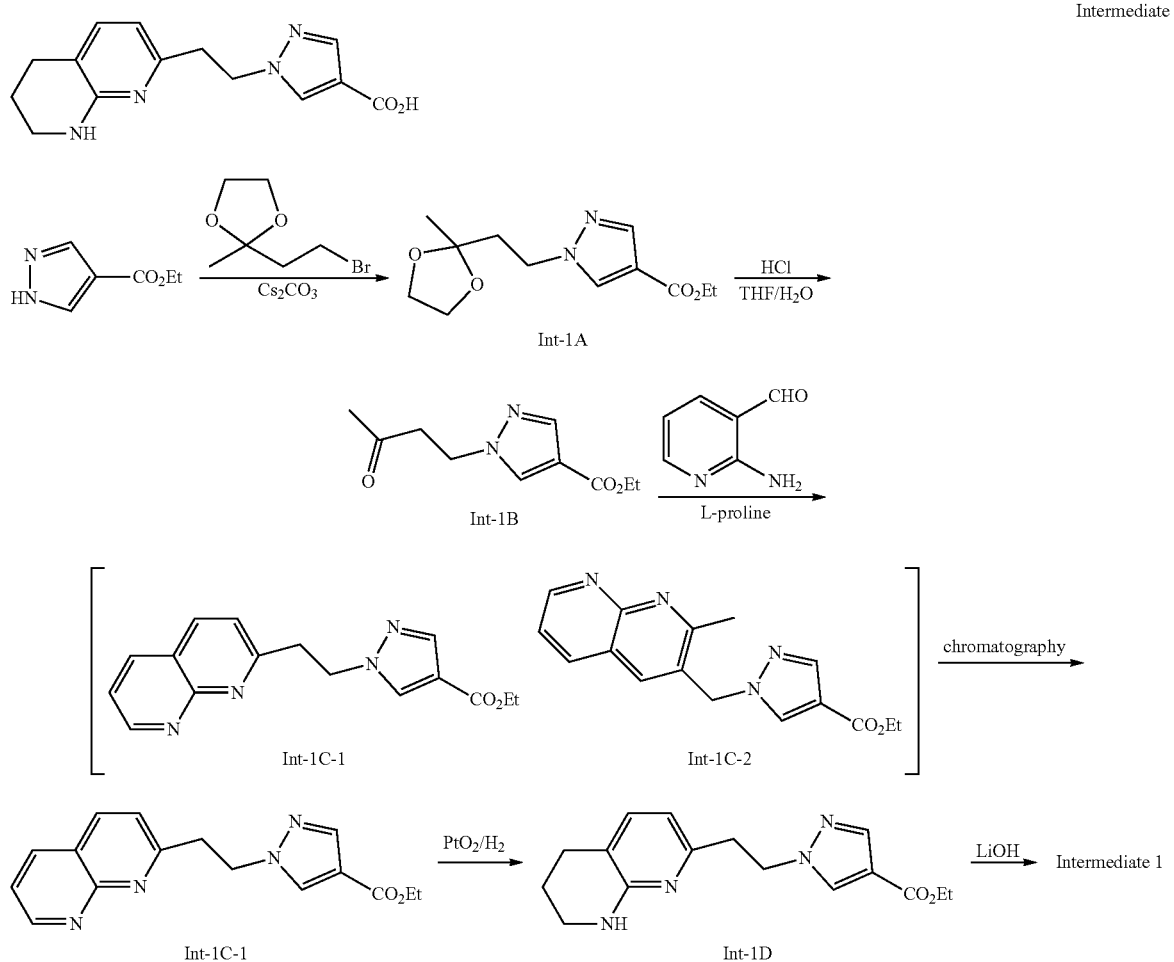

Intermediate 1

Intermediate 1A: Ethyl (E)-4-(2-(1,8-naphthyridin-2-yl)vinyl)-1H-pyrrole-2-carboxylate. A mixture of commercially available ethyl 1H-pyrazole-4-carboxylate (1.7 g, 12.13 mmol), 2-(2-bromoethyl)-2-methyl-1,3-dioxolane (2.8 g, 14.35 mmol), and $Cs_2CO_3$ (5.93 g, 18.20 mmol) in acetonitrile (15 mL) was stirred at 65° C. in a sealed tube for 2 h. The solid was removed by filtration. The filtrate was concentrated in vacuo, dissolved in EtOAc (100 mL), and the organic layer washed with $H_2O$ (15 mL), brine, dried ($MgSO_4$), filtered and concentrated under reduced pressure to afford a crude residue. The residue was purified by flash chromatography (silica gel, hexanes:EtOAc, 100:0 to 40:60) to afford 3.0 g (97% yield) of Intermediate 1A as a yellow oil: LCMS (ES): m/z 255.1 [M+H]$^+$.

Intermediate 1B: A mixture of ethyl 1-(2-(2-methyl-1,3-dioxolan-2-yl)ethyl)-1H-pyrazole-4-carboxylate (3.0 g, 11.80 mmol) in THF (15 mL) and HCl (25 mL, 25.00 mmol) (aq. 1N) was stirred at RT for 16 h. After evaporation of the solvents, the crude product was diluted with $H_2O$ (30 mL), and extracted with EtOAc (250 mL). The organic layer was separated, dried over $MgSO_4$, and concentrated to give 2.5 g (100% yield) of crude Intermediate 1B as an oil. LCMS (ES): m/z 211.0 [M+H]$^+$.

Intermediate 1C-1: A mixture of ethyl 1-(3-oxobutyl)-1H-pyrazole-4-carboxylate (2.5 g, 11.89 mmol, Intermediate 1B), 2-aminonicotinaldehyde (1.89 g, 15.46 mmol) and L-proline (1.37 g, 11.89 mmol) in EtOH (70 mL) was heated at 78° C. for 24 h. After cooling down to room temperature, solvent was evaporated, and crude product dissolved in minimum amount of $CH_2Cl_2$. Purification by silica gel chromatography (Hexane/EtOAc, 100:0 to 0:100, then MeOH/EtOAc, 0:100 to 15:85) yielded Intermediate 1C-1 as an orange oil (1.5 g, 43% yield). $^1$H NMR (500 MHz, Chloroform-d) δ 9.12 (dd, J=4.2, 2.0 Hz, 1H), 8.18 (dd, J=8.2, 2.0 Hz, 1H), 8.08 (d, J=8.2 Hz, 1H), 7.91 (d, J=0.6 Hz, 1H), 7.81 (d, J=0.6 Hz, 1H), 7.49 (dd, J=8.2, 4.2 Hz, 1H), 7.23 (d, J=8.2 Hz, 1H), 4.82 (t, J=6.9 Hz, 2H), 4.23 (q, J=7.1 Hz, 2H), 3.64 (t, J=6.9 Hz, 2H), 1.29 (t, J=7.1 Hz, 3H). LCMS (ES): m/z 297.2 [M+H]$^+$.

Intermediate 1D: To a solution of ethyl 1-(2-(1,8-naphthyridin-2-yl)ethyl)-1H-pyrazole-4-carboxylate (1.5 g, 5.06 mmol, Intermediate 1C-1) in EtOH (150 mL) was added and $PtO_2$ (230 mg, 1.013 mmol). The suspension was hydrogenated (1 atm. H$_2$, balloon) at room temperature for 20 h.

After filtration of the reaction mixture through a Celite® pad and subsequent washing of the cake with EtOH, the filtrate was concentrated in vacuo and air-dried under vacuum to yield 1.42 g (93% yield) of Intermediate 1D as a beige solid. $^1$H NMR (500 MHz, Chloroform-d) δ 7.89 (s, 1H), 7.75 (s, 1H), 7.00 (d, J=7.2 Hz, 1H), 6.19 (d, J=7.2 Hz, 1H), 4.47 (t, J=7.1 Hz, 2H), 4.26 (q, J=7.2 Hz, 2H), 3.45-3.35 (m, 2H), 3.07 (t, J=7.1 Hz, 2H), 2.68 (t, J=6.3 Hz, 2H), 1.96-1.84 (m, 2H), 1.32 (t, J=7.1 Hz, 3H). LCMS (ES): m/z 301.2 [M+H]$^+$.

Intermediate 1: A mixture of ethyl 1-(2-(5,6,7,8-tetrahydro-1,8-naphthyridin-2-yl)ethyl)-1H-pyrazole-4-carboxylate (2.0 g, 6.66 mmol, Intermediate 1D), lithium hydroxide (1.8 g, 75 mmol) in THF (30 ml), H$_2$O (15 mL) and MeOH (3 mL) was stirred at RT for 26 h. The solvent was removed in vacuo. The aqueous residue was acidified with conc HCl to give a solid which was filtered and further dried under vacuum to give 1.8 g (91% yield) of crude Intermediate 1 as a white solid. $^1$H NMR (400 MHz, DMSO-d$_6$) δ 8.12 (s, 1H), 7.76 (s, 1H), 7.02 (d, J=7.3 Hz, 1H), 6.35 (bs, 1H), 6.21 (d, J=7.3 Hz, 1H), 4.41 (t, J=7.3 Hz, 2H), 3.25 (td, J=5.8, 2.7 Hz, 2H), 2.97 (t, J=7.4 Hz, 2H), 2.61 (t, J=6.3 Hz, 2H), 1.83-1.66 (m, 2H). LCMS (ES): m/z 273.2 [M+H]$^+$.

Intermediate 2. 1-(2-(8-(tert-Butoxycarbonyl)-5,6,7,8-tetrahydro-1,8-naphthyridin-2-yl)ethyl)-1H-pyrazole-4-carboxylic acid

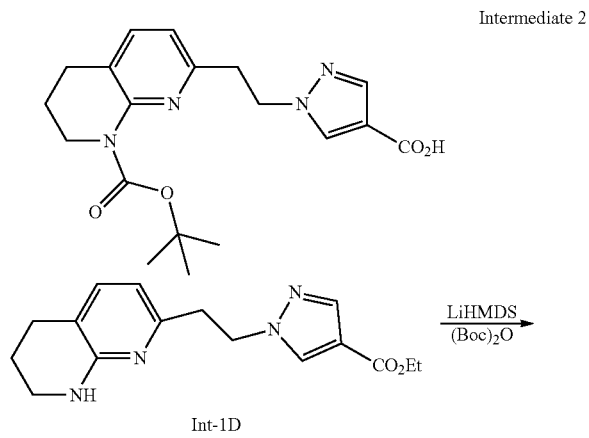

Int-1D

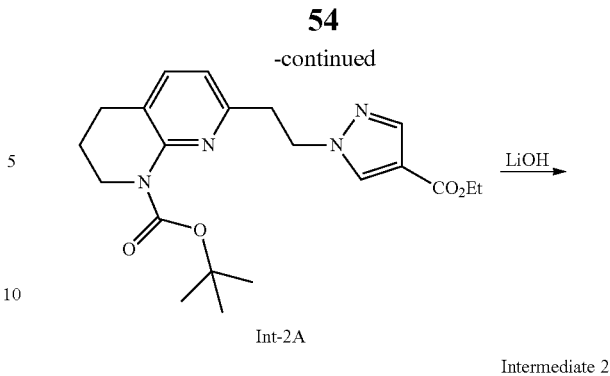

Int-2A

Intermediate 2

Intermediate 2A: To mixture of ethyl 1-(2-(5,6,7,8-tetrahydro-1,8-naphthyridin-2-yl)ethyl)-1H-pyrazole-4-carboxylate (0.369 g, 1.229 mmol), Boc$_2$O (0.371 mL, 1.597 mmol) in THF (6.5 mL) was added LiHMDS (1.597 mL, 1.597 mmol, 1M in THF) dropwise at 0° C. The reaction mixture was stirred at this temperature for 30 min at which point it was quenched with sat. NH$_4$Cl and extracted with EtOAc (3×15 mL). The combined organic layers were washed with brine, dried over anhydrous Na$_2$SO$_4$, filtered and concentrated under reduced pressure to afford a crude residue. The residue was purified by flash chromatography (silica gel, hexanes:EtOAc, 100:0 to 0:100) to afford 278 mg (57% yield) of Intermediate 2A as a yellow oil: $^1$H NMR (500 MHz, Chloroform-d) δ 7.89 (s, 1H), 7.83 (s, 1H), 7.24 (d, J=7.5 Hz, 1H), 6.63 (d, J=7.5 Hz, 1H), 4.59 (t, J=6.9 Hz, 2H), 4.25 (q, J=7.1 Hz, 2H), 3.83-3.62 (m, 2H), 3.26 (t, J=6.9 Hz, 2H), 2.72 (t, J=6.7 Hz, 2H), 1.98-1.88 (m, 2H), 1.55 (s, 9H), 1.31 (t, J=7.1 Hz, 3H). LCMS (ES): m/z 401.3 [M+H]$^+$.

Intermediate 2: A mixture of intermediate 2A (278 mg, 0.694 mmol), lithium hydroxide (225 mg, 9.40 mmol) in THF (4 mL), H$_2$O (3 mL) and MeOH (2 ml) was stirred at RT for 16 h. The volatiles were removed in vacuo and the aqueous residue was acidified with 1N aq. HCl. The mixture was extracted with CHCl$_3$ (3×10 mL) and the organic layer was separated, dried over MgSO$_4$, and concentrated to give 230 mg (89% yield) of crude Intermediate 2 as a foam solid. LCMS (ES): m/z 373.2 [M+H]$^+$.

Intermediate 3. 5-(tert-Butoxymethyl)-1-(2-(5,6,7,8-tetrahydro-1,8-naphthyridin-2-yl)ethyl)-1H-pyrazole-4-carboxylic acid Intermediate 3

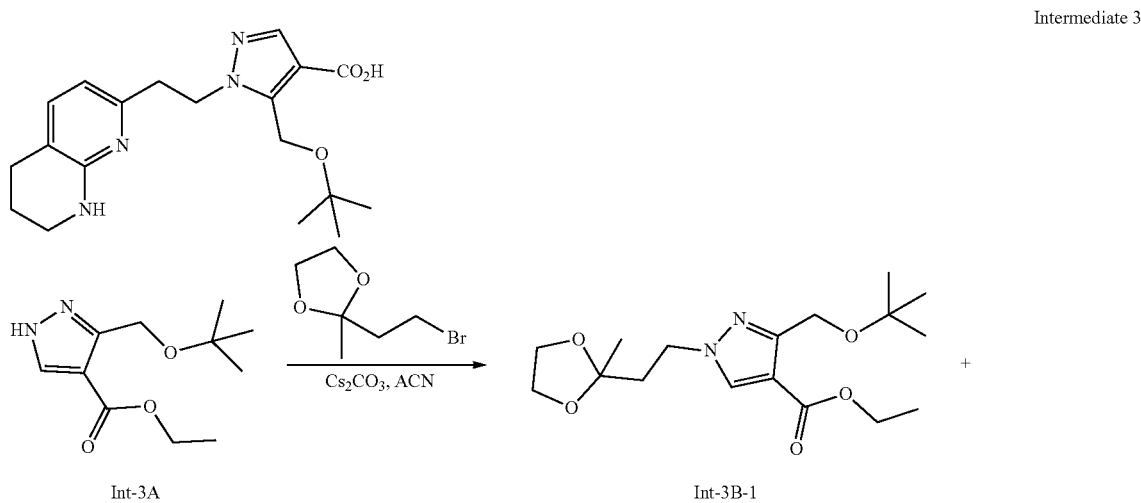

Int-3A

Int-3B-1

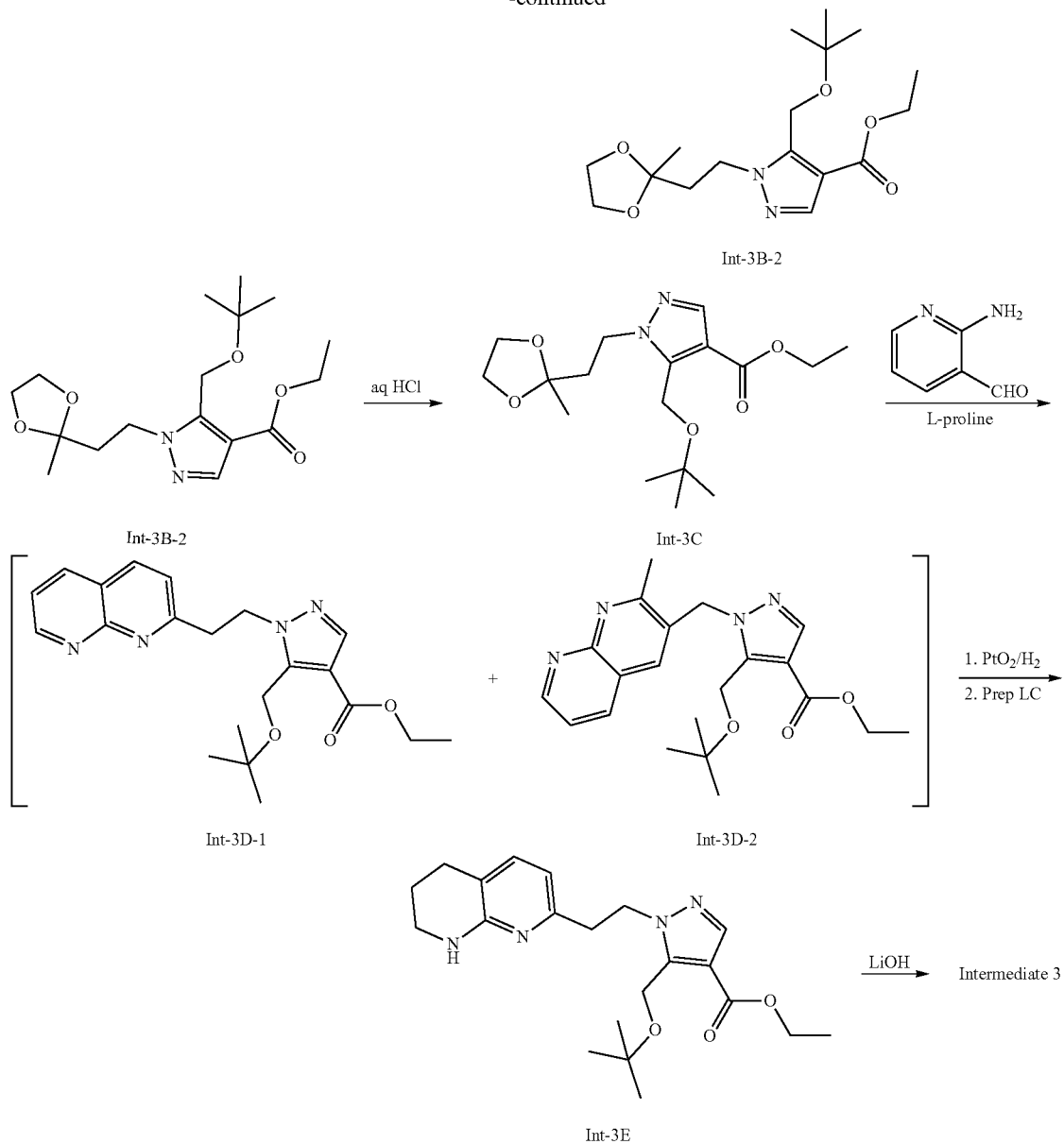

Intermediate 3A: Ethyl 3-(tert-butoxymethyl)-1H-pyrazole-4-carboxylate. Intermediate 3A was prepared according to the procedure described in WO 2014/064134. $^1$H NMR (400 MHz, Chloroform-d) δ 7.95 (s, 1H), 4.85 (s, 2H), 4.32 (q, J=7.1 Hz, 2H), 1.38 (t, J=7.2 Hz, 3H), 1.32 (s, 9H). LCMS (ES): m/z 227.2 [M+H]$^+$.

Intermediate 3B-1: A mixture of ethyl 3-(tert-butoxymethyl)-1H-pyrazole-4-carboxylate (75 mg, 0.331 mmol), 2-(2-bromoethyl)-2-methyl-1,3-dioxolane (97 mg, 0.497 mmol), and Cs$_2$CO$_3$ (162 mg, 0.497 mmol) in acetonitrile (2 mL) was stirred at 65° C. in a sealed tube for 2 h. The solid was removed by filtration. The filtrate was concentrated in vacuo to give a crude product which was dissolved in EtOAc (10 mL). The organic layer was washed with H$_2$O (2 mL), brine, dried (MgSO$_4$), filtered and concentrated under reduced pressure to afford a crude residue. The residue was purified by flash chromatography (silica gel, hexanes:EtOAc, 75:25 to 34:66) to afford 21 mg (18% yield) of Intermediate 3B-1 as a yellow oil (faster-eluting product): $^1$H NMR (400 MHz, Chloroform-d) δ 7.78 (s, 1H), 4.76 (s, 2H), 4.31-4.12 (m, 4H), 4.01-3.79 (m, 4H), 2.31-2.12 (m, 2H), 1.28 (s, 3H), 1.27 (t, J=7.3 Hz, 3H), 1.23 (s, 9H). LCMS (ES): m/z 341.3 [M+H]$^+$.

Intermediate 3B-2: The reaction also gave 16 mg (14% yield) of Intermediate 3B-2 as a yellow oil (slower eluting product): $^1$H NMR (400 MHz, Chloroform-d) δ 7.78 (s, 1H), 4.61 (s, 2H), 4.21 (q, J=7.1 Hz, 2H), 4.17-4.11 (m, 2H), 3.94-3.80 (m, 4H), 2.26-2.15 (m, 2H), 1.26 (t, J=7.3 Hz, 3H), 1.25 (s, 3H), 1.24 (s, 9H). LCMS (ES): m/z 341.3 [M+H]$^+$.

Intermediate 3C: A mixture of ethyl 5-(tert-butoxymethyl)-1-(2-(2-methyl-1,3-dioxolan-2-yl)ethyl)-1H-pyrazole-4-carboxylate (1.82 g, 5.35 mmol, Int-3B-2) in THF (7 mL) and HCl (6 mL, 6.00 mmol) (aq. 1N) was stirred at RT for 16 h. Solvent was evaporated and the crude product was diluted with H$_2$O (20 mL), and extracted with EtOAc (100 mL). The organic layer was separated, dried over MgSO$_4$, and concentrated to give 1.58 g (100% yield) of crude Intermediate 3C as an oil. LCMS (ES): m/z 297.5[M+H]$^+$.

Intermediate [3D-1+3D-2]: A mixture of ethyl 5-(tert-butoxymethyl)-1-(3-oxobutyl)-1H-pyrazole-4-carboxylate (1.58 g, 5.33 mmol), 2-aminonicotinaldehyde (846 mg, 6.93 mmol) and L-proline (614 mg, 5.33 mmol) in EtOH (70 mL) was heated at 78° C. in a sealed tube for 24 h. After cooling down to room temperature, the solvent was evaporated. The crude product was dissolved in a minimum amount of CH$_2$Cl$_2$ and subjected to silica gel chromatography (Hexane/EtOAc, 100:0 to 0:100, then MeOH/EtOAc, 0:100 to 10:90) to give a mixture of Int-3D-1 and Int-3D-2 as an orange oil (1.85 g, 91% yield). LCMS (ES): m/z 383.4 [M+H]$^+$.

Intermediate 3E: To a solution of a mixture of Intermediates [3D-1+3D-2] (1.85 g, 4.84 mmol) in EtOH (200 mL) was added and PtO$_2$ (296 mg, 0.863 mmol). The suspension was hydrogenated (1 atm. H$_2$, balloon) at room temperature for 22 h. After filtration of the reaction mixture through a Celite® pad and subsequent washing of the cake with EtOH, the filtrate was concentrated in vacuo and air-dried under vacuum to give a crude product which was purified by preparative HPLC (Column: Sunfire Prep C18, 30×100 mm, 5-µm particles; Mobile Phase A: 100% H$_2$O with 10-mM ammonium acetate; Mobile Phase B: 100% acetonitrile with 10-mM ammonium acetate; Gradient: 25-100% B over 10 minutes; Flow: 40 mL/min.) to afford Intermediate 3E (621 mg, 33% yield) as a white solid: $^1$H NMR (500 MHz, Chloroform-d) δ 7.84 (s, 1H), 7.07 (d, J=7.2 Hz, 1H), 6.12 (d, J=7.2 Hz, 1H), 4.67 (s, 2H), 4.54 (t, J=6.8 Hz, 2H), 4.27 (q, J=7.1 Hz, 2H), 3.44 (t, J=5.8 Hz, 2H), 3.21 (t, J=6.8 Hz, 2H), 2.70 (t, J=6.3 Hz, 2H), 1.99-1.80 (m, 2H), 1.34 (t, J=7.1 Hz, 3H), 1.26 (s, 9H). LCMS (ES): m/z 387.5 [M+H]$^+$.

Intermediate 3: A mixture of ethyl 5-(tert-butoxymethyl)-1-(2-(5,6,7,8-tetrahydro-1,8-naphthyridin-2-yl)ethyl)-1H-pyrazole-4-carboxylate (560 mg, 1.449 mmol, Int-3E), lithium hydroxide (318 mg, 13.28 mmol) in THF (27 mL), H$_2$O (8.6 mL) and MeOH (2.7 mL) was stirred at RT for 15 h. The solvent was removed in vacuo. The aqueous residue was acidified with conc HCl and the mixture extracted with EtOAc (2×50 mL) and CHCl$_3$ (2×50 mL). The organic layer was separated, dried over MgSO$_4$ and concentrated to give 520 mg (100% yield) of crude Intermediate 3 as a foam solid. LCMS (ES): m/z 359.4 [M+H]$^+$.

Intermediate 4. 3-(tert-Butoxymethyl)-1-(2-(5,6,7,8-tetrahydro-1,8-naphthyridin-2-yl)ethyl)-1H-pyrazole-4-carboxylic acid Intermediate 4

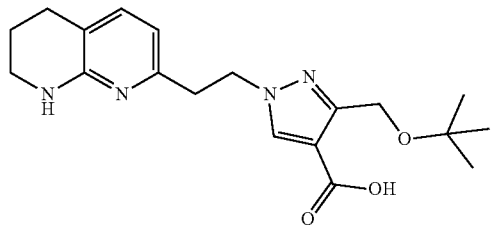

Intermediate 4 was prepared in a manner analogous to Intermediate 3 above, except that Intermediate 3B-2 was replaced by Intermediate 3B-1. LCMS (ES): m/z 359.4 [M+H]$^+$.

Intermediate 5. 1-(3-(5,6,7,8-Tetrahydro-1,8-naphthyridin-2-yl)propyl)-1H-pyrazole-4-carboxylic acid Intermediate 5

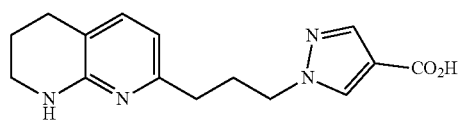

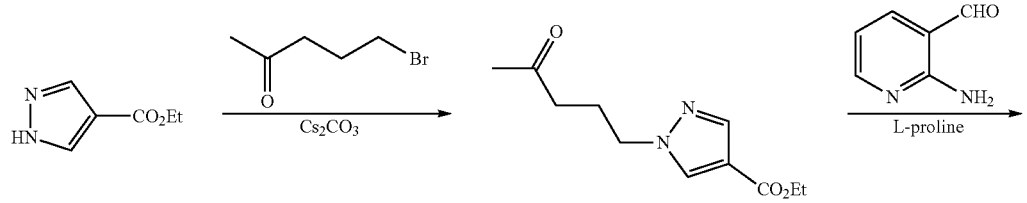

Int-5A

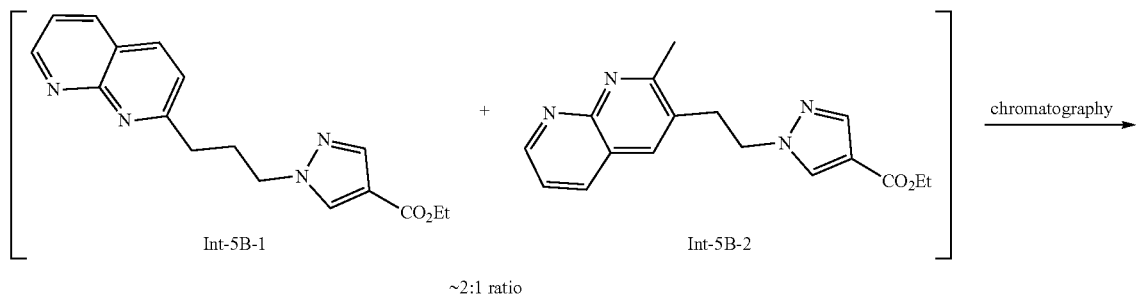

Int-5B-1    Int-5B-2

~2:1 ratio

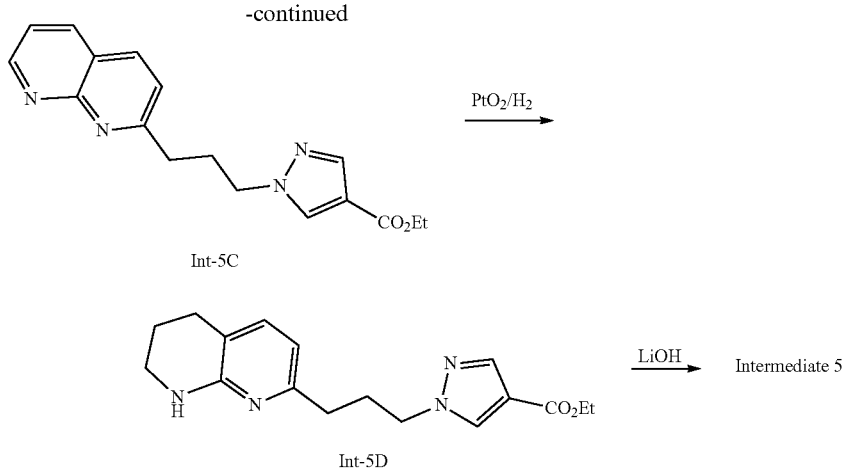

Int-5C

Int-5D

Intermediate 5 was prepared in a manner analogous to Intermediate 1 above, except that during alkylation step, 2-(2-bromoethyl)-2-methyl-1,3-dioxolane was replaced by 5-bromopentan-2-one. LCMS (ES): m/z 287.2 [M+H]⁺.

Intermediate 6. 1-(2-(5,6,7,8-Tetrahydro-1,8-naphthyridin-2-yl)ethyl)-1H-imidazole-4-carboxylic acid

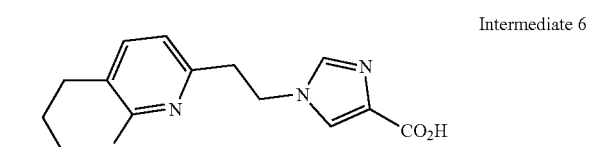

Intermediate 6

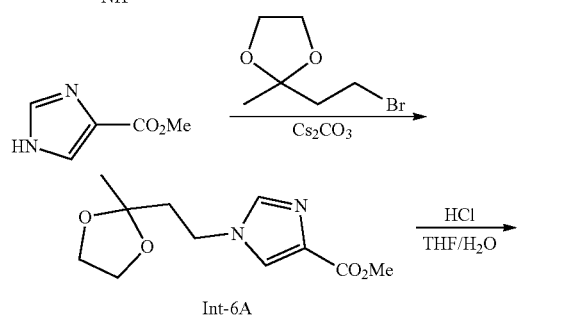

Int-6A

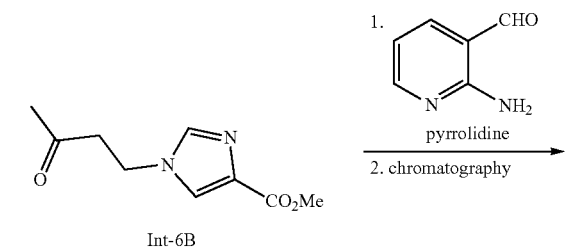

Int-6B

Int-6C

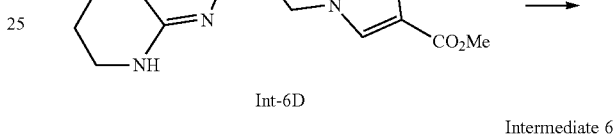

Int-6D

Intermediate 6

Intermediate 6 was prepared in a manner analogous to Intermediate 1 above except for the following specific variations:

Intermediate 6A was prepared in a manner analogous to Intermediate 1A above, except that during alkylation step, ethyl 1H-pyrazole-4-carboxylate was replaced by methyl 1H-imidazole-4-carboxylate. $^1$H NMR (400 MHz, Chloroform-d) δ 7.56 (d, J=1.4 Hz, 1H), 7.47 (d, J=1.4 Hz, 1H), 4.06-3.99 (m, 2H), 3.96-3.83 (m, 4H), 3.81 (s, 3H), 2.19-2.07 (m, 2H), 1.25 (s, 3H). LCMS (ES): m/z 241.1 [M+H]⁺.

Intermediate 6B: A mixture of methyl 1-(2-(2-methyl-1,3-dioxolan-2-yl)ethyl)-1H-imidazole-4-carboxylate (0.7 g, 2.91 mmol) in THF (1 mL) and HCl (4 mL, 4.00 mmol) (aq. 1N) was stirred at RT for 16 h. After evaporation of the solvents, the crude product was diluted with $H_2O$ (30 mL), and extracted with EtOAc (250 mL). The organic layer was separated, dried over $MgSO_4$, and concentrated to give 0.572 g (100% yield) of crude Intermediate 6B as an oil. LCMS (ES): m/z 197.1 [M+H]⁺.

Intermediate 6C: A mixture of methyl 1-(3-oxobutyl)-1H-imidazole-4-carboxylate (286 mg, 1.458 mmol, Intermediate 6B), 2-aminonicotinaldehyde (231 mg, 1.89 mmol) and pyrrolidine (0.265 mL, 3.21 mmol) in EtOH (5 mL) was heated at 78° C. in a sealed tube for 7 h. After cooling down to room temperature, solvent was evaporated and crude was dissolved in minimum amount $CH_2Cl_2$ and subjected to silica gel chromatography (MeOH/EtOAc, 10:90 to 50:50) to give Intermediate 6C as a yellow oil (600 mg, 146% yield, contains pyrrolidine by $^1$H NMR). $^1$H NMR (400 MHz, Chloroform-d) δ 9.05 (dd, J=4.3, 2.0 Hz, 1H), 8.14 (dd, J=8.1, 2.0 Hz, 1H), 8.07 (d, J=8.3 Hz, 1H), 7.58 (d, J=1.4 Hz, 1H), 7.54 (d, J=1.4 Hz, 1H), 7.45 (dd, J=8.1, 4.2 Hz, 1H), 7.22 (d, J=8.3 Hz, 1H), 4.67 (t, J=6.9 Hz, 2H), 3.76 (s, 3H), 3.47 (t, J=6.9 Hz, 2H). LCMS (ES): m/z 283.1 [M+H]⁺.

Intermediate 6D: To a solution of Intermediate 6C (600 mg) in EtOH (30 mL) was added and $PtO_2$ (97 mg, 0.425 mmol). The suspension was hydrogenated (1 atm. H₂, balloon) at room temperature for 7 h. After filtration of the reaction mixture through a Celite® pad and subsequent washing of the cake with EtOH, the filtrate was concentrated in vacuo and air-dried under vacuum to give a crude product which was purified by preparative HPLC (Column: Sunfire Prep C18, 30×100 mm, 5-μm particles; Mobile Phase A: 100% water with 10-mM ammonium acetate; Mobile Phase B: 100% acetonitrile with 10-mM ammonium acetate; Gradient: 5-100% B over 10 minutes; Flow: 40 mL/min.) to afford Intermediate 6D (175 mg, 29% yield) as a yellow oil: $^1$H NMR (500 MHz, Methanol-d4) δ 7.81 (bs, 1H), 7.64 (bs, 1H), 7.20 (d, J=7.3 Hz, 1H), 6.30 (d, J=7.3 Hz, 1H), 4.40 (t, J=6.9 Hz, 2H), 3.84 (s, 3H), 3.42 (t, J=6.3 Hz, 2H), 3.05 (t, J=6.9 Hz, 2H), 2.73 (t, J=6.3 Hz, 2H), 1.95-1.83 (m, 2H). LCMS (ES): m/z 287.2 [M+H]⁺.

Intermediate 6: A mixture of Intermediate 6D (175 mg, 0.611 mmol), lithium hydroxide (80 mg, 3.34 mmol) in THF (4 mL), H₂O (2 mL) and MeOH (0.2 mL) was stirred at RT for 16 h. The solvent was removed in vacuo. The aqueous residue was acidified with aq. 1M HCl and the mixture was extracted with CHCl₃ (3×50 ml). The organic layer was separated, dried over MgSO₄ and concentrated to give 167 mg (100% yield) of crude Intermediate 6 as a foam solid. LCMS (ES): m/z 287.2 [M+H]⁺.

Intermediate 7. 1-((5,6,7,8-Tetrahydro-1,8-naphthyridin-2-yl)methyl)-1H-pyrazole-3-carboxylic acid

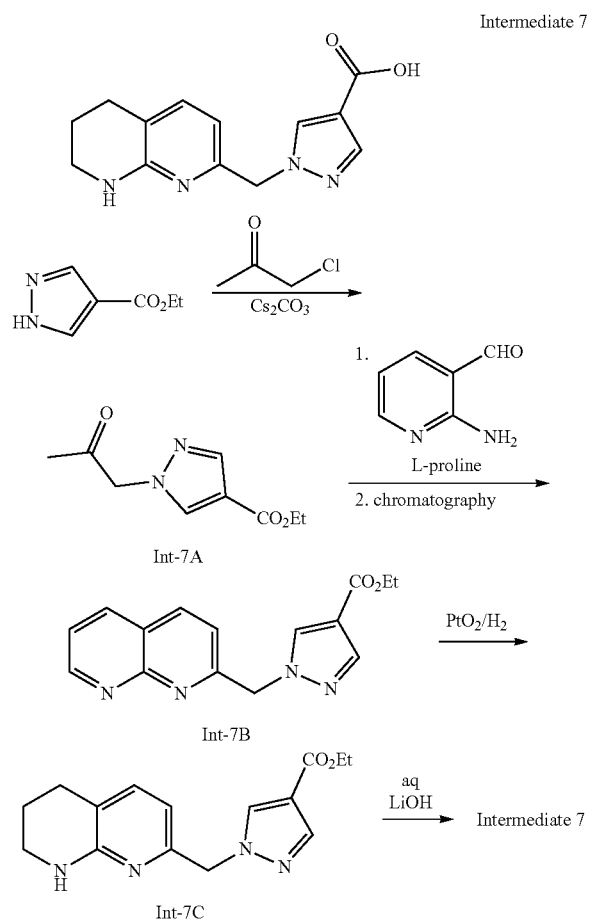

Intermediate 7A: A mixture of commercially available ethyl 1H-pyrazole-4-carboxylate (1.5 g, 10.70 mmol), 1-chloropropan-2-one (1.45 g, 15.67 mmol) and Cs₂CO₃ (4.5 g, 13.80 mmol) in acetonitrile (30 mL) was stirred at 65° C. in a sealed tube for 5 h. The mixture was allowed to stirred at RT for another 15 h. The solid was removed by filtration. The filtrate was concentrated in vacuo to give a crude product which was dissolved in EtOAc (100 mL). The organic layer was washed with H₂O (15 mL), brine, dried (MgSO₄), filtered and concentrated under reduced pressure to afford a crude residue. The residue was purified by flash chromatography (silica gel, hexanes:EtOAc, 100:0 to 0:100) to afford Intermediate 7A (600 mg, 29% yield) as a light brown oil: LCMS (ES): m/z 197.1 [M+H]⁺.

Intermediate 7B: A mixture of Intermediate 7A (600 mg, 3.06 mmol), 2-aminonicotinaldehyde (486 mg, 3.98 mmol) and L-proline (352 mg, 3.06 mmol) in EtOH (5 mL) was heated at 78° C. in a sealed tube for 24 h. After cooling down to room temperature, solvent was evaporated and crude residue was dissolved in minimum amount CH₂Cl₂ and subjected to silica gel chromatography (MeOH/EtOAc, 10:90) to give Intermediate 7B (140 mg, 16% yield) as an orange oil. $^1$H NMR (500 MHz, Chloroform-d) δ 9.35 (bs, 1H), 8.60 (d, J=8.3 Hz, 1H), 8.35 (d, J=8.3 Hz, 1H), 8.13 (s, 1H), 7.96 (s, 1H), 7.83 (bt, J=6.4 Hz, 1H), 7.47 (d, J=8.5 Hz, 1H), 5.71 (s, 2H), 4.23 (q, J=7.1 Hz, 2H), 1.27 (t, J=7.1 Hz, 3H). LCMS (ES): m/z 283.2 [M+H]⁺.

Intermediate 7C: To a solution of Intermediate 7B (140 mg, 0.946 mmol) in EtOH (15 mL) was added and PtO₂ (16 mg, 0.070 mmol). The suspension was hydrogenated (1 atm. H₂, balloon) at room temperature for 1 h. After filtration of the reaction mixture through a Celite® pad and subsequent washing of the cake with EtOH, the filtrate was concentrated in vacuo and air-dried under vacuum to afford intermediate 7C (142 mg, 100% yield) as a beige solid: $^1$H NMR (500 MHz, Chloroform-d) δ 7.92 (s, 1H), 7.84 (s, 1H), 7.02 (d, J=7.3 Hz, 1H), 6.23 (d, J=7.3 Hz, 1H), 5.08 (s, 2H), 4.20 (q, J=7.1 Hz, 2H), 3.39-3.22 (m, 2H), 2.62 (t, J=6.3 Hz, 2H), 1.87-1.76 (m, 2H), 1.26 (t, J=7.1 Hz, 3H). LCMS (ES): m/z 287.3 [M+H]⁺.

Intermediate 7: A mixture of Intermediate 7C (142 mg, 0.496 mmol), lithium hydroxide (80 mg, 3.34 mmol) in THF (2 mL), H₂O (1 mL) and MeOH (0.4 mL) was stirred at RT for 16 h. The volatiles were removed in vacuo and the aqueous residue was acidified with conc HCl. The mixture was extracted with CH₂Cl₂ (2×30 mL) and CHCl₃ (50 ml). The organic layer was separated, dried over MgSO₄ and concentrated to give 128 mg (100% yield) of crude Intermediate 7 as a white solid. LCMS (ES): m/z 259.2 [M+H]⁺.

Intermediate 8. Methyl 2-(2-(2-methyl-1,3-dioxolan-2-yl)ethyl)-2H-1,2,3-triazole-4-carboxylate (Int-8) and Intermediate 9. Methyl 1-(2-(2-methyl-1,3-dioxolan-2-yl)ethyl)-1H-1,2,3-triazole-4-carboxylate (Int-9)

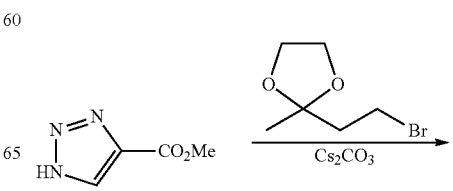

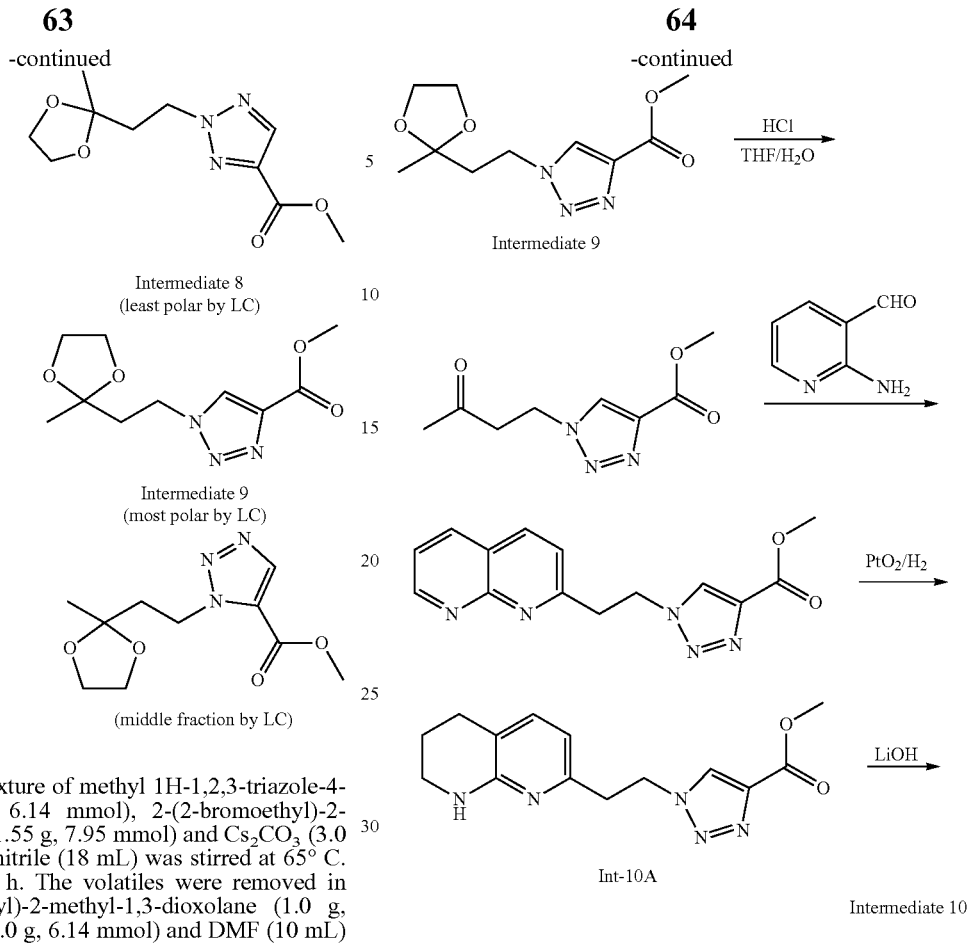

Intermediate 8 (least polar by LC)

Intermediate 9 (most polar by LC)

(middle fraction by LC)

Intermediate 8: A mixture of methyl 1H-1,2,3-triazole-4-carboxylate (780 mg, 6.14 mmol), 2-(2-bromoethyl)-2-methyl-1,3-dioxolane (1.55 g, 7.95 mmol) and Cs$_2$CO$_3$ (3.0 g, 9.21 mmol) in acetonitrile (18 mL) was stirred at 65° C. in a sealed tube for 2 h. The volatiles were removed in vacuo. 2-(2-Bromoethyl)-2-methyl-1,3-dioxolane (1.0 g, 5.12 mmol), Cs$_2$CO$_3$ (2.0 g, 6.14 mmol) and DMF (10 mL) were added. The resulting mixture was stirred at 65° C. in a sealed tube for 3 h. The solid was removed by filtration. The filtrate was concentrated in vacuo to give a crude product which was dissolved in EtOAc (80 mL). The organic layer was washed with H$_2$O (15 mL), brine, dried (MgSO$_4$), filtered and concentrated under reduced pressure to afford a crude residue. The residue was purified by preparative HPLC (Column: Phenomenex Axia C18, 30×100 mm, 5-μm particles; Mobile Phase A: 5:95 MeOH: water with 0.1% TFA; Mobile Phase B: 95:5 MeOH: water with 0.1% TFA; Gradient: 20-100% B over 10 minutes, then a 5-minute hold at 100% B; Flow: 40 mL/min. to afford Intermediate 8 (600 mg, 41% yield) as a colorless oil: $^1$H NMR (500 MHz, Chloroform-d) δ 8.06 (s, 1H), 4.69-4.55 (m, 2H), 4.05-3.91 (m, 4H), 3.97 (s, J=1.4 Hz, 3H), 2.52-2.38 (m, 2H), 1.36 (s, 3H). LCMS (ES): m/z 242.1 [M+H]$^+$.

Intermediate 9: The above separation also yielded Intermediate 9 (360 mg, 24% yield, RT 4.4 min) as a colorless oil: $^1$H NMR (500 MHz, Chloroform-d) δ 8.16 (s, 1H), 4.61-4.49 (m, 2H), 4.06-3.91 (m, 4H), 3.97 (s, 3H), 2.49-2.29 (m, 2H), 1.36 (s, 3H). LCMS (ES): m/z 242.1 [M+H]$^+$.

Intermediate 10. 1-(2-(5,6,7,8-Tetrahydro-1,8-naphthyridin-2-yl)ethyl)-1H-1,2,3-triazole-4-carboxylic acid

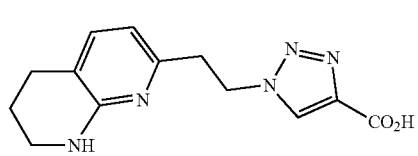

Intermediate 10

Intermediate 10A was prepared in a manner analogous to Intermediate 1A above starting from Intermediate 9.

Intermediate 10A: $^1$H NMR (400 MHz, Chloroform-d) δ 7.95 (s, 1H), 6.94 (d, J=7.3 Hz, 1H), 6.17 (d, J=7.3 Hz, 1H), 4.76 (t, J=6.9 Hz, 2H), 3.87 (s, 3H), 3.33 (t, J=5.6 Hz, 2H), 3.16 (t, J=7.5 Hz, 2H), 2.61 (t, J=6.3 Hz, 2H), 1.98-1.73 (m, 2H). LCMS (ES): m/z 288.2 [M+H]$^+$.

Intermediate 10: A mixture of Intermediate 10A (40 mg, 0.139 mmol), lithium hydroxide 6.67 mg, 0.278 mmol) in THF (1 mL) and H$_2$O (0.5 mL) was stirred at RT for 16 h. The solvent was removed in vacuo. The aqueous residue was acidified with 1N aq. HCl. The mixture was extracted with CHCl$_3$ (3×10 mL). The organic layer was separated, dried over MgSO$_4$ and concentrated to give Intermediate 10 (38 mg, 100%) as a white solid. LCMS (ES): m/z 274.2 [M+H]$^+$.

Intermediate 11. 1-(2-(5,6,7,8-Tetrahydro-1,8-naphthyridin-2-yl)ethyl)-1H-pyrazole-3-carboxylic acid

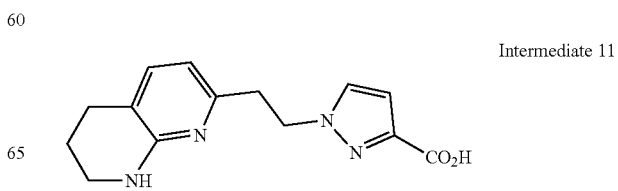

Intermediate 11

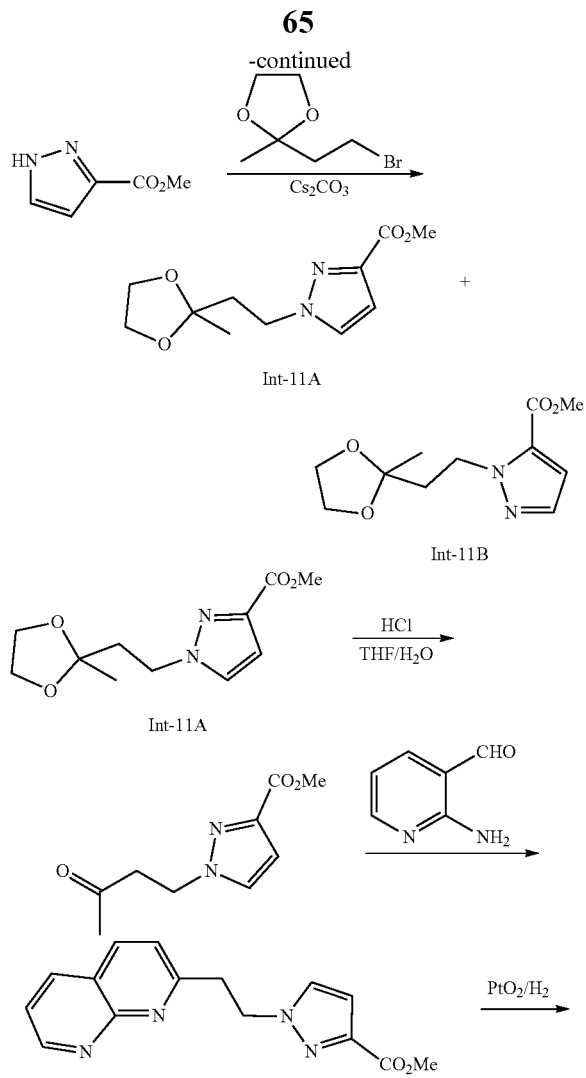
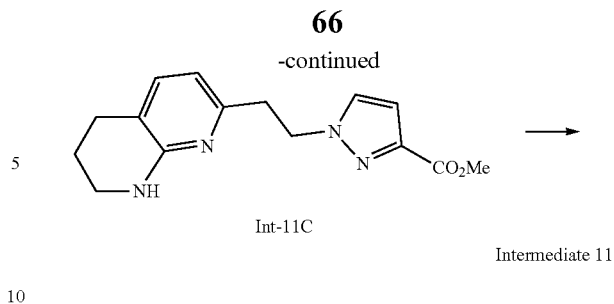

Intermediate 11A was prepared in a manner analogous to Intermediate 1A above, except that during the alkylation step, ethyl 1H-pyrazole-4-carboxylate was replaced by methyl 1H-pyrazole-3-carboxylate.

Intermediate 11A: $^1$H NMR (500 MHz, Chloroform-d) δ 7.41 (d, J=2.4 Hz, 1H), 6.77 (d, J=2.4 Hz, 1H), 4.34-4.24 (m, 2H), 3.98-3.87 (m, 4H), 3.89 (s, 3H), 2.33-2.22 (m, 2H), 1.29 (s, 3H). LCMS (ES): m/z 241.2 [M+H]$^+$.

Intermediate 11B: $^1$H NMR (500 MHz, Chloroform-d) δ 7.48 (d, J=2.0 Hz, 1H), 6.83 (d, J=2.0 Hz, 1H), 4.90-4.42 (m, 2H), 4.04-3.92 (m, 4H), 3.89 (s, 3H), 2.42-2.03 (m, 2H), 1.40 (s, 3H). LCMS (ES): m/z 241.2 [M+H]$^+$.

Intermediate 11C: $^1$H NMR (400 MHz, Chloroform-d) δ 7.37 (d, J=2.3 Hz, 1H), 7.06 (d, J=7.2 Hz, 1H), 6.65 (d, J=2.3 Hz, 1H), 6.14 (dd, J=7.3, 1.6 Hz, 1H), 4.58 (t, J=7.2 Hz, 2H), 3.85 (s, 3H), 3.49-3.35 (m, 2H), 3.15 (t, J=7.1 Hz, 2H), 2.65 (t, J=6.3 Hz, 2H), 1.86 (p, J=5.9 Hz, 2H). LCMS (ES): m/z 287.2 [M+H]$^+$.

Intermediate 11: A mixture of Intermediate 11C (120 mg, 0.419 mmol), lithium hydroxide (20.1 mg, 0.838 mmol) in THF (2 mL) and H$_2$O (1 mL) was stirred at RT for 18 h. The volatiles were removed in vacuo and the aqueous residue was acidified with 1N aq. HCl. The mixture was extracted with CHCl$_3$ (3×20 mL). The organic layer was separated, dried over MgSO$_4$ and concentrated to give crude Intermediate 11 (110 mg, 96% yield) as a white solid. LCMS (ES): m/z 273.2 [M+H]$^+$.

Intermediate 12. 1-(2-(5,6,7,8-Tetrahydro-1,8-naphthyridin-2-yl)ethyl)-1H-pyrazole-5-carboxylic acid

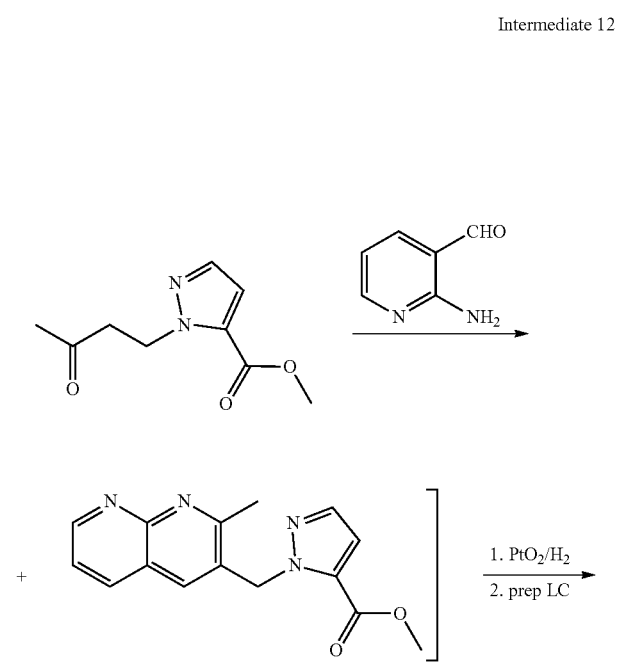

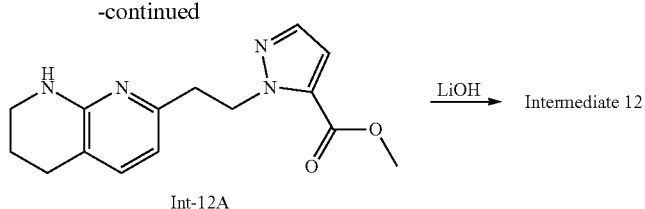

Int-12A

Intermediate 12 was prepared in a manner analogous to Intermediate 3 above except that Intermediate 11B was used starting material.

Intermediate 12A: $^1$H NMR (400 MHz, Chloroform-d) δ 7.48 (d, J=2.1 Hz, 1H), 7.25 (d, J=7.3 Hz, 1H), 6.84 (d, J=2.1 Hz, 1H), 6.15 (d, J=7.3 Hz, 1H), 4.93 (t, J=6.5 Hz, 2H), 3.88 (s, 3H), 3.52 (t, J=5.6 Hz, 2H), 3.26 (t, J=6.5 Hz, 2H), 2.75 (t, J=6.3 Hz, 2H), 2.02-1.84 (m, 2H). LCMS (ES): m/z 287.2 [M+H]$^+$.

Intermediate 12: A mixture of Intermediate 12A (45 mg, 0.157 mmol), lithium hydroxide (10.0 mg, 0.418 mmol) in THF (1 mL) and H$_2$O (0.5 mL) was stirred at RT for 24 h. The volatiles were removed in vacuo and the aqueous residue was acidified with 1N aq. HCl. The mixture was extracted with CHCl$_3$ (3×10 mL). The organic layer was separated, dried over MgSO$_4$ and concentrated to give Intermediate 12 (42 mg, 100%) as a white solid. LCMS (ES): m/z 273.2 [M+H]$^+$.

Intermediate 13. 1-(2-(5,6,7,8-Tetrahydro-1,8-naphthyridin-2-yl)ethyl)-1H-1,2,4-triazole-3-carboxylic acid Intermediate 13 was prepared in a manner analogous to intermediate 3, except that during alkylation step, ethyl 3-(tert-butoxymethyl)-1H-pyrazole-4-carboxylate was replaced by methyl 1H-1,2,4-triazole-3-carboxylate.

Intermediate 13A: $^1$H NMR (400 MHz, Chloroform-d) δ 8.35 (s, 1H), 4.52 (t, J=5.9 Hz, 2H), 4.00 (s, 3H), 3.13 (t, J=5.9 Hz, 2H), 2.17 (s, 3H). LCMS (ES): m/z 198.1 [M+H]$^+$.

Intermediate 13B: $^1$H NMR (400 MHz, Methanol-d$_4$) δ 8.54 (s, 1H), 7.53 (d, J=7.3 Hz, 1H), 6.49 (d, J=7.3 Hz, 1H), 4.68 (t, J=6.7 Hz, 2H), 3.95 (s, 3H), 3.58-3.45 (m, 2H), 3.39-3.27 (m, 2H), 2.83 (t, J=6.3 Hz, 2H), 2.00-1.92 (m, 2H). LCMS (ES): m/z 288.2 [M+H]$^+$.

Intermediate 13: A mixture of Intermediate 13B (22 mg, 0.077 mmol), lithium hydroxide (4.58 mg, 0.191 mmol) in THF (1 mL) and H$_2$O (0.5 mL) was stirred at RT for 24 h. The volatiles were removed in vacuo and the aqueous residue was acidified with 1N aq. HCl. The mixture was extracted with CHCl$_3$ (3×8 mL). The organic layer was separated, dried over MgSO$_4$ and concentrated to give Intermediate 13 (21 mg, 100%) as a white solid. LCMS (ES): m/z 274.1 [M+H]$^+$.

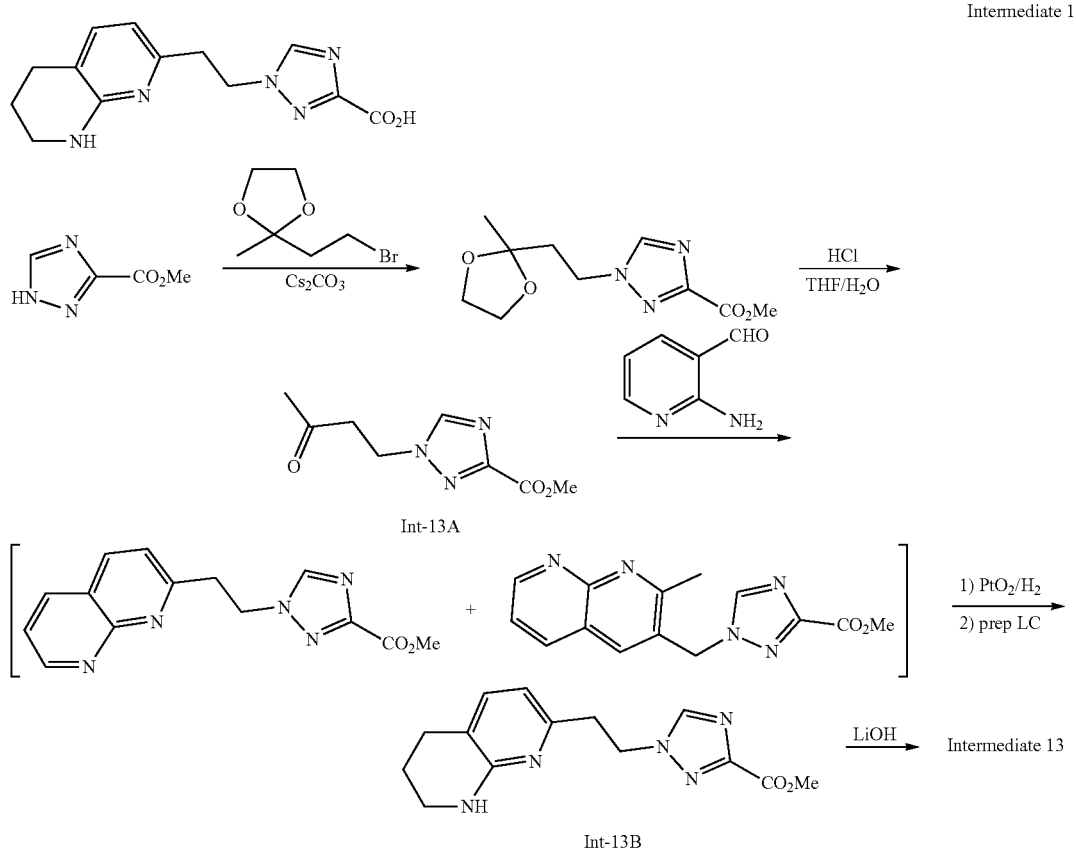

Intermediate 13

Intermediate 14. 1-(2-(5,6,7,8-Tetrahydro-1,8-naphthyridin-2-yl)ethyl)-3-(trifluoromethyl)-1H-pyrazole-4-carboxylic acid

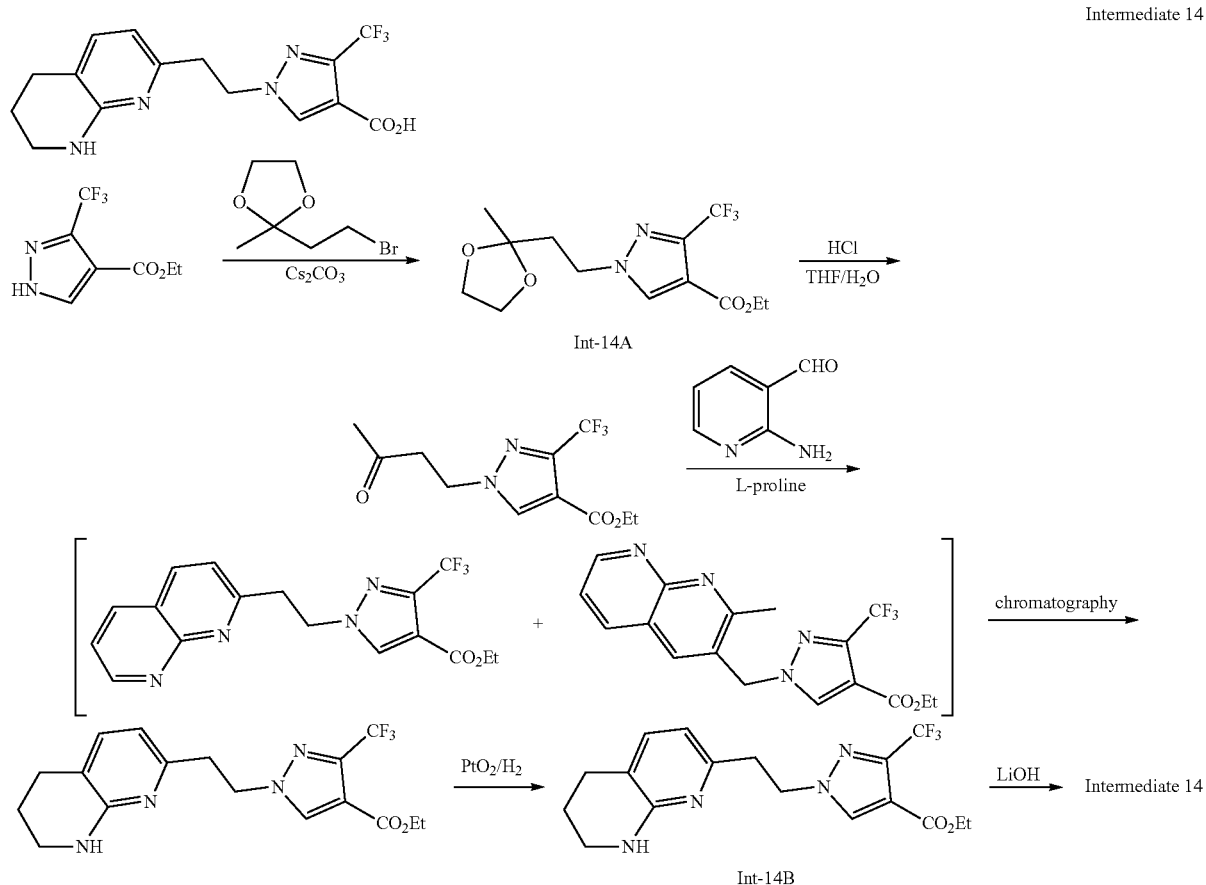

Intermediate 14 was prepared in a manner analogous to Intermediate 1, except that during alkylation step, ethyl 1H-pyrazole-4-carboxylate was replaced by ethyl 3-(trifluoromethyl)-1H-pyrazole-4-carboxylate.

Intermediate 14A: $^1$H NMR (500 MHz, Chloroform-d) δ 8.01 (s, 1H), 4.34 (q, J=7.1 Hz, 2H), 4.31-4.28 (m, 2H), 4.07-3.91 (m, 4H), 2.46-2.22 (m, 2H), 1.37 (t, J=7.1 Hz, 3H), 1.35 (s, 3H). LCMS (ES): m/z 323.1 [M+H]$^+$.

Intermediate 14B: $^1$H NMR (500 MHz, Chloroform-d) δ 7.89 (s, 1H), 7.07 (d, J=7.3 Hz, 1H), 6.22 (d, J=7.3 Hz, 1H), 4.56 (t, J=7.0 Hz, 2H), 4.29 (q, J=7.1 Hz, 2H), 3.44 (td, J=5.7, 2.4 Hz, 2H), 3.13 (t, J=7.0 Hz, 2H), 2.70 (t, J=6.3 Hz, 2H), 1.95-1.89 (m, 2H), 1.33 (t, J=7.1 Hz, 3H). LCMS (ES): m/z 288.2 [M+H]$^+$.

Intermediate 14: A mixture of Intermediate 14B (128 mg, 0.347 mmol), lithium hydroxide (80 mg, 3.34 mmol) in THF (2 mL), MeOH (0.4 mL) and H$_2$O (1 mL) was stirred at RT for 6 h. The volatiles were removed in vacuo and the aqueous residue was acidified with 1N aq. HCl. The mixture was extracted with CHCl$_3$ (3×15 mL). The organic layer was separated, dried over MgSO$_4$ and concentrated to give Intermediate 14 (108 mg, 91% yield) as a white solid. LCMS (ES): m/z 341.2 [M+H]$^+$.

Intermediate 15. Ethyl 3-(tert-butoxymethyl)-1-(4-oxopentyl)-1H-pyrazole-4-carboxylate and Intermediate 16. Ethyl 5-(tert-butoxymethyl)-1-(4-oxopentyl)-1H-pyrazole-4-carboxylate

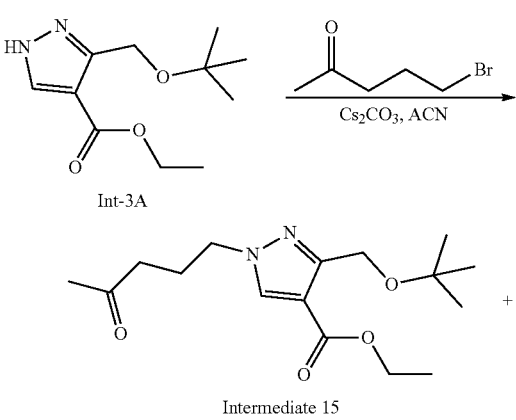

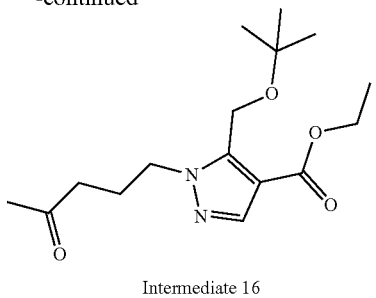

Intermediate 16

Intermediate 15: A mixture of ethyl 3-(tert-butoxymethyl)-1H-pyrazole-4-carboxylate (300 mg, 1.326 mmol, Int-3A), 5-bromopentan-2-one (390 mg, 2.363 mmol) and Cs$_2$CO$_3$ (800 mg, 2.46 mmol) in acetonitrile (8 mL) was stirred at 65° C. in a sealed tube for 20 h. The solid was removed by filtration. The filtrate was concentrated in vacuo to give a crude product which was dissolved in EtOAc (30 mL). The organic layer was washed with H$_2$O (10 mL), brine, dried (MgSO$_4$), filtered and concentrated under reduced pressure to afford a crude residue. The residue was purified by preparative HPLC (Column: Phenomenex Axia C18, 30×100 mm, 5-μm particles; Mobile Phase A: 5:95 MeOH: H$_2$O with 0.1% TFA; Mobile Phase B: 95:5 MeOH: water with 0.1% TFA; Gradient: 20-100% B over 10 minutes, then a 5-minute hold at 100% B; Flow: 40 mL/min. to afford Intermediate 15 (106 mg, 26% yield) as a colorless oil: $^1$H NMR (400 MHz, Chloroform-d) δ 7.83 (s, 1H), 4.69 (s, 2H), 4.28 (q, J=7.1 Hz, 2H), 4.14 (t, J=7.0 Hz, 2H), 2.45 (t, J=6.9 Hz, 2H), 2.14 (s, 3H), 2.11 (t, J=6.9 Hz, 2H), 1.34 (t, J=7.1 Hz, 3H), 1.31 (s, 9H). LCMS (ES): m/z 311.5 [M+H]$^+$.

Intermediate 16: The above preparative HPLC purification also yielded Intermediate 16 (100 mg, 24% yield, faster-eluting fraction) as a colorless oil: $^1$H NMR (400 MHz, Chloroform-d) δ 7.86 (s, 1H), 4.82 (s, 2H), 4.29 (q, J=7.1 Hz, 2H), 4.23 (t, J=6.8 Hz, 2H), 2.49 (t, J=7.1 Hz, 2H), 2.20-2.14 (m, 2H), 2.13 (s, 3H), 1.35 (t, J=7.1 Hz, 3H), 1.29 (s, 9H). LCMS (ES): m/z 311.5 [M+H]$^+$.

Intermediate 17. 1-(3-((tert-Butoxycarbonyl)amino)propyl)-1H-pyrazole-4-carboxylic acid

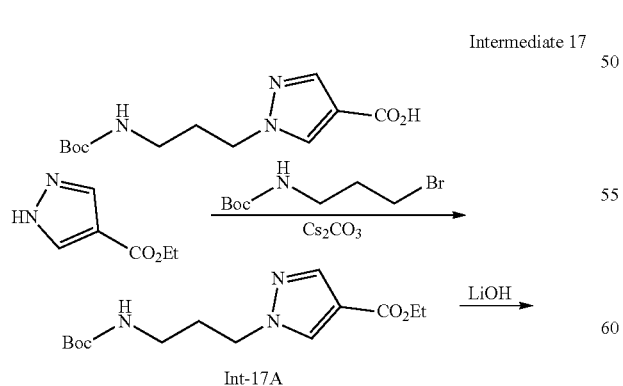

Intermediate 17

Intermediate 17A: A mixture of commercially available ethyl 1H-pyrazole-4-carboxylate (50 mg, 0.357 mmol), tert-butyl (3-bromopropyl)carbamate (70 mg, 0.294 mmol) and Cs$_2$CO$_3$ (240 mg, 0.737 mmol) in acetonitrile (3 mL) was stirred at 65° C. in a sealed tube for 2 h. The solid was removed by filtration. The filtrate was concentrated in vacuo to give a crude product which was purified by flash chromatography (silica gel, hexanes:EtOAc, 100:0 to 50:50) to afford Intermediate 17A (100 mg, 94% yield) as a yellow oil: $^1$H NMR (400 MHz, Chloroform-d) δ 7.84 (s, 1H), 7.83 (s, 1H), 4.22 (q, J=7.1 Hz, 2H), 4.13 (t, J=6.7 Hz, 2H), 3.04 (bt, J=6.5 Hz, 2H), 2.02-1.94 (m, 2H), 1.37 (s, 9H), 1.27 (t, J=7.2 Hz, 3H). LCMS (ES): m/z 298.3 [M+H]$^+$.

Intermediate 17: A mixture of Intermediate 17A (100 mg, 0.336 mmol), lithium hydroxide (18 mg, 0.752 mmol) in THF (3 mL), H$_2$O (1 mL) and MeOH (0.2 mL) was stirred at RT for 15 h. The volatiles were removed in vacuo and the aqueous residue was acidified with aq. 1N HCl. The mixture was extracted with CHCl$_3$ (3×10 mL). The organic layer was separated, dried over MgSO$_4$ and concentrated to give crude Intermediate 17 (91 mg, 100% yield) as a white solid. LCMS (ES): m/z 270.3 [M+H]$^+$.

Intermediate 18. Ethyl 3-methyl-1-(2-(2-methyl-1,3-dioxolan-2-yl)ethyl)-1H-pyrazole-4-carboxylate and Intermediate 19. Ethyl 5-methyl-1-(2-(2-methyl-1,3-dioxolan-2-yl)ethyl)-1H-pyrazole-4-carboxylate

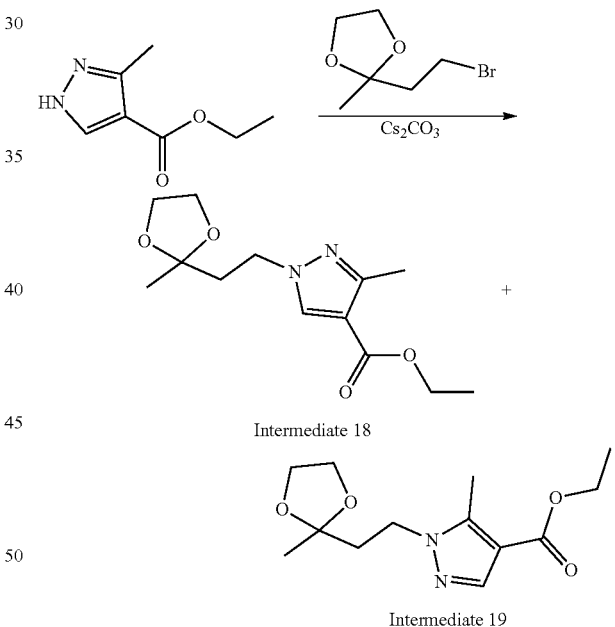

Intermediate 18

Intermediate 19

Intermediate 18. Ethyl 3-methyl-1-(2-(2-methyl-1,3-dioxolan-2-yl)ethyl)-1H-pyrazole-4-carboxylate: A mixture of ethyl 3-methyl-1H-pyrazole-4-carboxylate (79.3 mg, 0.514 mmol), 2-(2-bromoethyl)-2-methyl-1,3-dioxolane (140 mg, 0.718 mmol and Cs$_2$CO$_3$ (251 mg, 0.772 mmol) in acetonitrile (8 mL) was stirred at 65° C. in a sealed tube for 2 h. The solid was removed by filtration. The filtrate was concentrated in vacuo to give a crude product which was dissolved in EtOAc (30 mL). The organic layer was washed with H$_2$O (10 mL), brine, dried (MgSO$_4$), filtered and concentrated under reduced pressure to afford a crude residue. The residue was purified by flash chromatography (silica gel, hexanes: EtOAc, 100:0 to 50:50) to afford Intermediate 18 (60 mg, 43% yield) as a yellow oil: ¹H NMR (500 MHz, Chloroform-d) δ 7.75 (s, 1H), 4.19 (q, J=7.1 Hz, 2H), 4.12-4.05 (m, 2H), 3.95-3.82 (m, 4H), 2.38 (s, 3H), 2.21-2.15 (m, 2H), 1.26 (t, J=7.1 Hz, 3H), 1.25 (s, 3H). LCMS (ES): m/z 269.4 [M+H]

Intermediate 19. Ethyl 5-methyl-1-(2-(2-methyl-1,3-dioxolan-2-yl)ethyl)-1H-pyrazole-4-carboxylate: The above chromatography also yielded Intermediate 19 (25 mg, 18% yield): ¹H NMR (500 MHz, Chloroform-d) δ 7.75 (s, 1H), 4.19 (q, J=7.1 Hz, 2H), 4.12-4.05 (m, 2H), 3.94-3.83 (m, 4H), 2.37 (s, 3H), 2.22-2.14 (m, 2H), 1.26 (t, J=7.1 Hz, 3H), 1.25 (s, 3H). LCMS (ES): m/z 269.4 [M+H]⁺.

Intermediate 20. Ethyl 3,5-dimethyl-1-(2-(2-methyl-1,3-dioxolan-2-yl)ethyl)-1H-pyrazole-4-carboxylate

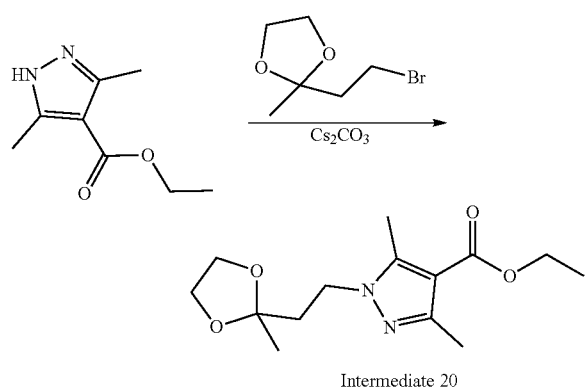

Intermediate 20

Intermediate 20. A mixture of ethyl 3,5-dimethyl-1H-pyrazole-4-carboxylate (200 mg, 1.189 mmol), 2-(2-bromoethyl)-2-methyl-1,3-dioxolane (300 mg, 1.53 mmol) and Cs₂CO₃ (581 mg, 1.78 mmol) in acetonitrile (3 mL) was stirred at 65° C. in a sealed tube for 4 h. The solid was removed by filtration. The filtrate was concentrated in vacuo to give a crude product which was dissolved in EtOAc (30 mL). The organic layer was washed with H₂O (10 mL), brine, dried (MgSO₄), filtered, and concentrated under reduced pressure to afford a crude residue. The residue was purified by flash chromatography (silica gel, hexanes:EtOAc, 100:0 to 50:50) to afford Intermediate 20 (330 mg, 98% yield) as a yellow oil: ¹H NMR (500 MHz, Chloroform-d) δ 4.30 (qd, J=7.2, 1.4 Hz, 2H), 4.18-4.10 (m, 2H), 4.05-3.92 (m, 4H), 2.52 (s, 3H), 2.42 (s, 3H), 2.25-2.14 (m, 2H), 1.37 (t, J=7.2 Hz, 3H), 1.34 (s, 3H). LCMS (ES): m/z 283.4 [M+H]⁺.

Intermediate 21. Methyl 1-(2-(2-methyl-1,3-dioxolan-2-yl)ethyl)-3-phenyl-1H-pyrazole-4-carboxylate
and
Intermediate 22. Methyl 1-(2-(2-methyl-1,3-dioxolan-2-yl)ethyl)-5-phenyl-1H-pyrazole-4-carboxylate

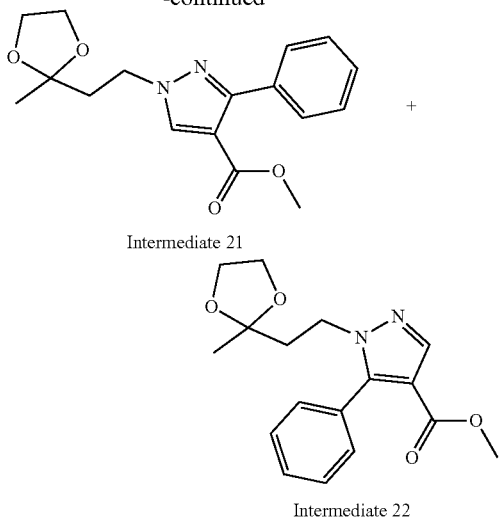

Intermediate 21

Intermediate 22

Intermediate 21. Methyl 1-(2-(2-methyl-1,3-dioxolan-2-yl)ethyl)-3-phenyl-1H-pyrazole-4-carboxylate: A mixture of methyl 3-phenyl-1H-pyrazole-4-carboxylate (200 mg, 0.989 mmol), 2-(2-bromoethyl)-2-methyl-1,3-dioxolane (300 mg, 1.53 mmol) and Cs₂CO₃ (483 mg, 1.48 mmol) in acetonitrile (5 mL) was stirred at 65° C. in a sealed tube for 2 h. The solid was removed by filtration. The filtrate was concentrated in vacuo to give a crude product which was dissolved in EtOAc (30 mL). The organic layer was washed with H₂O (10 mL), brine, dried (MgSO₄), filtered, and concentrated under reduced pressure to afford a crude residue. The residue was purified by preparative HPLC (Column: Sunfire Prep C18, 30×100 mm, 5-μm particles; Mobile Phase A: 100% water with 0.1% TFA; Mobile Phase B: 100% acetonitrile with 0.1% TFA; Gradient: 10-100% B over 10 minutes; Flow: 40 mL/min.) to afford Intermediate 21 (100 mg, 32% yield) as a yellow oil: ¹H NMR (500 MHz, Chloroform-d) δ 7.98 (s, 1H), 7.80-7.72 (m, 2H), 7.43-7.37 (m, 3H), 4.33-4.21 (m, 2H), 4.04-3.89 (m, 4H), 3.76 (s, 3H), 2.38-2.28 (m, 2H), 1.34 (s, 3H). LCMS (ES): m/z 317.05 [M+H]⁺.

Intermediate 22. The above preparative HPLC purification also gave Intermediate 21 (85 mg, 27% yield): ¹H NMR (500 MHz, Chloroform-d) δ 7.99 (s, 1H), 7.52-7.46 (m, 2H), 7.40-7.33 (m, 2H), 4.13-4.03 (m, 2H), 3.90-3.83 (m, 2H), 3.80-3.72 (m, 2H), 3.68 (s, 3H), 2.21-2.04 (m, 2H), 1.21 (s, 3H). LCMS (ES): m/z 317.05 [M+H]⁺.

Intermediate 23. tert-Butyl (S)-2-amino-3-(1-(2-(5,6,7,8-tetrahydro-1,8-naphthyridin-2-yl)ethyl)-1H-pyrazole-4-carboxamido)propanoate

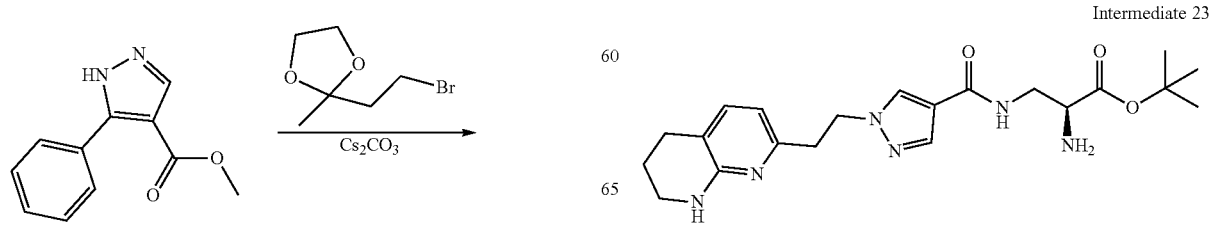

Intermediate 23

75
-continued

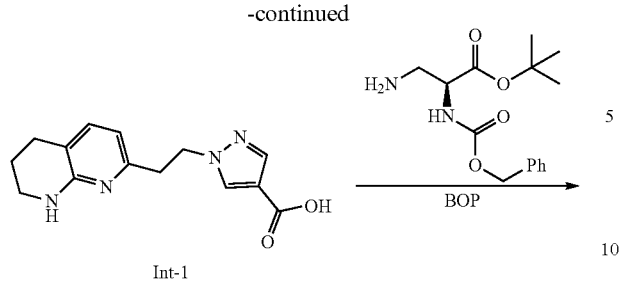

Int-1

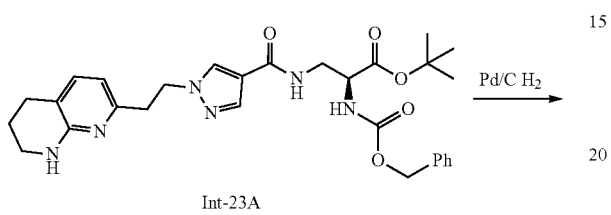

Int-23A

Intermediate 23

Intermediate 23A: To a solution of 1-(2-(5,6,7,8-tetrahydro-1,8-naphthyridin-2-yl)ethyl)-1H-pyrazole-4-carboxylic acid (Intermediate 1, 589 mg, 2.16 mmol) and (S)-tert-butyl 3-amino-2-(((benzyloxy)carbonyl)amino)propanoate (667 mg, 2.266 mmol) in DMF (10 ml) were added BOP (1435 mg, 3.24 mmol) and DIPEA (1.51 mL, 8.65 mmol). The reaction mixture was stirred at room temperature for 2 h. The volatiles were removed in vacuo and the residue was purified by preparative HPLC (Column: Sunfire C18 OBD, 30×100 mm, 5-μm particles; Mobile Phase A: 5:95 acetonitrile: water with 0.1% TFA; Mobile Phase B: 95:5 acetonitrile: water with 0.1% TFA; Gradient: 25-100% B over 10 minutes, then a 5-minute hold at 100% B; Flow: 40 mL/min) to afford 1.08 g (75% yield) of Intermediate 23A as a foam solid: $^1$H NMR (500 MHz, Methanol-$d_4$) δ 8.01 (s, 1H), 7.88 (s, 1H), 7.50 (d, J=7.3 Hz, 1H), 7.41-7.23 (m, 5H), 6.43 (d, J=7.3 Hz, 1H), 5.17-5.04 (m, 2H), 4.54 (t, J=6.6 Hz, 2H), 4.34 (dd, J=7.4, 5.3 Hz, 1H), 3.75 -3.62 (m, 2H), 3.50 (t, J=6.6, 4.8 Hz, 2H), 3.27 (t, J=6.6 Hz, 2H), 2.80 (t, J=6.2 Hz, 2H), 2.00-1.87 (m, 2H), 1.44 (s, 9H). LCMS (ES): m/z 549.5 [M+H]$^+$.

Intermediate 23: To a solution of Intermediate 23A (1.7 g, 2.57 mmol) in MeOH (90 mL) was added and 10% Pd on carbon (342 mg, 0.321 mmol). The suspension was hydrogenated (1 atm., H$_2$ balloon) at room temperature for 1 h. After filtration of the reaction mixture through a Celite® pad and subsequent washing of the cake with MeOH, the filtrate was concentrated in vacuo and air-dried under vacuum to give 1.41 g (100% yield) of product as a white foam solid: $^1$H NMR (500 MHz, Methanol-$d_4$) δ 8.09 (s, 1H), 7.91 (s, 1H), 7.45 (d, J=7.3 Hz, 1H), 6.42 (d, J=7.4 Hz, 1H), 4.55 (t, J=6.8 Hz, 2H), 4.15 (dd, J=6.3, 4.5 Hz, 1H), 3.83 (dd, J=14.6, 4.5 Hz, 1H), 3.79 (dd, J=14.6, 6.3 Hz, 1H), 3.53-3.46 (m, 2H), 3.25 (t, J=6.7 Hz, 2H), 2.80 (t, J=6.3 Hz, 2H), 2.07-1.87 (m, 2H), 1.52 (s, 9H). LCMS (ES): m/z 415.3 [M+H]$^+$.

76

Intermediate 24. Ethyl (S)-3-amino-3-(3-fluoro-4-methoxyphenyl)propanoate

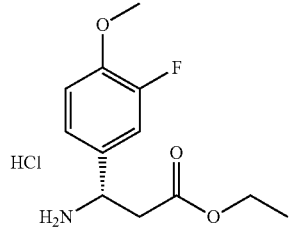

Intermediate 24

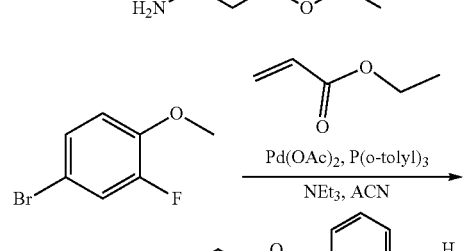

Int-24A

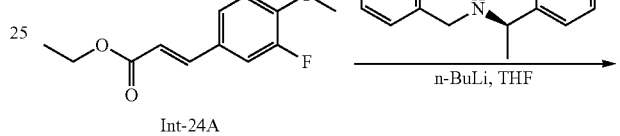

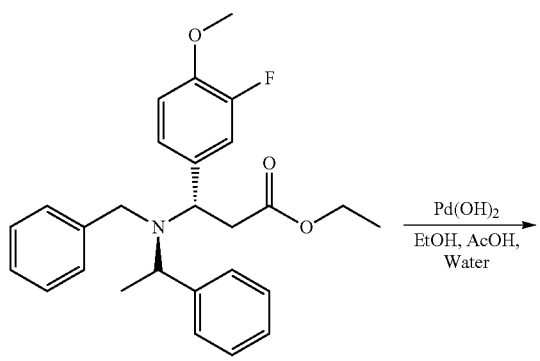

Int-24B

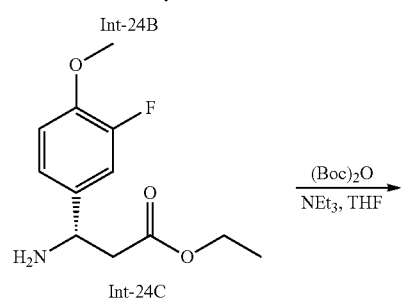

Int-24C

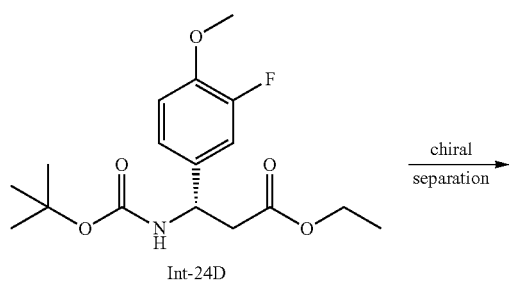

Int-24D

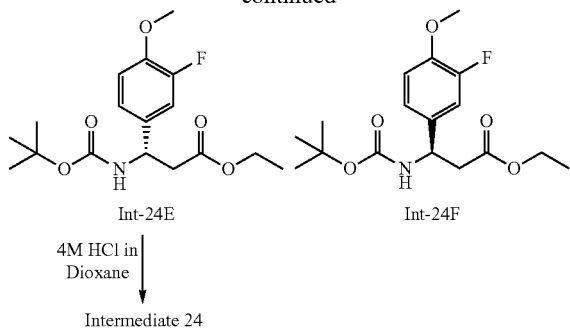

Intermediate 24A, 24B, and 24C were prepared according to the procedure described in: Hutchinson, J. H. et. al., *J. Med. Chem.* 2003, 46, 4790.

Intermediate 24A. Ethyl (E)-3-(3-fluoro-4-methoxyphenyl)acrylate: $^1$H NMR (500 MHz, CDCl3) δ 7.59 (d, J=16.0 Hz, 1H), 7.33-7.21 (m, 2H), 6.96 (t, J=8.5 Hz, 1H), 6.30 (d, J=15.7 Hz, 1H), 4.27 (q, J=7.2 Hz, 2H), 3.93 (s, 3H), 1.34 (t, J=7.2 Hz, 3H). LCMS (ES): m/z 225 [M+H]$^+$.

Intermediate 24B. Ethyl (S)-3-(benzyl((S)-1-phenylethyl)amino)-3-(3-fluoro-4-methoxyphenyl)propanoate: $^1$H NMR (500 MHz, CDCl$_3$) δ 7.59 (d, J=16.0 Hz, 1H), 7.33-7.21 (m, 2H), 6.96 (t, J=8.5 Hz, 1H), 6.30 (d, J=15.7 Hz, 1H), 4.27 (q, J=7.2 Hz, 2H), 3.93 (s, 3H), 1.34 (t, J=7.2 Hz, 3H). LCMS (ES): m/z 436 [M+H]$^+$.

Intermediate 24C. Ethyl (S)-3-amino-3-(3-fluoro-4-methoxyphenyl)propanoate: Intermediate 24C was prepared according to the procedure described in: Hutchinson, J. H. et. al., *J. Med Chem.* 2003, 46, 4790. $^1$H NMR (500 MHz, CDCl$_3$) δ 7.12 (dd, J=12.4, 2.2 Hz, 1H), 7.07 (dd, J=8.4, 1.2 Hz, 1H), 6.92 (t, J=8.5 Hz, 1H), 4.37 (t, J=6.7 Hz, 1H), 4.14 (qd, J=7.2, 0.8 Hz, 2H), 3.88 (s, 3H), 2.66-2.53 (m, 2H), 1.74-1.62 (m, 2H), 1.24 (t, J=7.2 Hz, 3H). LCMS (ES): m/z 242 [M+H]$^+$.

Intermediate 24D. Ethyl (S)-3-(tert-butoxycarbonyl)amino)-3-(3-fluoro-4-methoxyphenyl)propanoate: To a solution of (S)-ethyl 3-amino-3-(3-fluoro-4-methoxyphenyl)propanoate (Intermediate 24C, 31.75 g, 132 mmol) in THF (189 mL) at 0° C. were added triethylamine (20.18 mL, 145 mmol) and (Boc)$_2$O (30.6 mL, 132 mmol). The reaction mixture was warmed to room temperature and stirred for 18.5 h whereupon it was diluted with EtOAc. The reaction mixture was washed with water, 10% citric acid and brine. The organic layer was dried over anhydrous Na$_2$SO$_4$, concentrated and air-dried under vacuum to give Intermediate 24D.

Intermediate 24E: Intermediate 24D was purified by preparative chiral SFC (Column: Whelko-RR (5×50 cm, 10 uM, #4080), BPR Pressure: 100 bars, Temperature: 35° C., Flow rate: 300 mL/min, Mobile Phase: CO$_2$/MeOH (70/30), Detector Wavelength: 220 nm; Separation Program: stack injection; Injection: 4 mL with cycle time: 2 mins; Sample preparation: 44.4 g/310 mL MeOH:DCM (9:1), 143.2 mg/mL; Throughput: 16.3 g/hr) to afford 41.1 g (91%) of the Intermediate 24E as a white solid: $^1$H NMR (500 MHz, CDCl$_3$) δ 7.09-6.97 (m, 2H), 6.94-6.87 (m, 1H), 5.47 (br. s., 1H), 5.03 (br. s., 1H), 4.09 (q, J=7.2 Hz, 2H), 3.88 (s, 3H), 2.92-2.70 (m, 2H), 1.44 (s, 9H), 1.20 (t, J=7.2 Hz, 3H). LCMS (ES): m/z 364 [M+Na]$^+$. >99% ee.

[α]$_{20}^D$−27.36° (c 2.09, CHCl$_3$)

Intermediate 24F. Ethyl (R)-3-((tert-butoxycarbonyl)amino)-3-(3-fluoro-4-methoxyphenyl)propanoate: The above preparative chiral SFC separation yielded the (R)-enantiomer (Intermediate 24F, 1.5 g, 3%) as a white solid: $^1$H NMR (500 MHz, CDCl$_3$) δ 7.10-6.97 (m, 2H), 6.95-6.86 (m, 1H), 5.47 (br. s., 1H), 5.02 (d, J=8.0 Hz, 1H), 4.09 (q, J=7.0 Hz, 2H), 3.88 (s, 3H), 2.91-2.69 (m, 2H), 1.47-1.37 (m, 9H), 1.20 (t, J=7.2 Hz, 3H). LCMS (ES): m/z 364 [M+Na]$^+$. 96.4% ee.

[α]$_{20}^D$+20.76° (c 2.08, CHCl$_3$)

Intermediate 24. Ethyl (S)-3-amino-3-(3-fluoro-4-methoxyphenyl)propanoate, HCl: A solution of (S)-ethyl 3-((tert-butoxycarbonyl)amino)-3-(3-fluoro-4-methoxyphenyl)propanoate (Intermediate 24E, 1.0 g, 2.93 mmol) in 4M HCl in dioxane (48 mL) was stirred at room temperature for 1 h. The solvent was removed in vacuo and the residue was air-dried under vacuum. The residue was then dissolved in EtOH (10 mL), concentrated in vacuo and dried under vacuum to yield 0.801 g (98%) of Intermediate 24E as a white solid as the HCl salt: $^1$H NMR (500 MHz, CDCl$_3$) δ 8.80 (br. s, 3H), 7.37-7.28 (m, 2H), 6.95 (t, J=8.5 Hz, 1H), 4.68 (t, J=6.9 Hz, 1H), 4.08 (q, J=7.1 Hz, 2H), 3.88 (s, 3H), 3.22 (dd, J=16.6, 6.2 Hz, 1H), 3.00 (dd, J=16.5, 7.7 Hz, 1H), 1.18 (t, J=7.2 Hz, 3H). LCMS (ES): m/z 242 [M+H]$^+$. >99% ee.

[α]$_{20}^D$+11.82° (c 1.54, CHCl$_3$)

Intermediate 25. Ethyl (R)-3-amino-3-(3-fluoro-4-methoxyphenyl)propanoate, HCl

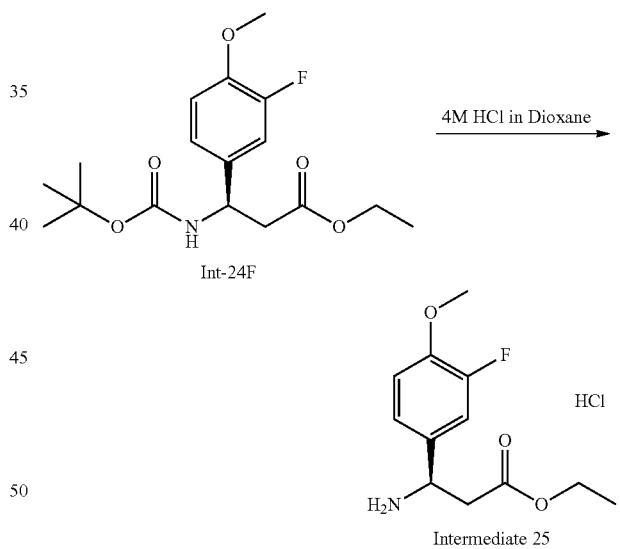

Intermediate 25. Ethyl (R)-3-((tert-butoxycarbonyl)amino)-3-(3-fluoro-4-methoxyphenyl)propanoate: Using the procedure described for synthesis of Intermediate 24, (R)-ethyl 3-((tert-butoxycarbonyl)amino)-3-(3-fluoro-4-methoxyphenyl)propanoate (Int-24F, 1.5 g, 4.39 mmol) and 4M HCl in dioxane (48 mL) yielded Intermediate 25, HCl salt (1.16 g, 95% yield) as a white solid: $^1$H NMR (500 MHz, CDCl$_3$) δ 8.81 (br. s, 3H), 7.37-7.27 (m, 2H), 7.01-6.88 (m, 1H), 4.68 (br. s., 1H), 4.08 (q, J=7.1 Hz, 2H), 3.88 (s, 3H), 3.23 (dd, J=16.6, 6.2 Hz, 1H), 3.01 (dd, J=16.6, 7.6 Hz, 1H), 1.18 (t, J=7.0 Hz, 3H). LCMS (ES): m/z 242 [M+H]$^+$. 96.4% ee.

[α]$_{20}^D$−11.26° (c 2.45, CHCl$_3$)

Intermediate 26. Methyl (S)-3-amino-3-(3-bromo-5-(tert-butyl)phenyl)propanoate and Intermediate 27. Ethyl (S)-3-amino-3-(3-bromo-5-(tert-butyl)phenyl)propanoate

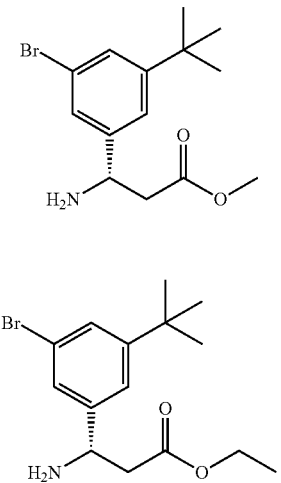

Intermediate 26

Intermediate 27

Intermediate 26 and Intermediate 27 were prepared according to the procedure described in Henderson, N. C. et. al., *Nature Medicine* 2013 19, 1617.

Intermediate 28. Methyl (S)-3-(3,5-dichlorophenyl)-3-(methylamino)propanoate and Intermediate 29. Methyl (R)-3-(3,5-dichlorophenyl)-3-(methylamino)propanoate

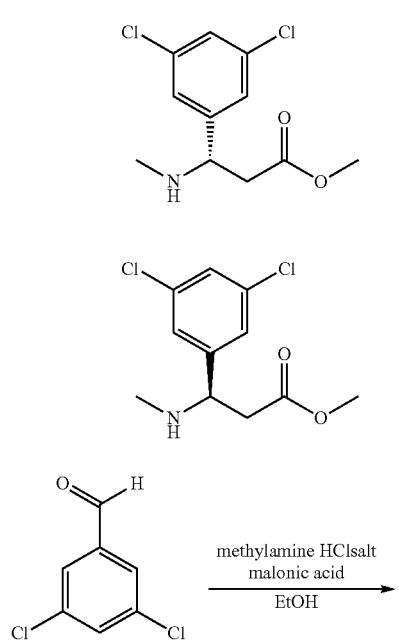

Intermediate 28

Intermediate 29

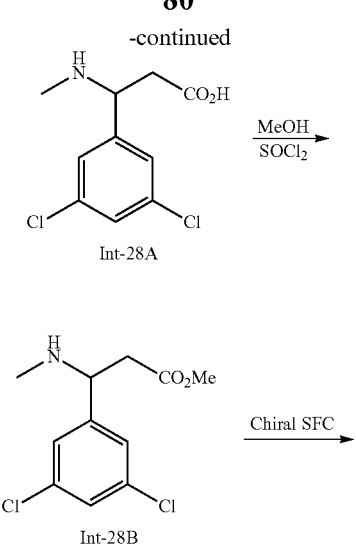

Int-28A

Int-28B

Intermediate 28 and Intermediate 29

Intermediate 28A: 3-(3,5-Dichlorophenyl)-3-(methylamino)propanoic acid: A mixture of methylamine hydrochloride (2.0 g, 29.6 mmol) and sodium acetate (2.46 g, 30.0 mmol) in EtOH (4 mL) was stirred at RT for 30 min. 3,5-Dichlorobenzaldehyde (1.06 g, 6.06 mmol), malonic acid (1.04 g, 9.99 mmol) were added. The mixture was heated at reflux for 3.5 h. The solid was removed by filtration. The filtrate was concentrated in vacuo to give a crude product which was purified by preparative HPLC (Column: Phenomenex Axia C18, 30×100 mm, 5-μm particles; Mobile Phase A: 5:95 MeOH: water with 0.1% TFA; Mobile Phase B: 95:5 MeOH: water with 0.1% TFA; Gradient: 20-100% B over 10 minutes, then a 5-minute hold at 100% B; Flow: 40 mL/min) to afford Intermediate 28A (910 mg, 42% yield) as a white solid: $^1$H NMR (400 MHz, Methanol-$d_4$) δ 7.60 (t, J=1.8 Hz, 1H), 7.53 (d, J=1.8 Hz, 2H), 4.63 (t, J=6.9 Hz, 1H), 3.14 (dd, J=17.2, 6.9 Hz, 1H), 3.03 (dd, J=17.2, 6.9 Hz, 1H), 2.62 (s, 3H). LCMS (ES): m/z 248.3 [M+H]$^+$.

Intermediate 28B: To a mixture Intermediate 28A (910 mg, 2.51 mmol) in MeOH (15-mL) was added SOCl$_2$ (0.7 mL, 9.59 mmol). The reaction mixture was stirred at RT for 2 h. Solvent was evaporated to give 0.75 g (100% yield) of crude Intermediate 28B as a white solid. $^1$H NMR (500 MHz, Methanol-$d_4$) δ 7.60 (t, J=1.9 Hz, 1H), 7.55 (d, J=1.9 Hz, 2H), 4.68 (dd, J=7.5, 6.4 Hz, 1H), 3.69 (s, 3H), 3.25 (dd, J=17.1, 6.4 Hz, 1H), 3.13 (dd, J=17.1, 7.5 Hz, 1H), 2.63 (s, 3H). LCMS (ES): m/z 262.1 [M+H]$^+$.

Intermediate 28: Intermediate 28B was purified by preparative chiral SFC (Column: Chiralpak ID, 21×250 mm, 5 micron, BPR Pressure: 100 bars, Temperature: 40° C., Flow rate: 45 mL/min, Mobile Phase: CO$_2$/MeOH (95/5)+0.1% DEA, Detector Wavelength: 220 nm) to afford Intermediate 28 (60 mg, 16% yield) as a yellow oil.

Intermediate 29: The above chiral SFC separation also yielded Intermediate 29 (350 mg, 93% yield) as a yellow oil.

Intermediate 30. Methyl 3-amino-3-(3,5-dichlorophenyl)propanoate

Intermediate 31. Methyl (S)-3-amino-3-(3,5-dichlorophenyl)propanoate and

Intermediate 32. Methyl (R)-3-amino-3-(3,5-dichlorophenyl)propanoate

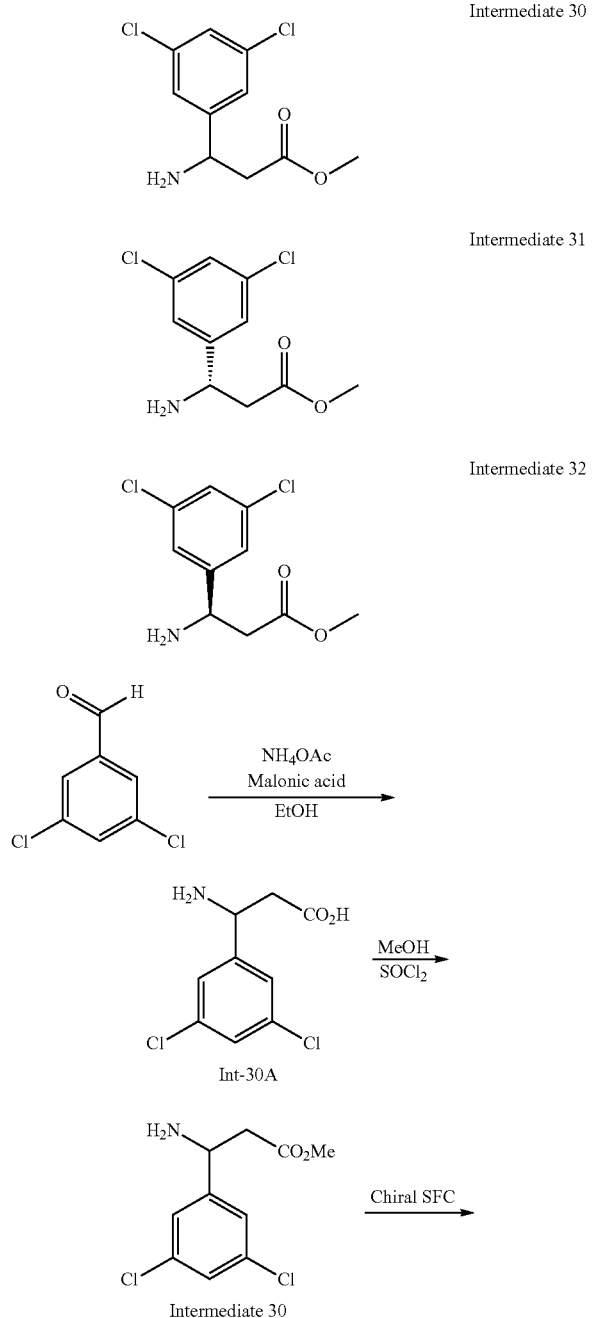

Intermediate 30A: 3-Amino-3-(3,5-dichlorophenyl)propanoic acid: A mixture of ammonium acetate (14.09 g, 183 mmol), 3,5-dichlorobenzaldehyde (8.0 g, 45.7 mmol), malonic acid (5.23 g, 50.3 mmol) in EtOH (90 mL) was heated at reflux for 16 h. After cooling down to room temperature, the solid was collected by filtration, washed with EtOH (15 mL), and dried to give crude Intermediate 30A (7.0 g, 66% yield) as a white solid. LCMS (ES): m/z 234.3 $[M+H]^+$.

Intermediate 30: To a mixture of Intermediate 30A (7.0 mg, 29.9 mmol) in MeOH (50 mL) was added $SOCl_2$ (5.02 mL, 68.8 mmol). The reaction mixture was stirred at RT for 6 h. The solid was removed by filtration. The filtrate was concentrated in vacuo to give a crude product which was dissolved in EtOAc (150 mL). The organic layer was washed with sat. $NaHCO_3$ solution, brine, dried ($MgSO_4$), filtered, and concentrated under reduced pressure to afford the crude product which was purified by flash chromatography (silica gel, $CH_2Cl_2$:MeOH, 100:0 to 95:5) to afford Intermediate 30 (3.3 g, 46% yield) as a yellow oil: $^1$H NMR (500 MHz, Chloroform-d) δ 7.31 (d, J=1.9 Hz, 2H), 7.28 (t, J=1.9 Hz, 1H), 4.44 (t, J=6.7 Hz, 1H), 3.69 (s, 3H), 2.81-2.63 (m, 2H). LCMS (ES): m/z 248.3 $[M+H]^+$.

Intermediate 31: Intermediate 30 (3.3 g) was purified by preparative chiral SFC (Column: Chiralpak AD, 30×250 mm, 5 micron, BPR Pressure: 150 bars, Temperature: 40° C., Flow rate: 80 mL/min, Mobile Phase: $CO_2$/MeOH (95/5)+0.1% DEA, Detector Wavelength: 220 nm) to afford Intermediate 31 (2.3 g) as a yellow oil. $^1$H NMR (500 MHz, Chloroform-d) δ 7.28 (d, J=1.9 Hz, 1H), 7.26 (t, J=1.9 Hz, 1H), 4.43-4.34 (m, 1H), 3.70 (s, 3H), 2.76-2.56 (m, 2H).

Intermediate 32: Intermediate 30 (3.3 g) was purified by preparative chiral SFC (Column: Chiralpak AD, 30×250 mm, 5 micron, BPR Pressure: 150 bars, Temperature: 40° C., Flow rate: 80 mL/min, Mobile Phase: $CO_2$/MeOH (95/5)+0.1% DEA, Detector Wavelength: 220 nm) to afford Intermediate 32 (1.31 g) as a yellow oil. $^1$H NMR (500 MHz, Chloroform-d) δ 7.27 (d, J=1.9 Hz, 1H), 7.26 (t, J=1.9 Hz, 1H), 4.38 (dd, J=8.7, 4.8 Hz, 1H), 3.70 (s, 3H), 2.65 (dd, J=16.0, 4.8 Hz, 1H), 2.60 (dd, J=16.0, 8.7 Hz, 1H).

Intermediate 33. Ethyl (S)-3-amino-2-((2,4,6-trimethylphenyl)sulfonamido) propanoate

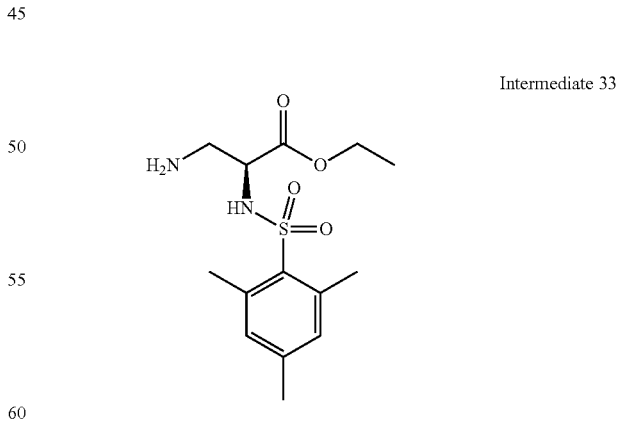

Intermediate 33 was prepared according to the procedure described in Pitts, J. W. et. al., *J. Med. Chem.* 2000 43, 27. $^1$H NMR (500 MHz, Chloroform-d) δ 6.95 (s, 2H), 5.63 (br. s., 1H), 5.31 (s, 1H), 3.97-4.05 (m, 2H), 3.82 (t, J=4.68 Hz, 1H), 2.94-3.05 (m, 2H), 2.66 (s, 6H), 2.29 (s, 3H), 1.14 (t, J=7.15 Hz, 3H), LCMS (ES): m/z 315 $[M+H]^+$.

Intermediate 34. 1-(2-(5,6,7,8-Tetrahydro-1,8-naphthyridin-2-yl)ethyl)-1H-pyrazole-4-carboxylic acid

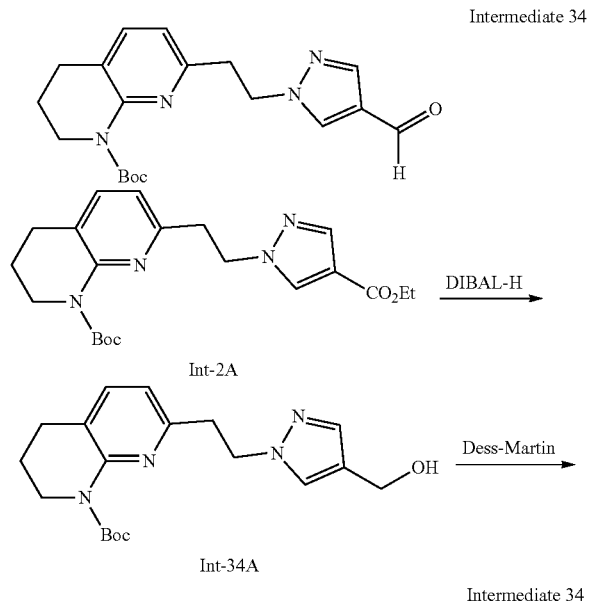

Int-2A

Int-34A

Intermediate 34

Intermediate 34A: To a solution of tert-butyl 7-(2-(4-(ethoxycarbonyl)-1H-pyrazol-1-yl)ethyl)-3,4-dihydro-1,8-naphthyridine-1(2H)-carboxylate (Int-2A, 276 mg, 0.689 mmol) in THF (10 mL) was added DIBAL-H solution (3.45 mL, 3.45 mmol, 1M in THF) at −78° C. The reaction mixture was stirred at room temperature for 0.5 h. The resulting mixture was quenched with aqueous satu. $NH_4Cl$ solution (2 mL). After filtration, the filtrate was dried over $MgSO_4$ and concentrated to give the crude product which was further purified by silica gel chromatography to give Intermediate 34A (0.19 g, 77% yield) as a white solid. $^1$H NMR (500 MHz, Chloroform-d) δ 7.48 (s, 1H), 7.39 (s, 1H), 7.27 (d, J=7.7 Hz, 1H), 6.70 (d, J=7.5 Hz, 1H), 4.56-4.50 (m, 4H), 3.83-3.70 (m, 2H), 3.25 (t, J=7.1 Hz, 2H), 2.73 (t, J=6.7 Hz, 2H), 1.93 (p, J=6.5 Hz, 2H), 1.56 (s, 9H). LCMS (ES): m/z 359.3 $[M+H]^+$.

Intermediate 34: To a solution of tert-butyl 7-(2-(4-(hydroxymethyl)-1H-pyrazol-1-yl)ethyl)-3,4-dihydro-1,8-naphthyridine-1(2H)-carboxylate (0.154 g, 0.363 mmol, Int-34A) in $CH_2Cl_2$ (5 mL) was added Dess-Martin Periodinane (154 mg, 0.363 mmol). The reaction mixture was stirred at room temperature for 2 h. After filtration of the reaction mixture through a Celite® pad and subsequent washing of the cake with EtOAc, the filtrate was concentrated in vacuo to give a crude product which was further purified by silica gel chromatography to give Intermediate 34 (0.1 g, 77% yield) as a viscous oil. LCMS (ES): m/z 357.2 $[M+H]^+$.

Example 1. (S)-3-(3-(tert-Butoxymethyl)-1-(2-(5,6,7,8-tetrahydro-1,8-naphthyridin-2-yl)ethyl)-1H-pyrazole-4-carboxamido)-3-(3-fluoro-4-methoxyphenyl)propanoic acid Example 1

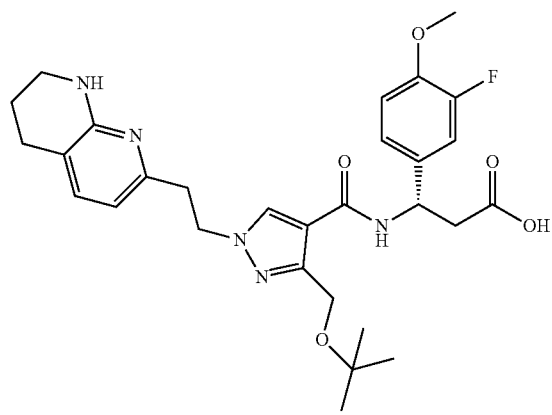

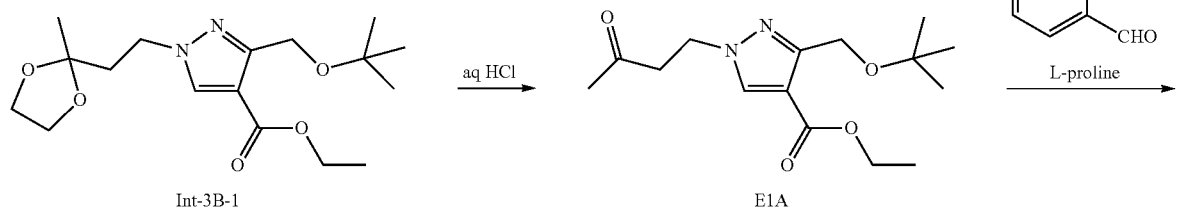

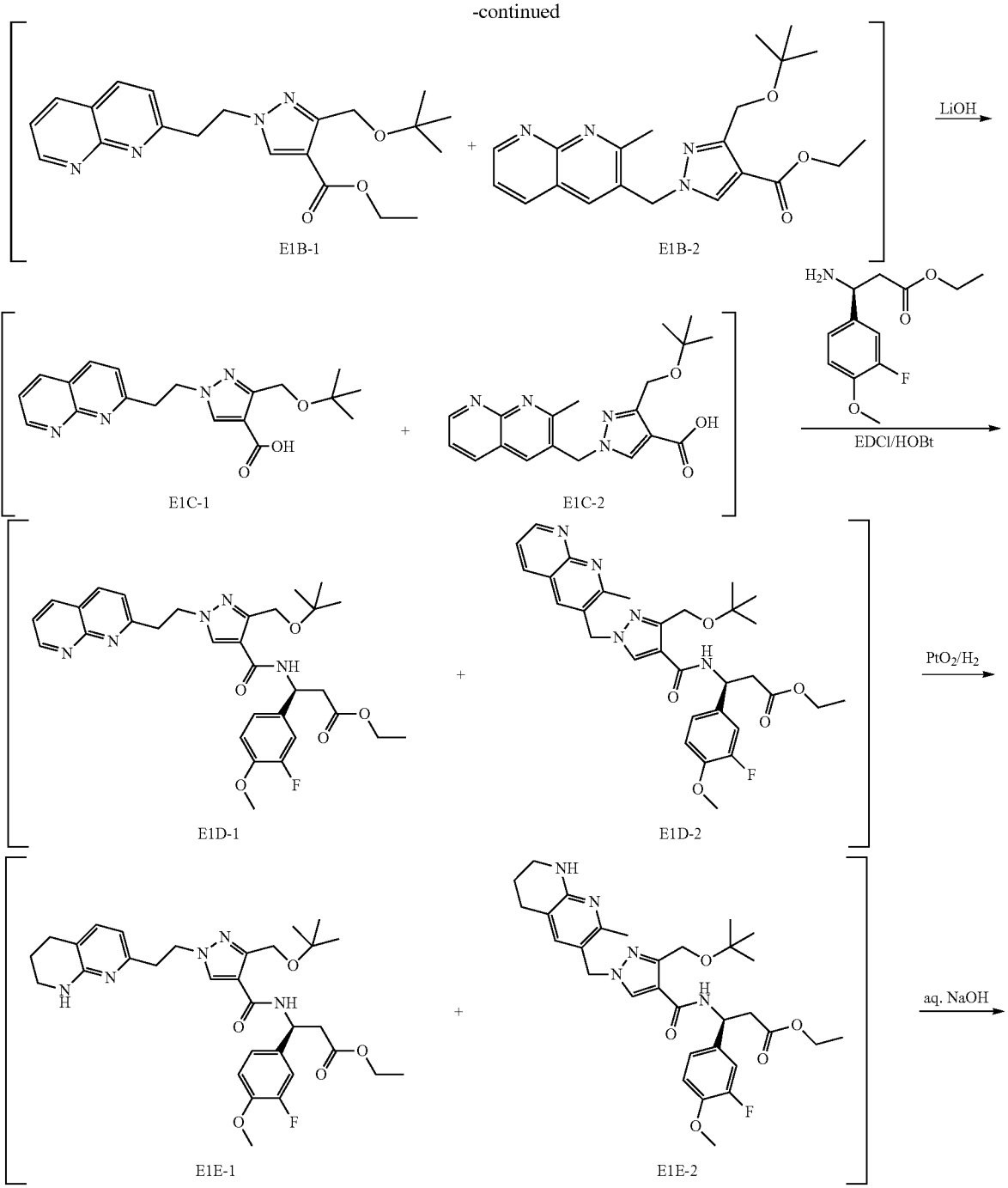

Example 1

Example 1A: A mixture of ethyl 3-(tert-butoxymethyl)-1-(2-(2-methyl-1,3-dioxolan-2-yl)ethyl)-1H-pyrazole-4-carboxylate (367 mg, 1.08 mmol, Int-3B-1) in THF (3 mL) and 1N HCl (2 mL) was stirred at RT for 16 h. Solvent was evaporated and the crude product was diluted with H₂O (20 mL), and extracted with EtOAc (100 mL). The organic layer was separated, dried over MgSO₄, and concentrated to give 0.32 g (100% yield) of the crude product as an oil. The crude product was used for the next step without further purification. $^1$H NMR (400 MHz, Chloroform-d) δ 7.82 (s, 1H), 4.60 (s, 2H), 4.28 (t, J=6.3 Hz, 2H), 4.20 (q, J=7.1 Hz, 2H), 2.99 (t, J=6.3 Hz, 2H), 2.09 (s, 3H), 1.26 (t, J=6.3 Hz, 3H), 1.24 (s, 9H). LCMS (ES): m/z 297.3 [M+H]⁺.

Example [E1B-1+E1B-2]: A mixture of ethyl 3-(tert-butoxymethyl)-1-(3-oxobutyl)-1H-pyrazole-4-carboxylate (320 mg, 1.080 mmol), 2-aminonicotinaldehyde (171 mg, 1.40 mmol) and L-proline (124 mg, 1.08 mmol) in EtOH (5 mL) was heated at 78° C. in a sealed tube for 24 h. After cooling down to room temperature, the solvent was evaporated and the crude residue was dissolved in minimum amount of CH₂Cl₂ and subjected to silica gel chromatography (Hexane/EtOAc, 100:0 to 0:100) then (MeOH/EtOAc, 0:100 to 10:90) to give a mixture of E1B-1 and E1B-2 as an orange oil (280 mg, 68% yield) in a ~2.2:1 ratio (by $^1$H NMR). LCMS (ES): m/z 383.3 [M+H]$^+$.

Example [E1C-1+E1C-2]: A mixture of Example [E1B-1+E1B-2] (100 mg, 0.26 mmol), lithium hydroxide (20 mg, 0.8 mmol) in THF (1 mL), H$_2$O (0.6 mL) and MeOH (0.4 mL) was stirred at RT for 20 h. The solvent was removed in vacuo. The aqueous residue was acidified with aq HCl (1N). Solvents were evaporated and the crude residue was dissolved in a minimum amount of CH$_2$Cl$_2$ and subjected to silica gel chromatography (MeOH/CH$_2$Cl$_2$, 20:80) to give a mixture of E1C-1 and E1C-2 as a yellow foam solid (93 mg, 100% yield). LCMS (ES): m/z 355.5 [M+H]$^+$.

Example [E1D-1+E1D-2]: To a solution of Example [E1C-1+E1C-2] (93 mg, 0.262 mmol), ethyl (S)-3-amino-3-(3-fluoro-4-methoxyphenyl)propanoate (63.3 mg, 0.262 mmol) in CH$_2$Cl$_2$ (1.2 mL), and DMF (0.5 ml) was added EDC (78 mg, 0.407 mmol), HOBT (48.2 mg, 0.315 mmol) and Et$_3$N (0.070 mL, 0.500 mmol). The reaction mixture was stirred at room temperature for 23 h. Solvents were evaporated and the crude product was subjected to silica gel chromatography (EtOAc 100%, then MeOH/EtOAc, 20:80) to give a mixture of E1D-1 and E1D-2 as a pink foam (100 mg, 66% yield). LCMS (ES): m/z 578.6 [M+H]$^+$.

Example [E1E-1+E1E-2]: To a solution of Example [E1D-1+E1D-2] (60 mg, 0.104 mmol) in EtOH (3.5 mL) was added PtO$_2$ (4.72 mg, 0.021 mmol). The suspension was hydrogenated (1 atm, H$_2$ balloon) at room temperature for 16 h. After filtration of the reaction mixture through a Celite® pad and subsequent washing of the cake with EtOH, the filtrate was concentrated in vacuo and air-dried under vacuum to give (60 mg, 100% yield) of a mixture of E1E-1 and E1E-2 as a grey oil. LCMS (ES): m/z 582.7 [M+H]$^+$.

Example 1: To a mixture of Example [E1E-1+E1E-2] (20 mg, 0.053 mmol) in THF (1.0 mL) and MeOH (1 ml) at room temperature was added 1M aq. NaOH (0.103 mL, 0.103 mmol) and the reaction mixture stirred for 8 h. The volatiles were removed in vacuo. The residue was acidified to pH ~5 with 1M HCl. The volatiles were removed in vacuo and the residue was purified by preparative HPLC (Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-50% B over 25 minutes, then a 5-minute hold at 100% B; Flow: 20 mL/min) to afford Example 1 (4.3 mg, 22% yield): $^1$H NMR (500 MHz, DMSO-d$_6$) δ 8.27 (d, J=8.0 Hz, 1H), 8.12 (s, 1H), 7.50 (bs, 1H), 7.26-7.00 (m, 4H), 6.49 (d, J=7.1 Hz, 1H), 5.30 (q, J=8.1 Hz, 1H), 4.51 (d, J=12.0 Hz, 1H), 4.48 (d, J=12.0 Hz, 1H), 4.41 (t, J=7.4 Hz, 2H), 3.81 (s, 3H), 3.38-3.11 (m, 1H, three protons missing due to H$_2$O suppression), 2.82-2.74 (m, 2H), 2.73-2.67 (m, 2H), 1.87-1.75 (m, 2H), 1.13 (s, 9H). LCMS (ES): m/z 554.5 [M+H]$^+$ Human αVβ6 IC50 (nM)=771.

Example 2. (S)-3-(3-Fluoro-4-methoxyphenyl)-3-(3-(hydroxymethyl)-1-(2-(5,6,7,8-tetrahydro-1,8-naphthyridin-2-yl)ethyl)-1H-pyrazole-4-carboxamido)propanoic acid

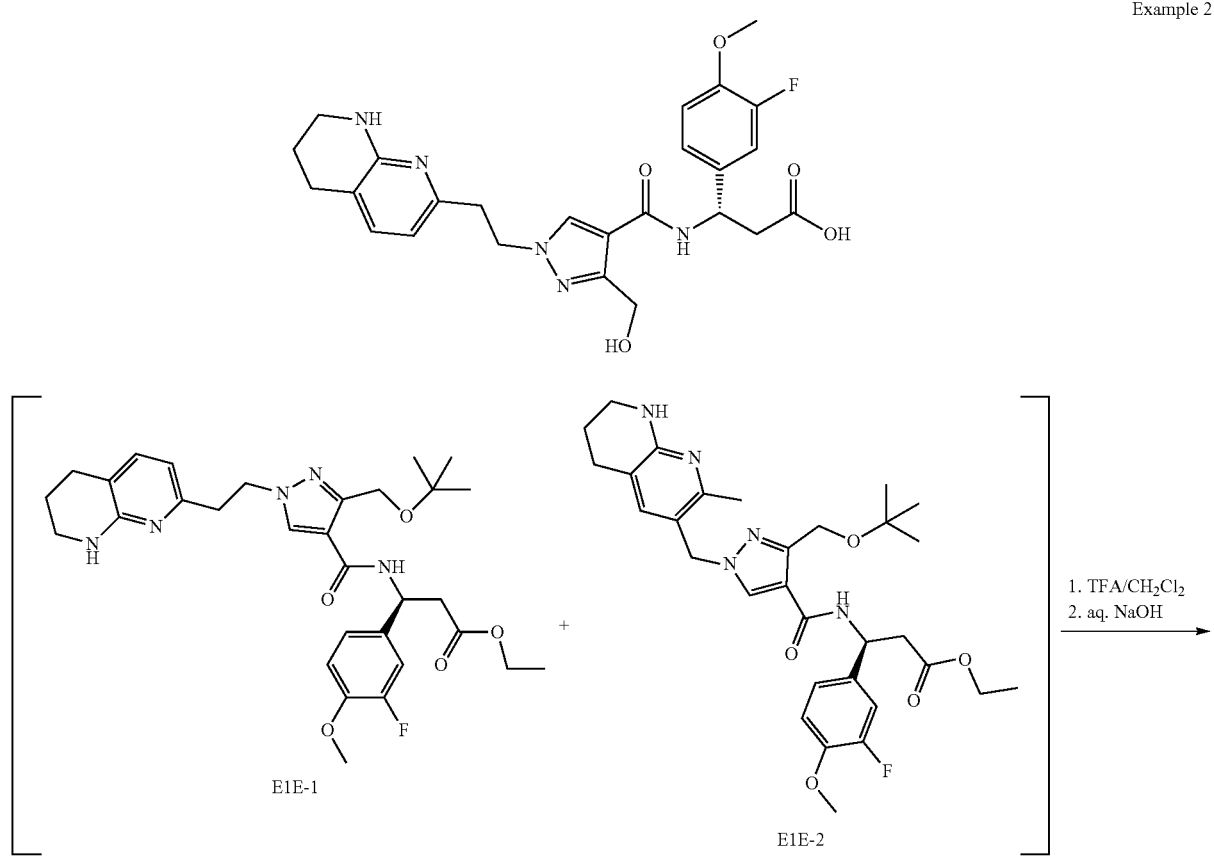

Example 2

Example 2. Step 1: A mixture of Example [E1E-1+E1E-2] (20 mg, 0.034 mmol) in TFA (0.8 mL) and CH$_2$Cl$_2$ (0.5 mL) was stirred at RT for 2 h. The solvent was removed in vacuo to give the crude product (20 mg, contained TFA) as a viscous oil which was used for the next step without further purification. LCMS (ES): m/z 526.6 [M+H]$^+$.

Step 2: To the product mixture from Step 1 (28 mg, 0.053 mmol) in THF (1.0 mL) and MeOH (0.2 ml) at room temperature was added 1M aq. NaOH (0.230 mL, 0.230 mmol) and the reaction mixture stirred for 3 h. The volatiles were removed in vacuo. The residue was acidified to pH ~5 with 1M HCl. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-45% B over 22 minutes, then a 5-minute hold at 100% B; Flow: 20 mL/min) to afford Example 2 (20.2 mg, 100%): $^1$H NMR (500 MHz, DMSO-d$_6$) δ 8.73 (d, J=8.1 Hz, 1H), 8.16 (s, 1H), 7.41-7.06 (m, 4H), 6.38 (bs, 1H), 5.35-5.24 (m, 1H), 4.53 (s, 2H), 4.36 (t, J=7.5 Hz, 2H), 3.82 (s, 3H), 3.38-3.06 (m, 1H, three protons missing due to H$_2$O suppression), 2.86-2.61 (m, 4H), 1.85-1.73 (m, 2H). LCMS (ES): m/z 498.4 [M+H]$^+$. Human αVβ6 IC50 (nM)=349.

Example 3. (3-(3-(tert-Butoxymethyl)-1-(2-(5,6,7,8-tetrahydro-1,8-naphthyridin-2-yl)ethyl)-1H-pyrazole-4-carboxamido)-3-(3,5-dichlorophenyl)propanoic acid Example 3

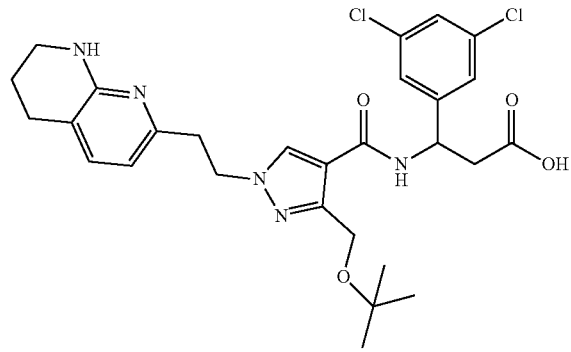

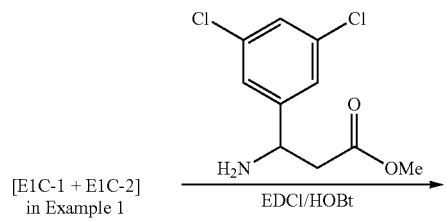

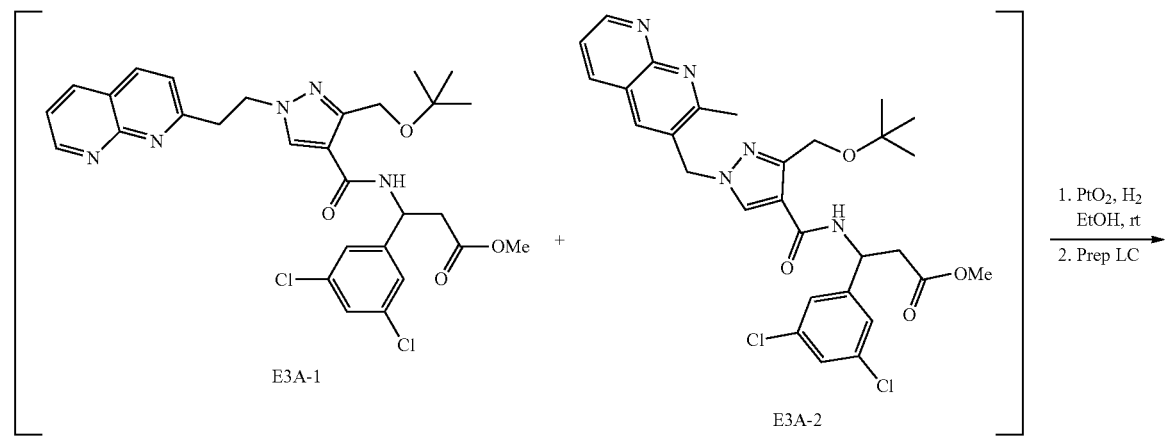

-continued

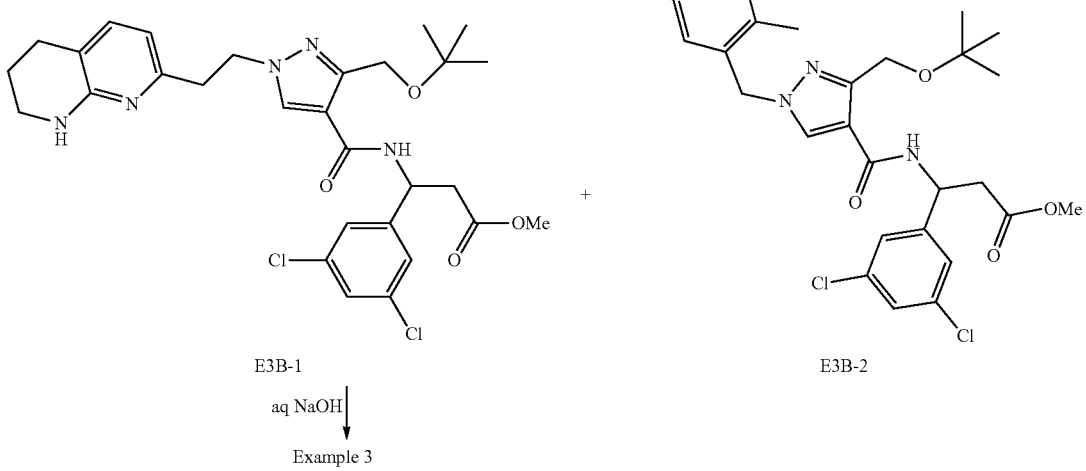

E3B-1

E3B-2 aq NaOH ↓

Example 3

Example [E3A-1+E3A-2]: To a solution of Example [E1C-1+E1C-2] (148 mg, 0.418 mmol) and methyl 3-amino-3-(3,5-dichlorophenyl)propanoate, TFA (151 mg, 0.418 mmol) in $CH_2Cl_2$ (4.5 mL) and DMF (0.5 ml) were added EDC (125 mg, 0.65 mmol), HOBT (77 mg, 0.501 mmol) and $Et_3N$ (0.058 mL, 0.418 mmol). The reaction mixture was stirred at room temperature for 20 h. Solvent was evaporated and the crude product was subjected to silica gel chromatography (MeOH/$CH_2Cl_2$, 0:100 to 5:95) to give the product as a pink foam (168 mg, 69%). LCMS (ES): m/z 584.5 [M+H]$^+$.

Example E3B-1: To a solution of Example [E3A-1+E3A-2] (168 mg, 0.287 mmol) in EtOH (10 mL) was added $PtO_2$ (13.1 mg, 0.057 mmol). The suspension was hydrogenated (1 atm. H$_2$, balloon) at room temperature for 16 h. After filtration of the reaction mixture through a Celite® pad and subsequent washing of the cake with EtOH, the filtrate was concentrated in vacuo and dried under vacuum to give a crude product which was purified by preparative HPLC (Column: Sunfire Prep C18, 30×100 mm, 5-nm particles; Mobile Phase A: 100% water with 10-mM ammonium acetate; Mobile Phase B: 100% acetonitrile with 10-mM ammonium acetate; Gradient: 20-100% B over 10 minutes; Flow: 40 mL/min.) to afford E3A-1 (36 mg, 21% yield) as a foamy solid: $^1$H NMR (400 MHz, Methanol-d$_4$) δ 7.90 (s, 1H), 7.41-7.37 (m, 3H), 7.13 (d, J=7.3 Hz, 1H), 6.26 (d, J=7.3 Hz, 1H), 5.48 (dd, J=8.1, 6.6 Hz, 1H), 4.66 (s, 2H), 4.43 (t, J=6.9 Hz, 2H), 3.67 (s, 3H), 3.43-3.47 (m, 2H), 3.07 (t, J=6.9 Hz, 2H), 2.99 (dd, J=16.0, 6.6 Hz, 1H), 2.94 (dd, J=16.0, 8.1 Hz, 1H), 2.70 (t, J=6.3 Hz, 2H), 1.93-1.81 (m, 2H), 1.25 (s, 9H). LCMS (ES): m/z 588.5 [M+H]$^+$.

Example E3B-2: The above preparative HPLC purification also gave E3B-2 (20 mg, 12% yield) as a foamy solid: $^1$H NMR (400 MHz, Methanol-d$_4$) δ 7.98 (s, 1H), 7.38 (s, 3H), 7.23 (s, 1H), 5.51 (s, 2H), 5.49 (t, J=7.2 Hz, 1H), 4.66 (s, 2H), 3.67 (s, 3H), 3.54-3.35 (m, 2H), 2.99 (dd, J=16.0, 6.7 Hz, 1H), 2.95 (dd, J=16.0, 8.2 Hz, 1H), 2.74 (t, J=6.2 Hz, 2H), 2.35 (s, 3H), 1.95-1.84 (m, 2H), 1.25 (s, 9H). LCMS (ES): m/z 588.5 [M+H]$^+$.

Example 3: To a mixture of Example E3B-1 (17 mg, 0.029 mmol) in THF (1.0 mL) and MeOH (0.1 mL) at room temperature was added 1M aq. NaOH (0.087 mL, 0.087 mmol) and the reaction mixture stirred for 8 h. The volatiles were removed in vacuo. The residue was acidified to pH ~5 with 1M HCl. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 5-minute hold at 100% B; Flow: 20 mL/min. to afford Example 3 (12.2 mg, 74%): $^1$H NMR (500 MHz, DMSO-d$_6$) δ 8.37 (d, J=6.5 Hz, 1H), 8.05 (s, 1H), 7.49 (s, 1H), 7.38 (s, 2H), 7.04 (d, J=7.3 Hz, 1H), 6.25 (d, J=7.3 Hz, 1H), 5.30 (q, J=8.3 Hz, 1H), 4.50 (s, 2H), 4.33 (t, J=8.5 Hz, 2H), 3.25 (t, 6.2 Hz, 2H), 2.96 (t, J=8.2 Hz, 2H), 2.91-2.67 (m, 2H), 2.63-2.75 (m, 2H), 1.80-1.67 (m, 2H), 1.14 (s, 9H). LCMS (ES): m/z 574.5 [M+H]$^+$. Human αVβ6 IC50 (nM)= 312.

Example 4. 3-(3,5-Dichlorophenyl)-3-(3-(hydroxymethyl)-1-(2-(5,6,7,8-tetrahydro-1,8-naphthyridin-2-yl)ethyl)-1H-pyrazole-4-carboxamido)propanoic acid Example 4

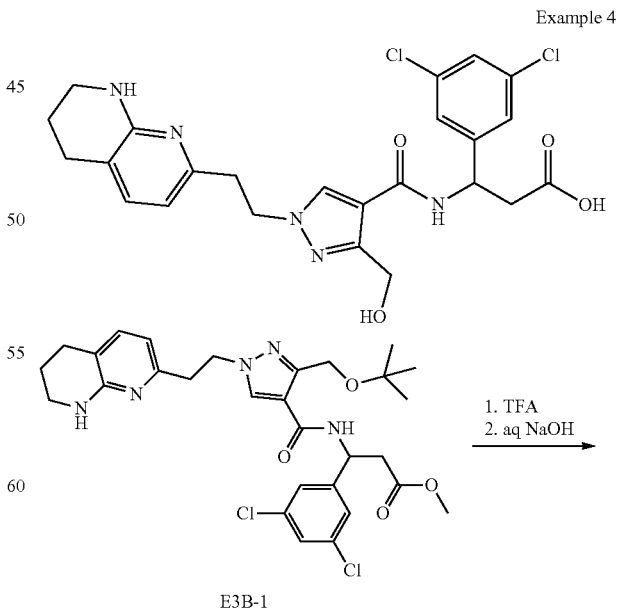

E3B-1

1. TFA
2. aq NaOH

Example 4

Example 4 was prepared from Example E3B-1 in a manner analogous to preparation of Example 2 above: $^1$H NMR (500 MHz, DMSO-$d_6$) δ 8.80 (d, J=7.8 Hz, 1H), 8.16 (s, 1H), 7.50 (t, J=2.0 Hz, 1H), 7.41 (d, J=2.0 Hz, 2H), 7.10 (d, J=7.0 Hz, 1H), 6.28 (d, J=7.3 Hz, 1H), 5.30 (q, J=7.4 Hz, 1H), 4.54 (s, 1H), 4.53 (s, 1H), 4.35 (t, J=7.4 Hz, 2H), 3.37-3.30 (two protons missing due to H$_2$O supression), 2.99 (t, J=6.5 Hz, 2H), 2.80 (d, J=7.3 Hz, 2H), 2.62 (t, J=6.3 Hz, 2H), 1.76 (p, J=6.2 Hz, 2H). LCMS (ES): m/z 518.5 [M+H]$^+$. Human αVβ6 IC50 (nM)=141.

Example 5. 3-(3-(tert-Butoxymethyl)-1-(3-(5,6,7,8-tetrahydro-1,8-naphthyridin-2-yl)propyl)-1H-pyrazole-4-carboxamido)-3-(3,5-dichlorophenyl)propanoic acid

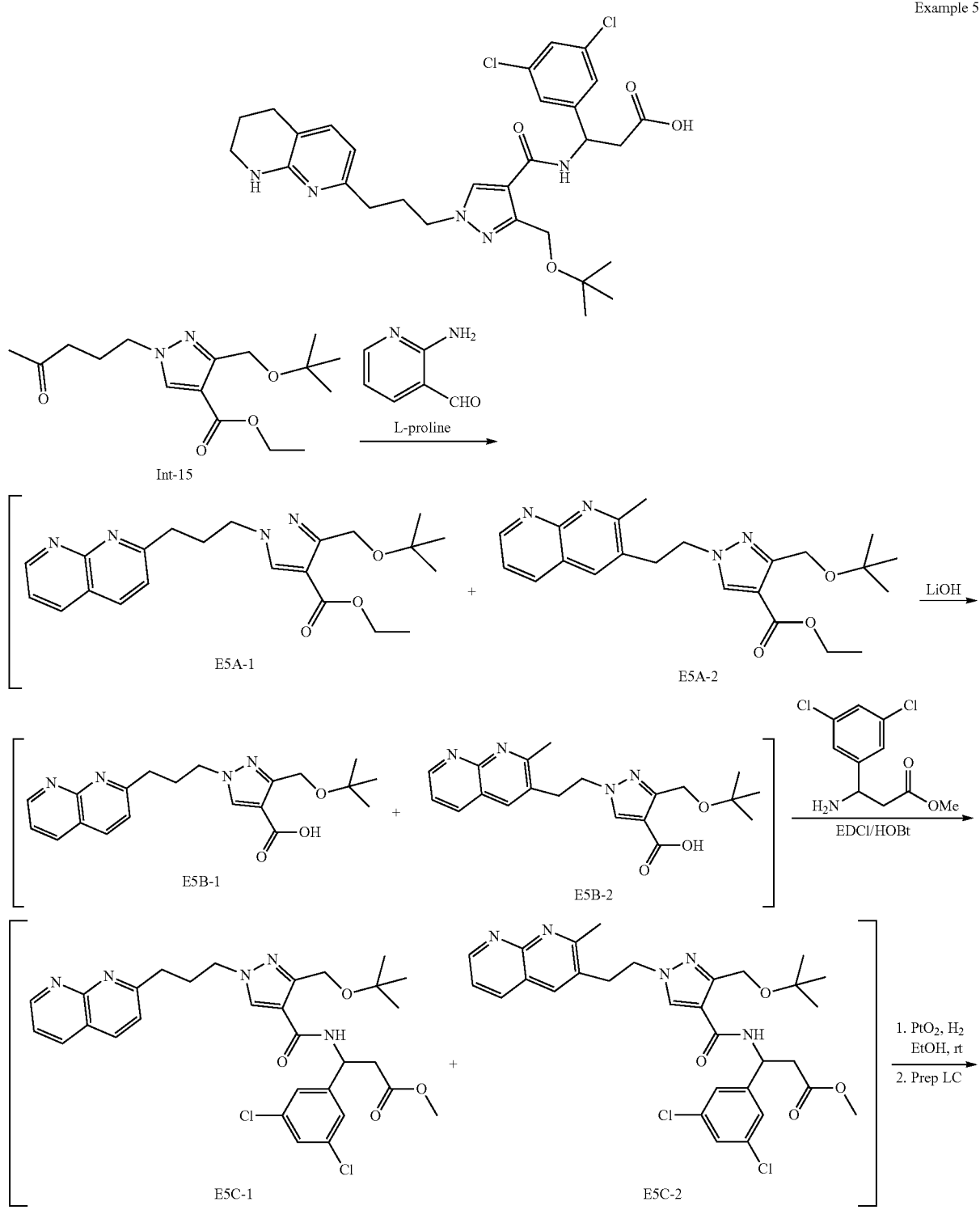

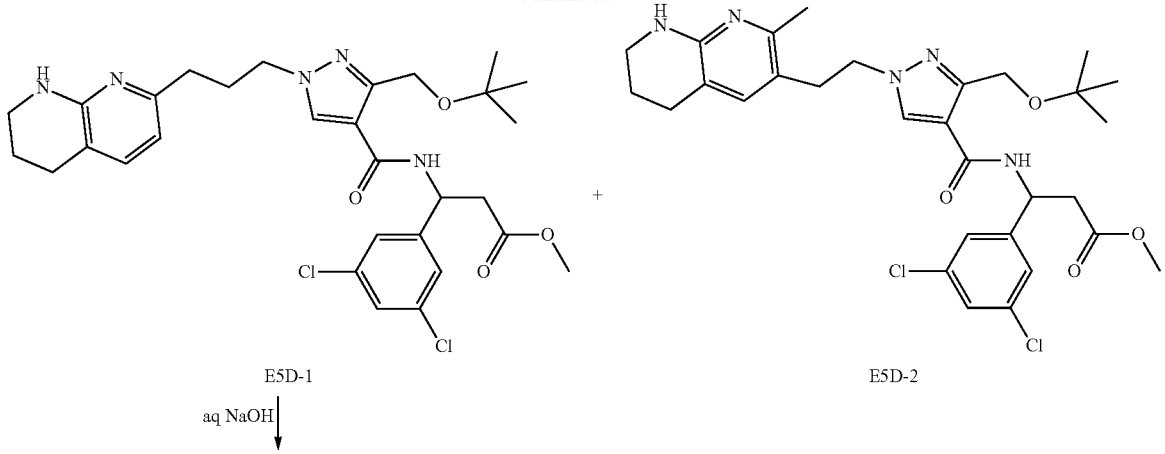 [SMILES: COC(=O)CC(NC(=O)c1cn(CCCc2ccc3c(n2)NCCC3)nc1COC(C)(C)C)c1cc(Cl)cc(Cl)c1 ; COC(=O)CC(NC(=O)c1cn(CCc2cc3c(nc2C)NCCC3)nc1COC(C)(C)C)c1cc(Cl)cc(Cl)c1]

-continued

E5D-1 aq NaOH ↓

E5D-2

Example [E5A-1+E5A-2]: A mixture of 5-(3-(tert-butoxymethyl)-4-(ethoxycarbonyl)-1H-pyrazol-1-yl)-2-oxopentan-1-ylium (Intermediate 15, 106 mg, 0.343 mmol), 2-aminonicotinaldehyde (54.4 mg, 0.445 mmol) and L-proline (39.4 mg, 0.343 mmol) in EtOH (2.5 mL) was heated at 78° C. in a sealed tube for 24 h. After cooling down to room temperature, solvent was evaporated and the crude product was dissolved in a minimum amount of $CH_2Cl_2$ and subjected to silica gel chromatography (Hexane/EtOAc, 100:0 to 0:100) then (MeOH/EtOAc, 0:100 to 10:90) to give the product mixture as an orange oil (91 mg, 67%, ratio ~1:1 by HPLC). LCMS (ES): m/z 397.5 $[M+H]^+$.

Example [E5B-1+E5B-2]: A mixture of Example [E5A-1+E5A-2] (91 mg, 0.232 mmol), lithium hydroxide (19 mg, 0.793 mmol) in THF (1 mL), $H_2O$ (0.6 mL) and MeOH (0.6 ml) was stirred at RT for 60 h. The solvent was removed in vacuo. The aqueous residue was acidified with aq HCl (1N). Volatiles were evaporated and the crude product was dissolved in a minimum amount of $CH_2Cl_2$ and subjected to silica gel chromatography (MeOH/$CH_2Cl_2$, 20:80) to give the product as yellow foamy solid (85 mg, 99%). LCMS (ES): m/z 369.5 $[M+H]^+$.

Example [E5C-1+E5C-2]: To a solution of Example [E5B-1+E5B-2] (85 mg, 0.231 mmol) and methyl 3-amino-3-(3,5-dichlorophenyl)propanoate, TFA (84 mg, 0.231 mmol) in $CH_2Cl_2$ (4.5 mL) and DMF (0.5 ml) were added EDC (80 mg, 0.417 mmol), HOBT (42.4 mg, 0.277 mmol) and $Et_3N$ (0.032 mL, 0.231 mmol). The reaction mixture was stirred at room temperature for 23 h. Solvents were evaporated and the crude product was subjected to silica gel chromatography ($CH_2Cl_2$ 100%) then (MeOH:$CH_2Cl_2$, 5:95) to give the product mixture as a light yellow foam (168 mg, 122%, contains impurity). LCMS (ES): m/z 598.5 $[M+H]^+$.

Example E5D-1: To a solution of Example [E5C-1+E5C-2] (168 mg, 0.287 mmol) in EtOH (10 mL) was added $PtO_2$ (12.75 mg, 0.056 mmol). The suspension was hydrogenated (1 atm. $H_2$, balloon) at room temperature for 16 h. After filtration of the reaction mixture through a Celite® pad and subsequent washing of the cake with EtOH, the filtrate was concentrated in vacuo and dried under vacuum to give a crude product which was purified by preparative HPLC (Column: Sunfire Prep C18, 30×100 mm, 5-μm particles; Mobile Phase A: 100% water with 10-mM ammonium acetate; Mobile Phase B: 100% acetonitrile with 10-mM ammonium acetate; Gradient: 25-100% B over 10 minutes; Flow: 40 mL/min.) to afford E5D-1 (44 mg, 26% yield) as a foamy solid: $^1$H NMR (400 MHz, Methanol-$d_4$) δ 8.03 (s, 1H), 7.40 (s, 4H), 7.25 (d, J=7.3 Hz, 1H), 6.42 (d, J=7.3 Hz, 1H), 5.50 (dd, J=8.2, 6.5 Hz, 1H), 4.65 (s, 2H), 4.18 (t, J=6.8 Hz, 2H), 3.68 (s, 3H), 3.44-3.36 (m, 2H), 3.01 (dd, J=16.0, 6.5 Hz, 1H), 2.96 (dd, J=16.0, 8.2 Hz, 1H), 2.71 (t, J=6.3 Hz, 2H), 2.59 (t, J=7.4 Hz, 2H), 2.31-2.16 (m, 2H), 1.95-1.81 (m, 2H), 1.27 (s, 9H). LCMS (ES): m/z 602.6 $[M+H]^+$.

Example E5D-2: The above preparative HPLC purification also give E5D-2 (34 mg, 20% yield) as a foamy solid: $^1$H NMR (400 MHz, Methanol-$d_4$) δ 7.85 (s, 1H), 7.43-7.33 (m, 3H), 7.01 (s, 1H), 5.49 (dd, J=8.4, 6.4 Hz, 1H), 4.67 (s, 2H), 4.30 (t, J=6.7 Hz, 2H), 3.67 (s, 3H), 3.40 (dd, J=6.5, 4.8 Hz, 2H), 3.10-2.89 (m, 4H), 2.66 (t, J=6.4 Hz, 2H), 2.24 (s, 3H), 1.87 (p, J=6.1 Hz, 2H), 1.28 (s, 9H). LCMS (ES): m/z 602.6 $[M+H]^+$.

Example 5: To a mixture of Example E5D-1 (22 mg, 0.053 mmol) in THF (1.0 mL) and MeOH (0.1 mL) at room temperature was added 1M aq. NaOH (0.110 mL, 0.110 mmol) and the reaction mixture was stirred for 16 h. The volatiles were removed in vacuo. The residue was acidified to pH ~5 with 1M HCl. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 5-minute hold at 100% B; Flow: 20 mL/min). to afford Example 5 (15.0 mg, 69%): $^1$H NMR (500 MHz, DMSO-$d_6$) δ 8.39 (d, J=7.8 Hz, 1H), 8.14 (s, 1H), 7.50 (d, J=1.8 Hz, 1H), 7.41 (d, J=1.8 Hz, 2H), 7.04 (d, J=7.2 Hz, 1H), 6.26 (d, J=7.2 Hz, 1H), 5.32 (dd, J=8.9, 6.4 Hz, 1H), 4.53 (d, J=12.0 Hz, 1H), 4.50 (d, J=12.0 Hz, 1H), 4.10 (t, J=7.1 Hz, 2H), 3.27-3.20 (t, J=5.9 Hz, 1H, one proton missing due to $H_2O$ supression), 2.84 (dd, J=15.5, 8.9 Hz, 1H), 2.79 (dd, J=15.9, 6.4 Hz, 1H), 2.61 (t, J=6.3 Hz, 2H), 2.42 (t, J=7.6 Hz, 2H), 2.07 (p, J=7.4 Hz, 2H), 1.75 (p, J=6.1

Hz, 2H), 1.16 (s, 9H). LCMS (ES): m/z 588.6 [M+H]+. Human αVβ6 IC50 (nM)=159.

Example 6. 3-(3,5-Dichlorophenyl)-3-(3-(hydroxymethyl)-1-(3-(5,6,7,8-tetrahydro-1,8-naphthyridin-2-yl)propyl)-1H-pyrazole-4-carboxamido)propanoic acid

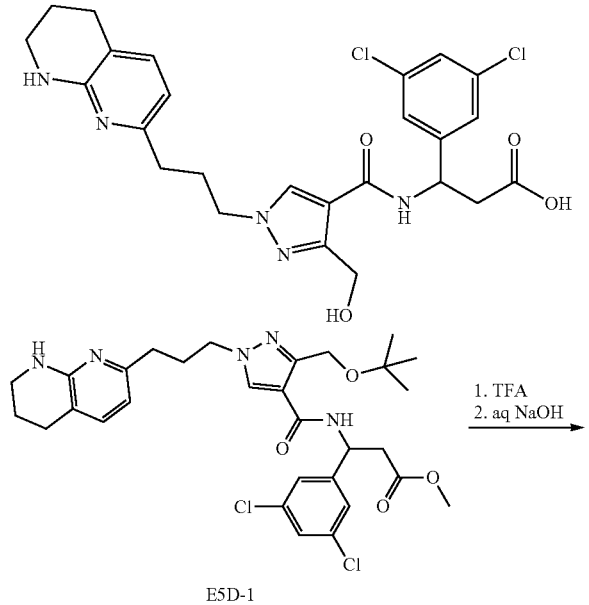

Example 6

Example 6 was prepared from Example E5D-1 in a manner analogous to preparation of Example 2 above: ¹H NMR (500 MHz, DMSO-d₆) δ 8.89 (d, J=7.8 Hz, 1H), 8.12 (s, 1H), 7.53-7.45 (m, 2H), 7.39 (d, J=2.0 Hz, 2H), 6.56 (d, J=7.4 Hz, 1H), 5.28 (q, J=7.4 Hz, 1H), 4.52 (s, 2H), 4.13 (t, J=6.6 Hz, 2H), 3.35 (t, J=5.6 Hz, 2H), 2.81 (d, J=7.4 Hz, 2H), 2.68-2.60 (m, 4H), 2.14 (t, J=7.2 Hz, 2H), 1.77 (t, J=6.0 Hz, 2H). LCMS (ES): m/z 532.5 [M+H]+. Human αVβ6 IC50 (nM)=178.

Example 7. (S)-3-(3,5-Dichlorophenyl)-3-(1-(3-(pyridin-2-ylamino)propyl)-1H-pyrazole-4-carboxamido)propanoic acid

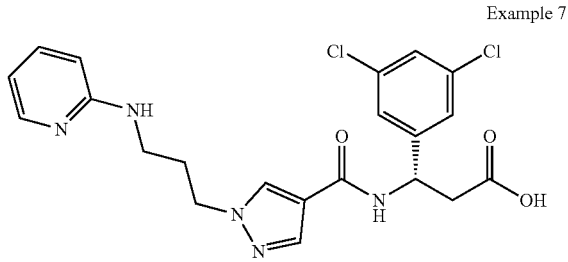

Example 7

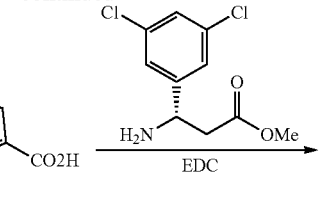

Int-17

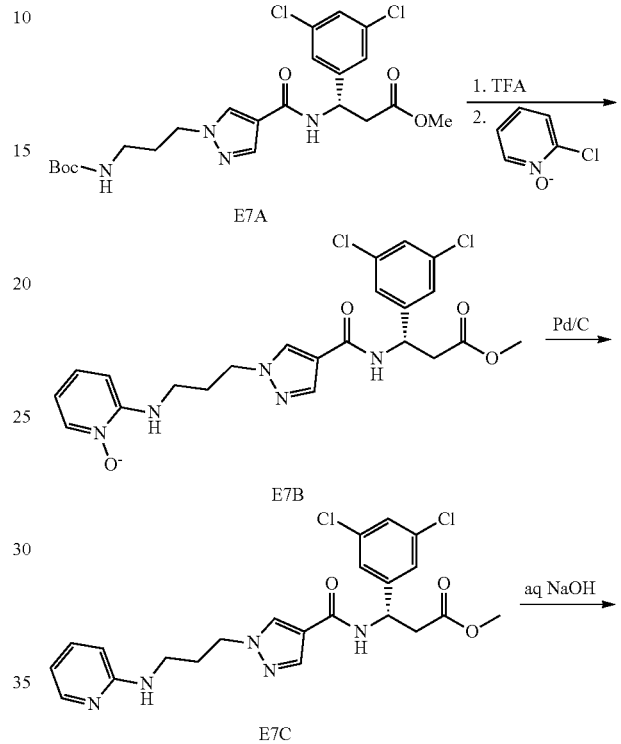

Example 7

Example E7A: To a solution of 1-(3-((tert-butoxycarbonyl)amino)propyl)-1H-pyrazole-4-carboxylic acid (45 mg, 0.167 mmol, Intermediate 17) and (S)-methyl 3-amino-3-(3,5-dichlorophenyl)propanoate, 2 HCl (60 mg, 0.187 mmol) in CH₂Cl₂ (2 mL) were added EDC (50 mg, 0.261 mmol), HOBT (30.7 mg, 0.201 mmol) and Et₃N (0.028 mL, 0.198 mmol). The reaction mixture was stirred at room temperature for 18 h. Solvents were evaporated and the crude product was purified by preparative HPLC to give Example E7A (100 mg, 96% yield) as a yellow foam. ¹H NMR (400 MHz, Chloroform-d) δ 7.95 (s, 1H), 7.85 (s, 1H), 7.41 (d, J=8.3 Hz, 1H), 7.28 (t, J=1.9 Hz, 1H), 7.25 (d, J=1.8 Hz, 2H), 5.52 (dt, J=8.2, 5.6 Hz, 1H), 4.22 (t, J=6.7 Hz, 2H), 3.70 (s, 3H), 3.13 (q, J=6.3 Hz, 2H), 2.96 (dd, J=16.0, 5.8 Hz, 1H), 2.92 (dd, J=16.0, 5.6 Hz, 1H), 2.06 (p, J=6.6 Hz, 2H), 1.47 (s, 9H). LCMS (ES): m/z 499.4 [M+H]+.

Example E7B. Step 1: A mixture of Intermediate E7A (80 mg, 0.16 mmol) in TFA (1 mL) and CH₂Cl₂ (1 mL) was stirred at RT for 2 h. The solvent was removed in vacuo to give (63 mg, 100% yield) of the crude product as a viscous oil. The product was used for the next step without further purification. LCMS (ES): m/z 399.3 [M+H]+.

Step 2: A mixture of the product obtained from Step 1 (63 mg, 0.158 mmol), 2-chloropyridine N-oxide hydrochloride (33.2 mg, 0.2 mmol) and sodium bicarbonate (66.3 mg, 0.789 mmol) in tert-amyl alcohol (1 mL) was heated at reflux in a sealed tube for 3 days. The mixture was cooled down to room temperature and diluted with CH$_2$Cl$_2$ (5 mL). After filtration of the reaction mixture through a Celite® pad and subsequent washing of the cake with EtOH, the filtrate was concentrated in vacuo and air-dried under vacuum to give a crude product which was purified by preparative HPLC to afford E7B (29.1 mg, 38% yield) as a foamy solid: $^1$H NMR (400 MHz, Methanol-d$_4$) δ 8.13 (dd, J=6.7, 1.5 Hz, 1H), 8.00 (s, 1H), 7.95 (s, 1H), 7.62 (t, J=8.1 Hz, 1H), 7.47 (bs, 1H), 7.37 (bt, J=5.9 Hz, 1H), 7.29-7.27 (m, 2H), 7.26-7.24 (m, 2H), 6.80-6.70 (m, 2H), 5.52 (dt, J=8.1, 6.0 Hz, 1H), 4.35 (t, J=6.2 Hz, 2H), 3.69 (s, 3H), 3.46-3.31 (m, 2H), 2.96 (dd, J=16.1, 6.1 Hz, 1H), 2.90 (dd, J=16.1, 6.0 Hz, 1H), 2.34 (p, J=6.3 Hz, 2H). LCMS (ES): m/z 492.4 [M+H]$^+$.

Example E7C: To a solution of E7B (30 mg, 0.061 mmol) in EtOH (1 mL) was added cyclohexene (0.037 mL, 0.366 mmol) and 10% Pd on carbon (3.24 mg, 3.05 μmop. The suspension was heated at 78° C. in a sealed tube for 8 h. After filtration of the reaction mixture through a Celite® pad and subsequent washing of the cake with MeOH, the filtrate was concentrated in vacuo and air-dried under vacuum to give Example E7C (29 mg, 100%) as a foamy solid. LCMS (ES): m/z 476.4 [M+H]$^+$.

Example 7: To a mixture of E7C (29 mg, 0.061 mmol) in THF (1.0 mL) at room temperature was added 1M aq. NaOH (0.091 mL, 0.091 mmol) and the reaction mixture stirred for 6 h. The volatiles were removed in vacuo. The residue was acidified to pH ~5 with 1M aq. HCl. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 4-minute hold at 100% B; Flow: 20 mL/min.) to afford Example 7 (14.7 mg, 51%): $^1$H NMR (500 MHz, DMSO-d$_6$) δ 8.64 (d, J=8.0 Hz, 1H), 8.17 (s, 1H), 7.91 (d, J=5.3 Hz, 1H), 7.87 (s, 1H), 7.46 (d, J=1.9 Hz, 1H), 7.38 (d, J=1.9 Hz, 2H), 7.35 (t, J=7.6 Hz, 1H), 6.52-6.44 (m, 1H), 6.43 (d, J=8.5 Hz, 1H), 5.28 (q, J=7.6 Hz, 1H), 4.18 (t, J=7.0 Hz, 2H), 3.16 (q, J=6.8, 6.3 Hz, 2H), 2.83-2.70 (m, 2H), 2.05-1.96 (m, 2H). LCMS (ES): m/z 462.3 [M+H]$^+$. Human αVβ6 IC50 (nM)=63.

Example 8. (S)-3-(3,5-Dichlorophenyl)-3-(1-(3-((4, 5-dihydro-1H-imidazol-2-yl)amino)propyl)-1H-pyrazole-4-carboxamido)propanoic acid

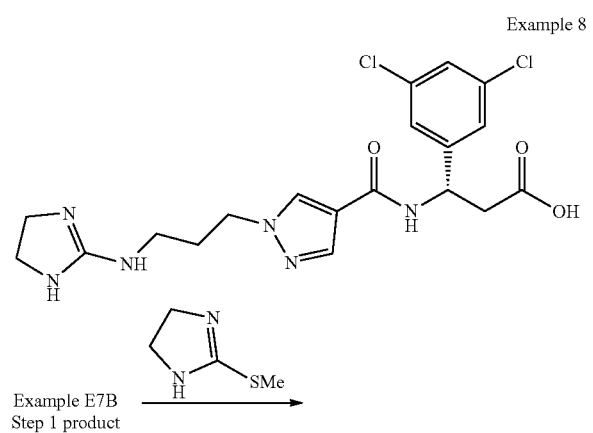

Example 8

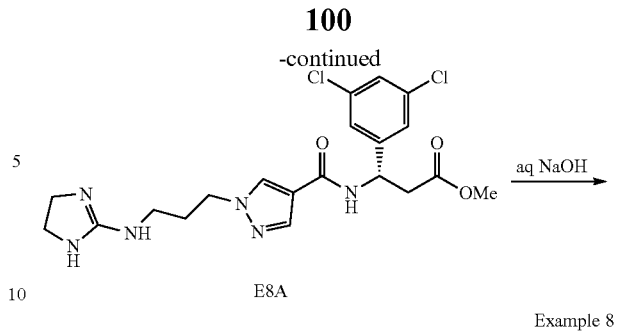

Example 8

Example E8A: A mixture of Example E7B, step 1 product (39 mg, 0.098 mmol), 2-(methylthio)-2-imidazoline (17.02 mg, 0.147 mmol) and DIPEA (0.068 mL, 0.391 mmol) in EtOH (4 mL) was heated in a sealed vial under microwave at 150° C. for 25 min. The mixture was cooled down to room temperature. The volatiles were removed in vacuo to give a crude product which was purified by preparative HPLC to afford E8A (38 mg, 83%) as a viscous oil: $^1$H NMR (400 MHz, Methanol-d$_4$) δ 8.13 (s, 1H), 7.98 (s, 1H), 7.39 (d, J=1.8 Hz, 2H), 7.36 (t, J=1.9 Hz, 1H), 5.54-5.45 (m, 1H), 4.28 (t, J=6.6 Hz, 2H), 3.71 (s, 4H), 3.68 (s, 3H), 3.25-3.18 (m, 2H), 3.00 (dd, J=16.0, 8.6 Hz, 1H), 2.93 (dd, J=16.0, 6.4 Hz, 1H), 2.15 (p, J=6.7 Hz, 2H). LCMS (ES): m/z 467.4 [M+H]$^+$.

Example 8: To a mixture of E8A (38 mg, 0.081 mmol) in THF (1.0 mL) at room temperature was added 1M aq. NaOH (0.25 mL, 0.25 mmol) and the reaction mixture stirred for 15 h. The volatiles were removed in vacuo. The residue was acidified to pH ~5 with 1M aq. HCl. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min.) to afford Example 8 (8.6 mg, 23%) as: $^1$H NMR (500 MHz, Methanol-d$_4$) δ 8.14 (d, J=0.8 Hz, 1H), 7.97 (d, J=0.7 Hz, 1H), 7.40 (d, J=1.9 Hz, 2H), 7.30 (t, J=1.9 Hz, 1H), 5.38 (t, J=6.8 Hz, 1H), 4.27 (t, J=6.5 Hz, 2H), 3.70 (s, 4H), 3.20 (t, J=6.7 Hz, 2H), 2.72 (d, J=6.7 Hz, 2H), 2.15 (p, J=6.6 Hz, 2H). LCMS (ES): m/z 453.4[M+H]$^+$. Human αVβ6 IC50 (nM)=41.

Example 9. 3-(3-Chlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid Example 9

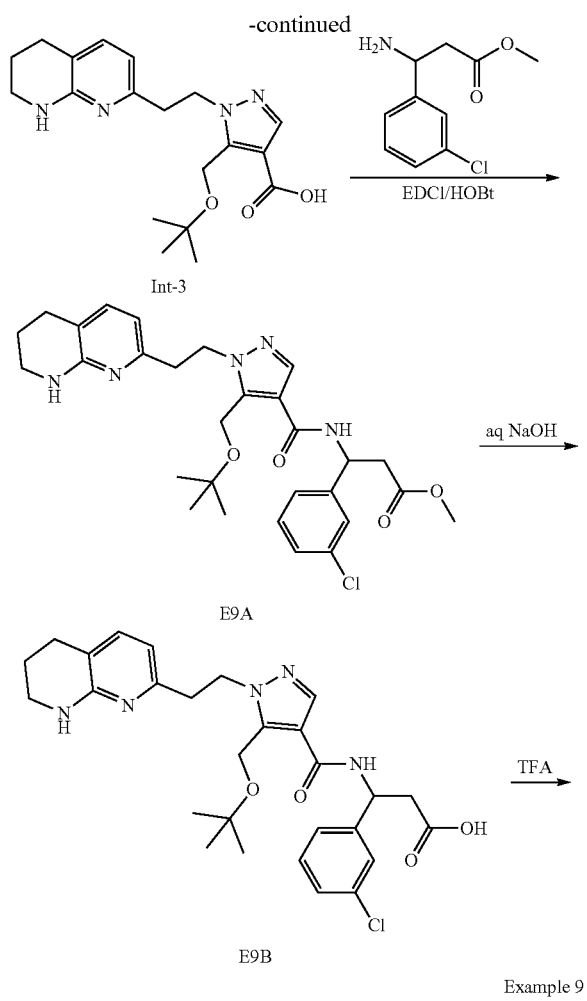

Example 9

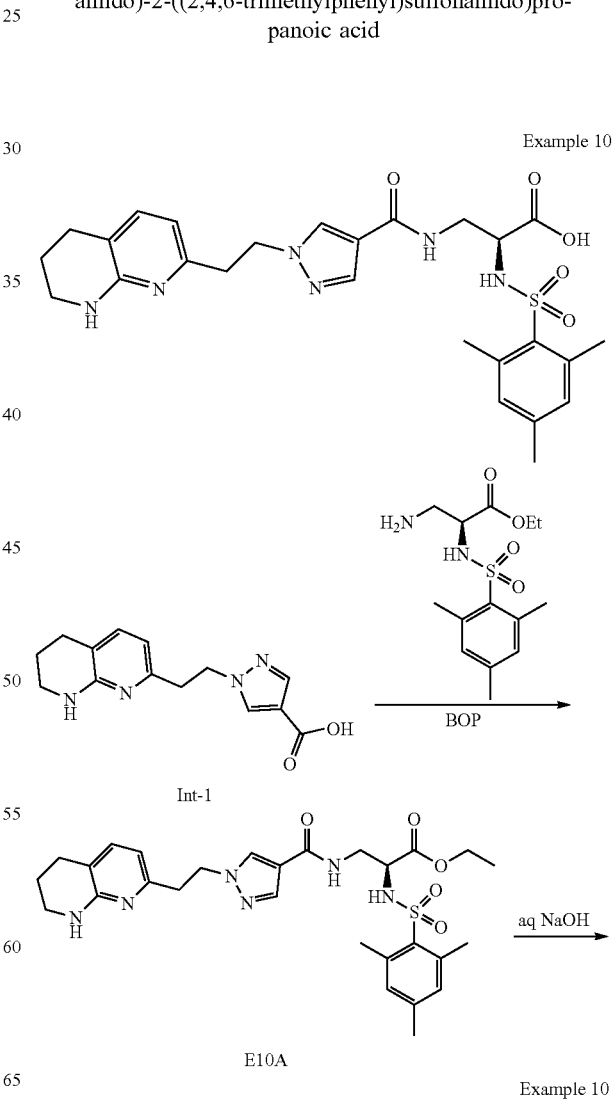

Example 9: A mixture of Example E9B (18 mg, 0.034 mmol) in TFA (1 mL) and CH₂Cl₂ (0.5 mL) was stirred at RT for 4 h. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min.) to afford Example 9 (15 mg, 93%): ¹H NMR (500 MHz, Methanol-d₄) δ 7.80 (s, 1H), 7.31 (s, 1H), 7.23 (d, J=7.7 Hz, 1H), 7.19 (t, J=7.7 Hz, 1H), 7.12 (d, J=7.7 Hz, 1H), 7.01 (d, J=7.3 Hz, 1H), 6.06 (d, J=7.3 Hz, 1H), 5.32 (t, J=6.9 Hz, 1H), 4.53 (d, J=13.8 Hz, 1H), 4.49 (d, J=13.8 Hz, 1H), 4.38 (t, J=6.9 Hz, 2H), 3.28 (t, J=5.6 Hz, 2H), 2.94 (t, J=6.7 Hz, 2H), 2.70-2.62 (m, 2H), 2.59 (t, J=6.3 Hz, 2H), 1.76 (p, J=6.0 Hz, 2H). LCMS (ES): m/z 484.2 [M+H]⁺. Human αVβ6 IC50 (nM)=22.

Example 10. (S)-3-(1-(2-(5,6,7,8-Tetrahydro-1,8-naphthyridin-2-yl)ethyl)-1H-pyrazole-4-carboxamido)-2-((2,4,6-trimethylphenyl)sulfonamido)propanoic acid Example E9A: To a solution of 5-(tert-butoxymethyl)-1-(2-(5,6,7,8-tetrahydro-1,8-naphthyridin-2-yl)ethyl)-1H-pyrazole-4-carboxylic acid (Intermediate 3, 20 mg, 0.056 mmol) and methyl 3-amino-3-(3-chlorophenyl)propanoate, HCl (25 mg, 0.100 mmol) in DMF (1.5 ml) were added EDC (20 mg, 0.104 mmol), HOBT (10.3 mg, 0.067 mmol) and Et₃N (0.028 mL, 0.198 mmol). The reaction mixture was stirred at room temperature for 24 h. The volatiles were removed in vacuo and the residue was purified by preparative HPLC to give Example E9A (22.2 mg, 60% yield) as a foamy solid. ¹H NMR (500 MHz, Chloroform-d) δ 9.68 (bs, 1H), 7.86 (s, 1H), 7.36-7.33 (m, 1H), 7.32-7.19 (m, 4H), 6.22 (d, J=7.3 Hz, 1H), 5.57 (dd, J=6.7, 6.1 Hz, 1H), 4.70 (d, J=12.5 Hz, 1H), 4.64 (d, J=12.5 Hz, 1H), 4.59 (t, J=6.7 Hz, 2H), 3.67 (s, 3H), 3.54 (t, J=5.7 Hz, 2H), 3.29 (t, J=6.7 Hz, 2H), 2.98 (dd, J=15.8, 6.7 Hz, 1H), 2.93 (dd, J=15.8, 6.1 Hz, 1H), 2.77 (t, J=6.2 Hz, 2H), 2.04-1.89 (m, 2H), 1.23 (s, 9H). LCMS (ES): m/z 554.3 [M+H]⁺.

Example E9B: A mixture of Example E9A (22.2 mg, 0.036 mmol) in THF (1.0 mL) and MeOH (0.1 mL) at room temperature was added 1M aq. NaOH (0.25 mL, 0.25 mmol) and the reaction mixture stirred for 2 h. The solvents were removed in vacuo to give 18 mg (100%) of the crude product as a gummy solid. The product was used for the next step without further purification. LCMS (ES): m/z 526.6 [M+H]⁺.

Example E10A: To a solution of 1-(2-(5,6,7,8-tetrahydro-1,8-naphthyridin-2-yl)ethyl)-1H-pyrazole-4-carboxylic acid (Intermediate 1, 70 mg, 0.257 mmol) and (S)-ethyl 3-amino-2-(2,4,6-trimethylphenylsulfonamido)propanoate, HCl (95 mg, 0.271 mmol) in DMF (3.5 mL) were added BOP (171 mg, 0.386 mmol) and Et$_3$N (0.18 mL, 1.028 mmol). The reaction mixture was stirred at room temperature for 2 h. The volatiles were removed in vacuo and the residue was purified by preparative HPLC (Column: Sunfire C18 OBD, 30×100 mm, 5-μm particles; Mobile Phase A: 5:95 acetonitrile: water with 0.1% TFA; Mobile Phase B: 95:5 acetonitrile: water with 0.1% TFA; Gradient: 20-100% B over 10 minutes, then a 5-minute hold at 100% B; Flow: 40 mL/min.) to afford Example E10A (108 mg, 74%) as a foamy solid: $^1$H NMR (400 MHz, Methanol-d$_4$) δ 7.97 (s, 1H), 7.82 (s, 1H), 7.52 (d, J=7.2 Hz, 1H), 6.95 (s, 2H), 6.44 (d, J=7.3 Hz, 1H), 4.55 (t, J=6.6 Hz, 2H), 4.08 (dd, J=8.2, 5.7 Hz, 1H), 3.89 (q, J=7.1 Hz, 2H), 3.66 (dd, J=13.6, 5.7 Hz, 1H), 3.53-3.48 (m, 2H), 3.44 (dd, J=13.7, 8.2 Hz, 1H), 3.27 (t, J=6.6 Hz, 2H), 2.80 (t, J=6.2 Hz, 2H), 2.61 (s, 6H), 2.27 (s, 3H), 1.94 (dq, J=7.0, 5.6 Hz, 2H), 1.06 (t, J=7.1 Hz, 3H). LCMS (ES): m/z 569.4 [M+H]$^+$.

Example 10: To a mixture of Example 10A (75 mg, 0.132 mmol) in THF (2.5 mL) at room temperature was added 1M aq. NaOH (0.330 mL, 0.330 mmol) and the reaction mixture stirred for 15 h. The volatiles were removed in vacuo. The residue was acidified to pH ~5 with 1M aq. HCl. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min.) to afford Example 10 (41.3 mg, 57%): $^1$H NMR (400 MHz, DMSO-d$_6$) δ 12.63 (bs, 1H), 8.01-7.95 (m, 2H), 7.91 (d, J=9.1 Hz, 1H), 7.69 (s, 1H), 7.04 (d, J=7.3 Hz, 1H), 6.87 (s, 2H), 6.39 (bs, 1H), 6.24 (d, J=7.2 Hz, 1H), 4.38 (t, J=7.3 Hz, 2H), 3.96-3.78 (m, 1H), 3.48-3.35 (m, 1H), 3.35-3.26 (m, 3H), 2.97 (t, J=7.3 Hz, 2H), 2.61 (t, J=6.2 Hz, 2H), 2.52 (s, 6H), 2.19 (s, 3H), 1.84-1.65 (m, 2H). LCMS (ES): m/z 541.3 [M+H]$^+$. Human αVβ6 IC50 (nM)=0.5; Human αVβ1 IC50 (nM)=6.3; Human αVβ3 IC50 (nM)=1.9; Human αVβ5 IC50 (nM)=0.2; and Human αVβ8 IC50 (nM)=14.

Example 11. (S)-2-Amino-3-(1-(2-(5,6,7,8-tetrahydro-1,8-naphthyridin-2-yl)ethyl)-1H-pyrazole-4-carboxamido)propanoic acid

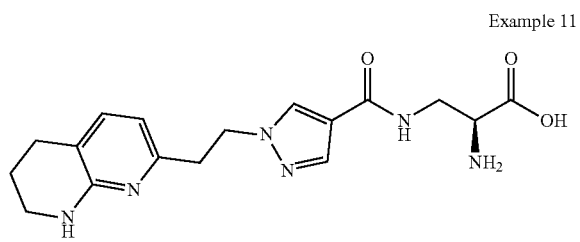 [SMILES: N[C@@H](CNC(=O)c1cnn(CCc2ccc3c(n2)NCCC3)c1)C(=O)O]

Example 11

Example 11: A mixture of Intermediate 23 (15 mg, 0.036 mmol) in TFA (0.5 mL) and CH$_2$Cl$_2$ (0.5 mL) was stirred at RT for 4 h. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-30% B over 20 minutes, then a 3-minute hold at 100% B; Flow: 20 mL/min.) to afford Example 11 (9.8 mg, 76%): $^1$H NMR (500 MHz, Methanol-d$_4$) δ 8.04 (s, 1H), 7.87 (s, 1H), 7.48 (d, J=7.3 Hz, 1H), 6.44 (d, J=7.3 Hz, 1H), 4.48 (t, J=6.9 Hz, 2H), 3.92-3.80 (m, 2H), 3.74 (dd, J=15.3, 7.0 Hz, 1H), 3.48 (t, J=5.7 Hz, 2H), 3.26-3.22 (m, 2H), 2.79 (t, J=6.3 Hz, 2H), 1.98-1.87 (m, 2H). LCMS (ES): m/z 359.2 [M+H]$^+$. Human αVβ6 IC50 (nM)=121.

Example 12. (S)-2-(((Benzyloxy)carbonyl)amino)-3-(1-(2-(5,6,7,8-tetrahydro-1,8-naphthyridin-2-yl)ethyl)-1H-pyrazole-4-carboxamido)propanoic acid

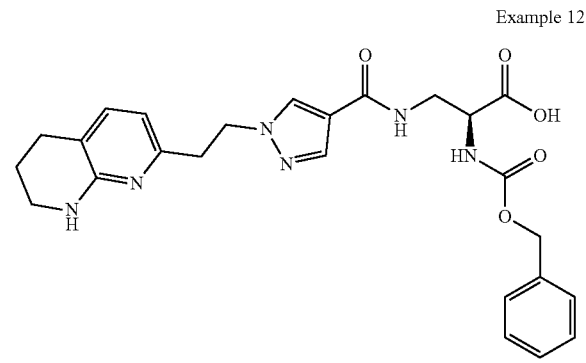 [SMILES: O=C(N[C@@H](CNC(=O)c1cnn(CCc2ccc3c(n2)NCCC3)c1)C(=O)O)OCc1ccccc1]

Example 12

Example 12: A mixture of Intermediate 23A (9 mg, 0.016 mmol) in TFA (1 mL) and CH$_2$Cl$_2$ (0.5 mL) was stirred at RT for 4 h. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-50% B over 20 minutes, then a 3-minute hold at 100% B; Flow: 20 mL/min.) to afford Example 12 (5.5 mg, 64%): $^1$H NMR (500 MHz, Methanol-d$_4$) δ 8.02 (s, 1H), 7.83 (s, 1H), 7.39-7.12 (m, 6H), 6.35 (d, J=7.3 Hz, 1H), 5.08 (d, J=13.0 Hz, 1H), 5.03 (d, J=13.0 Hz, 1H), 4.39 (td, J=7.1, 1.8 Hz, 2H), 4.34-4.29 (m, 1H), 3.79-3.68 (m, 2H), 3.43 (t, J=5.7 Hz, 2H), 3.14-3.03 (m, 2H), 2.74 (t, J=6.3 Hz, 2H), 1.89 (p, J=6.1 Hz, 2H). LCMS (ES): m/z 493.4 [M+H]$^+$ Human αVβ6 IC50 (nM)=1.1; Human αVβ1 IC50 (nM)=TBD; Human αVβ3 IC50 (nM)=2.1; Human αVβ5 IC50 (nM)=0.2; and Human αVβ8 IC50 (nM)=49.

Example 13. (S)-3-(3,5-Dichlorophenyl)-3-(2-(2-(5,6,7,8-tetrahydro-1,8-naphthyridin-2-yl)ethyl)-2H-1,2,3-triazole-4-carboxamido)propanoic acid and
Example 14. (S)-3-(3,5-Dichlorophenyl)-3-(2-((2-methyl-5,6,7,8-tetrahydro-1,8-naphthyridin-3-yl)methyl)-2H-1,2,3-triazole-4-carboxamido)propanoic acid
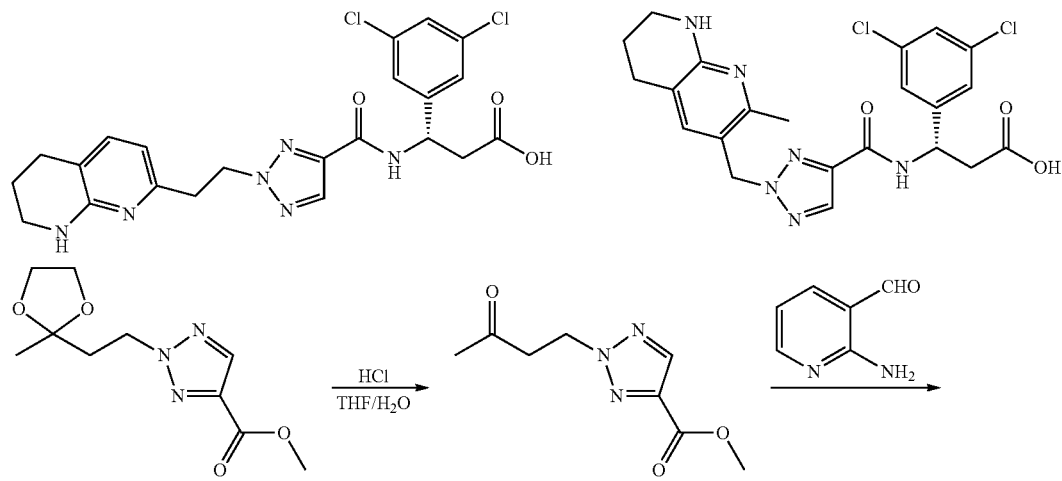
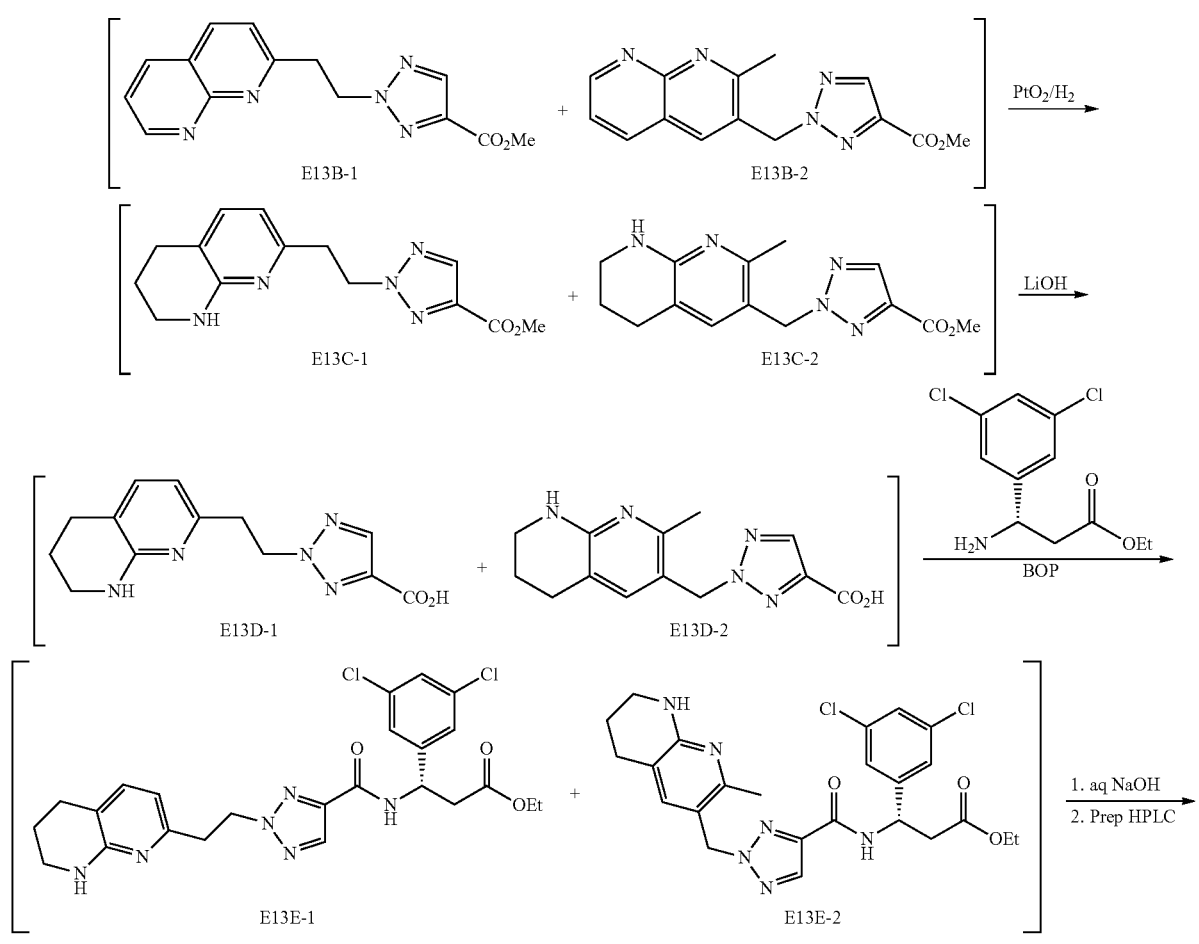

Example 13A: A mixture of methyl 2-(2-(2-methyl-1,3-dioxolan-2-yl)ethyl)-2H-1,2,3-triazole-4-carboxylate (Intermediate 8, 600 mg, 2.487 mmol) in THF (3 mL) and aq. 1N HCl (1.5 mL, 1.5 mmol) was stirred at RT. After 4 h, aq. 1N HCl (1.5 mL, 1.5 mmol) was added. The reaction mixture was stirred at RT for 16 h. Solvent was evaporated and the crude product was dried under vacuum to give Example 13A (0.49 g, 100%) as an oil. This product was used for the next step without further purification.

Example [E13B-1+E13B-2]: A mixture of methyl 2-(3-oxobutyl)-2H-1,2,3-triazole-4-carboxylate (490 mg, 2.485 mmol), 2-aminonicotinaldehyde (395 mg, 3.23 mmol) and L-proline (315 mg, 2.73 mmol) in EtOH (1 mL) was heated at 78° C. in a sealed tube for 48 h. After cooling down to room temperature, the solvent was evaporated and the crude residue was dissolved in a minimum amount of $CH_2Cl_2$ and subjected to silica gel chromatography (Hexane/EtOAc, 100:0 to 0:100, then MeOH/EtOAc, 0:100 to 10:90) to give Example [E13B-1+E13B-2] (220 mg, 31% yield, ~1:1 ratio by $^1H$ NMR) as a yellow solid. LCMS (ES): m/z 284.2 $[M+H]^+$.

Example [E13C-1+E13C-2]: To a solution of Example [E13B-1+E13B-2] (192 mg, 0.104 mmol) in EtOH (20 mL) was added and $PtO_2$ (30.8 mg, 0.136 mmol). The suspension was hydrogenated (1 atm. $H_2$, balloon) at room temperature for 18 h. After filtration of the reaction mixture through a Celite® pad and subsequent washing of the cake with EtOH, the filtrate was concentrated in vacuo and air-dried under vacuum to give a crude product which was purified by preparative HPLC (Column: Sunfire Prep C18, 30×100 mm, 5-µm particles; Mobile Phase A: 100% water with 10-mM ammonium acetate; Mobile Phase B: 100% acetonitrile with 10-mM ammonium acetate; Gradient: 15-100% B over 10 minutes; Flow: 40 mL/min.) to afford Example [E13C-1+E13C-2] (104 mg, 53% yield) as a white solid: $^1H$ NMR (400 MHz, Methanol-$d_4$) δ 8.08 (s, 1H), 7.25 (d, J=7.3 Hz, 1H), 6.33 (d, J=7.3 Hz, 1H), 4.85-4.81 (m, 2H), 3.92 (s, 3H), 3.50-3.41 (m, 2H), 3.28 (t, J=6.9 Hz, 2H), 2.74 (t, J=6.2 Hz, 2H), 1.95-1.86 (m, 2H). $^1H$ NMR indicated presence of 30% E13C-2 in the mixture; LCMS (ES): m/z 288.7 $[M+H]^+$.

Example [E13D-1+E13D-2]: A mixture of Example [E13C-1+E13C-2] (104 mg, 0.362 mmol), lithium hydroxide (30 mg, 1.25 mmol) in THF (2 mL), $H_2O$ (1 mL) and MeOH (0.06 ml) was stirred at RT for 16 h. The solvent was removed in vacuo. The aqueous residue was acidified with 1N aq. HCl. The mixture was extracted with $CHCl_3$ (3×10 ml). The organic layer was separated, dried over $MgSO_4$ and concentrated to give crude [E13D-1+E13D-2] (99 mg, 100% yield) as a foamy solid. LCMS (ES): m/z 274.2 $[M+H]^+$.

Example [E13E-1+E13E-2]: To a solution of [E13D-1+E13D-2] (35 mg, 0.128 mmol) and (S)-ethyl 3-amino-3-(3,5-dichlorophenyl)propanoate (33.6 mg, 0.128 mmol) in DMF (2 mL) were added BOP (88 mg, 0.119 mmol) and $Et_3N$ (0.122 mL, 0.696 mmol). The reaction mixture was stirred at room temperature for 24 h. The volatiles were removed in vacuo and the residue was purified by preparative HPLC (Column: Sunfire C18 OBD, 30×100 mm, 5-µm particles; Mobile Phase A: 5:95 acetonitrile: water with 0.1% TFA; Mobile Phase B: 95:5 acetonitrile: water with 0.1% TFA; Gradient: 30-100% B over 10 minutes, then a 5-minute hold at 100% B; Flow: 40 mL/min.) to afford Example [E13E-1+E13E-2] (23 mg, 35%) as a foamy solid: $^1H$ NMR (400 MHz, Chloroform-d) δ 8.02 (s, 1H), 7.98 (d, J=8.5 Hz, 1H), 7.35-7.17 (m, 4H), 6.16 (d, J=7.2 Hz, 1H), 5.57-5.46 (m, 1H), 4.87 (t, J=6.3 Hz, 2H), 4.15 (q, J=7.1 Hz, 3H), 3.63-3.50 (m, 2H), 3.43 (t, J=6.4 Hz, 2H), 2.99 (dd, J=16.2, 6.2 Hz, 1H), 2.93 (dd, J=16.2, 5.6 Hz, 1H), 2.76 (t, J=6.3 Hz, 2H), 2.08-1.79 (m, 2H), 1.23 (t, J=7.1 Hz, 3H). $^1H$ NMR indicated presence of ~30% E13E-2 in the mixture. LCMS (ES): m/z 517.3.4 $[M+H]^+$.

Example 13: To a mixture of Example [E13E-1+E13E-2] (23 mg, 0.044 mmol) in THF (1 mL) at room temperature was added 1M aq. NaOH (0.1 mL, 0.1 mmol) and the reaction mixture stirred for 16 h. The volatiles were removed in vacuo. The residue was acidified to pH ~5 with 1M HCl. The volatiles were removed in vacuo and the residue was purified by preparative HPLC (Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 19 minutes, then a 5-minute hold at 100% B; Flow: 20 mL/min.) to afford Example 13 (8.6 mg, 39%): $^1H$ NMR (500 MHz, Methanol-$d_4$) δ 7.97 (s, 1H), 7.42 (d, J=1.9 Hz, 2H), 7.34 (t, J=1.9 Hz, 1H), 7.29 (d, J=7.3 Hz, 1H), 6.38 (d, J=7.3 Hz, 1H), 5.44 (dd, J=7.0. 5.8 Hz, 1H), 4.88-4.78 (m, 2H), 3.42 (dd, J=6.4, 4.9 Hz, 2H), 3.34-3.29 (m, 2H), 2.90 (dd, J=15.9, 7.0 Hz, 1H), 2.86 (dd, J=15.9, 5.8 Hz, 1H), 2.74 (t, J=6.3 Hz, 2H), 1.89 (ddd, J=11.1, 6.9, 5.7 Hz, 2H). LCMS (ES): m/z 489.3 $[M+H]^+$. Human αVβ6 IC50 (nM)=7.1.

Example 14: The above preparative HPLC purification also gave Example 14 (3.4 mg, 16%): $^1H$ NMR (500 MHz, Methanol-$d_4$) δ 8.04 (s, 1H), 7.43 (s, 1H), 7.40 (d, J=1.9 Hz, 2H), 7.31 (t, J=1.9 Hz, 1H), 5.60 (d, J=14.9 Hz, 1H), 5.57 (d, J=14.9 Hz, 1H), 5.45 (t, J=6.4 Hz, 1H), 3.46-3.30 (m, 2H), 2.93-2.86 (m, 2H), 2.76 (t, J=6.2 Hz, 2H), 2.48 (s, 3H), 1.96-1.83 (m, 2H). LCMS (ES): m/z 489.3 $[M+H]^+$. Human αVβ6 IC50 (nM)=2211.

Example 15. (S)-3-(1-(2-(5,6,7,8-Tetrahydro-1,8-naphthyridin-2-yl)ethyl)-1H-pyrazole-4-carboxamido)-2-(2,4,6-trimethylbenzamido)propanoic acid Example 15

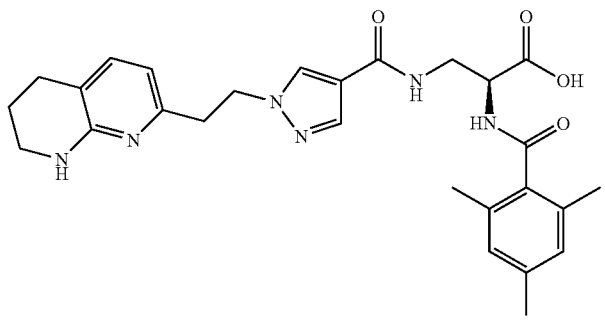

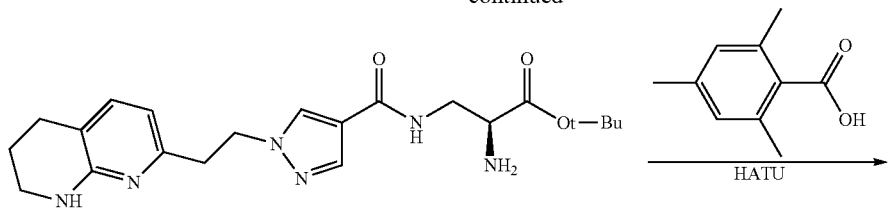

Int-23

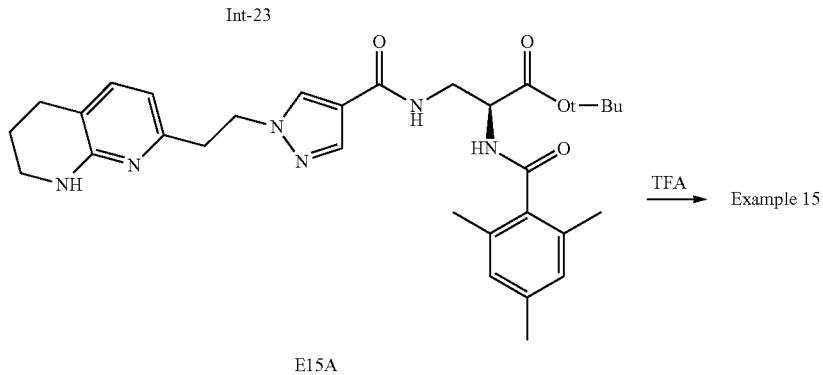

E15A

Example 15A: To a solution of (S)-tert-butyl 2-amino-3-(1-(2-(5,6,7,8-tetrahydro-1,8-naphthyridin-2-yl)ethyl)-1H-pyrazole-4-carboxamido)propanoate (Intermediate 23, 25.2 mg, 0.061 mmol) and of 2,4,6-trimethylbenzoic acid (10 mg, 0.061 mmol) in DMF (1.5 ml) were added HATU (23.2 mg, 0.061 mmol) and DIPEA (10.7 μL, 0.061 mmol). The reaction mixture was stirred at room temperature for 4 h. The volatiles were removed in vacuo and the residue was purified by preparative HPLC (Column: Sunfire C18 OBD, 30×100 mm, 5-μm particles; Mobile Phase A: 5:95 acetonitrile: water with 0.1% TFA; Mobile Phase B: 95:5 acetonitrile: water with 0.1% TFA; Gradient: 25-100% B over 10 minutes, then a 5-minute hold at 100% B; Flow: 40 mL/min.) to afford Example 15A (7.0 mg, 21%) as a foamy solid: $^1$H NMR (400 MHz, Chloroform-d) δ 8.67 (bs, 1H), 8.11 (s, 1H), 7.95 (s, 1H), 7.63 (t, J=5.4 Hz, 1H), 7.32 (d, J=7.3 Hz, 1H), 7.14 (d, J=7.4 Hz, 1H), 6.85 (s, 2H), 6.32 (d, J=7.3 Hz, 1H), 4.94-4.85 (m, 1H), 4.56 (t, J=6.8 Hz, 2H), 3.98-3.74 (m, 2H), 3.53 (t, J=5.7 Hz, 2H), 3.27 (t, J=6.9 Hz, 2H), 2.76 (t, J=6.2 Hz, 2H), 2.29 (s, 3H), 2.21 (s, 6H), 2.03-1.87 (m, 2H), 1.53 (s, 9H). LCMS (ES): m/z 561.5 [M+H]$^+$.

Example 15: A mixture of Example 15A (7 mg, 0.012 mmol) in TFA (1 mL) and CH$_2$Cl$_2$ (0.5 mL) was stirred at RT for 5 h. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-100% B over 19 minutes, then a 5-minute hold at 100% B; Flow: 20 mL/min.) to afford Example 15 (2.9 mg, 71%): $^1$H NMR (500 MHz, Methanol-d$_4$) δ 8.04 (s, 1H), 7.81 (d, J=0.7 Hz, 1H), 7.30 (d, J=7.3 Hz, 1H), 6.83 (s, 2H), 6.36 (d, J=7.2 Hz, 1H), 4.73 (dd, J=7.6, 4.3 Hz, 1H), 4.44-4.37 (m, 2H), 3.86 (dd, J=13.9, 7.6 Hz, 1H), 3.65 (dd, J=13.8, 4.3 Hz, 1H), 3.46-3.42 (m, 2H), 3.06 (t, J=7.2 Hz, 2H), 2.75 (t, J=6.2 Hz, 2H), 2.27 (s, 3H), 2.20 (s, 6H), 1.95-1.85 (m, 2H). LCMS (ES): m/z 505.4 [M+H]$^+$. Human αVβ6 IC50 (nM)=0.9.

Example 16. (S)-3-(3,5-Dichlorophenyl)-3-(1-(2-(5,6,7,8-tetrahydro-1,8-naphthyridin-2-yl)ethyl)-1H-pyrazole-4-carboxamido)propanoic acid Example 16

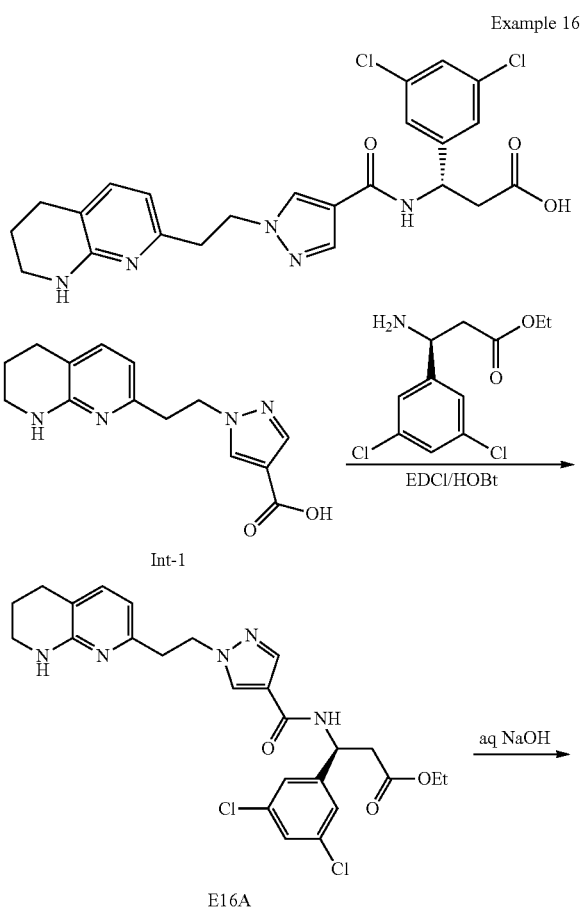

Int-1

E16A

Example 16

Example E16A: To a solution of 1-(2-(5,6,7,8-tetrahydro-1,8-naphthyridin-2-yl)ethyl)-1H-pyrazole-4-carboxylic acid (58 mg, 0.213 mmol, Intermediate 1) and (S)-ethyl 3-amino-3-(3,5-dichlorophenyl)propanoate (70 mg, 0.209 mmol) in DMF (2.5 ml) were added EDC (60 mg, 0.313 mmol), HOBT (39.1 mg, 0.256 mmol) and Et$_3$N (0.10 mL, 0.717 mmol). The reaction mixture was stirred at room temperature for 24 h. The volatiles were removed in vacuo and the residue was purified by preparative HPLC (Column: Sunfire C18 OBD, 30×100 mm, 5-μm particles; Mobile Phase A: 5:95 acetonitrile: water with 0.1% TFA; Mobile Phase B: 95:5 acetonitrile: water with 0.1% TFA; Gradient: 25-100% B over 10 minutes, then a 5-minute hold at 100% B; Flow: 40 mL/min.) to give Example E16A (110 mg, 82%) as a foamy solid. $^1$H NMR (400 MHz, Methanol-d$_4$) δ 7.94 (s, 1H), 7.81 (s, 1H), 7.36 (d, J=7.4 Hz, 1H), 7.25 (d, J=1.9 Hz, 2H), 7.23 (t, J=1.9 Hz, 1H), 6.30 (d, J=7.4 Hz, 1H), 5.35 (dd, J=8.5, 6.5 Hz, 1H), 4.42 (t, J=6.5 Hz, 2H), 4.00 (qd, J=7.2, 1.1 Hz, 2H), 3.40-3.34 (m, 2H), 3.15 (t, J=6.6 Hz, 2H), 2.84 (dd, J=15.5, 8.5 Hz, 1H), 2.78 (dd, J=15.5, 6.5 Hz, 1H), 2.67 (t, J=6.2 Hz, 2H), 1.87-1.73 (m, 2H), 1.07 (t, J=7.1 Hz, 3H). LCMS (ES): m/z 516.3 [M+H]$^+$.

Example 16: To a mixture of Example 16A (58 mg, 0.094 mmol) in THF (2.5 mL) at room temperature was added 1M aq. NaOH (0.235 mL, 0.235 mmol) and the reaction mixture stirred for 16 h. The volatiles were removed in vacuo. The residue was acidified to pH ~5 with 1M aq. HCl. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-100% B over 20 minutes, then a 5-minute hold at 100% B; Flow: 20 mL/min.) to afford Example 16 (39.1 mg, 85%): $^1$H NMR (500 MHz, Methanol-d$_4$) δ 7.96 (s, 1H), 7.91 (s, 1H), 7.38 (d, J=1.8 Hz, 2H), 7.32 (t, J=1.9 Hz, 1H), 7.22 (d, J=7.3 Hz, 1H), 6.27 (d, J=7.3 Hz, 1H), 5.43 (dd, J=7.9, 6.4 Hz, 1H), 4.51-4.39 (m, 2H), 3.46-3.38 (m, 2H), 3.11 (t, J=6.8 Hz, 2H), 2.90-2.75 (m, 2H), 2.72 (t, J=6.3 Hz, 2H), 1.93-1.85 (m, 2H). LCMS (ES): m/z 488.2 [M+H]$^+$. Human αVβ6 IC50 (nM)=4.2.

Example 17. 3-(N-Ethyl-1-(2-(5,6,7,8-tetrahydro-1,8-naphthyridin-2-yl)ethyl)-1H-pyrazole-4-carboxamido)-3-(6-methoxypyridin-3-yl)propanoic acid Example 17

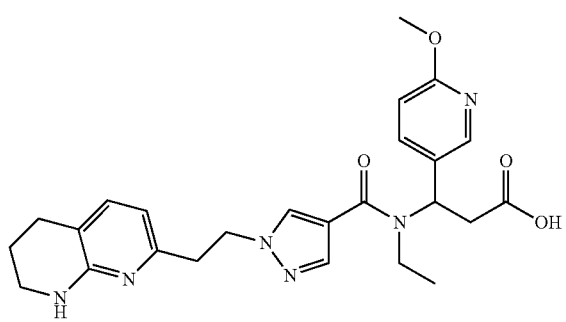

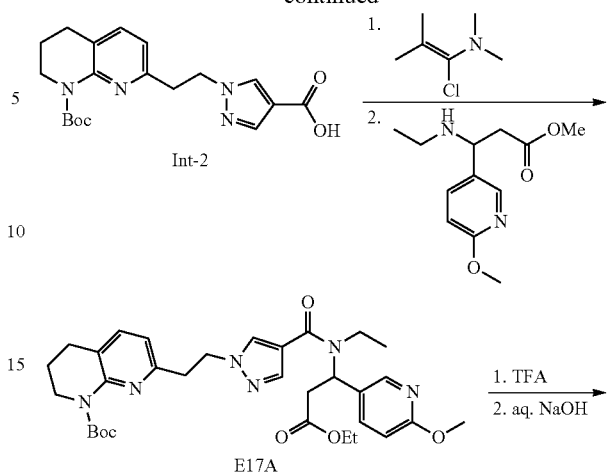

Example 17

Example E17A: To a mixture of 1-(2-(8-(tert-butoxycarbonyl)-5,6,7,8-tetrahydro-1,8-naphthyridin-2-yl)ethyl)-1H-pyrazole-4-carboxylic acid (25 mg, 0.067 mmol, Intermediate 2) in DCM (0.7 mL) was added 1-chloro-N,N,2-trimethylprop-1-en-1-amine (46 mg, 0.344 mmol). The mixture was stirred at RT for 20 min. Then a preformed mixture of methyl 3-(ethylamino)-3-(6-methoxypyridin-3-yl)propanoate, 3 TFA (38 mg, 0.065 mmol), triethylamine (0.036 mL, 0.26 mmol) in THF (0.5 mL) and DCM (0.5 mL) was added. The reaction mixture was stirred at room temperature for 2 h. The volatiles were removed in vacuo and the residue was purified by preparative HPLC (Column: Sunfire C18 OBD, 30×100 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-100% B over 10 minutes, then a 5-minute hold at 100% B; Flow: 40 mL/min.) to give Example E17A (11 mg, 28%) as a viscous oil. LCMS (ES): m/z 593.5 [M+H]$^+$.

Example 17: A mixture of Example 17A (19 mg, 0.030 mmol) in TFA (1 mL) and CH$_2$Cl$_2$ (0.5 mL) was stirred at RT for 2 h. The volatiles were removed in vacuo and the residue was dissolved in THF (1 mL) and MeOH (0.1 mL). Then 1M aq. NaOH (0.107 mL, 0.107 mmol) was added and the reaction mixture stirred for 2 h. The volatiles were removed in vacuo. The residue was acidified to pH ~5 with aq. 1M HCl. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min.) to afford Example 17 (9.6 mg, 51%) as a white solid: $^1$H NMR (500 MHz, DMSO-d6) δ 8.28-7.38 (m, 4H), 6.95 (bs, 1H), 6.78 (d, J=7.3 Hz, 1H), 6.14 (d, J=7.3 Hz, 1H), 5.67 (bs, 1H), 4.38 (t, J=7.0 Hz, 2H). 3.87-3.68 (m, 3H), 3.37-3.25 (two protons missing due to H$_2$O supression), 3.24-3.07 (m, 4H), 2.98-2.88 (m, 2H), 2.59-2.52 (m, 2H), 1.77-1.63 (m, 2H), 0.85 (t, J=7.1 Hz, 3H). LCMS (ES): m/z 479.5 [M+H]$^+$. Human αVβ6 IC50 (nM)=363.

Example 18. (S)-3-(6-Methoxypyridin-3-yl)-3-(N-methyl-1-(2-(5,6,7,8-tetrahydro-1,8-naphthyridin-2-yl)ethyl)-1H-pyrazole-4-carboxamido)propanoic acid

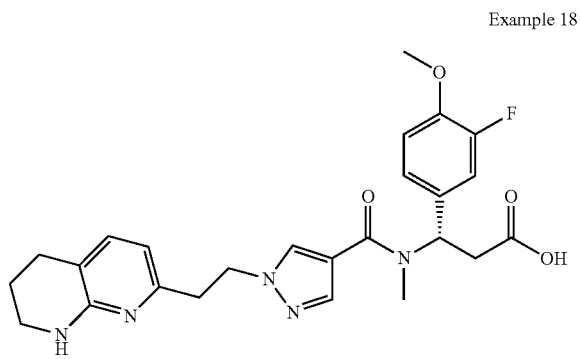

Example 18

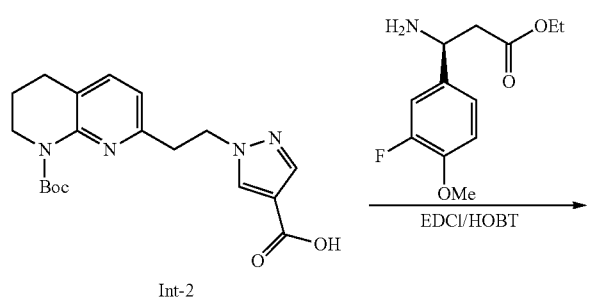

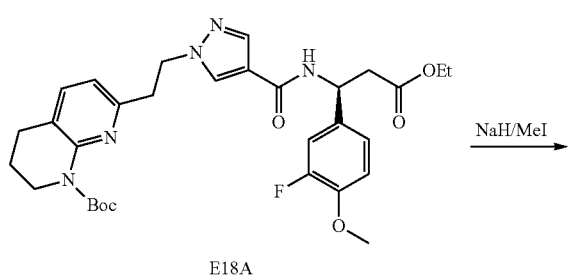

Example 18

Example E18A: To a mixture of 1-(2-(8-(tert-butoxycarbonyl)-5,6,7,8-tetrahydro-1,8-naphthyridin-2-yl)ethyl)-1H-pyrazole-4-carboxylic acid (50 mg, 0.134 mmol, Intermediate 2) and (S)-ethyl 3-amino-3-(3-fluoro-4-methoxyphenyl)propanoate, HCl (48.5 mg, 0.175 mmol) in CH$_2$Cl$_2$ (3 mL) were added EDC (40 mg, 0.209 mmol), HOBT (24.7 mg, 0.161 mmol) and Et$_3$N (0.028 mL, 0.201 mmol). The reaction mixture was stirred at room temperature for 16 h. The volatiles were removed in vacuo and the residue was purified by silica gel chromatography (MeOH/CH$_2$Cl$_2$, 5:95) to give crude Example E18A (80 mg, 100%) as a yellow foamy solid. $^1$H NMR (500 MHz, Chloroform-d) δ 7.90 (s, 1H), 7.80 (s, 1H), 7.24 (d, J=7.5 Hz, 1H), 7.08-6.83 (m, 3H), 6.63 (d, J=7.5 Hz, 1H), 5.53-5.43 (m, 1H), 4.60 (t, J=6.8 Hz, 2H), 4.14 (qd, J=7.1, 0.9 Hz, 2H), 3.87 (s, 3H), 3.77 (td, J=5.7, 2.6 Hz, 2H), 3.23 (t, J=6.8 Hz, 2H), 2.90 (dd, J=15.7, 5.9 Hz, 1H), 2.83 (dd, J=15.7, 5.9 Hz, 1H), 2.71 (t, J=6.6 Hz, 2H), 1.92 (p, J=6.5 Hz, 2H), 1.54 (s, 9H), 1.24 (t, J=7.1 Hz, 3H). LCMS (ES): m/z 596.4 [M+H]$^+$.

Example 18: To mixture of tert-butyl (S)-7-(2-(4-((3-ethoxy-1-(6-methoxypyridin-3-yl)-3-oxopropyl)carbamoyl)-1H-pyrazol-1-yl)ethyl)-3,4-dihydro-1,8-naphthyridine-1(2H)-carboxylate (Example 18A, 40 mg, 0.067 mmol) in THF (1 mL) was added NaH (2.69 mg, 0.067 mmol, 60% in mineral oil) at 0° C. The reaction mixture was stirred at this temperature for 10 min and iodomethane (0.013 mL, 0.201 mmol) was added. The reaction mixture was allowed to warm to RT and stirred at this temperature for 1 h at which point it was quenched with sat. NH$_4$Cl and extracted with EtOAc (3×8 mL). The combined organic layer was washed with brine, dried over anhydrous Na$_2$SO$_4$, filtered, and concentrated under reduced pressure to afford a crude residue. The residue was purified by preparative HPLC (Column: Phenomenex Axia, 30×200 mm, 5-µm particles; Mobile Phase A: 5:95 MeOH: water with 0.1% TFA; Mobile Phase B: 95:5 MeOH: water with 0.1% TFA; Gradient: 25-100% B over 10 minutes, then a 5-minute hold at 100% B; Flow: 40 mL/min.) to afford Example 18 (5.0 mg, 10%): $^1$H NMR (500 MHz, Methanol-d$_4$) δ 7.96 (s, 1H), 7.78 (s, 1H), 7.58-7.26 (m, 1H), 7.23-6.82 (m, 3H), 6.53-6.32 (m, 1H), 6.20 (bs, 0.66H), 5.32 (bs, 0.33H), 4.52 (t, J=6.5 Hz, 2H), 3.87 (s, 3H), 3.54-3.43 (m, 2H), 3.24 (t, J=6.5 Hz, 2H), 3.20-2.59 (m, 7H), 1.97-1.82 (m, 2H). LCMS (ES): m/z 482.3 [M+H]$^+$. Human αVβ6 IC50 (nM)=13.

Example 19. (S)-2-((4-Methoxyphenyl)sulfonamido)-3-(1-(2-(5,6,7,8-tetrahydro-1,8-naphthyridin-2-yl)ethyl)-1H-pyrazole-4-carboxamido)propanoic acid

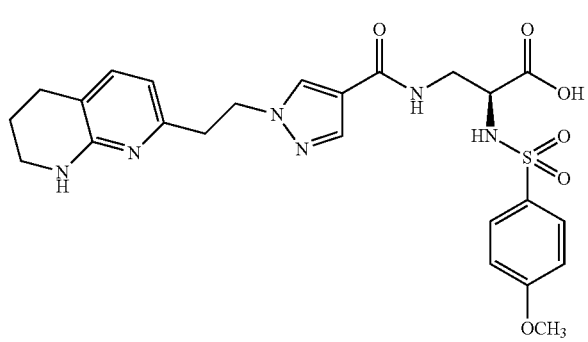

Example 19

-continued

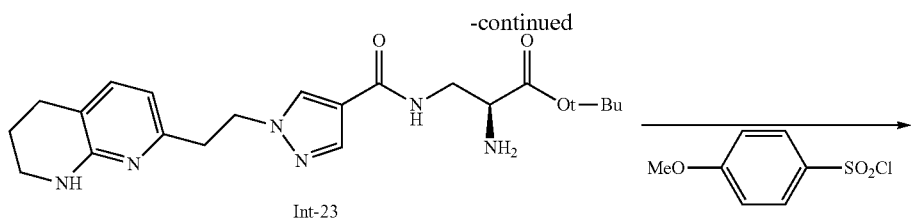

Int-23

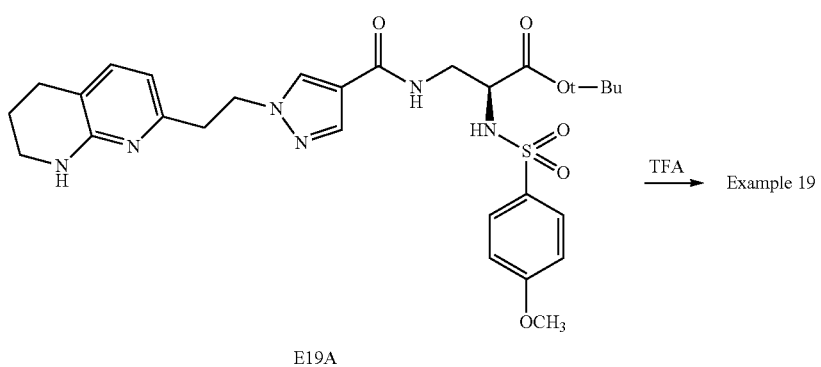

E19A

TFA → Example 19

Example 19A: To a mixture of Intermediate 23 (16 mg, 0.039 mmol), sodium bicarbonate (16 mg, 0.190 mmol) in THF (1 mL) and H$_2$O (0.5 mL) was added 4-methoxybenzene-1-sulfonyl chloride (16 mg, 0.077 mmol). The reaction mixture was stirred at RT for 1 h. The volatiles were removed in vacuo and the residue was purified by preparative HPLC (Column: Sunfire C18 OBD, 30×100 mm, 5-μm particles; Mobile Phase A: 5:95 acetonitrile: water with 0.1% TFA; Mobile Phase B: 95:5 acetonitrile: water with 0.1% TFA; Gradient: 20-100% B over 10 minutes, then a 5-minute hold at 100% B; Flow: 40 mL/min.) to afford Example 19A (20.4 mg, 90%) as a foamy solid: $^1$H NMR (500 MHz, Methanol-d$_4$) δ 7.99 (s, 1H), 7.86 (s, 1H), 7.79-7.73 (m, 2H), 7.51 (d, J=7.3 Hz, 1H), 7.03-6.98 (m, 2H), 6.43 (d, J=7.2 Hz, 1H), 4.55 (t, J=6.5 Hz, 2H), 4.04 (dd, J=8.3, 5.5 Hz, 1H), 3.86 (s, 3H), 3.64 (dd, J=13.6, 5.5 Hz, 1H), 3.50 (dd, J=6.5, 4.9 Hz, 2H), 3.39 (dd, J=13.6, 8.3 Hz, 1H), 3.27 (t, J=6.5 Hz, 2H), 2.80 (t, J=6.2 Hz, 2H), 2.04-1.84 (m, 2H), 1.27 (s, 9H). LCMS (ES): m/z 585.2 [M+H]$^+$.

Example 19: A mixture of Example 19A (16 mg, 0.027 mmol) in TFA (1 mL) and CH$_2$Cl$_2$ (0.5 mL) was stirred at RT for 4 h. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-45% B over 20 minutes, then a 5-minute hold at 100% B; Flow: 20 mL/min.) to afford Example 19 (7.1 mg, 46%): $^1$H NMR (500 MHz, DMSO-d$_6$) δ 8.04-7.97 (m, 2H), 7.90 (d, J=8.3 Hz, 1H), 7.73 (s, 1H), 7.69-7.62 (m, 2H), 7.03 (d, J=7.3 Hz, 1H), 7.00-6.91 (m, 2H), 6.37 (bs, 1H), 6.23 (d, J=7.3 Hz, 1H), 4.38 (t, J=7.4 Hz, 2H), 3.90-3.82 (m, 1H), 3.78 (s, 3H), 3.44-3.36 (m, 1H), 3.31-3.20 (m, 3H), 2.97 (t, J=7.4 Hz, 2H), 2.60 (t, J=6.3 Hz, 2H), 1.81-1.60 (m, 2H). LCMS (ES): m/z 529. [M+H]$^+$. Human αVβ6 IC50 (nM)=1.3.

Example 20. (S)-2-((Butoxycarbonyl)amino)-3-(1-(2-(5,6,7,8-tetrahydro-1,8-naphthyridin-2-yl)ethyl)-1H-pyrazole-4-carboxamido)propanoic acid Example 20

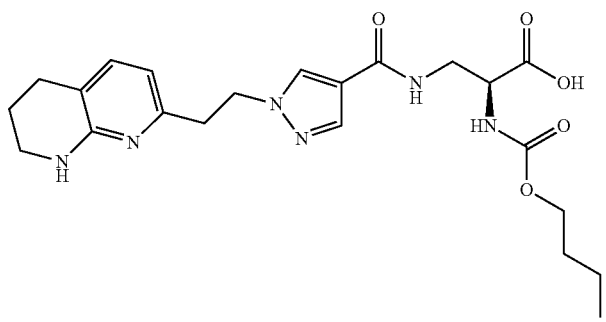

-continued

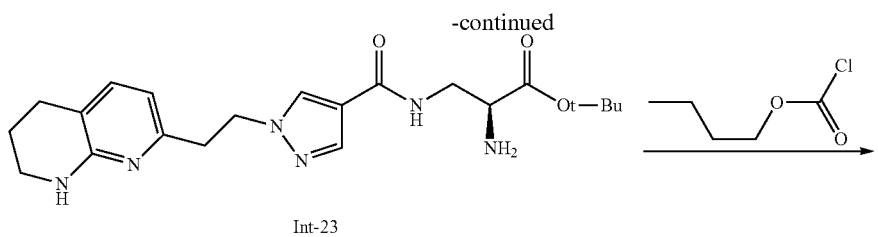

Int-23

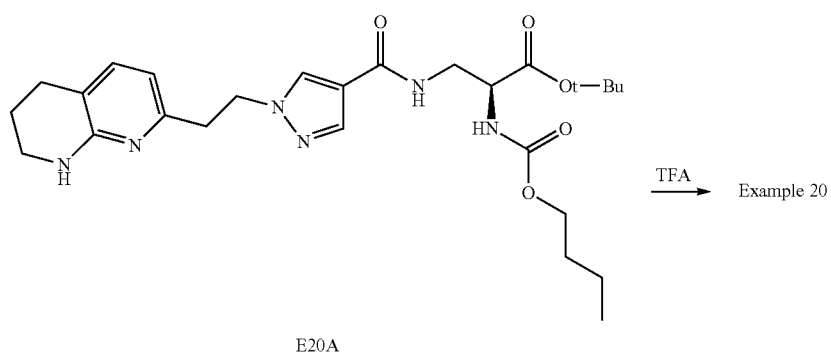

E20A

TFA ⟶ Example 20

Example 20A: To a mixture of Intermediate 23 (12 mg, 0.029 mmol), sodium bicarbonate (12 mg, 0.143 mmol) in THF (1 mL) and H$_2$O (0.5 mL) was added butyl carbonochloridate (18 mg, 0.132 mmol). The reaction mixture was stirred at RT for 1 h. The volatiles were removed in vacuo and the residue was purified by preparative HPLC (Column: Sunfire C18 OBD, 30×100 mm, 5-μm particles; Mobile Phase A: 5:95 acetonitrile: water with 0.1% TFA; Mobile Phase B: 95:5 acetonitrile: water with 0.1% TFA; Gradient: 20-100% B over 10 minutes, then a 5-minute hold at 100% B; Flow: 40 mL/min.) to afford Example 20A (13 mg, 87%) as a foamy solid: $^1$H NMR (500 MHz, Methanol-d$_4$) δ 8.03 (s, 1H), 7.89 (s, 1H), 7.53 (d, J=7.3 Hz, 1H), 6.47 (d, J=7.3 Hz, 1H), 4.54 (t, J=6.6 Hz, 2H), 4.30 (dd, J=7.2, 5.4 Hz, 1H), 4.09-4.02 (m, 2H), 3.72-3.60 (m, 2H), 3.52 (t, J=6.4, Hz, 2H), 3.27 (t, J=6.6 Hz, 2H), 2.82 (t, J=6.3 Hz, 2H), 2.08-1.87 (m, 2H), 1.61 (p, J=7.0 Hz, 2H), 1.46 (s, 9H), 1.45-1.36 (m, 2H), 0.95 (t, J=7.4 Hz, 3H). LCMS (ES): m/z 515.3 [M+H]$^+$.

Example 20: A mixture of Example 20A (13 mg, 0.025 mmol) in TFA (1 mL) and CH$_2$Cl$_2$ (0.5 mL) was stirred at RT for 4 h. The volatiles were removed in vacuo and the residue was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-100% B over 10 minutes, then a 5-minute hold at 100% B; Flow: 20 mL/min.) to afford Example 20 (8.6 mg, 71%): $^1$H NMR (500 MHz, Methanol-d$_4$) δ 8.05 (s, 1H), 7.87 (s, 1H), 7.40 (d, J=7.3 Hz, 1H), 6.42 (d, J=7.3, 1H), 4.46 (t, J=7.0 Hz, 2H), 4.38-4.25 (m, 1H), 4.04 (t, J=6.5 Hz, 2H), 3.82-3.67 (m, 2H), 3.60-3.40 (m, 2H), 3.17 (t, J=7.1 Hz, 2H), 2.78 (t, J=6.2 Hz, 2H), 1.98-1.89 (m, 2H), 1.63-1.55 (m, 2H), 1.46-1.35 (m, 2H), 0.93 (t, J=7.4 Hz, 3H). LCMS (ES): m/z 459.2 [M+H]$^+$. Human αVβ6 IC50 (nM)=1.1; Human αVβ1 IC50 (nM)=27.0; Human αVβ3 IC50 (nM)=1.8; Human αVβ5 IC50 (nM)=0.2; and Human αVβ8 IC50 (nM)=86.

The following examples (in Table A) were prepared using methods analogous to the ones as indicated in the table.

TABLE A

| Example No. | Structure | Data | Method |
|---|---|---|---|
| 21 | (S)-2-((S)-1-(phenylsulfonyl)pyrrolidine-2-carboxamido)-3-(1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 8.02 (s, 1H), 7.95-7.92 (m, 2H), 7.86 (s, 1H), 7.75-7.68 (m, 1H), 7.67-7.61 (m, 2H), 7.28-7.22 (m, 1H), 6.27 (d, J = 7.3 Hz, 1H), 4.40-4.42 (m, 3H), 4.15 (dd, J = 8.7, 4.0 Hz, 1H), 3.97 (dd, J = 13.7, 4.3 Hz, 1H), 3.69 (dd, J = 13.7, 7.5 Hz, 1H), 3.51 (ddd, J = 10.0, 6.9, 4.7 Hz, 1H), 3.42 (td, J = 5.2, 2.0 Hz, 2H), 3.24 (dt, J = 10.1, 7.2 Hz, 1H), 3.13 (dp, J = 21.4, 7.3 Hz, 2H), 2.72 (t, J = 6.3 Hz, 2H), 1.99-1.95 (m, 1H), 1.93-1.81 (m, 3H), 1.81-1.71 (m, 1H), 1.58-1.46 (m, 1H). LCMS (ES): m/z 596.4 [M + H]$^+$. Human αVβ6 IC50 (nM) = 1.4. | Same method as for Example 15 |

TABLE A-continued

| Example No. | Structure | Data | Method |
|---|---|---|---|
| 22 | 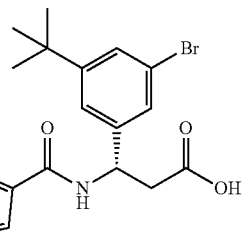<br>(S)-3-(3-bromo-5-(tert-butyl)phenyl)-3-(1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 7.96 (s, 1H), 7.91 (s, 1H), 7.50-7.35 (m, 3H), 7.22 (d, J = 7.1 Hz, 1H), 6.27 (d, J = 7.1 Hz, 1H), 5.47 (m, 1H), 4.53-4.41 (m, 2H), 3.46-3.38 (m, 2H), 3.15-3.04 (m, 2H), 2.90 2.78 (m, 2H), 2.76-2.70 (m, 2H), 1.94-1.85 (m, 2H), 1.31 (s, 9H). LCMS (ES): m/z 554.2 [M + H]$^+$. Human αVβ6 IC50 (nM) = 1.9. | Same method as for Example 16 |
| 23 | 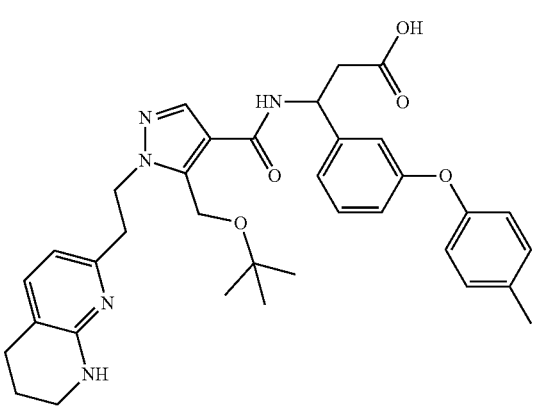<br>3-(5-(tert-Butoxymethyl)-1-(2-(5,6,7,8-tetrahydro-1,8-naphthyridin-2-yl)ethyl)-1H-pyrazole-4-carboxamido)-3-(3-(p-tolyloxy)phenyl)propanoic acid | $^1$H NMR (500 MHz, Methanol-d$_4$) δ 7.71 (s, 1H), 7.17 (t, J = 7.9 Hz, 1H), 7.09-6.97 (m, 4H), 6.91 (s, 1H), 6.75 (d, J = 8.1 Hz, 2H), 6.70 (d, J = 8.2 Hz, 2H), 6.05 (d, J = 7.3 Hz, 1H), 5.34 (t, J = 7.4 Hz, 1H), 4.45 (d, J = 12.0 Hz, 1H), 4.40 (d, J = 12.0 Hz, 1H), 4.37 (t, J = 6.7 Hz, 2H), 3.30 (t, J = 5.6 Hz, 2H), 2.98 (t, J = 6.7 Hz, 2H), 2.73-2.67 (m, 2H), 2.60 (t, J = 6.3 Hz, 2H), 2.20 (s, 3H), 1.81-1.77 (m, 2H), 1.09 (s, 9H). LCMS (ES): m/z 612.4 [M + H]$^+$. Human αVβ6 IC50 (nM) = 2.3. | Same method as for Example 16 By using intermediate 16 |
| 24 | 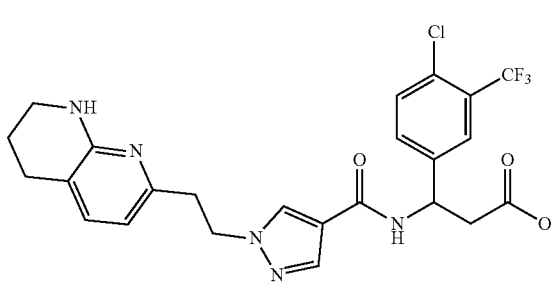<br>3-(4-Chloro-3-(trifluoromethyl)phenyl)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.59 (d, J = 8.0 Hz, 1H), 8.14 (s, 1H), 7.88 (s, 1H), 7.86-7.80 (m, 1H), 7.75-7.65 (m, 2H), 7.43 (d, J = 7.3 Hz, 1H), 6.42 (d, J = 7.3 Hz, 1H), 5.38 (q, J = 7.7 Hz, 1H), 4.46 (t, J = 6.9 Hz, 2H), 3.43-3.32 (two protons missing due to H$_2$O suppression) (t, J = 6.9 Hz, 2H), 2.84 (qd, J = 17.0, 16.0, 8.5 Hz, 2H), 2.70 (t, J = 6.3 Hz, 2H), 1.86-1.74 (m, 2H). LCMS (ES): m/z 522.3 [M + H]$^+$. Human αVβ6 IC50 (nM) = 3.1. | Same method as for Example 16 |
| 25 | 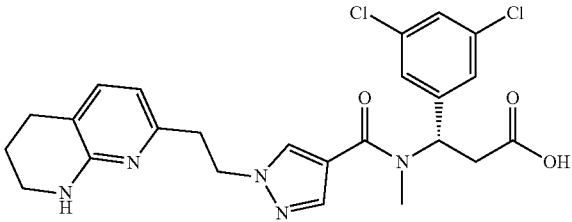<br>(S)-3-(3,5-Dichlorophenyl)-3-(N-methyl-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 8.30-7.70 (m, 2H), 7.57-6.97 (m, 4H), 6.40-5.80 (m, 2H), 4.52-4.30 (m, 2H), 3.35-3.42 (m, 2H), 3.09-3.14 (m, 2H), 3.06-2.75 (m, 5H), 2.72-2.65 (m, 2H), 1.91-1.80 (m, 2H). LCMS (ES): m/z 502.2 [M + H]$^+$. Human αVβ6 IC50 (nM) = 3.1. | Same method as for Example 16 By using intermediate 16 |

TABLE A-continued

| Example No. | Structure | Data | Method |
|---|---|---|---|
| 26 | (S)-3-(3-Bromo-5-(tert-butyl)phenyl-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 7.77 (s, 1H), 7.33 (s, 1H), 7.30 (s, 1H), 7.27 (s, 1H), 7.05 (d, J = 7.2 Hz, 1H), 6.08 (d, J = 7.3 Hz, 1H), 5.33 (t, J = 7.0 Hz, 1H), 4.56 (d, J = 13.6 Hz, 1H), 4.52 (d, J = 13.7 Hz, 1H), 4.36 (t, J = 6.9 Hz, 2H), 3.29 (t, J = 5.6 Hz, 2H), 2.95 (t, J = 6.7 Hz, 2H), 2.65 (t, J = 6.8 Hz, 2H), 2.59 (t, J = 6.4 Hz, 2H), 1.77 (p, J = 6.1 Hz, 2H), 1.20 (s, 9H). LCMS (ES): m/z 585.1 [M + H]$^+$. Human αVβ6 IC50 (nM) = 5.0. | Same method as for Example 9 |
| 27 | 3-(5-(Hydroxymethyl)-1-(2-(5,6,7,8-tetrahydro-1,8-naphthyridin-2-yl)ethyl)-1H-pyrazole-4-carboxamido)-3-(3-(p-tolyloxy)phenyl)propanoic acid | $^1$H NMR (500 MHz, Methanol-d$_4$) δ 7.84 (s, 1H), 7.29 (t, J = 7.9 Hz, 1H), 7.20 (d, J = 7.3 Hz, 1H), 7.15 (d, J = 7.7 Hz, 3H), 7.04 (s, 1H), 6.88 (d, J = 8.1 Hz, 2H), 6.82 (d, J = 7.9 Hz, 2H), 6.22 (d, J = 7.3 Hz, 1H), 5.46 (t, J = 7.2 Hz, 1H), 4.67 (d, J = 13.8 Hz, 1H), 4.62 (d, J = 13.9 Hz, 1H), 4.48 (t, J = 6.8 Hz, 2H), 3.42 (t, J = 5.7 Hz, 2H), 3.08 (t, J = 6.7 Hz, 2H), 2.88-2.75 (m,, 2H), 2.72 (t, J = 6.3 Hz, 2H), 2.32 (s, 3H), 1.93-1.81 (m., 2H). LCMS (ES): m/z 556.3 [M + H]$^+$. Human αVβ6 IC50 (nM) = 5.1. | Same method as for Example 9 |
| 28 | (S)-3-(1-(3-(5,6,7,8-Tetrahydro-1,8-naphthyridin-2-yl)propyl)-1H-pyrazole-4-carboxamido)-2-((2,4,6-trimethylphenyl)sulfonamido)propanoic acid | $^1$H NMR (500 MHz, Methanol-d$_4$) δ 8.08 (s, 1H), 7.80 (s, 1H), 7.41 (d, J = 7.3 Hz, 1H), 6.92 (s, 2H), 6.49 (d, J = 7.3 Hz, 1H), 4.24 (t, J = 6.4 Hz, 2H), 3.73 (t, J = 6.3 Hz, 1H), 3.63 (d, J = 6.4 Hz, 2H), 3.41 (td, J = 5.3, 2.3 Hz, 2H), 2.75 (t, J = 6.3 Hz, 2H), 2.64 (s, 6H), 2.61 (t, J = 8.0 Hz, 2H), 2.29-2.21 (m, 2H), 2.20 (s, 3H), 1.94-1.85 (m, 2H). LCMS (ES): m/z 555.4 [M + H]$^+$. Human αVβ6 IC50 (nM) = 6.1. | Same method as for Example 10 By using intermediate 5 |

TABLE A-continued

| Example No. | Structure | Data | Method |
|---|---|---|---|
| 29 | 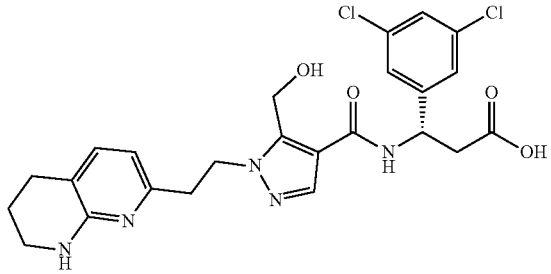<br>(S)-3-(3,5-dichlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.58 (d, J = 8.4 Hz, 1H), 7.95 (s, 1H), 7.67-7.12 (m, 4H), 6.33 (d, J = 7.1 Hz, 1H), 5.32 (q, J = 7.8 Hz, 1H), 4.76 (d, J = 13.4 Hz, 1H), 4.72 (d, J = 13.4 Hz, 1H), 4.46 (t, J = 7.4 Hz, 2H), 3.43-3.32 (two protons missing due to H$_2$O suppression), 3.14-3.07 (m, 2H), 2.94-2.76 (m, 2H), 2.73-2.63 (m, 2H), 1.84-1.73 (m, 2H). LCMS (ES): m/z 518.0 [M + H]$^+$. Human αVβ6 IC50 (nM) = 6.4. | Same method as for Example 9 |
| 30 | 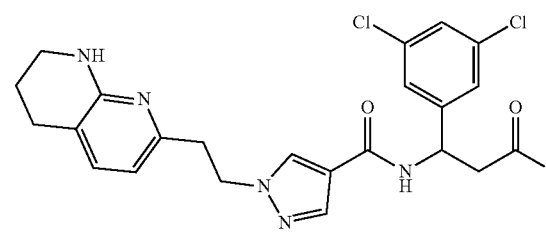<br>3-(3,5-Dichlorophenyl)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.53 (d, J = 8.1 Hz, 1H), 8.17 (s, 1H), 7.89 (s, 1H), 7.54-7.48 (m, 2H), 7.41 (s, 2H), 6.47 (d, J = 7.3 Hz, 1H), 5.31 (q, J = 7.9 Hz, 1H), 4.48 (t, J = 7.0 Hz, 2H), 3.43-3.32 (two protons missing due to H$_2$O suppression), 3.19 (t, J = 6.9 Hz, 2H), 2.87-2.76 (m, 2H), 2.75-2.67 (m, 2H), 1.86-1.75 (m, 2H). LCMS (ES): m/z 488.3 [M + H]$^+$. Human αVβ6 IC50 (nM) = 7.3. | Same method as for Example 3 |
| 31 | 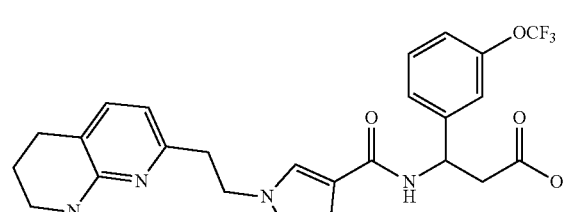<br>3-(1-(2-(5,6,7,8-Tetrahydro-1,8-naphthyridin-2-yl)ethyl)-1H-pyrazole-4-carboxamido)-3-(3-(trifluoromethoxy)phenyl)propanoic acid | $^1$H NMR (500 MHz, Methanol-d$_4$) δ 8.03 (s, 1H), 7.94 (s, 1H), 7.51-7.38 (m, 3H), 7.32 (s, 1H), 7.19 (d, J = 7.8 Hz, 1H), 6.43 (d, J = 7.3 Hz, 1H), 5.55 (t, J = 7.5 Hz, 1H), 4.53 (t, J = 6.7 Hz, 2H), 3.49 (t, J = 5.8 Hz, 2H), 3.25 (t, J = 6.7 Hz, 2H), 2.92 (qd, J = 16.0, 8.0 Hz, 2H), 2.79 (t, J = 6.3 Hz, 2H), 1.99-1.86 (m, 2H). LCMS (ES): m/z 488.3 [M + H]$^+$. Human αVβ6 IC50 (nM) = 7.6. | Same method as for Example 9 |
| 32 | 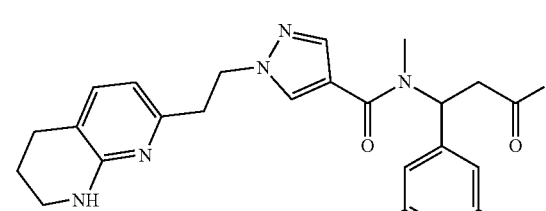<br>3-(3,5-Dichlorophenyl)-3-(N-methyl-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 8.30-7.70 (m, 2H), 7.57-6.97 (m, 4H), 6.40-5.80 (m, 2H), 4.52-4.30 (m, 2H), 3.35-3.42 (m, 2H), 3.09-3.14 (m, 2H), 3.06-2.75 (m, 5H), 2.72-2.65 (m, 2H), 1.91-1.80 (m, 2H). LCMS (ES): m/z 502.2 [M + H]$^+$. Human αVβ6 IC50 (nM) = 7.6. | Same method as for Example 16 |

TABLE A-continued

| Example No. | Structure | Data | Method |
|---|---|---|---|
| 33 | 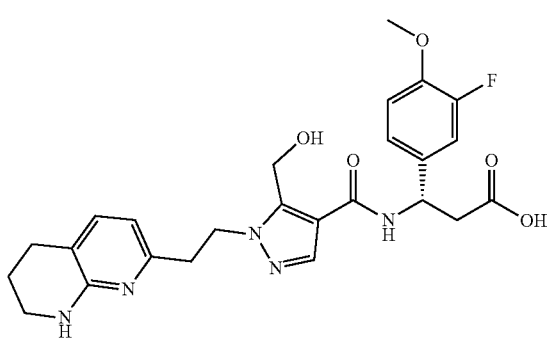<br>(S)-3-(3-Fluoro-4-methoxyphenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.51 (d, J = 8.3 Hz, 1H), 7.92 (s, 1H), 7.43 (d, J = 7.3 Hz, 1H), 7.20 (d, J = 12.8 Hz, 1H), 7.16-7.04 (m., 2H), 6.40 (d, J = 7.3 Hz, 1H), 5.30 (q, J = 7.9 Hz, 1H), 4.75 (d, J = 2.8 Hz, 1H), 4.72 (d, J = 2.8 Hz, 1H), 4.47 (t, J = 7.1 Hz, 2H), 3.81 (s, 3H), 3.37 (t, J = 5.5 Hz, 2H), 3.13 (t, J = 7.2 Hz, 2H), 2.88-2.72 (m, 2H), 2.69 (t, J = 6.5 Hz, 2H), 1.87-1.74 (m, 2H). LCMS (ES): m/z 498.5 [M + H]$^+$. Human αVβ6 IC50 (nM) = 9.4. | Same method as for Example 2 |
| 34 | 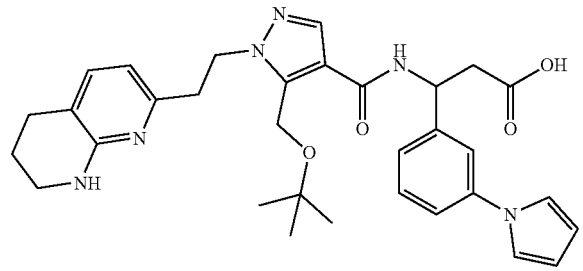<br>3-(3-(1H-Pyrrol-1-yl)phenyl)-3-(5-(tert-butoxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 7.79 (s, 1H), 7.40 (s, 1H), 7.36-7.14 (m, 3H), 7.11-7.01 (m, 3H), 6.17 (s, 2H), 6.07 (d, J = 7.2 Hz, 1H), 5.51-5.38 (m, 1H), 4.57-4.28 (m, 4H), 3.33-3.27 (m, 2H), 2.98 (t, J = 6.5 Hz, 2H), 2.84-2.71 (m, 2H), 2.65-2.57 (m, 2H), 1.81-1.70 (m, 2H), 1.07 (s, 9H). LCMS (ES): m/z 571.4 [M + H]$^+$. Human αVβ6 IC50 (nM) = 10. | Same method as for Example 9 |
| 35 | 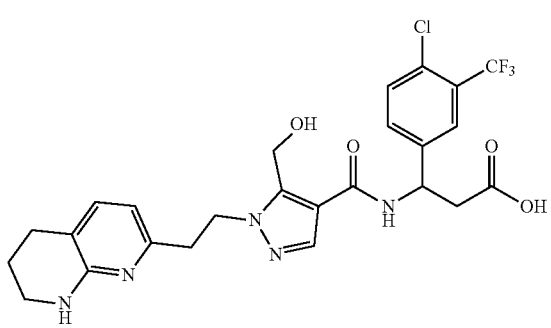<br>3-(4-Chloro-3-(trifluoromethyl)phenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 7.79 (s, 1H), 7.71 (d, J = 2.1 Hz, 1H), 7.54 (dd, J = 8.3, 2.1 Hz, 1H), 7.44 (d, J = 8.3 Hz, 1H), 7.02 (d, J = 7.3 Hz, 1H), 6.07 (d, J = 7.3 Hz, 1H), 5.35 (t, J = 6.9 Hz, 1H), 4.54 (d, J = 13.7 Hz, 1H), 4.50 (d, J = 13.7 Hz, 1H), 4.38 (t, J = 6.9 Hz, 2H), 3.28 (t, J = 5.6 Hz, 2H), 2.94 (t, J = 6.9 Hz, 2H), 2.74-2.61 (m, 2H), 2.59 (t, J = 6.3 Hz, 2H), 1.77 (p, J = 6.1 Hz, 2H). LCMS (ES): m/z 552.2 [M + H]$^+$. Human αVβ6 IC50 (nM) = 10. | Same method as for Example 9 |

TABLE A-continued

| Example No. | Structure | Data | Method |
|---|---|---|---|
| 36 | 3-(5-(Hydroxymethyl)-1-(2-(5,6,7,8-tetrahydro-1,8-naphthyridin-2-yl)ethyl)-1H-pyrazole-4-carboxamido)-3-(3-(trifluoromethoxy)phenyl)propanoic acid | $^1$H NMR (500 MHz, Methanol-d$_4$) δ 7.78 (s, 1H), 7.36-7.26 (m, 2H), 7.21 (s, 1H), 7.09-7.00 (m, 2H), 6.07 (d, J = 7.3 Hz, 1H), 5.39 (t, J = 7.0 Hz, 1H), 4.54 (d, J = 13.7 Hz, 1H), 4.50 (d, J = 13.6 Hz, 1H), 4.37 (t, J = 6.8 Hz, 2H), 3.29 (t, J = 5.6 Hz, 2H), 2.95 (t, J = 6.8 Hz, 2H), 2.75-2.62 (m, 2H), 2.59 (t, J = 6.3 Hz, 2H), 1.76 (p, J = 6.0 Hz, 2H). LCMS (ES): m/z 534.2 [M + H]$^+$. Human αVβ6 IC50 (nM) = 11. | Same method as for Example 9 |
| 37 | 3-(5-(tert-Butoxymethyl)-1-(2-(5,6,7,8-tetrahydro-1,8-naphthyridin-2-yl)ethyl)-1H-pyrazole-4-carboxamido)-3-(3-(3,5-dimethyl-1H-pyrazol-1-yl)phenyl)propanoic acid | $^1$H NMR (500 MHz, Methanol-d$_4$) δ 7.79 (s, 1H), 7.41-7.32 (m, 3H), 7.25-7.16 (m, 1H), 6.98 (d, J = 7.3 Hz, 1H), 6.00 (d, J = 7.3 Hz, 1H), 5.95 (s, 1H), 5.42 (t, J = 7.1 Hz, 1H), 4.44 (d, J = 11.9 Hz, 1H), 4.39 (d, J = 11.9 Hz, 1H), 4.37 (t, J = 6.6 Hz, 2H), 3.28 (t, J = 5.7 Hz, 2H), 2.95 (t, J = 6.7 Hz, 2H), 2.79-2.68 (m, 2H), 2.59 (t, J = 6.6 Hz, 2H), 2.14 (s, 3H), 2.13 (s, 3H), 1.81-1.68 (m, 2H), 1.08 (s, 9H). LCMS (ES): m/z 600.4 [M + H]$^+$. Human αVβ6 IC50 (nM) = 12. | Same method as for Example 9 |
| 38 | 3-(3-(3,5-Dichlorophenoxy)phenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 7.76 (s, 1H), 7.29 (t, J = 7.9 Hz, 1H), 7.18 (d, J = 7.7 Hz, 1H), 7.07-6.98 (m, 3H), 6.84 (d, J = 8.4 Hz, 1H), 6.81 (s, 2H), 6.08 (d, J = 7.2 Hz, 1H), 5.36 (t, J = 7.1 Hz, 1H), 4.52 (s, 2H), 4.37 (t, J = 6.8 Hz, 2H), 3.29 (t, J = 5.7 Hz, H), 2.94 (t, J = 27.0 Hz, 2H), 2.75-2.65 (m, 2H), 2.62-2.58 (m, 2H), 1.80-1.71 (m, 2H). LCMS (ES): m/z 610.2 [M + H]$^+$. Human αVβ6 IC50 (nM) = 13. | Same method as for Example 9 |
| 39 | (S)-3-(3-Fluoro-4-methoxyphenyl)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.42 (d, J = 8.5 Hz, 1H), 8.15 (s, 1H), 7.88 (s, 1H), 7.53 (d, J = 7.4 Hz, 1H), 7.28 (s, 1H), 7.35-6.99 (m, 3H), 6.46 (d, J = 7.3 Hz, 1H), 5.31 (q, J = 8.0 Hz, 1H), 4.47 (t, J = 6.8 Hz, 2H), 3.81 (s, 3H), 3.43-3.32 (two protons missing due to H$_2$O suppression), 3.19 (t, J = 6.8 Hz, 2H), 2.88-2.65 (m, 4H), 1.88-1.76 (m, 2H). LCMS (ES): m/z 468.2 [M + H]$^+$. Human αVβ6 IC50 (nM) = 15. | Same method as for Example 3 |

TABLE A-continued

| Example No. | Structure | Data | Method |
|---|---|---|---|
| 40 | 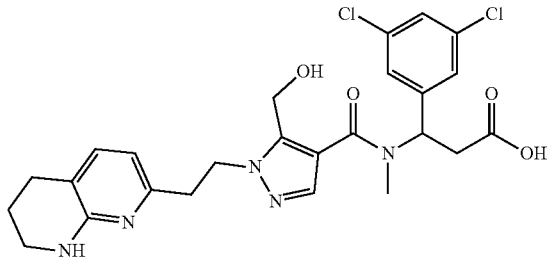 3-(3,5-Dichlorophenyl)-3-(5-(hydroxymethyl)-N-methyl-1-(2-(5,6,7,8-tetrahydro-1,8-naphthyridin-2-yl)ethyl)-1H-pyrazole-4-carboxamido)propanoic acid | $^1$H NMR (500 MHz, Methanol-$d_4$) δ 7.78-7.00 (m, 5H), 6.43 (bs, 1H), 6.14 (bs, 0.66H), 5.50 (bs, 0.33H), 4.65 (s, 2H), 4.58 (t, J = 6.5 Hz, 2H), 3.43-3.52 (m, 2H), 3.28 (t, J = 6.8 Hz, 2H), 3.21-2.67 (m, 7H), 1.97-1.85 (m, 2H). LCMS (ES): m/z 532.2 [M + H]$^+$. Human αVβ6 IC50 (nM) = 14. | Same method as for Example 9 |
| 41 | 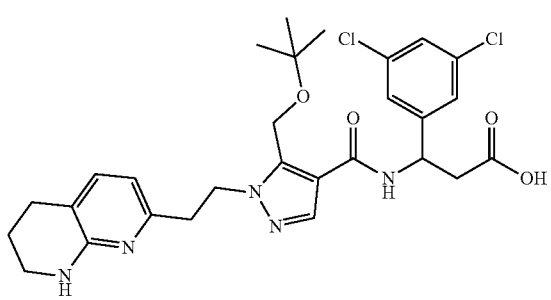 3-(5-(tert-Butoxymethyl)-1-(2-(5,6,7,8-tetrahydro-1,8-naphthyridin-2-yl)ethyl)-1H-pyrazole-4-carboxamido)-3-(3,5-dichlorophenyl)propanoic acid | $^1$H NMR (500 MHz, DMSO-$d_6$) δ 8.52 (d, J = 7.9 Hz, 1H), 7.93 (s, 1H), 7.53 (d, J = 7.3 Hz, 1H), 7.48 (d, J = 2.0 Hz, 1H), 7.41 (d, J = 2.0 Hz, 2H), 6.43 (d, J = 7.4 Hz, 1H), 5.30 (q, J = 7.6 Hz, 1H), 4.74 (d, J = 11.8 Hz, 1H), 4.69 (d, J = 11.6 Hz, 1H), 4.46 (t, J = 6.6 Hz, 2H), 3.45-3.36 (m, 2H), 3.22 (t, J = 6.8 Hz, 2H), 2.94-2.75 (m, 2H), 2.75-2.67 (m, 2H), 1.89-1.76 (m, 2H), 1.15 (s, 9H). LCMS (ES): m/z 574.4 [M + H]$^+$. Human αVβ6 IC50 (nM) = 14. | Same method as for Example 9 |
| 42 | 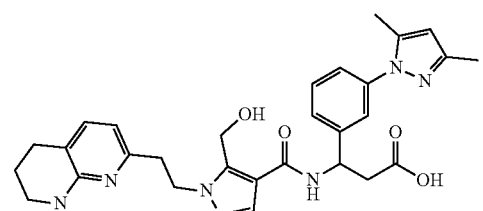 3-(3-(3,5-Dimethyl-1H-pyrazol-1-yl)phenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-$d_4$) δ 7.90 (s, 1H), 7.55-7.46 (m, 3H), 7.38-7.30 (m, 1H), 7.18 (d, J = 7.3 Hz, 1H), 6.22 (d, J = 7.3 Hz, 1H), 6.07 (s, 1H), 5.57 (t, J = 7.1 Hz, 1H), 4.68 (d, J = 13.8 Hz, 1H), 4.63 (d, J = 13.8 Hz, 1H), 4.50 (t, J = 6.8 Hz, 2H), 3.42 (t, J = 5.7 Hz, 2H), 3.08 (t, J = 6.8 Hz, 2H), 2.98-2.83 (m, 2H), 2.72 (t, J = 6.5 Hz, 2H), 2.27 (s, 3H), 2.25 (s, 3H), 1.92-1.83 (m, 2H). LCMS (ES): m/z 544.3 [M + H]$^+$. Human αVβ6 IC50 (nM) = 16. | Same method as for Example 9 |
| 43 | 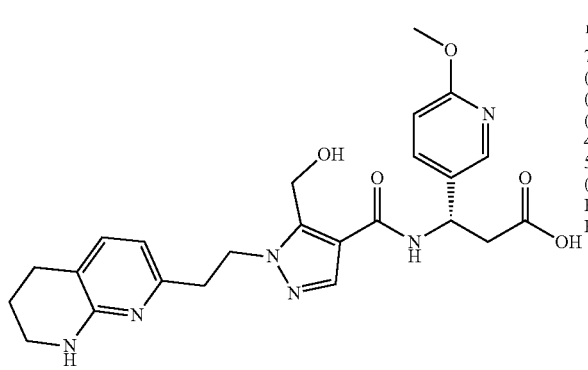 (S)-3-(5-(Hydroxymethyl)-1-(2-(5,6,7,8-tetrahydro-1,8-naphthyridin-2-yl)ethyl)-1H-pyrazole-4-carboxamido)-3-(6-methoxypyridin-3-yl)propanoic acid | $^1$H NMR (500 MHz, Methanol-$d_4$) δ 8.06 (s, 1H), 7.76 (s, 1H), 7.64 (dd, J = 8.6, 2.8 Hz, 1H), 7.36 (d, J = 7.3 Hz, 1H), 6.69 (d, J = 8.8 Hz, 1H), 6.30 (d, J = 7.3 Hz, 1H), 5.36 (t, J = 7.5 Hz, 1H), 4.72 (d, J = 10.3 Hz, 1H), 4.69 (d, J = 10.3 Hz, 1H), 4.46 (t, J = 6.6 Hz, 2H), 3.79 (s, 3H), 3.38 (t, J = 5.7 Hz, 2H), 3.15 (t, J = 6.5 Hz, 2H), 2.93-2.72 (m, 2H), 2.68 (t, J = 6.2 Hz, 2H), 1.83 (p, J = 5.9 Hz, 2H). LCMS (ES): m/z 481.3 [M + H]$^+$. Human αVβ6 IC50 (nM) = 16. | Same method as for Example 9 |

TABLE A-continued

| Example No. | Structure | Data | Method |
|---|---|---|---|
| 44 | 3-(5-(Hydroxymethyl)-1-(2-(5,6,7,8-tetrahydro-1,8-naphthyridin-2-yl)ethyl)-1H-pyrazole-4-carboxamido)-3-(3-(trifluoromethyl)phenyl)propanoic acid | $^1$H NMR (500 MHz, Methanol-d$_4$) δ 7.78 (s, 1H), 7.61 (s, 1H), 7.57 (d, J = 7.3 Hz, 1H), 7.48-7.37 (m, 2H), 7.06 (d, J = 7.2 Hz, 1H), 6.09 (d, J = 7.3 Hz, 1H), 5.43 (t, J = 7.1 Hz, 1H), 4.56 (d, J = 13.6 Hz, 1H), 4.50 (d, J = 13.6 Hz, 1H), 4.37 (t, J = 6.7 Hz, 2H), 3.30 (t, J = 5.6 Hz, 2H), 2.96 (t, J = 6.8 Hz, 2H), 2.79-2.65 (m, 2H), 2.60 (t, J = 6.3 Hz, 2H), 1.77 (p, J = 6.1 Hz, 2H). LCMS (ES): m/z 518.3 [M + H]$^+$. Human αVβ6 IC50 (nM) = 16. | Same method as for Example 9 |
| 45 | (S)-3-(3,5-Dichlorophenyl)-3-(N-methyl-1-(3-(5,6,7,8-tetrahydro-1,8-naphthyridin-2-yl)propyl)-1H-pyrazole-4-carboxamido)propanoic acid | $^1$H NMR (500 MHz, Methanol-d$_4$) δ 8.19 (s, 1H), 7.76 (s, 1H), 7.55-7.45 (m, 1H), 7.43 (s, 1H), 7.30 (bs, 2H), 6.62-6.52 (m, 1H), 6.26-6.00 (m, 1H), 4.39-4.18 (m, 2H), 3.47 (t, J = 5.6 Hz, 2H), 3.02 (dd, J = 15.0, 7.3 Hz, 1H), 2.93-2.36 (m, 8H), 2.36-2.19 (m, 2H), 1.98-1.89 (m, 2H). LCMS (ES): m/z 516.4 [M + H]$^+$. Human αVβ6 IC50 (nM) = 18. | Same method as for Example 16 By using intermediate 5 |
| 46 | (S)-3-(6-Methoxypyridin-3-yl)-3-(1-(2-(5,6,7,8-tetrahydro-1,8-naphthyridin-2-yl)ethyl)-1H-pyrayole-4-carboxamido)propanoic acid | $^1$H NMR (500 MHz, Methanol-d$_4$) δ 8.05 (d, J = 2.5 Hz, 1H), 7.88 (s, 1H), 7.80 (s, 1H), 7.62 (dd, J = 8.5, 2.6 Hz, 1H), 7.30 (d, J = 7.3 Hz, 1H), 6.67 (d, J = 8.7 Hz, 1H), 6.27 (d, J = 7.3 Hz, 1H), 5.36 (t, J = 7.4 Hz, 1H), 4.39 (t, J = 6.6 Hz, 2H), 3.78 (s, 3H), 3.35 (t, J = 5.7 Hz, 2H), 3.09 (t, J = 6.7 Hz, 2H), 2.88-2.71 (m, 2H), 2.66 (t, J = 6.3 Hz, 2H), 1.87-1.66 (m, 2H). LCMS (ES): m/z 451.1 [M + H]$^+$. Human αVβ6 IC50 (nM) = 21. | Same method as for Example 16 |
| 47 | 3-(3,5-Dichlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.58 (d, J = 8.1 Hz, 1H), 7.94 (s, 1H), 7.57-7.47 (d, 2H), 7.43 (s, 2H), 6.47 (d, J = 7.4 Hz, 1H), 5.32 (q, J = 7.7 Hz, 1H), 4.80 (d, J = 13.5 Hz, 1H), 4.75 (d, J = 13.5 Hz, 1H), 4.50 (t, J = 7.0 Hz, 2H), 3.43-3.32 (two protons missing due to H$_2$O suppression), 3.18 (t, J = 7.0 Hz, 2H), 2.90-2.76 (m, 2H), 2.72 (t, J = 6.2 Hz, 2H), 1.88-1.72 (m, 2H). LCMS (ES): m/z 518.4 [M + H]$^+$. Human αVβ6 IC50 (nM) = 22. | Same method as for Example 4 |

TABLE A-continued

| Example No. | Structure | Data | Method |
|---|---|---|---|
| 48 | (S)-3-(3,5-Dichlorophenyl)-3-(N-methyl-1-(2-(5,6,7,8-tetrahydro-1,8-naphthyridin-2-yl)ethyl)-3-(trifluoromethyl)-1H-pyrazole-4-carboxamido)propanoic acid | $^1$H NMR (500 MHz, Chloroform-d) δ 8.23 (bs, 0.5H), 7.73 (bs, 0.5H), 7.44-7.32 (m, 2H), 7.22-7.03 (m, 2H), 6.40 (bs, 0.5H), 6.28-6.11 (m, 1H), 5.44 (bs, 0.5H), 4.63-4.44 (m, 2H), 3.41-3.32 (m, 2H), 3.18-3.05 (m, 2H), 2.95-2.57 (m, 7H), 1.90-1.77 (m, 2H). LCMS (ES): m/z 570.2 [M + H]$^+$. Human αVβ6 IC50 (nM) = 22. | Same method as for Example 16 By using intermediate 14 |
| 49 | 3-(3,5-Dichlorophenyl)-3-(5-methyl-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 7.90 (s, 1H), 7.52 (dt, J = 7.4, 1.3 Hz, 1H), 7.42-7.33 (m, 3H), 6.45 (d, J = 7.3 Hz, 1H), 5.47-5.41 (m, 1H), 4.46 (t, J = 6.6 Hz, 2H), 3.56-3.47 (m, 2H), 3.21 (t, J = 6.7 Hz, 2H), 2.93 (dd, J = 16.0, 8.4 Hz, 1H), 2.87 (dd, J = 16.0, 6.5 Hz, 1H), 2.82 (t, J = 6.4 Hz, 2H), 2.44 (s, 3H), 2.00-1.92 (m, 2H). LCMS (ES): m/z 502.1 [M + H]$^+$. Human αVβ6 IC50 (nM) = 23. | Same method as for Example 3 By using intermediate 19 |
| 50 | (S)-3-(5-(tert-Butoxymethyl)-1-(2-(5,6,7,8-tetrahydro-1,8-naphthyridin-2-yl)ethyl)-1H-pyrazole-4-carboxamido)-3-(3-fluoro-4-methoxyphenyl)propanoic acid | $^1$H NMR (500 MHz, DMSO-d$_6$) δ 8.39 (d, J = 8.3 Hz, 1H), 7.94 (s, 1H), 7.51 (d, J = 7.3 Hz, 1H), 7.30-7.02 (m, 3H), 6.40 (d, J = 7.3 Hz, 1H), 5.32 (q, J = 7.8 Hz, 1H), 4.77 (d, J = 11.6 Hz, 1H), 4.71 (d, J = 11.6 Hz, 1H), 4.46 (t, J = 6.8 Hz, 2H), 3.82 (s, 3H), 3.43-3.32 (two protons missing due to H$_2$O suppression), 3.21 (t, J = 6.8 Hz, 2H), 2.89-2.66 (m, 4H), 1.86-1.77 (m, 2H), 1.17 (d, J = 5.3 Hz, 9H). LCMS (ES): m/z 554.5 [M + H]$^+$. Human αVβ6 IC50 (nM) = 26. | Same method as for Example 3 |
| 51 | 3-(5-(tert-Butoxymethyl)-1-(2-(5,6,7,8-tetrahydro-1,8-naphthyridin-2-yl)ethyl)-1H-pyrazole-4-carboxamido)-3-(3-(3,5-dichlorophenoxy)phenyl)propanoic acid | $^1$H NMR (500 MHz, Methanol-d$_4$) δ 7.73 (s, 1H), 7.29 (t, J = 7.8 Hz, 1H), 7.18 (d, J = 7.8 Hz, 1H), 7.03 (d, J = 6.5 Hz, 3H), 6.84 (d, J = 8.2 Hz, 1H), 6.79 (s, 2H), 6.03 (d, J = 7.3 Hz, 1H), 5.37 (t, J = 7.0 Hz, 1H), 4.46 (d, J = 12.0 Hz, 1H), 4.41 (d, J = 12.0 Hz, 1H), 4.36 (t, J = 6.8 Hz, 2H), 3.29 (t, J = 5.6 Hz, 2H), 2.96 (t, J = 6.8 Hz, 2H), 2.81-2.64 (m, 2H), 2.60 (t, J = 6.3 Hz, 2H), 1.77 (t, J = 6.0 Hz, 2H), 1.09 (s, 9H). LCMS (ES): m/z 666.3 [M + H]$^+$. Human αVβ6 IC50 (nM) = 28. | Same method as for Example 9 |

TABLE A-continued

| Example No. | Structure | Data | Method |
|---|---|---|---|
| 52 | 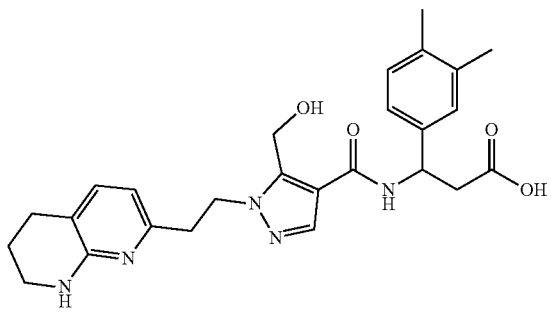<br>3-(3,4-Dimethylphenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 7.89 (s, 1H), 7.22-7.14 (m, 2H), 7.14-7.10 (m, 1H), 7.08 (d, J = 7.8 Hz, 1H), 6.21 (d, J = 7.3 Hz, 1H), 5.44 (dd, J = 8.6, 6.0 Hz, 1H), 4.66 (d, J = 13.6 Hz, 1H), 4.62 (d, J = 13.6 Hz, 1H), 4.48 (t, J = 6.8 Hz, 2H), 3.41 (t, J = 5.6 Hz, 2H), 3.07 (t, J = 6.8 Hz, 2H), 2.84 (dd, J = 15.4, 8.6 Hz, 1H), 2.78 (dd, J = 15.3, 6.0 Hz, 1H), 2.72 (t, J = 6.3 Hz, 2H), 2.26 (s, 3H), 2.23 (s, 3H), 1.92-1.85 (m, 2H). LCMS (ES): m/z 478.3 [M + H]$^+$. Human αVβ6 IC50 (nM) = 29. | Same method as for Example 9 |
| 53 | 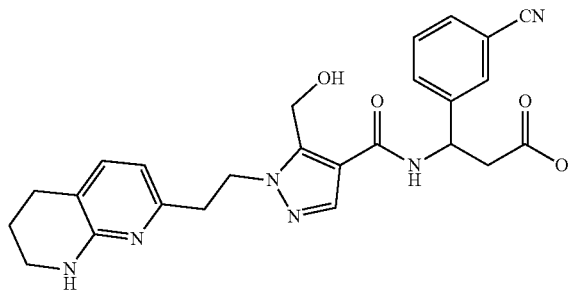<br>3-(3-Cyanophenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 7.80 (s, 1H), 7.65 (s, 1H), 7.62 (d, J = 7.7 Hz, 1H), 7.52 (d, J = 7.5 Hz, 1H), 7.42 (t, J = 7.9 Hz, 1H), 7.12 (d, J = 7.3 Hz, 1H), 6.16 (d, J = 7.3 Hz, 1H), 5.38-5.35 (m, 1H), 4.60 (d, J = 15.0 Hz, 1H), 4.55 (d, J = 15.0 Hz, 1H), 4.41 (t, J = 6.7 Hz, 2H), 3.33-3.29 (m, 2H), 3.00 (t, J = 6.9 Hz, 2H), 2.84-2.68 (m, 2H), 2.62 (t, J = 6.3 Hz, 2H), 1.84-1.74 (m, 2H). LCMS (ES): m/z 475.2 [M + H]$^+$. Human αVβ6 IC50 (nM) = 30. | Same method as for Example 9 |
| 54 | 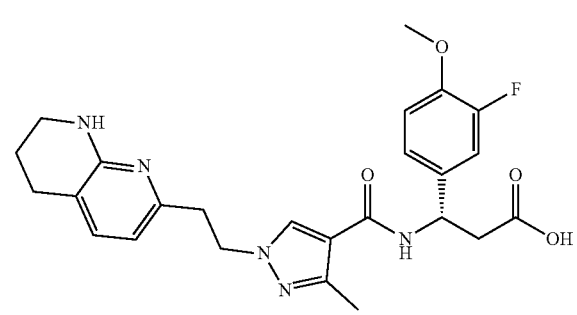<br>(S)-3-(3-Fluoro-4-methoxyphenyl)-3-(3-methyl-1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.12 (s, 1H), 7.20 (d, J = 12.6 Hz, 1H), 7.16-6.97 (m, 3H), 6.24 (d, J = 7.2 Hz, 1H), 5.33-5.23 (m, 1H), 4.29 (t, J = 7.6 Hz, 2H), 3.82 (s, 3H), 3.31-3.20 (m, 2H), 2.95 (t, J = 7.5 Hz, 2H), 2.83-2.67 (m, 2H), 2.62 (t, J = 6.1 Hz, 2H), 2.28 (s, 3H), 1.82-1.71 (m,, 2H). LCMS (ES): m/z 482.5 [M + H]$^+$. Human αVβ6 IC50 (nM) = 30. | Same method as for Example 3 By using intermediate 18 |
| 55 | 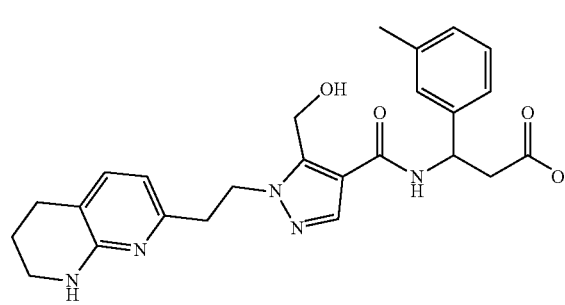<br>3-(5-(Hydroxymethyl)-1-(2-(5,6,7,8-tetrahydro-1,8-naphthyridin-2-yl)ethyl)-1H-pyrazole-4-carboxamido)-3-(m-tolyl)propanoic acid | $^1$H NMR (500 MHz, Methanol-d$_4$) δ 7.90 (s, 1H), 7.26-7.15 (m, 4H), 7.07 (d, J = 6.7 Hz, 1H), 6.22 (d, J = 7.3 Hz, 1H), 5.47 (dd, J = 8.6, 5.8 Hz, 1H), 4.67 (d, J = 13.7 Hz, 1H), 4.63 (d, J = 13.7 Hz, 1H), 4.49 (t, J = 6.8 Hz, 2H), 3.42 (t, J = 5.6 Hz, 2H), 3.08 (t, J = 6.8 Hz, 2H), 2.86 (dd, J = 15.2, 8.6 Hz, 1H), 2.79 (dd, J = 15.2, 5.8 Hz, 1H), 2.72 (t, J = 6.3 Hz, 2H), 2.34 (s, 3H), 1.89 (p, J = 6.1 Hz, 2H). LCMS (ES): m/z 464.3 [M + H]$^+$. Human αVβ6 IC50 (nM) = 32. | Same method as for Example 9 |

TABLE A-continued

| Example No. | Structure | Data | Method |
|---|---|---|---|
| 56 | 3-(Benzo[d][1,3]dioxol-5-yl)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-$d_6$) δ 8.34 (d, J = 8.5 Hz, 1H), 8.11 (s, 1H), 7.86 (s, 1H), 7.19 (s, 1H), 6.95 (s, 1H), 6.85 (d, J = 8.0 Hz, 1H), 6.82 (d, J = 8.1 Hz, 1H), 6.31 (d, J = 7.2 Hz, 1H), 5.98 (d, J = 4.5 Hz, 2H), 5.29 (q, J = 8.0 Hz, 1H), 4.42 (t, J = 7.2 Hz, 2H), 3.34-3.25 (m, 1H, one proton missing due to H$_2$O suppression), 3.04 (t, J = 6.8 Hz, 2H), 2.78 (dd, J = 15.6, 8.5 Hz, 1H), 2.70 (dd, J = 15.6, 6.6 Hz, 1H), 2.65 (t, J = 6.2 Hz, 2H), 1.78 (t, J = 6.1 Hz, 2H). LCMS (ES): m/z 464.3 [M + H]$^+$. Human αVβ6 IC50 (nM) = 37. | Same method as for Example 16 |
| 57 | 3-(3,4-Dichlorophenyl)-3-(3,5-dimethyl-1-(2-(5,6,7,8-tetrahydro-1,8-naphthyridin-2-yl)ethyl)-1H-pyrazole-4-carboxamido)propanoic acid | $^1$H NMR (500 MHz, DMSO-$d_6$) δ 8.03 (d, J = 8.1 Hz, 1H), 7.64 (s, 1H), 7.61 (d, J = 8.4 Hz, 1H), 7.57 (d, J = 7.3 Hz, 1H), 7.39 (d, J = 8.3 Hz, 1H), 6.56 (d, J = 7.3 Hz, 1H), 5.29 (q, J = 7.7 Hz, 1H), 4.28 (t, J = 7.3 Hz, 2H), 3.51-3.25 (two protons missing due to H$_2$O suppression), 3.11 (t, J = 7.3 Hz, 2H), 2.88-2.77 (m, 2H), 2.74 (t, J = 6.2 Hz, 2H), 2.27 (s, 3H), 2.20 (s, 3H), 1.83 (p, J = 6.0 Hz, 2H). LCMS (ES): m/z 516.1 [M + H]$^+$. Human αVβ6 IC50 (nM) = 40. | Same method as for Example 3 By using intermediate 20 |
| 58 | 3-(3,4-Dichlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-$d_4$) δ 7.78 (s, 1H), 7.45 (d, J = 2.2 Hz, 1H), 7.35 (d, J = 8.4 Hz, 1H), 7.23 (dd, J = 8.4, 2.2 Hz, 1H), 7.06 (d, J = 7.3 Hz, 1H), 6.09 (d, J = 7.3 Hz, 1H), 5.31 (t, J = 7.1 Hz, 1H), 4.56 (d, J = 13.7 Hz, 1H), 4.51 (d, J = 13.6 Hz, 1H), 4.37 (t, J = 6.8 Hz, 2H), 3.29 (t, J = 5.6 Hz, 2H), 2.96 (t, J = 6.8 Hz, 2H), 2.73-2.62 (m, 2H), 2.60 (t, J = 6.3 Hz, 2H), 1.77 (p, J = 6.1 Hz, 2H). LCMS (ES): m/z 518.2 [M + H]$^+$. Human αVβ6 IC50 (nM) = 40. | Same method as for Example 9 |
| 59 | 3-(5-(tert-Butoxymethyl)-1-(3-(5,6,7,8-tetrahydro-1,8-naphthyridin-2-yl)propyl)-1H-pyrazole-4-carboxamido)-3-(3,5-dichlorophenyl)propanoic acid | $^1$H NMR (500 MHz, DMSO-$d_6$) δ 8.46 (d, J = 7.9 Hz, 1H), 7.94 (s, 1H), 7.48 (d, J = 2.0 Hz, 1H), 7.43 (d, J = 2.0 Hz, 2H), 7.04 (d, J = 7.3 Hz, 1H), 6.27 (d, J = 6.8 Hz, 1H), 5.36-5.29 (m, 1H), 4.72 (d, J = 11.4 Hz, 1H), 4.67 (d, J = 11.4 Hz, 1H), 4.09 (t, J = 7.3 Hz, 2H), 3.27-3.20 (m, 2H), 2.85 (dd, J = 16.0, 8.4 Hz, 1H), 2.79 (dd, J = 16.0, 6.6 Hz, 1H), 2.61 (t, J = 6.3 Hz, 2H), 2.46 (t, J = 7.4 Hz, 2H), 2.20-2.04 (m, 2H), 1.81-1.70 (m, 2H), 1.12 (s, 9H). LCMS (ES): m/z 588.5 [M + H]$^+$. Human αVβ6 IC50 (nM) = 40. | Same method as for Example 5 |

TABLE A-continued

| Example No. | Structure | Data | Method |
|---|---|---|---|
| 60 | (S)-3-(3,5-Dichlorophenyl)-3-(1-(3-(5,6,7,8-tetrahydro-1,8-naphthyridin-2-yl)propyl)-1H-pyrazole-4-carboxamido)propanoic acid | $^1$H NMR (500 MHz, Methanol-d$_4$) δ 8.16 (d, J = 0.7 Hz, 1H), 7.93 (d, J = 0.7 Hz, 1H), 7.40 (d, J = 1.9 Hz, 2H), 7.35 (d, J = 7.3 Hz, 1H), 7.31 (t, J = 1.9 Hz, 1H), 6.47 (d, J = 7.3 Hz, 1H), 5.43 (t, J = 7.2 Hz, 1H), 4.24 (t, J = 6.5 Hz, 2H), 3.40 (td, J = 5.2, 1.7 Hz, 2H), 2.83-2.73 (m, 2H), 2.71 (t, J = 6.3 Hz, 2H), 2.61 (t, J = 7.5 Hz, 2H), 2.30-2.17 (m, 2H), 1.93-1.83 (m, 2H). LCMS (ES): m/z 502.2 [M + H]$^+$. Human αVβ6 IC50 (nM) = 46. | Same method as for Example 16 By using intermediate 5 |
| 61 | (S)-3-(3-Bromo-5-(tert-butyl)phenyl)-3-(1-(3-(5,6,7,8-tetrahydro-1,8-naphthyridin-2-yl)propyl)-1H-pyrazole-4-carboxamido)propanoic acid | $^1$H NMR (500 MHz, Methanol-d$_4$) δ 8.14 (s, 1H), 7.91 (s, 1H), 7.47 (t, J = 1.7 Hz, 1H), 7.42 (d, J = 1.7 Hz, 2H), 7.33 (d, J = 7.3 Hz, 1H), 6.46 (d, J = 7.3 Hz, 1H), 5.47 (dd, J = 8.0, 6.5 Hz, 1H), 4.23 (t, J = 6.5 Hz, 2H), 3.43-3.35 (m, 2H), 2.80 (d, J = 8.0 Hz, 1H), 2.75 (t, J = 6.5 Hz, 2H), 2.70 (t, J = 6.3 Hz, 2H), 2.61 (t, J = 7.5 Hz, 2H), 2.23 (pd, J = 6.9, 2.4 Hz, 2H), 1.93-1.80 (m, 2H), 1.30 (s, 9H). LCMS (ES): m/z 468.4 [M + H]$^+$. Human αVβ6 IC50 (nM) = 49. | Same method as for Example 16 By using intermediate 5 |
| 62 | 3-(5-(Hydroxymethyl)-1-(2-(5,6,7,8-tetrahydro-1,8-naphthyridin-2-yl)ethyl)-1H-pyrazole-4-carboxamido)-3-(4-(trifluoromethyl)phenyl)propanoic acid | $^1$H NMR (500 MHz, Methanol-d$_4$) δ 7.78 (s, 1H), 7.52 (d, J = 8.5 Hz, 2H), 7.49 (d, J = 8.5 Hz, 2H), 7.08 (d, J = 7.3 Hz, 1H), 6.10 (d, J = 7.3 Hz, 1H), 5.43 (dd, J = 8.2, 5.9 Hz, 1H), 4.58 (d, J = 13.6 Hz, 1H), 4.51 (d, J = 13.6 Hz, 1H), 4.37 (t, J = 6.8 Hz, 2H), 3.30 (t, J = 5.6 Hz, 2H), 2.97 (t, J = 6.8 Hz, 2H), 2.81-2.66 (m, 2H), 2.60 (t, J = 6.3 Hz, 2H), 1.77 (p, J = 6.1 Hz, 2H). LCMS (ES): m/z 518.3 [M + H]$^+$. Human αVβ6 IC50 (nM) = 49. | Same method as for Example 9 |
| 63 | (S)-3-(3-Bromo-5-(tert-butyl)phenyl)-3-(1-(2-(5,6,7,8-tetrahydro-1,8-naphthyridin-2-yl)ethyl)-3-(trifluoromethyl)-1H-pyrazole-4-carboxamido)propanoic acid | $^1$H NMR (500 MHz, Methanol-d$_4$) δ 8.16 (s, 1H), 7.53 (d, J = 7.3 Hz, 1H), 7.46 (s, 1H), 7.43 (s, 1H), 7.38 (s, 1H), 6.50 (d, J = 7.3 Hz, 1H), 5.45 (t, J = 7.2 Hz, 1H), 4.60 (t, J = 6.7 Hz, 2H), 3.51 (t, J = 5.7 Hz, 2H), 3.29 (t, J = 6.7 Hz, 2H), 2.97-2.84 (m, 2H), 2.82 (t, J = 6.4 Hz, 2H), 2.03-1.90 (m, 2H), 1.33 (s, 9H). LCMS (ES): m/z 622.2 [M + H]$^+$. Human αVβ6 IC50 (nM) = 56. | Same method as for Example 16 By using intermediate 14 |

TABLE A-continued

| Example No. | Structure | Data | Method |
|---|---|---|---|
| 64 | 3-(3-(1H-pyrrol-1-yl)phenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-$d_4$) δ 7.93 (s, 1H), 7.53 (s, 1H), 7.41 (d, J = 7.9 Hz, 1H), 7.36 (d, J = 7.9 Hz, 1H), 7.31 (d, J = 7.9 Hz, 1H), 7.19 (s, 2H), 7.12 (d, J = 7.4 Hz, 1H), 6.28 (s, 2H), 6.19 (d, J = 7.4 Hz, 1H), 5.56-5.49 (m, 1H), 4.63 (s, 2H), 4.51 (t, J = 6.9 Hz, 2H), 3.43-3.36 (m, 2H), 3.05 (t, J = 7.1 Hz, 2H), 2.92-2.83 (m, 2H), 2.71-2.68 (m, 2H), 1.90-1.82 (m, 2H). LCMS (ES): m/z 515.4 [M + H]$^+$. Human αVβ6 IC50 (nM) = 64. | Same method as for Example 9 |
| 65 | 3-(Benzo[d][1,3]dioxol-5-yl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, DMSO-$d_6$) δ 8.45 (d, J = 8.4 Hz, 1H), 7.95 (s, 1H), 7.02 (d, J = 7.3 Hz, 1H), 6.97 (s, 1H), 6.89-6.79 (m, 2H), 6.38 (s, 1H), 6.19 (d, J = 7.3 Hz, 1H), 5.99 (d, J = 3.7 Hz, 2H), 5.31 (q, J = 7.9 Hz, 1H), 4.71 (d, J = 13.5 Hz, 1H), 4.67 (d, J = 13.5 Hz, 1H), 4.41 (t, J = 7.5 Hz, 2H), 3.32-3.21 (m, 2H), 2.94 (t, J = 7.5 Hz, 2H), 2.81 (dd, J = 15.6, 8.6 Hz, 1H), 2.71 (dd, J = 15.6, 6.5 Hz, 1H), 2.61 (t, J = 6.3 Hz, 2H), 1.75 (q, J = 6.0 Hz, 2H). LCMS (ES): m/z 494.3 [M + H]$^+$. Human αVβ6 IC50 (nM) = 64. | Same method as for Example 9 |
| 66 | 3-(5-(Hydroxymethyl)-1-(2-(5,6,7,8-tetrahydro-1,8-naphthyridin-2-yl)ethyl)-1H-pyrazole-4-carboxamido)-3-(p-tolyl)propanoic acid | $^1$H NMR (500 MHz, Methanol-$d_4$) δ 7.90 (s, 1H), 7.29 (d, J = 7.7 Hz, 2H), 7.18 (d, J = 7.0 Hz, 1H), 7.15 (d, J = 7.7 Hz, 2H), 6.24 (d, J = 7.0 Hz, 1H), 5.52-5.41 (m, 1H), 4.66 (s, 2H), 4.54-4.48 (m, 2H), 3.44-3.40 (m, 2H), 3.11-3.05 (m, 2H), 2.93-2.77 (m, 2H), 2.75-2.70 (m, 2H), 2.32 (s, 3H), 1.95-1.85 (m, 2H). LCMS (ES): m/z 464.3 [M + H]$^+$. Human αVβ6 IC50 (nM) = 91. | Same method as for Example 9 |
| 67 | 3-(4-Chlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-$d_4$) δ 7.92 (s, 1H), 7.40 (d, J = 8.2 Hz, 2H), 7.32 (d, J = 8.2 Hz, 2H), 7.12 (d, J = 7.4 Hz, 1H), 6.18 (d, J = 7.4 Hz, 1H), 5.44 (t, J = 7.2 Hz, 1H), 4.63 (t, J = 14.1 Hz, 2H), 4.50 (t, J = 6.9 Hz, 2H), 3.40 (t, J = 5.6 Hz, 2H), 3.05 (t, J = 6.9 Hz, 2H), 2.82-2.73 (m, 2H), 2.71 (t, J = 6.4 Hz, 2H), 1.88 (p, J = 5.9 Hz, 2H). LCMS (ES): m/z 484.2 [M + H]$^+$. Human αVβ6 IC50 (nM) = 95. | Same method as for Example 9 |

TABLE A-continued

| Example No. | Structure | Data | Method |
|---|---|---|---|
| 68 | 3-(3,5-Dichlorophenyl)-3-(5-(hydroxymethyl)-1-(3-(5,6,7,8-tetrahydro-1,8-naphthyridin-2-yl)propyl)-1H-pyrazole-4-carboxamido)propanoic acid | $^1$H NMR (500 MHz, DMSO-d$_6$) δ 8.57 (d, J = 7.9 Hz, 1H), 7.97 (s, 1H), 7.56 (d, J = 7.3 Hz, 1H), 7.51 (d, J = 2.0 Hz, 1H), 7.44 (d, J = 2.0 Hz, 2H), 6.60 (d, J = 7.3 Hz, 1H), 5.33 (q, J = 7.7 Hz, 1H), 4.81 (d, J = 13.2 Hz, 1H), 4.78 (d, J = 13.2 Hz, 1H), 4.21 (t, J = 6.8 Hz, 2H), 3.42-3.33 (two protons missing due to H$_2$O supression), 2.86 (dd, J = 16.4, 8.9 Hz, 1H), 2.80 (dd, J = 16.4, 7.7 Hz, 1H), 2.70 (t, J = 6.2 Hz, 2H), 2.67 (t, J = 7.7 Hz, 2H), 2.22-2.10 (m, 2H), 1.86-1.75 (m, 2H). LCMS (ES): m/z 532.5 [M + H]$^+$. Human αVβ6 IC50 (nM) = 98. | Same method as for Example 6 |
| 69 | 3-(3,5-Dichlorophenyl)-3-(5-phenyl-1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.24 (d, J = 8.0 Hz, 1H), 8.05 (s, 1H), 7.51-7.36 (m, 4H), 7.32 (d, J = 1.9 Hz, 2H), 7.17 (bs, 1H), 7.11 (d, J = 7.3 Hz, 2H), 6.06 (d, J = 7.3 Hz, 1H), 5.17 (q, J = 7.6 Hz, 1H), 4.21 (t, J = 6.7 Hz, 2H), 3.33-3.30 (m, 1H, one proton missing due to H$_2$O suppression), 2.93 (t, J = 6.3 Hz, 2H), 2.77 (dd, J = 16.0, 8.2 Hz, 1H), 2.71 (dd, J = 16.0, 6.4 Hz, 1H), 2.65 (s, J = 5.8 Hz, 2H), 1.82-1.71 (m, 2H). LCMS (ES): m/z 564.3 [M + H]$^+$. Human αVβ6 IC50 (nM) = 111. | Same method as for Example 3 By using intermediate 22 |
| 70 | 3-(3,5-Dichlorophenyl)-3-(3-methyl-1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.30 (d, J = 8.2 Hz, 1H), 8.12 (s, 1H), 7.56 (d, J = 7.4 Hz, 1H), 7.49 (s, 1H), 7.41 (s, 2H), 6.52 (d, J = 7.4 Hz, 1H), 5.32-5.24 (m, 1H), 4.38 (t, J = 7.1 Hz, 2H), 3.46-3.37 (two protons missing due to H$_2$O supression), 3.18 (t, J = 7.1 Hz, 2H), 2.88-2.75 (m, 2H), 2.73 (t, J = 6.3 Hz, 2H), 2.28 (s, 3H), 1.87-1.75 (m, 2H). LCMS (ES): m/z 502.0 [M + H]$^+$. Human αVβ6 IC50 (nM) = 112. | Same method as for Example 3 By using intermediate 18 |
| 71 | 3-(4-Fluorophenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 7.77 (s, 1H), 7.31 (dd, J = 8.8, 5.4 Hz, 2H), 7.03 (d, J = 7.3 Hz, 1H), 6.93 (t, J = 8.8 Hz, 2H), 6.07 (d, J = 7.3 Hz, 1H), 5.35 dd, J = 8.3, (6.1 Hz, 1H), 4.54 (d, J = 13.7 Hz, 1H), 4.50 (d, J = 13.7 Hz, 1H), 4.37 (t, J = 6.8 Hz, 2H), 3.29 (t, J = 5.6 Hz, 2H), 2.94 (t, J = 6.8 Hz, 2H), 2.71 (dd, J = 15.2, 8.3 Hz, 1H), 2.65 (dd, J = 15.2, 6.1 Hz, 1H), 2.59 (t, J = 6.3 Hz, 2H), 1.77 (p, J = 6.1 Hz, 2H). LCMS (ES): m/z 468.3 [M + H]$^+$. Human αVβ6 IC50 (nM) = 120. | Same method as for Example 9 |

TABLE A-continued

| Example No. | Structure | Data | Method |
|---|---|---|---|
| 72 | 3-(5-(Hydroxymethyl)-1-(2-(5,6,7,8-tetrahydro-1,8-naphthyridin-2-yl)ethyl)-1H-pyrazole-4-carboxamido)-3-phenylpropanoic acid | $^1$H NMR (500 MHz, Methanol-$d_4$) δ 7.90 (s, 1H), 7.41 (d, J = 7.7 Hz, 2H), 7.33 (t, J = 7.6 Hz, 2H), 7.25 (t, J = 7.3 Hz, 1H), 7.18 (d, J = 7.3 Hz, 1H), 6.21 (d, J = 7.3 Hz, 1H), 5.51 (dd, J = 8.6, 6.0 Hz, 1H), 4.67 (d, J = 13.6 Hz, 1H), 4.62 (d, J = 13.6 Hz, 1H), 4.49 (t, J = 6.8 Hz, 2H), 3.42 (t, J = 5.6 Hz, 2H), 3.08 (t, J = 6.9 Hz, 2H), 2.87 (dd, J = 15.5, 8.6 Hz, 1H), 2.81 (dd, J = 15.4, 6.0 Hz, 1H), 2.72 (t, J = 6.3 Hz, 2H), 1.94-1.80 (m, 2H). LCMS (ES): m/z 450.3 [M + H]$^+$. Human αVβ6 IC50 (nM) = 124. | Same method as for Example 9 |
| 73 | 3-(5-(Hydroxymethyl)-1-(2-(5,6,7,8-tetrahydro-1,8-naphthyridin-2-yl)ethyl)-1H-pyrazole-4-carboxamido)-3-(4-methoxyphenyl)propanoic acid | $^1$H NMR (500 MHz, DMSO-$d_6$) δ 8.60 (d, J = 8.4 Hz, 1H), 7.94 (s, 1H), 7.29 (d, J = 8.2 Hz, 2H), 7.02 (d, J = 7.3 Hz, 1H), 6.88 (d, J = 8.3 Hz, 2H), 6.36 (bs, 1H), 6.19 (d, J = 7.2 Hz, 1H), 5.33 (dd, J = 8.2, 6.4 Hz, 1H), 4.70 (d, J = 14.3 Hz, 1H), ), 4.66 (d, J = 14.3 Hz, 1H), 4.40 (t, J = 7.5 Hz, 2H), 3.74 (s, 3H), 3.30-3.22 (two protons missing due to H$_2$O suppression), 2.93 (t, J = 7.6 Hz, 2H), 2.79 (dd, J = 15.7, 8.2 Hz, 1H), 2.69 (dd, J = 15.7, 6.4 Hz, 1H), 2.61 (t, J = 6.2 Hz, 2H), 1.84-1.68 (m, 2H). LCMS (ES): m/z 480.3 [M + H]$^+$. Human αVβ6 IC50 (nM) = 124. | Same method as for Example 9 |
| 74 | (S)-3-(3-Fluoro-4-methoxyphenyl)-3-(1-(3-(5,6,7,8-tetrahydro-1,8-naphthyridin-2-yl)propyl)-1H-pyrazole-4-carboxamido)propanoic acid | $^1$H NMR (500 MHz, Methanol-$d_4$) δ 8.14 (s, 1H), 7.90 (s, 1H), 7.33 (d, J = 7.3 Hz, 1H), 7.22-7.11 (m, 2H), 7.08-6.97 (m, 1H), 6.44 (d, J = 7.3 Hz, 1H), 5.45 (t, J = 6.4 Hz, 1H), 4.21 (t, J = 6.8 Hz, 2H), 3.84 (s, 3H), 3.42-3.35 (m, 2H), 2.85-2.73 (m, 2H). 2.73-2.65 (m, 2H), 2.62-2.55 (m, 2H), 2.28-2.22 (m, 2H), 1.91-1.79 (m, 2H). LCMS (ES): m/z 482.4 [M + H]$^+$. Human αVβ6 IC50 (nM) = 125. | Same method as for Example 16 By using intermediate 5 |
| 75 | 3-(3-Fluorophenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-$d_4$) δ 7.79 (s, 1H), 7.22 (td, J = 8.0, 5.9 Hz, 1H), 7.11 (d, J = 7.7 Hz, 1H), 7.07-6.98 (m, 2H), 6.85 (td, J = 8.5, 2.6 Hz, 1H), 6.07 (d, J = 7.2 Hz, 1H), 5.36 (t, J = 7.0 Hz, 1H), 4.54 (d, J = 13.6 Hz, 1H), 4.50 (d, J = 13.6 Hz, 1H), 4.37 (t, J = 6.8 Hz, 2H), 3.29 (t, J = 5.4 Hz 2H), 2.94 (t, J = 6.8 Hz, 2H), 2.72-2.61 (m,, 2H), 2.59 (t, J = 6.3 Hz, 2H), 1.77 (p, J = 6.1 Hz, 2H). LCMS (ES): m/z 468.2 [M + H]$^+$. Human αVβ6 IC50 (nM) = 130. | Same method as for Example 9 |

TABLE A-continued

| Example No. | Structure | Data | Method |
|---|---|---|---|
| 76 | 3-(3,4-Dimethoxyphenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.45 (d, J = 8.4 Hz, 1H), 7.94 (s, 1H), 7.06-6.98 (m, 2H), 6.92-6.86 (m, 2H), 6.37 (bs, 1H), 6.19 (d, J = 7.2 Hz, 1H), 5.33 (dd, J = 8.7, 6.4 Hz, 1H), 4.70 (d, J = 13.7 Hz, 1H), 4.66 (d, J = 13.7 Hz, 1H), 4.40 (t, J = 7.5 Hz, 2H), 3.76 (s, 3H), 3.73 (s, 3H), 3.41-3.30 (two protons missing due to H$_2$O suppression), 2.93 (t, J = 7.5 Hz, 2H), 2.81 (dd, J = 15.5, 8.7 Hz, 1H), 2.72 (dd, J = 15.5, 6.4 Hz, 1H), 2.61 (t, J = 6.3 Hz, 2H), 1.75 (t, J = 6.0 Hz, 2H). LCMS (ES): m/z 510.3 [M + H]$^+$. Human αVβ6 IC50 (nM) = 131. | Same method as for Example 9 |
| 77 | 3-(3,5-Dimethyl-1-(2-(5,6,7,8-tetrahydro-1,8-naphthyridin-2-yl)ethyl)-1H-pyrazole-4-carboxamido)-3-(4-(trifluoromethyl)phenyl)propanoic acid | $^1$H NMR (500 MHz, DMSO-d$_6$) δ 8.09 (d, J = 8.1 Hz, 1H), 7.72 (d, J = 8.2 Hz, 2H), 7.62 (d, J = 8.1 Hz, 2H), 7.58 (d, J = 7.3 Hz, 1H), 6.57 (d, J = 7.3 Hz, 1H), 5.39 (dd, J = 8.6, 6.0 Hz, 1H), 4.29 (t, J = 7.3 Hz, 2H), 3.41-3.30 (two protons missing due to H$_2$O suppression), 3.11 (t, J = 7.3 Hz, 2H), 2.87 (dd, J = 16.0, 8.6 Hz, 1H), 2.81 (dd, J = 16.0, 6.0 Hz, 1H), 2.74 (t, J = 6.3 Hz, 2H), 2.28 (s, 3H), 2.21 (s, 3H), 1.83 (p, J = 6.0 Hz, 2H). LCMS (ES): m/z 516.2 [M + H]$^+$. Human αVβ6 IC50 (nM) = 134. | Same method as for Example 3 By using intermediate 20 |
| 78 | 3-(3,4-Dichlorophenyl)-3-(3-phenyl-1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.52 (d, J = 8.1 Hz, 1H), 8.17 (s, 1H), 7.66-7.55 (m, 4H), 7.48 (bs, 1H), 7.37 (d, J = 8.4 Hz, 1H), 7.35-7.28 (m, 3H), 6.53 (d, J = 7.3 Hz, 1H), 5.32 (q, J = 7.8 Hz, 1H), 4.51 (t, J = 7.2 Hz, 2H), 3.43-3.35 (two protons missing due to H$_2$O suppression), 3.27-3.16 (m, 2H), 2.89-2.65 (m, 4H), 1.86-1.75 (m, 2H). LCMS (ES): m/z 564.3 [M + H]$^+$. Human αVβ6 IC50 (nM) = 137. | Same method as for Example 3 By using intermediate 21 |

TABLE A-continued

| Example No. | Structure | Data | Method |
|---|---|---|---|
| 79 | (S)-3-(3-Fluoro-4-methoxyphenyl)-3-(3-phenyl-1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.41 (d, J = 8.4 Hz, 1H), 8.15 (s, 1H), 7.65-7.53 (m, 3H), 7.37-7.28 (m, 3H), 7.23-7.07 (m, 3H), 6.57 (d, J = 7.4 Hz, 1H), 5.30 (q, J = 7.8 Hz, 1H), 4.51 (t, J = 7.2 Hz, 2H), 3.75 (s, 3H), 3.40-3.32 (two protons missing due to H$_2$O suppression), 3.24 (t, J = 7.3 Hz, 2H), 2.84-2.62 (m, 4H), 1.88-1.78 (m, 2H). LCMS (ES): m/z 564.3 [M + H]$^+$. Human αVβ6 IC50 (nM) = 169. | Same method as for Example 3 By using intermediate 21 |
| 80 | 3-(3,5-Difluorophenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 7.81 (s, 1H), 7.01 (d, J = 7.3 Hz, 1H), 6.90 (d, J = 7.6 Hz, 2H), 6.69 (t, J = 9.2 Hz, 1H), 6.06 (d, J = 7.3 Hz, 1H), 5.31 (t, J = 6.9 Hz, 1H), 4.54 (d, J = 13.6 Hz, 1H), 4.50 (d, J = 13.8 Hz, 1H), 4.38 (t, J = 6.8 Hz, 2H), 3.29 (t, J = 5.6 Hz, 2H), 2.94 (t, J = 6.8 Hz, 2H), 2.63 (d, J = 6.9 Hz, 2H), 2.59 (t, J = 6.3 Hz, 2H), 1.81-1.71 (m, 2H). LCMS (ES): m/z 486.3 [M + H]$^+$. Human αVβ6 IC50 (nM) = 178. | Same method as for Example 9 |
| 81 | (S)-3-(1-(2-(2-Methyl-5,6,7,8-tetrahydro-1,8-naphthyridin-3-yl)ethyl)-1H-pyrazole-4-carboxamido)-2-((2,4,6-trimethylphenyl)sulfonamido)propanoic acid | $^1$H NMR (400 MHz, Methanol-d$_4$) δ 7.83 (d, J = 1.2 Hz, 2H), 7.31 (d, J = 1.3 Hz, 1H), 6.94 (s, 2H), 4.40 (td, J = 6.2, 1.6 Hz, 2H), 4.07 (dd, J = 9.0, 4.8 Hz, 1H), 3.76-3.63 (m, 1H), 3.48-3.43 (m, 2H), 3.40-3.37 (m, 1H), 3.07 (t, J = 6.4 Hz, 2H), 2.76 (t, J = 6.2 Hz, 2H), 2.62 (s, 6H), 2.26 (s, 3H), 2.20 (s, 3H), 2.00-1.83 (m, 2H). LCMS (ES): m/z 555.3 [M + H]$^+$. Human αVβ6 IC50 (nM) = 215. | Same method as for Example 5 |

TABLE A-continued

| Example No. | Structure (name) | Data | Method |
|---|---|---|---|
| 82 | 3-(3,5-Dichlorophenyl)-3-(3-phenyl-1-(2-(5,6,7,8-tetrahydro-1,8-naphthyridin-2-yl)ethyl)-1H-pyrazole-4-carboxamido)propanoic acid | $^1$H NMR (500 MHz, DMSO-$d_6$) δ 8.53 (d, J = 8.1 Hz, 1H), 8.18 (s, 1H), 7.68-7.53 (m, 3H), 7.51 (s, 1H), 7.42 (s, 2H), 7.38-7.28 (m, 3H), 6.57 (d, J = 7.3 Hz, 1H), 5.31 (q, J = 7.7 Hz, 1H), 4.52 (t, J = 7.0 Hz, 2H), 3.44-3.37 (two protons missing due to H$_2$O suppression), 3.24 (t, J = 7.0 Hz, 2H), 2.85-2.68 (m, 4H), 1.89-1.72 (m, 2H). LCMS (ES): m/z 564.3 [M + H]$^+$. Human αVβ6 IC50 (nM) = 244. | Same method as for Example 3 By using intermediate 21 |
| 83 | 3-(3,5-Dichlorophenyl)-3-(3,5-dimethyl-1-(2-(5,6,7,8-tetrahydro-1,8-naphthyridin-2-yl)ethyl)-1H-pyrazole-4-carboxamido)propanoic acid | $^1$H NMR (500 MHz, DMSO-$d_6$) δ 8.03 (d, J = 8.2 Hz, 1H), 7.57 (d, J = 7.3 Hz, 1H), 7.50 (d, J = 2.0 Hz, 1H), 7.45 (d, J = 2.0 Hz, 2H), 6.57 (d, J = 7.2 Hz, 1H), 5.37-5.14 (m, 1H), 4.28 (t, J = 7.3 Hz, 2H),), 3.44-3.37 (two protons missing due to H$_2$O suppression), 3.11 (t, J = 7.1 Hz, 2H), 2.89-2.77 (m, 2H), 2.73 (t, J = 6.3 Hz, 2H), 2.27 (s, 3H), 2.21 (s, 3H), 1.82 (s, 2H). LCMS (ES): m/z 516.1 [M + H]$^+$. Human αVβ6 IC50 (nM) = 278. | Same method as for Example 3 By using intermediate 20 |
| 84 | 3-(3-(tert-Butoxymethyl)-1-(2-(5,6,7,8-tetrahydro-1,8-naphthyridin-2-yl)ethyl)-1H-pyrazole-4-carboxamido)-3-(3,4-dichlorophenyl)propanoic acid | $^1$H NMR (500 MHz, DMSO-$d_6$) δ 8.44 (d, J = 7.9 Hz, 1H), 8.09 (s, 1H), 7.60 (d, J = 8.3 Hz, 1H), 7.57 (s, 1H), 7.51 (d, J = 7.4 Hz, 1H), 7.34 (d, J = 8.3 Hz, 1H), 6.50 (d, J = 7.4 Hz, 1H), 5.41-5.16 (m, 1H), 4.49 (s, 2H), 4.41 (t, J = 7.1 Hz, 2H), 3.38 (t, J = 5.6 Hz, 2H), 3.16 (t, J = 7.2 Hz, 2H), 2.92-2.73 (m, 2H), 2.70 (t, J = 6.1 Hz, 2H), 1.85-1.74 (s, 2H), 1.12 (s, 9H). LCMS (ES): m/z 574.4 [M + H]$^+$. Human αVβ6 IC50 (nM) = 284. | Same method as for Example 9 |
| 85 | 2-Phenyl-3-(1-(2-(5,6,7,8-tetrahydro-1,8-naphthyridin-2-yl)ethyl)-1H-pyrazole-4-carboxamido)propanoic acid | $^1$H NMR (500 MHz, Methanol-$d_4$) δ 7.88 (d, J = 0.7 Hz, 1H), 7.82 (d, J = 0.7 Hz, 1H), 7.42-7.35 (m, 2H), 7.35-7.29 (m, 2H), 7.29-7.21 (m, 1H), 7.17 (d, J = 7.3 Hz, 1H), 6.24 (d, J = 7.3 Hz, 1H), 4.45 (t, J = 6.9 Hz, 2H), 3.93 (dd, J = 8.4, 6.6 Hz, 1H), 3.70 (dd, J = 13.3, 8.4 Hz, 1H), 3.66 (dd, J = 13.3, 6.6 Hz, 1H), 3.44-3.37 (m, 2H), 3.08 (t, J = 6.9 Hz, 2H), 2.72 (t, J = 6.3 Hz, 2H), 1.93-1.85 (m, 2H). LCMS (ES): m/z 420.3 [M + H]$^+$. Human αVβ6 IC50 (nM) = 321. | Same method as for Example 16 |

TABLE A-continued

| Example No. | Structure | Data | Method |
|---|---|---|---|
| 86 | (S)-3-(3,5-Dichlorophenyl)-3-(1-(2-(5,6,7,8-tetrahydro-1,8-naphthyridin-2-yl)ethyl)-3-(trifluoromethyl)-1H-pyrazole-4-carboxamido)propanoic acid | $^1$H NMR (500 MHz, Methanol-$d_4$) δ 8.19 (s, 1H), 7.53 (d, J = 7.3 Hz, 1H), 7.38 (d, J = 2.0 Hz, 2H), 7.37 (d, J = 2.0 Hz, 1H), 6.49 (d, J = 7.3 Hz, 1H), 5.41 (t, J = 7.2 Hz, 1H), 4.60 (t, J = 6.7 Hz, 2H), 3.51 (t, J = 5.9 Hz, 2H), 3.30 (t, J = 7.2 Hz, 2H), 2.92 (dd, J = 16.0, 8.3 Hz, 1H), 2.87 (dd, J = 16.0, 6.7 Hz, 1H), 2.82 (t, J = 6.2 Hz, 2H), 1.95 (p, J = 6.3 Hz, 2H). LCMS (ES): m/z 504.3 [M + H]$^+$. Human αVβ6 IC50 (nM) = 331. | Same method as for Example 16 By using intermediate 14 |
| 87 | (S)-3-(6-Methoxypyridin-3-yl)-3-(1-(3-(5,6,7,8-tetrahydro-1,8-naphthyridin-2-yl)propyl)-1H-pyrazole-4-carboxamido)propanoic acid | $^1$H NMR (500 MHz, Methanol-$d_4$) δ 8.19 (d, J = 2.5 Hz, 1H), 8.12 (s, 1H), 7.90 (s, 1H), 7.76 (dd, J = 8.6, 2.5 Hz, 1H), 7.34 (d, J = 7.3 Hz, 1H), 6.77 (d, J = 8.6 Hz, 1H), 6.46 (d, J = 7.3 Hz, 1H), 5.47 (t, J = 7.2 Hz, 1H), 4.23 (t, J = 6.6 Hz, 2H), 3.89 (s, 3H), 3.40 (td, J = 5.3, 2.1 Hz, 2H), 2.87 (dd, J = 15.1, 8.0 Hz, 1H), 2.80 (dd, J = 15.1, 6.6 Hz, 1H), 2.71 (t, J = 6.3 Hz, 2H), 2.61 (t, J = 7.5 Hz, 2H), 2.24 (p, J = 7.5 Hz, 2H), 1.88 (q, J = 6.6 Hz, 2H). LCMS (ES): m/z 465.4 [M + H]$^+$. Human αVβ6 IC50 (nM) = 339. | Same method as for Example 16 By using intermediate 5 |
| 88 | (S)-3-(1-(3-((4,5-Dihydro-1H-imidazol-2-yl)amino)propyl)-1H-pyrazole-4-carboxamido)-3-(6-methoxypyridin-3-yl)propanoic acid | $^1$H NMR (500 MHz, Methanol-$d_4$) δ 8.18 (d, J = 2.5 Hz, 1H), 8.09 (s, 1H), 7.97 (s, 1H), 7.76 (dd, J = 8.7, 2.6 Hz, 1H), 6.81 (d, J = 8.6 Hz, 1H), 5.51 (t, J = 7.5 Hz, 1H), 4.27 (t, J = 6.6 Hz, 2H), 3.91 (s, 3H), 3.71 (s, 4H), 3.21 (t, J = 6.8 Hz, 2H), 2.99 (dd, J = 15.9, 8.2 Hz, 1H), 2.90 (dd, J = 15.8, 6.8 Hz, 1H), 2.14 (p, J = 6.7 Hz, 2H). LCMS (ES): m/z 416.3 [M + H]$^+$. Human αVβ6 IC50 (nM) = 378. | Same method as for Example 8 |
| 89 | 5-Methyl-3-(1-(2-(5,6,7,8-tetrahydro-1,8-naphthyridin-2-yl)ethyl)-1H-pyrazole-4-carboxamido)hexanoic acid | $^1$H NMR (500 MHz, Methanol-$d_4$) δ 7.91 (s, 1H), 7.88 (s, 1H), 7.14 (d, J = 7.3 Hz, 1H), 6.22 (d, J = 7.3 Hz, 1H), 4.53-4.47 (m, 1H), 4.45 (t, J = 6.9 Hz, 2H), 3.41 (t, J = 5.6 Hz, 2H), 3.07 (t, J = 6.9 Hz, 2H), 2.71 (t, J = 6.4 Hz, 2H), 2.55-2.41 (m, 2H), 1.89 (p, J = 6.3 Hz, 2H), 1.75-1.53 (m, 2H), 1.49-1.31 (m, 1H), 0.96 (t, J = 6.9 Hz, 6H). LCMS (ES): m/z 400.3 [M + H]$^+$. Human αVβ6 IC50 (nM) = 399. | Same method as for Example 16 |

TABLE A-continued

| Example No. | Structure | Data | Method |
|---|---|---|---|
| 90 | 5-Phenyl-3-(1-(2-(5,6,7,8-tetrahydro-1,8-naphthyridin-2-yl)ethyl)-1H-pyrazole-4-carboxamido)pentanoic acid | $^1$H NMR (500 MHz, Methanol-$d_4$) δ 7.82 (s, 1H), 7.78 (s, 1H), 7.15-7.10 (m, 3H), 7.10-7.06 (m, 2H), 7.06-7.04 (m, 1H), 6.20 (d, J = 7.2 Hz, 1H), 4.37 (t, J = 6.8 Hz, 2H), 4.33-4.23 (m, 1H), 3.31 (t, J = 5.7 Hz, 2H), 3.02 (d, J = 6.8 Hz, 2H), 2.65-2.51 (m, 4H), 2.49-2.43 (m, 2H), 1.87-1.71 (m, 4H). LCMS (ES): m/z 448.3 [M + H]$^+$. Human αVβ6 IC50 (nM) = 401. | Same method as for Example 16 |
| 91 | (S)-3-(3-Fluoro-4-methoxyphenyl)-3-(5-phenyl-1-(2-(5,6,7,8-tetrahydro-1,8-naphthyridin-2-yl)ethyl)-1H-pyrazole-4-carboxamido)propanoic acid | $^1$H NMR (500 MHz, DMSO-$d_6$) δ 8.11 (d, J = 8.3 Hz, 1H), 8.05 (s, 1H), 7.46-7.36 (m, 3H), 7.27 (bs, 1H), 7.13-6.96 (m, 5H), 6.09 (d, J = 7.4 Hz, 1H), 5.16 (q, J = 7.7 Hz, 1H), 4.29-4.19 (m, 2H), 3.80 (s, 3H), 3.37-3.29 (m, 1H, one proton missing due to H$_2$O suppression), 3.00-2.90 (m, 2H), 2.77-2.61 (m, 4H), 1.84-1.73 (m, 2H). LCMS (ES): m/z 544.3 [M + H]$^+$. Human αVβ6 IC50 (nM) = 410. | Same method as for Example 3 By using intermediate 22 |
| 92 | (S)-3-(5-(Hydroxymethyl)-1-(2-(5,6,7,8-tetrahydro-1,8-naphthyridin-2-yl)ethyl)-1H-pyrazole-4-carboxamido)-3-(o-tolyl)propanoic acid | $^1$H NMR (500 MHz, Methanol-$d_4$) δ 7.89 (s, 1H), 7.38 (d, J = 7.3 Hz, 1H), 7.23-7.11 (m, 4H), 6.21 (d, J = 7.3 Hz, 1H), 5.73 (dd, J = 8.6, 5.9 Hz, 1H), 4.65 (d, J = 13.5 Hz, 1H), 4.62 (d J = 13.5 Hz, 1H), 4.49 (t, J = 7.0 Hz, 2H), 3.42 (t, J = 5.6 Hz, 2H), 3.07 (t, J = 6.8 Hz, 2H), 2.82 (dd, J = 15.4, 8.6 Hz, 1H), 2.75 (dd, J = 15.4, 5.9 Hz, 1H), 2.72 (t, J = 6.2 Hz, 2H), 2.50 (s, 3H), 1.90 (q, J = 5.9 Hz, 2H). LCMS (ES): m/z 464.3 [M + H]$^+$. Human αVβ6 IC50 (nM) = 416. | Same method as for Example 9 |
| 93 | (R)-3-(3,5-Dichlorophenyl)-3-(N-methyl-1-(2-(5,6,7,8-tetrahydro-1,8-naphthyridin-2-yl)ethyl)-1H-pyrazole-4-carboxamido)propanoic acid | $^1$H NMR (500 MHz, Methanol-$d_4$) δ 8.30-7.70 (m, 2H), 7.57-6.97 (m, 4H), 6.40-5.80 (m, 2H), 4.52-4.30 (m, 2H), 3.35-3.42 (m, 2H), 3.09-3.14 (m, 2H), 3.06-2.75 (m, 5H), 2.72-2.65 (m, 2H), 1.91-1.80 (m, 2H). LCMS (ES): m/z 502.2 [M + H]$^+$. Human αVβ6 IC50 (nM) = 446. | Same method as for Example 16 By using intermediate 29 |

TABLE A-continued

| Example No. | Structure | Data | Method |
|---|---|---|---|
| 94 | (S)-3-(6-Methoxypyridin-3-yl)-3-(1-(3-(pyridin-2-ylamino)propyl)-1H-pyrazole-4-carboxamido)propanoic acid | $^1$H NMR (500 MHz, DMSO-d$_6$) δ 8.16 (d, J = 2.4 Hz, 1H), 8.10 (s, 1H), 7.92 (s, 1H), 7.88 (d, J = 5.4 Hz, 1H), 7.74 (dd, J = 8.6, 2.4 Hz, 1H), 7.47 (t, J = 7.9 Hz, 1H), 6.77 (d, J = 8.6 Hz, 1H), 6.62-6.52 (m, 2H), 5.46 (t, J = 7.4 Hz, 1H), 4.27 (t, J = 6.9 Hz, 2H), 3.88 (s, 3H), 3.32-3.22 (two protons missing due to H$_2$O suppression), 2.91 (dd, J = 15.5, 7.9 Hz, 1H), 2.83 (dd, J = 15.6, 6.9 Hz, 1H), 2.16 (p, J = 6.9 Hz, 2H). LCMS (ES): m/z 425.1 [M + H]$^+$. Human αVβ6 IC50 (nM) = 592. | Same method as for Example 7 |
| 95 | 3-(3-(tert-Butoxymethyl)-1-(2-(5,6,7,8-tetrahydro-1,8-naphthyridin-2-yl)ethyl)-1H-pyrazole-4-carboxamido)-3-(4-(trifluoromethyl)phenyl)propanoic acid | $^1$H NMR (500 MHz, DMSO-d$_6$) δ 8.50 (d, J = 7.9 Hz, 1H), 8.07 (s, 1H), 7.70 (d, J = 8.1 Hz, 2H), 7.56 (d, J = 8.1 Hz, 2H), 7.50 (d, J = 7.3 Hz, 1H), 6.49 (d, J = 7.3 Hz, 1H), 5.39 (q, J = 7.7 Hz, 1H), 4.48 (s, 2H), 4.40 (t, J = 6.9 Hz, 2H), 3.41-3.32 (m, 2H), 3.14 (t, J = 7.2 Hz, 2H),), 2.86 (dd, J = 16.0, 6.3 Hz, 1H), 2.80 (dd, J = 16.0, 8.6 Hz, 1H), 2.68 (t, J = 6.6 Hz, 2H), 1.83-1.73 (m, 2H), 1.10 (s, 9H). LCMS (ES): m/z 574.5 [M + H]$^+$. Human αVβ6 IC50 (nM) = 1054. | Same method as for Example 9 |
| 96 | Methyl (S)-3-(3-bromo-5-(tert-butyl)phenyl)-3-(1-(2-(5,6,7,8-tetrahydro-1,8-naphthyridin-2-yl)ethyl)-1H-pyrazole-4-carboxamido)propanoate | $^1$H NMR (500 MHz, Methanol-d$_4$) δ 7.90 (s, 2H), 7.43 (s, 1H), 7.38 (s, 1H), 7.34 (s, 1H), 7.06 (d, J = 7.3 Hz, 1H), 6.18 (d, J = 7.3 Hz, 1H), 5.47 (t, J =7.5 Hz, 1H), 4.44 (t, J = 7.0 Hz, 2H), 3.63 (s, 3H), 3.36 (t, J = 5.6 Hz, 2H), 3.04 (t, J = 6.9 Hz, 2H), 2.93 (dd, J = 15.6, 8.8 Hz, 1H), 2.87 (dd, J = 15.6, 6.5 Hz, 1H), 2.66 (t, J = 6.2 Hz, 2H), 1.85 (p, J = 6.0 Hz, 2H), 1.30 (s, 9H). LCMS (ES): m/z 568.0 [M + H]$^+$. Human αVβ6 IC50 (nM) = 1100. | Same method as for Example 16 without hydrolysis of ester |

TABLE A-continued

| Example No. | Structure | Data | Method |
|---|---|---|---|
| 97 | (S)-3-(3,5-Dichlorophenyl)-3-(1-((5,6,7,8-tetrahydro-1,8-naphthyridin-2-yl)methyl)-1H-pyrazole-4-carboxamido)propanoic acid | $^1$H NMR (500 MHz, Methanol-$d_4$) δ 8.16 (s, 1H), 7.95 (s, 1H), 7.39 (d, J = 1.9 Hz, 2H), 7.34 (t, J = 1.9 Hz, 1H), 7.20 (d, J = 7.3 Hz, 1H), 6.32 (d, J = 7.3 Hz, 1H), 5.46 (dd, J = 8.1, 6.5 Hz, 1H), 5.19 (s, 2H), 3.44-3.37 (m, 2H), 2.88 (dd, J = 15.8, 8.1 Hz, 1H), 2.84 (dd, J = 15.8, 6.5 Hz, 1H), 2.73 (t, J = 6.3 Hz, 2H), 1.92-1.85 (m, 2H). LCMS (ES): m/z 474.3 [M + H]$^+$. Human αVβ6 IC50 (nM) = 1167. | Same method as for Example 16 By using intermediate 7 |
| 98 | (S)-3-(3-Bromo-5-(tert-butyl)phenyl)-3-(1-((5,6,7,8-tetrahydro-1,8-naphthyridin-2-yl)methyl)-1H-pyrazole-4-carboxamido)propanoic acid | $^1$H NMR (500 MHz, Methanol-$d_4$) δ 8.15 (s, 1H), 7.95 (s, 1H), 7.46-7.42 (m, 2H), 7.39 (t, J = 1.7 Hz, 1H), 7.20 (d, J = 7.3 Hz, 1H), 6.31 (d, J = 7.3 Hz, 1H), 5.49 (dd, J = 8.3, 6.4 Hz, 1H), 5.18 (s, 2H), 3.42-3.35 (m, 2H), 2.90 (dd, J = 15.6, 8.3 Hz, 1H), 2.83 (dd, J = 15.6, 6.4 Hz, 1H), 2.73 (t, J = 6.3 Hz, 2H), 1.88 (dtd, J = 6.9, 5.7, 4.3 Hz, 2H), 1.32 (s, 9H). LCMS (ES): m/z 540.4 [M + H]$^+$. Human αVβ6 IC50 (nM) = 1414. | Same method as for Example 16 By using intermediate 7 |
| 99 | 4-Phenyl-3-(1-(2-(5,6,7,8-tetrahydro-1,8-naphthyridin-2-yl)ethyl)-1H-pyrazole-4-carboxamido)butanoic acid | $^1$H NMR (500 MHz, Methanol-$d_4$) δ 7.86 (s, 1H), 7.83 (s, 1H), 7.31-7.22 (m, 4H), 7.22-7.13 (m, 2H), 6.22 (d, J = 7.3 Hz, 1H), 4.71-4.55 (m, 1H), 4.42 (t, J = 6.9 Hz, 2H), 3.41 (t, J = 5.6 Hz, 2H), 3.07 (t, J = 6.9 Hz, 2H), 2.92 (d, J = 7.1 Hz, 2H), 2.71 (t, J = 6.4 Hz, 2H), 2.59-2.45 (m, 2H), 1.88 (p, J = 6.0 Hz, 2H). LCMS (ES): m/z 434.2 [M + H]$^+$. Human αVβ6 IC50 (nM) = 1419. | Same method as for Example 16 |
| 100 | 3-(3,5-Dichlorophenyl)-3-(3-methyl-1-((2-methyl-5,6,7,8-tetrahydro-1,8-naphthyridin-3-yl)methyl)-1H-pyrazole-4-carboxamido)propanoic acid | $^1$H NMR (500 MHz, DMSO-$d_6$) δ 8.33 (d, J = 8.0 Hz, 1H), 8.20 (s, 1H), 7.55 (s, 1H), 7.49 (d, J = 2.0 Hz, 1H), 7.41 (d, J = 2.0 Hz, 2H), 5.29 (q, J = 7.8 Hz, 1H), 5.17 (s, 2H), 3.44-3.35 (two protons missing due to H$_2$O suppression), 2.87-2.65 (m, 4H), 2.46 (s, 3H), 2.27 (s, 3H), 1.86-1.76 (m, 2H). LCMS (ES): m/z 502.0 [M + H]$^+$. Human αVβ6 IC50 (nM) = 1460. | Same method as for Example 3 By using intermediate 18 |

TABLE A-continued

| Example No. | Structure | Data | Method |
|---|---|---|---|
| 101 | Ethyl (S)-3-(3,5-dichlorophenyl)-3-(1-(2-(5,6,7,8-tetrahydro-1,8-naphthyridin-2-yl)ethyl)-1H-pyrazole-4-carboxamido)propanoate | $^1$H NMR (400 MHz, Methanol-d$_4$) δ 7.94 (s, 1H), 7.81 (s, 1H), 7.37 (d, J = 7.4 Hz, 1H), 7.25 (d, J = 1.9 Hz, 2H), 7.23 (t, J = 1.9 Hz, 1H), 6.30 (d, J = 7.4 Hz, 1H), 5.35 (dd, J = 8.5, 6.5 Hz, 1H), 4.42 (t, J = 6.5 Hz, 2H), 4.00 (qd, J = 7.2, 1.1 Hz, 2H), 3.42-3.34 (m, 2H), 3.15 (t, J = 6.6 Hz, 2H), 2.84 (dd, J = 15.9, 8.5 Hz, 1H), 2.78 (dd, J = 15.9, 6.5 Hz, 1H), 2.67 (t, J = 6.2 Hz, 2H), 1.88-1.70 (m, 2H), 1.07 (t, J = 7.1 Hz, 3H). LCMS (ES): m/z 516.4 [M + H]$^+$. Human αVβ6 IC50 (nM) = 1464. | Same method as for Example 16 without hydrolysis of ester |
| 102 | (S)-3-(6-Methoxypyridin-3-yl)-3-(1-((5,6,7,8-tetrahydro-1,8-naphthyridin-2-yl)methyl)-1H-pyrazole-4-carboxamido)propanoic acid | $^1$H NMR (500 MHz, Methanol-d$_4$) δ 8.18 (d, J = 2.4 Hz, 1H), 8.14 (s, 1H), 7.94 (s, 1H), 7.75 (dd, J = 8.6, 2.5 Hz, 1H), 7.19 (d, J = 7.3 Hz, 1H), 6.79 (d, J = 8.6 Hz, 1H), 6.29 (d, J = 7.3 Hz, 1H), 5.49 (dd, J = 7.9, 7.0 Hz, 1H), 5.17 (s, 2H), 3.90 (s, 3H), 3.41-3.36 (m, 2H), 2.94 (dd, J = 15.6, 7.9 Hz, 1H), 2.85 (dd, J = 15.6, 7.0 Hz, 1H), 2.73 (t, J = 6.3 Hz, 2H), 1.92-1.81 (m, 2H). LCMS (ES): m/z 436.9 [M + H]$^+$. Human αVβ6 IC50 (nM) = 1981. | Same method as for Example 16 By using intermediate 7 |
| 103 | 3-(2-Chlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid | $^1$H NMR (500 MHz, Methanol-d$_4$) δ 7.92 (s, 1H), 7.48 (d, J = 7.9 Hz, 1H), 7.39 (d, J = 7.9 Hz, 2H), 7.32-7.25 (m, 1H), 7.15 (d, J = 7.5 Hz, 1H), 6.19 (d, J = 7.5 Hz, 1H), 5.79 (dd, J = 8.7, 4.9 Hz, 1H), 4.65 (d, J = 13.9 Hz, 1H), 4.61 (d, J = 13.9 Hz, 1H), 4.49 (t, J = 6.7 Hz, 2H), 3.49-3.37 (m, 2H), 3.13-3.04 (m, 2H), 2.88-2.70 (m, 4H), 1.93-1.84 (m, 2H). LCMS (ES): m/z 484.3 [M + H]$^+$. Human αVβ6 IC50 (nM) = 2597. | Same method as for Example 9 |
| 104 | 3-(3,5-Dichlorophenyl)-3-(N-ethyl-1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 7.89 (s, 1H), 7.68 (s, 1H), 7.49 (s, 1H), 7.40-6.86 (m, 3H), 6.12 (d, J = 7.3 Hz, 1H), 5.65 (bs, 1H), 4.38 (t, J = 6.9 Hz, 2H), 3.37-3.25 (four protons missing due to H$_2$O suppression), 3.24-3.07 (m, 2H), 2.95-2.86 (m, 2H), 2.59-2.52 (m, 2H), 1.77-1.60 (m, 2H), 0.86 (t, J = 7.1 Hz, 3H). LCMS (ES): m/z 516.4 [M + H]$^+$. Human αVβ6 IC50 (nM) = 3813. | Same method as for Example 17 |

TABLE A-continued

| Example No. | Structure | Data | Method |
|---|---|---|---|
| 105 | 3-(3,5-Dichlorophenyl)-3-(3-(hydroxymethyl)-1-((2-methyl-5,6,7,8-tetrahydro-1,8-naphthyridin-3-yl)methyl)-1H-pyrazole-4-carboxamido)propanoic acid | $^1$H NMR (500 MHz, DMSO-d$_6$) δ 8.83 (d, J = 7.8 Hz, 1H), 8.18 (s, 1H), 7.50 (t, J = 1.9 Hz, 1H), 7.40 (d, J = 1.9 Hz, 2H), 7.33 (s, 1H), 5.30 (q, J = 7.5 Hz, 1H), 5.15 (s, 2H), 4.52 (s, 2H), 3.35-3.28 (two protons missing due to H$_2$O suppression), 2.80 (d, J = 7.3 Hz, 2H), 2.66 (t, J = 6.5 Hz, 2H), 2.34 (s, 3H), 1.85-1.71 (m, 2H). LCMS (ES): m/z 518.5 αVβ6 IC50 (nM) = 3928. | Same method as for Example 3 |
| 106 | Ethyl (S)-3-(3-bromo-5-(tert-butyl)phenyl)-3-(1-(2-(5,6,7,8-tetrahydro-1,8-naphthyridin-2-yl)ethyl)-1H-pyrazole-4-carboxamido)propanoate | $^1$H NMR (500 MHz, Methanol-d$_4$) δ 7.92 (s, 2H), 7.45 (s, 1H), 7.41 (s, 1H), 7.37 (s, 1H), 7.09 (d, J = 7.3 Hz, 1H), 6.20 (d, J = 7.3 Hz, 1H), 5.50 (t, J = 7.8 Hz, 1H), 4.46 (t, J = 6.9 Hz, 2H), 4.09 (q, J = 7.3 Hz, 2H), 3.39 (t, J = 5.5 Hz, 2H), 3.06 (t, J = 7.0 Hz, 2H), 2.98-2.82 (m, 2H), 2.69 (t, J = 7.1 Hz, 2H), 1.93-1.78 (m, 2H), 1.32 (s, 9H), 1.17 (t, J = 7.3 Hz, 3H). LCMS (ES): m/z 582.3 [M + H]$^+$. Human αVβ6 IC50 (nM) = 4309. | Same method as for Example 16 without hydrolysis of ester |
| 107 | 3-(3,5-Dichlorophenyl)-3-(5-(hydroxymethyl)-1-(2-(2-methyl-5,6,7,8-tetrahydro-1,8-naphthyridin-3-yl)ethyl)-1H-pyrazole-4-carboxamido)propanoic acid | $^1$H NMR (500 MHz, DMSO-d$_6$) δ 8.59 (d, J = 7.9 Hz, 1H), 7.98 (s, 1H), 7.51 (d, J = 2.0 Hz, 1H), 7.43 (d, J = 1.9 Hz, 2H), 7.39 (s, 1H), 5.32 (dd, J = 8.7, 6.4 Hz, 1H), 4.71 (d, J = 13.7 Hz, 1H), 4.67 (d, J = 13.7 Hz, 1H), 4.31 (t, J = 7.1 Hz, 2H), 3.43-3.33 (two protons missing due to H$_2$O suppression), 2.95 (t, J = 7.2 Hz, 2H), 2.86 (dd, J = 16.1, 8.7 Hz, 1H), 2.80 (dd, J = 16.1, 6.4 Hz, 1H), 2.68-2.61 (m, 2H), 2.24 (s, 3H), 1.88-1.65 (m, 2H). LCMS (ES): m/z 532.5 [M + H]$^+$. Human αVβ6 IC50 (nM) = 5000. | Same method as for Example 5 |
| 108 | 3-(5-(tert-Butoxymethyl)-1-(2-(2-methyl-5,6,7,8-tetrahydro-1,8-naphthyridin-3-yl)ethyl)-1H-pyrazole-4-carboxamido)-3-(3,5-dichlorophenyl)propanoic acid | $^1$H NMR (500 MHz, DMSO-d$_6$) δ 8.49 (d, J = 8.0 Hz, 1H), 7.97 (s, 1H), 7.50 (d, J = 1.9 Hz, 1H), 7.42 (d, J = 1.9 Hz, 2H), 6.83 (s, 1H), 5.32 (dd, J = 8.6, 6.7 Hz, 1H), 4.60 (d, J = 11.6 Hz, 1H), 4.50 (d, J = 11.4 Hz, 1H), 4.21 (t, J = 7.4 Hz, 2H), 3.48-3.37 (m, 1H, one proton missing due to H$_2$O suppression), 3.26-3.17 (m, 2H), 2.88 (t, J = 7.4 Hz, 2H), 2.83 (dd, J = 16.1, 8.6 Hz, 1H), 2.79 (dd, J = 16.1, 6.7 Hz, 1H), 2.11 (s, 3H), 1.78-1.68 (m, 2H), 1.14 (s, 9H). LCMS (ES): m/z 588.5 [M + H]$^+$. Human αVβ6 IC50 (nM) = 5000. | Same method as for Example 5 |

TABLE A-continued

| Example No. | Structure | Data | Method |
|---|---|---|---|
| 109 | 2-(2-(1-(2-(5,6,7,8-Tetrahydro-1,8-naphthyridin-2-yl)ethyl)-1H-pyrazole-4-carboxamido)-2,3-dihydro-1H-inden-2-yl)acetic acid | $^1$H NMR (500 MHz, Methanol-$d_4$) δ 7.92 (s, 1H), 7.87 (s, 1H), 7.22-7.17 (m, 2H), 7.17-7.11 (m, 2H), 7.09 (d, J = 7.3 Hz, 1H), 6.22 (d, J = 7.3 Hz, 1H), 4.44 (t, J = 6.9 Hz, 2H), 3.66 (d, J = 15.8 Hz, 2H), 3.41-3.37 (m, 2H), 3.16 (d, J = 15.8 Hz, 2H), 3.05 (t, J = 7.0 Hz, 2H), 2.84-2.76 (m, 2H), 2.68 (t, J = 6.1 Hz, 2H), 1.88 (p, J = 6.2 Hz, 2H). LCMS (ES): m/z 446.3 [M + H]$^+$. Human αVβ6 IC50 (nM) = 6436. | Same method as for Example 16 |
| 110 | Methyl 3-(3,5-dichloro-4-iodophenyl)-3-(1-(2-(5,6,7,8-tetrahydro-1,8-naphthyridin-2-yl)ethyl)-1H-pyrazole-4-carboxamido)propanoate | $^1$H NMR (500 MHz, Chloroform-d) δ 9.58 (bs, 1H), 8.03 (s, 1H), 7.79 (s, 1H), 7.32 (s, 2H), 7.28 (d, J = 7.2 Hz, 1H), 6.26 (d, J = 7.2 Hz, 1H), 5.42 (dt, J = 8.0, 5.8 Hz, 1H), 4.51 (t, J = 7.0 Hz, 2H), 3.68 (s, 3H), 3.52 (t, J = 5.7 Hz, 2H), 3.25 (t, J = 7.0 Hz, 2H), 2.95-2.86 (m, 2H), 2.76 (t, J = 6.3 Hz, 2H), 2.03-1.79 (m, 2H). LCMS (ES): m/z 628.3 [M + H]$^+$. Human αVβ6 IC50 (nM) NT. | Same method as for Example 16 without hydrolysis of ester |
| 111 | (S)-3-(1-(2-(5,6,7,8-Tetrahydro-1,8-naphthyridin-2-yl)ethyl)-1H-1,2,3-triazole-4-carboxamido)-2-((2,4,6-trimethylphenyl)sulfonamido)propanoic acid | $^1$H NMR (500 MHz, DMSO-$d_6$) δ 7.93 (s, 1H), 7.04 (d, J = 7.3 Hz, 1H), 6.80 (s, 2H), 6.25 (d, J = 7.3 Hz, 1H), 4.81-4.64 (m, 2H), 3.88 (dd, J = 8.0, 5.8 Hz, 1H), 3.52 (dd, J = 13.4, 5.8 Hz, 1H), 3.35 (dd, J = 13.4, 8.0 Hz, 1H), 3.25 (t, J = 5.6 Hz, 2H), 3.11 (t, J = 7.3 Hz, 2H), 2.61 (t, J = 6.3 Hz, 2H), 2.51 (s, 6H), 2.15 (s, 3H), 1.88-1.65 (m, 2H). LCMS (ES): m/z 542.4 [M + H]$^+$. Human αVβ6 IC50 (nM) = 0.8; Human αVβ1 IC50 (nM) = 46; Human αVβ3 IC50 (nM) = 6.4; Human αVβ5 IC50 (nM) = 1.1; and Human αVβ8 IC50 (nM) = 63. | Same method as for Example 16 By using intermediate 9 |
| 112 | (S)-3-(1-(2-(5,6,7,8-Tetrahydro-1,8-naphthyridin-2-yl)ethyl)-1H-pyrazole-3-carboxamido)-2-((2,4,6-trimethylphenyl)sulfonamido)propanoic acid | $^1$H NMR (500 MHz, Methanol-$d_4$) δ 7.49 (d, J = 2.3 Hz, 1H), 7.35-7.26 (m, 1H), 6.97 (s, 2H), 6.58 (d, J = 2.3 Hz, 1H), 6.44 (d, J = 7.3 Hz, 1H), 4.50 (td, J = 6.5, 2.7 Hz, 2H), 3.72 (dd, J = 12.9, 6.2 Hz, 1H), 3.65 (dd, J = 6.2, 5.3 Hz, 1H), 3.58 (dd, J = 12.9, 5.3 Hz, 1H), 3.43-3.38 (m, 2H), 3.5- 3.20 (m, 2H), 2.73 (t, J = 6.2 Hz, 2H), 2.66 (s, 6H), 2.27 (s, 3H), 1.88 (p, J = 6.1 Hz, 2H). LCMS (ES): m/z 541.4 [M + H]$^+$. Human αVβ6 IC50 (nM) = 1.0; Human αVβ1 IC50 (nM) = 45; Human αVβ3 IC50 (nM) = 2.0; Human αVβ5 IC50 (nM) = 0.4; and Human αVβ8 IC50 (nM) = 115. | Same method as for Example 16 By using intermediate 12 |

TABLE A-continued

| Example No. | Structure | Data | Method |
|---|---|---|---|
| 113 | (S)-3-(2-(2-(5,6,7,8-Tetrahydro-1,8-naphthyridin-2-yl)ethyl)-2H-1,2,3-triazole-4-carboxamido)-2-((2,4,6-trimethylphenyl)sulfonamido)propanoic acid | $^1$H NMR (500 MHz, DMSO-d$_6$) δ 8.24 (t, J = 5.9 Hz, 1H), 7.96 (s, 1H), 7.89 (bt, J = 8.4 Hz, 1H), 7.04 (d, J = 7.2 Hz, 1H), 6.82 (s, 2H), 6.44 (bs, 1H), 6.26 (d, J = 7.2 Hz, 1H), 4.73 (t, J = 7.4 Hz, 2H), 3.88 (p, J = 7.3 Hz, 1H), 3.65-3.47 (m, 1H), 3.38-3.31 (m, 1H), 3.25 (t, J = 5.6 Hz, 2H), 3.10 (dd, J = 8.2, 6.7 Hz, 2H), 2.60 (t, J = 6.3 Hz, 2H), 2.53 (s, 9H), 2.16 (s, 3H), 1.81-1.69 (m, 2H). LCMS (ES): m/z 542.2 [M + H]$^+$. Human αVβ6 IC50 (nM) = 1.3; Human αVβ1 IC50 (nM) = 111; Human αVβ3 IC50 (nM) = 3.0; Human αVβ5 IC50 (nM) = 0.3; and Human αVβ8 IC50 (nM) = 57. | Same method as for Example 13 By using intermediate 33 |
| 114 | (S)-3-(1-(2-(5,6,7,8-Tetrahydro-1,8-naphthyridin-2-yl)ethyl)-1H-imidazole-4-carboxamido)-2-((2,4,6-trimethylphenyl)sulfonamido)propanoic acid | $^1$H NMR (500 MHz, Methanol-d$_4$) δ 7.46 (d, J = 1.3 Hz, 1H), 7.41 (d, J = 1.3 Hz, 1H), 7.32 (d, J = 7.2 Hz, 1H), 6.94 (s, 2H), 6.34 (d, J = 7.3 Hz, 1H), 4.26 (td, J = 6.9, 3.0 Hz, 2H), 3.82-3.75 (m, 2H), 3.58 (q, J = 7.4 Hz, 1H), 3.43 (dd, J = 6.6, 4.7 Hz, 2H), 3.07-2.99 (m, 2H), 2.75 (t, J = 6.3 Hz, 2H), 2.65 (s, 6H), 2.22 (s, 3H), 1.95-1.84 (m, 2H). LCMS (ES): m/z 541.2 [M + H]$^+$. Human αVβ6 IC50 (nM) = 2.0; Human αVβ1 IC50 (nM) = TBD; Human αVβ4 IC50 (nM) = 4.4; Human αVβ5 IC50 (nM) = 0.5; and Human αVβ8 IC50 (nM) = 156. | Same method as for Example 16 By using intermediate 6 |
| 115 | (S)-3-(1-(2-(5,6,7,8-Tetrahydro-1,8-naphthyridin-2-yl)ethyl)-1H-pyrazole-5-carboxamido)-2-((2,4,6-trimethylphenyl)sulfonamido)propanoic acid | $^1$H NMR (500 MHz, Methanol-d$_4$) δ 7.48 (d, J = 2.0 Hz, 1H), 7.43 (d, J = 7.2 Hz, 1H), 7.00 (s, 2H), 6.66 (d, J = 2.0 Hz, 1H), 6.48 (d, J = 7.2 Hz, 1H), 4.78 (ddd, J = 14.6, 9.0, 6.0 Hz, 1H), 4.69 (ddd, J = 14.0, 9.0, 6.0 Hz, 1H), 3.72-3.65 (m, 2H), 3.65-3.60 (m, 1H), 3.46 (dd, J = 6.5, 4.9 Hz, 2H), 3.09 (ddd, J = 15.3, 9.2, 6.4 Hz, 1H), 3.00 (ddd, J = 14.1, 9.2, 5.9 Hz, 1H), 2.78 (t, J = 6.2 Hz, 2H), 2.67 (s, 6H), 2.28 (s, 3H), 1.97-1.88 (m, 2H). LCMS (ES): m/z 541.2 [M + H]$^+$. Human αVβ6 IC50 (nM) = 34. | Same method as for Example 16 By using intermediate 12 |
| 116 | (S)-3-(3,5-Dichlorophenyl)-3-(1-(2-(5,6,7,8-tetrahydro-1,8-naphthyridin-2-yl)ethyl)-1H-imidazole-4-carboxamido)propanoic acid | $^1$H NMR (500 MHz, DMSO-d$_6$) δ 8.67 (bs, 1H), 7.63 (d, J = 1.3 Hz, 1H), 7.61 (d, J = 1.3 Hz, 1H), 7.45 (d, J = 1.9 Hz, 1H), 7.43 (d, J = 1.9 Hz, 2H), 7.02 (d, J = 7.3 Hz, 1H), 6.29 (d, J = 2.6 Hz, 1H), 6.23 (d, J = 7.3 Hz, 1H), 5.28 (q, J = 7.4 Hz, 1H), 4.29 (t, J = 7.1 Hz, 2H), 3.27-3.18 (m, 2H), 2.94-2.85 (m, 3H), 2.78 (dd, J = 16.1, 6.2 Hz, 1H), 2.60 (t, J = 6.3 Hz, 2H), 1.79-1.68 (m, 2H). LCMS (ES): m/z 488.3 [M + H]$^+$. Human αVβ6 IC50 (nM) = 102. | Same method as for Example 16 By using intermediate 6 |
| 117 | Ethyl (S)-3-(1-(2-(5,6,7,8-tetrahydro-1,8-naphthyridin-2-yl)ethyl)-1H-imidazole-4-carboxamido)-2-((2,4,6-trimethylphenyl)sulfonamido)propanoate | $^1$H NMR (400 MHz, Methanol-d$_4$) δ 8.22 (d, J = 1.5 Hz, 1H), 7.79 (d, J = 1.5 Hz, 1H), 7.55 (d, J = 7.3 Hz, 1H), 6.97 (s, 2H), 6.52 (d, J = 7.3 Hz, 1H), 4.60-4.48 (m, 2H), 4.10 (dd, J = 8.2, 5.5 Hz, 1H), 3.89 (q, J = 7.1 Hz, 2H), 3.72 (dd, J = 13.7, 5.5 Hz, 1H), 3.57-3.44 (m, 3H), 3.26 (t, J = 6.9 Hz, 2H), 2.82 (t, J = 6.2 Hz, 2H), 2.61 (s, 6H), 2.28 (s, 3H), 1.95 (dq, J = 7.0, 5.6 Hz, 2H), 1.06 (t, J = 7.1 Hz, 3H). LCMS (ES): m/z 569.3 [M + H]$^+$. Human αVβ6 IC50 (nM) = 130. | Same method as for 16 By using intermediate 6 without hydrolysis of ester |

TABLE A-continued

| Example No. | Structure | Data | Method |
|---|---|---|---|
| 118 | (S)-3-(2-((2-Methyl-5,6,7,8-tetrahydro-1,8-naphthyridin-3-yl)methyl)-2H-1,2,3-triazole-4-carboxamido)-2-((2,4,6-trimethylphenyl)sulfonamido)propanoic acid | $^1$H NMR (500 MHz, DMSO-$d_6$) δ 8.13 (bt, J = 6.0 Hz, 1H), 7.93 (s, 1H), 7.80 (bs, 1H), 7.10 (s, 1H), 6.74 (s, 2H), 6.52 (bt, J = 2.6 Hz, 1H), 5.49 (d, J = 14.5 Hz, 1H), 5.46 (d, J = 14.5 Hz, 1H), 3.86-3.74 (m, 1H), 3.60-3.45 (m, 1H), 3.45-3.27 (1H, buried under H$_2$O peak), 3.26-3.19 (m, 2H), 2.61 (t, J = 6.2 Hz, 2H), 2.48 (s, 6H), 2.31 (s, 3H), 2.11 (s, 3H), 1.84-1.61 (m, 2H). LCMS (ES): m/z 542.2 [M + H]$^+$. Human αVβ6 IC50 (nM) = 223. | Same method as for Example 14 |
| 119 | (S)-3-(1-(2-(5,6,7,8-Tetrahydro-1,8-naphthyridin-2-yl)ethyl)-1H-pyrrole-3-carboxamido)-2-((2,4,6-trimethylphenyl)sulfonamido)propanoic acid | $^1$H NMR (500 MHz, DMSO-$d_6$) δ 7.33 (d, J = 7.3 Hz, 1H), 7.19 (s, 1H), 6.90 (s, 2H), 6.58 (s, 1H), 6.34-6.38 (m, 2H), 4.13 (t, J = 6.9 Hz, 2H), 3.73-3.65 (m, 1H), 3.64-3.48 (m, 2H), 3.45-3.37 (m, 1H, one proton missing due to H$_2$O suppression), 2.97 (t, J = 7.4 Hz, 2H), 2.73 (t, J = 6.4 Hz, 2H), 2.61 (s, 6H), 2.19 (s, 3H), 1.96-1.84 (m, 2H). LCMS (ES): m/z 540.4 [M + H]$^+$. Human αVβ6 IC50 (nM) = 0.5; Human αVβ1 IC50 (nM) = 6.3; Human αVβ3 IC50 (nM) = 1.5; Human αVβ5 IC50 (nM) = 0.2; and Human αVβ8 IC50 (nM) = 31. | Same method as for Example 13 from methyl 1H-pyrrole-3-carboxylate |
| 120 | (S)-3-(3,5-Dichlorophenyl)-3-(1-(2-(5,6,7,8-tetrahydro-1,8-naphthyridin-2-yl)ethyl)-1H-1,2,4-triazole-3-carboxamido)propanoic acid | $^1$H NMR (500 MHz, Methanol-$d_4$) δ 8.33 (s, 1H), 7.43 (d, J = 1.9 Hz, 2H), 7.35 (t, J = 1.9 Hz, 1H), 7.27 (d, J = 7.3 Hz, 1H), 6.37 (d, J = 7.3 Hz, 1H), 5.49 (t, J = 6.5 Hz, 1H), 4.62 (t, J = 6.8 Hz, 2H), 3.45-3.41 (m, 2H), 3.21 (t, J = 6.7 Hz, 2H), 3.03-2.83 (m, 2H), 2.80-2.70 (m, 2H), 1.93-1.81 (m, 2H). LCMS (ES): m/z 489.2 [M + H]$^+$. Human αVβ6 IC50 (nM) = 98. | Same method as for Example 16 By using intermediate 13 |
| 121 | (S)-2-(((Benzyloxy)carbonyl)amino)-3-(1-(2-(5,6,7,8-tetrahydro-1,8-naphthyridin-2-yl)ethyl)-1H-imidazole-4-carboxamido)propanoic acid | $^1$H NMR (500 MHz, DMSO-$d_6$) δ 7.62 (s, 1H), 7.61 (s, 1H), 7.40-7.27 (m, 5H), 7.02 (d, J = 7.3 Hz, 1H), 6.23 (d, J = 7.3 Hz, 1H), 5.02 (s, 2H), 4.30 (t, J = 7.0 Hz, 2H), 3.64-3.53 (m, 1H), 3.46 (dd, J = 13.5, 7.7 Hz, 1H), 3.39-3.27 (1H, buried under H$_2$O peak), 3.25 (t, J = 5.6 Hz, 2H), 2.92 (t, J = 7.1 Hz, 2H), 2.61 (t, J = 6.3 Hz, 2H), 1.75 (p, J = 6.0 Hz, 2H). LCMS (ES): m/z 493.2 [M + H]$^+$. Human αVβ6 IC50 (nM) = 2.3; Human αVβ1 IC50 (nM) = 77; Human αVβ3 IC50 (nM) = 1.6; Human αVβ5 IC50 (nM) = 0.3; and Human αVβ8 IC50 (nM) = 246. | Same method as for Example 12 |
| 122 | (S)-3-(1-((2-Methyl-5,6,7,8-tetrahydro-1,8-naphthyridin-3-yl)methyl)-1H-pyrrole-3-carboxamido)-2-((2,4,6-trimethylphenyl)sulfonamido)propanoic acid | $^1$H NMR (500 MHz, DMSO-$d_6$) δ 7.72 (bs, 1H), 7.13 (s, 1H), 7.04 (s, 1H), 6.86 (s, 2H), 6.72 (s, 1H), 6.30 (s, 1H), 4.89 (s, 2H), 3.48-3.29 (m, 1H, two protons missing due to H$_2$O suppression), 3.28-3.17 (m, 2H), 2.59 (t, J = 6.3 Hz, 2H), 2.47 (s, 6H), 2.18 (s, 3H), 2.14 (s, 3H), 1.76-1.63 (m, 2H). LCMS (ES): m/z 540.1 [M + H]$^+$. Human αVβ6 IC50 (nM) = 43. | Same method as for Example 13 From methyl 1H-pyrrole-3-carboxylate |

TABLE A-continued

| Example No. | Structure | Data | Method |
|---|---|---|---|
| 123 | (S)-3-(1-(2-(5,6,7,8-Tetrahydro-1,8-naphthyridin-2-yl)ethyl)-1H-1,2,3-triazole-4-carboxamido)-2-((2,4,6-trimethylphenyl)sulfonamido)propanoic acid | $^1$H NMR (500 MHz, Methanol-d$_4$) δ 8.30 (s, 1H), 7.35 (d, J = 7.2 Hz, 1H), 6.94 (s, 2H), 6.42 (d, J = 7.4 Hz, 1H), 4.58 (t, J = 6.7 Hz, 2H), 3.79-3.69 (m, 2H), 3.70-3.58 (m, 1H), 3.44 (t, J = 5.6 Hz, 2H), 3.22 (t, J = 6.7 Hz, 2H), 2.75 (t, J = 6.3 Hz, 2H), 2.65 (s, 6H), 2.24 (s, 3H), 1.90 (p, J = 6.1 Hz, 2H). LCMS (ES): m/z 542.3 [M + H]$^+$. Human αVβ6 IC50 (nM) = 2.0; Human αVβ1 IC50 (nM) = 126; Human αVβ3 IC50 (nM) = 2.1; Human αVβ5 IC50 (nM) = 902; and Human αVβ8 IC50 (nM) = 152. | Same method as for Example 16 By using intermediate 13 |
| 124 | (S)-2-(Butylsulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 7.94 (s, 1H), 7.86 (s, 1H), 7.24 (d, J = 7.3 Hz, 1H), 6.29 (d, J = 7.3 Hz, 1H), 4.45 (t, J = 6.8 Hz, 2H), 4.00 (dd, J = 8.2, 5.0 Hz, 1H), 3.75-3.51 (m, 2H), 3.45-3.37 (m, 2H), 3.15-2.98 (m, 4H), 2.72 (t, J = 6.3 Hz, 2H), 1.93-1.64 (m, 4H), 1.48-1.33 (m, 2H), 0.91 (t, J = 7.3 Hz, 3H) LCMS (ES): m/z 479.3 [M + H]$^+$. Human αVβ6 IC50 (nM) = 2.6. | Same method as for Example 19 |
| 125 | (S)-2-((Phenylmethyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (600 MHz, DMSO-d$_6$) δ 8.06 (s, 1H), 7.87-7.74 (m, 1H), 7.42-7.22 (m, 6H), 7.00 (d, J = 7.3 Hz, 1H), 6.19 (d, J = 7.3 Hz, 1H), 4.43-4.35 (m, 2H), 4.31 (s, 2H), 4.02 (br. s., 1H), 3.63-3.41 (m, 1H), 3.24 (t, J = 5.2 Hz, 2H), 2.94 (t, J = 7.3 Hz, 2H), 2.64-2.56 (m, 2H), 1.82-1.67 (m, 2H) LCMS (ES): m/z 513.3 [M + H ]$^+$. Human αVβ6 IC50 (nM) = 14. | Same method as for Example 19 |
| 126 | (S)-2-(Ethylsulfonamido)-3-(1-(2-(5,6,7,8-tetrahydro-1,8-naphthyridin-2-yl)ethyl)-1H-pyrazole-4-carboxamido)propanoic acid | $^1$H NMR (600 MHz, DMSO-d$_6$) δ 8.24-8.09 (m, 2H), 8.05 (s, 1H), 7.80 (s, 1H), 7.02 (d, J = 7.3 Hz, 1H), 6.20 (d, J = 7.1 Hz, 1H), 4.38 (t, J = 7.2 Hz, 2H), 3.52 (br. s., 4H), 3.32-3.19 (m, 1H), 2.95 (t, J = 7.1 Hz, 2H), 2.60 (s, 2H), 1.81-1.65 (m, 2H), 1.19-1.09 (m, 3H) LCMS (ES): m/z 451.0 [M + H]$^+$. Human αVβ6 IC50 (nM) = 10. | Same method as for Example 19 |
| 127 | (S)-2-((Propoxycarbonyl)amino)-3-(1-(2-(5,6,7,8-tetrahydro-1,8-naphthyridin-2-yl)ethyl)-1H-pyrazole-4-carboxamido)propanoic acid | $^1$H NMR (600 MHz, DMSO-d$_6$) δ 7.95 (s, 1H), 7.69 (s, 1H), 6.91 (d, J = 7.3 Hz, 1H), 6.10 (d, J = 7.3 Hz, 1H), 4.26 (t, J = 7.2 Hz, 2H), 3.77 (t, J = 5.8 Hz, 1H), 3.14 (t, J = 5.0 Hz, 2H), 2.86-2.77 (m, 2H), 2.53-2.46 (m, 3H), 1.63 (quin, J = 5.8 Hz, 3H), 1.47-1.32 (m, 3H), 0.81-0.66 (m, 4H). LCMS (ES): m/z 445.1 [M + H]$^+$. Human αVβ6 IC50 (nM) = 1.5. | Same method as for Example 19 |

TABLE A-continued

| Example No. | Structure | Data | Method |
|---|---|---|---|
| 128 | (S)-3-(1-(2-(5,6,7,8-Tetrahydro-1,8-naphthyridin-2-yl)ethyl)-1H-pyrazole-4-carboxamido)-2-(((2-(trifluoromethyl)phenyl)methyl)sulfonamido) propanoic acid | $^1$H NMR (500 MHz, DMSO-d$_6$) δ 8.08 (s, 1H), 7.83 (s, 1H), 7.77-7.44 (m, 4H), 7.00 (d, J = 7.2 Hz, 1H), 6.19 (d, J = 7.2 Hz, 1H), 4.52 (br. s., 2H), 4.37 (t, J = 7.2 Hz, 2H), 4.18-4.04 (m, 1H), 3.24 (br. s., 2H), 2.94 (t, J = 7.2 Hz, 2H), 2.65-2.56 (m, 4H), 1.74 (br. s., 2H) LCMS (ES): m/z 581.2 [M + H]$^+$. Human αVβ6 IC50 (nM) = 2.5. | Same method as for Example 19 |
| 129 | (S)-3-(1-(2-(5,6,7,8-Tetrahydro-1,8-naphthyridin-2-yl)ethyl)-1H-pyrazole-4-carboxamido)-2-(((3,3,3-trifluoropropyl)sulfonamido)propanoic acid | $^1$H NMR (500 MHz, DMSO-d$_6$) δ 8.08 (s, 1H), 7.83 (s, 1H), 7.06 (d, J = 7.2 Hz, 1H), 6.22 (d, J = 7.2 Hz, 1H), 4.38 (t, J = 7.2 Hz, 2H), 4.19-4.02 (m, 1H), 3.25 (d, J = 4.9 Hz, 4H), 2.96 (t, J = 7.2 Hz, 2H), 2.82-2.57 (m, 6H), 1.83-1.66 (m, 2H) LCMS (ES): m/z 519.3 [M + H]$^+$. Human αVβ6 IC50 (nM) = 3.0. | Same method as for Example 19 |
| 130 | (S)-2-((Methoxycarbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 7.98 (s, 1H), 7.86 (s, 1H), 7.25 (d, J = 7.3 Hz, 1H), 6.33-6.26 (m, 1H), 4.50-4.39 (m, 2H), 3.68-3.60 (m, 4H), 3.48-3.40 (m, 2H), 3.19-3.07 (m, 2H), 2.79-2.70 (m, 2H), 1.96-1.82 (m, 2H) LCMS (ES): m/z 417.2 [M + H]$^+$. Human αVβ6 IC50 (nM) = 13. | Same method as for Example 19 |
| 131 | (S)-2-((Isobutoxycarbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 8.04 (s, 1H), 7.86 (d, J = 0.6 Hz, 1H), 7.32 (d J = 7.0 Hz, 1H), 6.36 (d, J = 7.0 Hz, 1H), 4.44 (t, J = 7.1 Hz, 2H), 4.30 (t, J = 5.6 Hz, 1H), 3.90-3.67 (m, 4H), 3.48-3.40 (m, 2H), 3.17-3.06 (m, 2H), 2.82-2.70 (m, 2H), 1.97-1.79 (m, 3H), 0.92 (d, J = 6.7 Hz, 7H) LCMS (ES): m/z 459.0 [M + H]$^+$. Human αVβ6 IC50 (nM) = 0.9. | Same method as for Example 19 |
| 132 | (S)-2-((Ethoxycarbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 7.99 (s, 1H), 7.87 (s, 1H), 7.26 (s, 1H), 6.32 (d, J = 7.3 Hz, 1H), 4.46 (s, 2H), 4.33-4.21 (m, 1H), 4.13-4.00 (m, 2H), 3.78-3.64 (m, 2H), 3.44 (s, 2H), 3.11 (s, 2H), 2.74 (s, 2H), 1.96-1.85 (m, 2H), 1.22 (s, 3H) LCMS (ES): m/z 431.0 [M + H]$^+$. Human αVβ6 IC50 (nM) = 2.3. | Same method as for Example 19 |

TABLE A-continued

| Example No. | Structure | Data | Method |
|---|---|---|---|
| 133 | 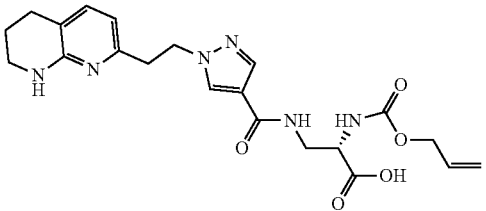<br>(S)-2-(((Allyloxy)carbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 8.10-7.97 (m, 1H), 7.86 (d, J = 0.6 Hz, 1H), 7.36-7.27 (m, 1H), 6.45-6.29 (m, 1H), 6.02-5.83 (m, 1H), 5.32 (d, J = 1.7 Hz, 1H), 5.19-5.10 (m, 1H), 4.53 (d, J = 5.3 Hz, 2H), 4.48-4.40 (m, 2H), 4.30 (s, 1H), 3.75 (d, J = 6.0 Hz, 2H), 3.48-3.41 (m, 2H), 3.13 (t, J = 6.8 Hz, 2H), 2.81-2.71 (m, 2H), 1.96-1.85 (m, 2H) LCMS (ES): m/z 443.2 [M + H]$^+$. Human αVβ6 IC50 (nM) = 2.6. | Same method as for Example 19 |
| 134 | 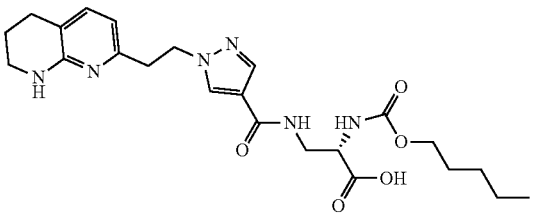<br>(S)-2-(((Pentyloxy)carbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 8.05 (s, 1H), 7.86 (s, 1H), 7.33 (d, J = 6.9 Hz, 1H), 6.36 (d, J = 7.0 Hz, 1H), 4.43 (t, J = 7.1 Hz, 2H), 4.34-4.22 (m, 1H), 4.02 (t, J = 6.6 Hz, 2H), 3.75 (br. s., 2H), 3.52-3.40 (m, 2H), 3.15-3.05 (m, 2H), 2.76 (t, J = 6.2 Hz, 2H), 1.96-1.84 (m, 2H), 1.61 (t, J = 6.9 Hz, 2H), 1.42-1.25 (m, 4H), 0.91 (br. s., 3H) LCMS (ES): m/z 473.3 [M + H]$^+$. Human αVβ6 IC50 (nM) = 0.8. | Same method as for Example 19 |
| 135 | 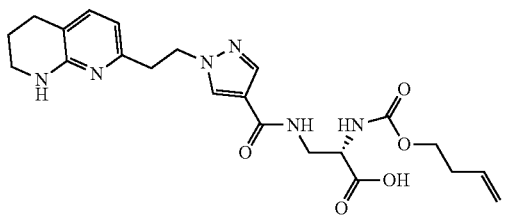<br>(S)-2-(((But-3-en-1-yloxy)carbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 8.02 (s, 1H), 7.86 (s, 1H), 7.29 (d, J = 7.2 Hz, 1H), 6.34 (d, J = 7.2 Hz, 1H), 5.81 (dd, J = 17.1, 10.4 Hz, 1H), 5.18-4.97 (m, 2H), 4.44 (t, J = 7.1 Hz, 2H), 4.27 (s, 1H), 4.07 (td, J = 6.7, 2.9 Hz, 2H), 3.74 (d, J = 5.8 Hz, 3H), 3.47-3.40 (m, 2H), 3.11 (s, 2H), 2.75 (t, J = 6.2 Hz, 2H), 2.35 (dt, J = 6.8, 1.3 Hz, 2H), 1.97-1.82 (m, 2H) LCMS (ES): m/z 457.2 [M + H]$^+$. Human αVβ6 IC50 (nM) = 1.4. | Same method as for Example 19 |
| 136 | 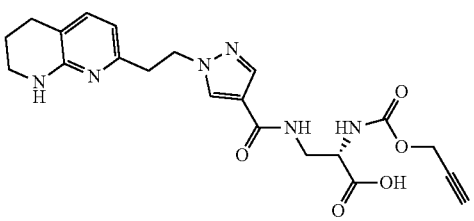<br>(S)-2-(((Prop-2-yn-1-yloxy)carbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 8.01 (s, 1H), 7.86 (d, J = 0.6 Hz, 1H), 7.33 (d, J = 6.9 Hz, 1H), 6.36 (d, J = 7.2 Hz, 1H), 4.66 (d, J = 1.2 Hz, 2H), 4.48-4.40 (m, 2H), 4.29 (s, 1H), 3.79-3.64 (m, 2H), 3.51-3.42 (m, 2H), 3.17-3.07 (m, 2H), 2.91-2.83 (m, 1H), 2.79-2.72 (m, 2H), 1.91 (br. s., 2H) LCMS (ES): m/z 441.0 [M + H]$^+$. Human αVβ6 IC50 (nM) = 2.0. | Same method as for Example 19 |
| 137 | 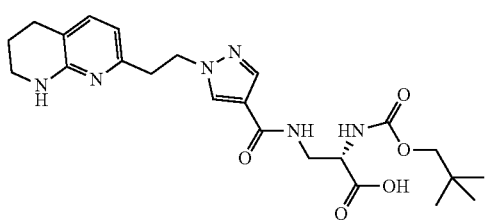<br>(S)-2-(((Neopentyloxy)carbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 8.03 (s, 1H), 7.86 (s, 1H), 7.30 (d, J = 6.9 Hz, 1H), 6.35 (d, J = 7.2 Hz, 1H), 4.44 (t, J = 7.0 Hz, 2H), 4.30 (t, J = 6.0 Hz, 1H), 3.86-3.65 (m, 4H), 3.51-3.38 (m, 2H), 3.11 (s, 2H), 2.75 (t, J = 6.2 Hz, 2H), 1.97-1.83 (m, 2H), 0.93 (s, 9H) LCMS (ES): m/z 473.3 [M + H]$^+$. Human αVβ6 IC50 (nM) = 0.8. | Same method as for Example 19 |

TABLE A-continued

| Example No. | Structure | Data | Method |
|---|---|---|---|
| 138 | (S)-2-(Propylsulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.07 (s, 1H), 7.81 (s, 1H), 7.02 (d, J = 7.2 Hz, 1H), 6.21 (d, J = 7.2 Hz, 1H), 4.38 (t, J = 7.2 Hz, 2H), 3.25 (br. s., 2H), 3.04-2.79 (m, 4H), 2.60 (t, J = 5.8 Hz, 2H), 1.80-1.54 (m, 4H), 1.33-1.12 (m, 3H), 0.84 (t, J = 7.3 Hz, 3H) LCMS (ES): m/z 465.2 [M + H]$^+$. Human αVβ6 IC50 (nM) = 4.1. | Same method as for Example 19 |
| 139 | (S)-2-((2-(Naphthalen-1-yl)ethyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.09-7.89 (m, 3H), 7.86-7.73 (m, 2H), 7.65-7.49 (m, 2H), 7.46-7.27 (m, 2H), 7.00 (d, J = 7.2 Hz, 1H), 6.17 (d, J = 7.2 Hz, 1H), 4.33 (t, J = 7.2 Hz, 2H), 4.14 (br. s., 1H), 3.40-3.21 (m, 5H), 3.17 (s, 2H), 2.91 (t, J = 7.2 Hz, 2H), 2.58 (t, J = 6.1 Hz, 2H), 1.74 (d, J = 5.5 Hz, 2H) LCMS (ES): m/z 577.2 [M + H]$^+$. Human αVβ6 IC50 (nM) = 0.9. | Same method as for Example 19 |
| 140 | (S)-2-(((3,5-Dichlorophenyl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.09-8.00 (m, 1H), 7.79 (s, 1H), 7.61-7.53 (m, 1H), 7.46 (s, 2H), 7.00 (d, J = 7.2 Hz, 1H), 6.20 (d, J = 7.2 Hz, 1H), 4.49-4.27 2H), 3.52-3.22 (m, 2H), 2.94 (br. s., 2H), 2.65-2.56 (m, 2H), 1.74 (br. s., 2H), 1.23 (s, 5H) LCMS (ES): m/z 581.1 [M + H]$^+$. Human αVβ6 IC50 (nM) = 6.2. | Same method as for Example 19 |
| 141 | (S)-2-(((3,4-Dichlorophenyl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.10-8.02 (m, 1H), 7.84-7.76 (m, 1H), 7.68-7.58 (m, 1H), 7.58-7.49 (m, 1H), 7.37 (s, 1H), 7.01 (d, J = 7.2 Hz, 1H), 6.19 (d, J = 7.2 Hz, 1H), 4.43-4.24 (m, 4H), 3.68-3.43 (m, 3H), 3.24 (br. s., 2H), 2.95 (t, J = 7.1 Hz, 2H), 2.57 (d, J = 6.1 Hz, 3H), 1.73 (br. s., 2H) LCMS (ES): m/z 581.1 [M + H]$^+$. Human αVβ6 IC50 (nM) = 3.6. | Same method as for Example 19 |

TABLE A-continued

| Example No. | Structure | Data | Method |
|---|---|---|---|
| 142 | (S)-2-(((3-Fluorophenyl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.13-8.03 (m, 1H), 7.87-7.79 (m, 1H), 7.51-7.08 (m, 6H), 6.44-6.28 (m, 1H), 4.52-4.29 (m, 4H), 4.16-4.02 (m, 1H), 3.34 (br. s., 4H), 3.12 (br. s., 2H), 2.66 (br. s., 2H), 1.83-1.70 (m, 2H) LCMS (ES): m/z 531.2 [M + H]$^+$. Human αVβ6 IC50 (nM) = 8.2. | Same method as for Example 19 |
| 143 | (S)-3-(1-(2-(5,6,7,8-Tetrahydro-1,8-naphthyridin-2-yl)ethyl)-1H-pyrazole-4-carboxamido)-2-((m-tolylmethyl)sulfonamido)propanoic acid | $^1$H NMR (500 MHz, DMSO-d$_6$) δ 8.07-7.99 (m, 1H), 7.80 (s, 1H), 7.35-7.07 (m, 4H), 6.99 (d, J = 7.2 Hz, 1H), 6.19 (d, J = 7.2 Hz, 1H), 4.51-4.21 (m, 2H), 3.47 (br. s., 2H), 3.26-3.12 (m, 4H), 2.94 (t, J = 7.1 Hz, 2H), 2.58 (d, J = 5.8 Hz, 2H), 2.26 (s, 2H), 1.91 (br. s., 3H), 1.73 (br. s., 2H) LCMS (ES): m/z 527.2 [M + H]$^+$. Human αVβ6 IC50 (nM) = 11. | Same method as for Example 19 |
| 144 | (S)-2-(Pentylsulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.08 (s, 1H), 7.83 (s, 1H), 7.03 (d, J = 7.2 Hz, 1H), 6.21 (d, J = 7.2 Hz, 1H), 4.38 (t, J = 7.2 Hz, 2H), 3.25 (br. s., 5H), 2.98-2.82 (m, 4H), 2.69-2.57 (m, 2H), 1.84-1.69 (m, 2H), 1.66-1.47 (m, 2H), 1.19 (br. s., 4H), 0.80 (br. s., 3H) LCMS (ES): m/z 493.2 [M + H]$^+$. Human αVβ6 IC50 (nM) = 2.1. | Same method as for Example 19 |
| 145 | (S)-2-((2-Methylpropyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.08 (s, 1H), 7.81 (s, 1H), 7.02 (d, J = 7.2 Hz, 1H), 6.21 (d, J = 7.2 Hz, 1H), 4.38 (t, J = 7.2 Hz, 2H), 3.24 (br. s., 2H), 3.01-2.80 (m, 3H), 2.65-2.56 (m, 2H), 2.17-1.99 (m, 1H), 1.74 (br. s., 2H), 1.23 (s, 4H), 0.97-0.82 (m, 6H) LCMS (ES): m/z 479.1 [M + H]$^+$. Human αVβ6 IC50 (nM) = 3.9. | Same method as for Example 19 |

TABLE A-continued

| Example No. | Structure | Data | Method |
|---|---|---|---|
| 146 | (S)-3-(1-(2-(5,6,7,8-Tetrahydro-1,8-naphthyridin-2-yl)ethyl)-1H-pyrazole-4-carboxamido)-2-(((4-(trifluoromethoxy)phenyl)methyl)sulfonamido) propanoic acid | $^1$H NMR (500 MHz, DMSO-d$_6$) δ 8.06 (s, 1H), 7.82 (s, 1H), 7.49 (d, J = 8.3 Hz, 2H), 7.30 (d, J = 8.1 Hz, 2H), 7.02 (d, J = 7.2 Hz, 1H), 6.19 (d, J = 7.2 Hz, 1H), 4.37 (s, 4H), 4.07 (br. s., 1H), 3.69-3.43 (m, 2H), 3.24 (br. s., 2H), 3.02-2.87 (m, 2H), 2.65-2.56 (m, 2H), 1.73 (br. s., 2H) LCMS (ES): m/z 597.2 [M + H]$^+$. Human αVβ6 IC50 (nM) = 8.6. | Same method as for Example 19 |
| 147 | (S)-2-((2-Methoxyethyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.06 (s, 1H), 7.81 (s, 1H), 7.02 (d, J = 7.2 Hz, 1H), 6.21 (d, J = 7.2 Hz, 1H), 4.38 (t, J = 7.2 Hz, 2H), 3.66-3.40 (m, 5H), 3.27-3.13 (m, 7H), 2.95 (t, J = 7.2 Hz, 2H), 2.65-2.56 (m, 2H), 1.78-1.69 (m, 2H) LCMS (ES): m/z 481.2 [M + H]$^+$. Human αVβ6 IC50 (nM) = 14. | Same method as for Example 19 |
| 148 | (S)-2-((2-Ethoxyethyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.07 (s, 1H), 7.82 (s, 1H), 7.03 (d, J = 7.2 Hz, 1H), 6.21 (d, J = 7.2 Hz, 1H), 4.38 (t, J = 7.2 Hz, 2H), 4.10-3.99 (m, 1H), 3.73-3.60 (m, 1H), 3.37 (q, J = 6.8 Hz, 1H), 3.30-3.19 (m, 6H), 3.02-2.91 (m, 3H), 2.66-2.57 (m, 3H), 1.84-1.65 (m, 2H), 1.06 (t, J = 7.0 Hz, 3H) LCMS (ES): m/z 495.0 [M + H]$^+$. Human αVβ6 IC50 (nM) = 8.9. | Same method as for Example 19 |
| 149 | (S)-2-(((2-Methoxyethoxy)carbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 8.00 (s, 1H), 7.87 (s, 1H), 7.30 (d, J = 7.0 Hz, 1H), 6.35 (d, J = 7.2 Hz, 1H), 4.45 (t, J = 6.9 Hz, 2H), 4.28 (t, J = 5.7 Hz, 1H), 4.17 (d, J = 5.2 Hz, 2H), 3.76-3.68 (m, 2H), 3.63-3.53 (m, 2H), 3.49-3.39 (m, 2H), 3.35 (s, 3H), 3.16-3.04 (m, 2H), 2.75 (t, J = 6.1 Hz, 2H), 2.68 (s, 2H) LCMS (ES): m/z 461.0 [M + H]$^+$. Human αVβ6 IC50 (nM) = 4.7. | Same method as for Example 19 |

TABLE A-continued

| Example No. | Structure | Data | Method |
|---|---|---|---|
| 150 | (S)-3-(1-(2-(5,6,7,8-Tetrahydro-1,8-naphthyridin-2-yl)ethyl)-1H-pyrazole-4-carboxamido)-2-(((4-(trifluoromethoxyl)phenyl)methyl)sulfonamido)propanoic acid | $^1$H NMR (500 MHz, DMSO-d$_6$) δ 8.09 (s, 1H), 7.83 (s, 1H), 7.74-7.57 (m, 4H), 7.00 (d, J = 7.2 Hz, 1H), 6.19 (d, J = 7.2 Hz, 1H), 4.65-4.32 (m, 6H), 4.12 (br. s., 1H), 3.50 (br. s., 1H), 3.24 (br. s., 1H), 2.95 (t, J = 7.2 Hz, 2H), 2.58 (t, J = 5.8 Hz, 2H), 1.73 (d, J = 5.1 Hz, 2H) LCMS (ES): m/z 581.3 [M + H]$^+$. Human αVβ6 IC50 (nM) = 5.7. | Same method as for Example 19 |
| 151 | (S)-2-((2-(1,3-Dioxoisoindolin-2-yl)ethyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.05 (s, 1H), 7.91-7.71 (m, 5H), 7.04 (d, J = 7.2 Hz, 1H), 6.20 (d, J = 7.2 Hz, 1H), 4.34 (t, J = 7.2 Hz, 2H), 4.10 (br. s., 1H), 3.96 (t, J = 6.9 Hz, 2H), 3.43-3.21 (m, 3H), 2.94 (t, J = 7.1 Hz, 2H), 2.59 (d, J = 5.6 Hz, 5H), 1.74 (br. s., 2H) LCMS (ES): m/z 596.2 [M + H]$^+$. Human αVβ6 IC50 (nM) = 1.2. | Same method as for Example 19 |
| 152 | (2S)-2-((((2-Ethylhexyl)oxy)carbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 8.09 (br. s., 1H), 7.86 (s, 1H), 7.35 (d, J = 6.7 Hz, 1H), 6.38 (d, J = 7.2 Hz, 1H), 4.47-4.21 (m, 3H), 4.06-3.63 (m, 4H), 3.53-3.39 (m, 2H), 3.22-3.02 (m, 2H), 2.84-2.68 (m, 2H), 1.96-1.81 (m, 2H), 1.62-1.17 (m, 9H), 0.96-0.70 (m, 6H) LCMS (ES): m/z 515.1 [M + H]$^+$. Human αVβ6 IC50 (nM) = 0.4. | Same method as for Example 19 |
| 153 | (S)-3-(1-(2-(5,6,7,8-Tetrahydro-1,8-naphthyridin-2-yl)ethyl)-1H-pyrazole-4-carboxamido)-2-(((2,2,2-trifluoroethoxy)carbonyl)amino)propanoic acid | $^1$H NMR (500 MHz, METHANOL-d$_4$) δ 7.99 (s, 1H), 7.86 (s, 1H), 7.29 (d, J = 7.3 Hz, 1H), 6.33 (d, J = 7.3 Hz, 1H), 4.65-4.39 (m, 4H), 4.28 (t, J = 5.9 Hz, 1H), 3.79-3.68 (m, 2H), 3.48-3.40 (m, 2H), 3.12 (t, J = 6.9 Hz, 2H), 2.75 (t, J = 6.2 Hz, 2H), 1.96-1.84 (m, 2H) LCMS (ES): m/z 485.2 [M + H]$^+$. Human αVβ6 IC50 (nM) = 1.6. | Same method as for Example 19 |

TABLE A-continued

| Example No. | Structure | Data | Method |
|---|---|---|---|
| 154 | (S)-3-(1-(2-(5,6,7,8-Tetrahydro-1,8-naphthyridin-2-yl)ethyl)-1H-pyrazole-4-carboxamido)-2-(((3-(trifluoromethoxyl)phenyl)methyl)sulfonamido)propanoic acid | $^1$H NMR (500 MHz, DMSO-d$_6$) δ 8.05 (s, 1H), 7.76 (d, J = 14.0 Hz, 2H), 7.68 (d, J = 7.6 Hz, 2H), 7.56 (d, J = 7.6 Hz, 1H), 7.00 (d, J = 7.3 Hz, 1H), 6.19 (d, J = 7.0 Hz, 1H), 4.50 (br. s., 2H), 4.37 (t, J = 7.2 Hz, 2H), 3.52 (d, J = 11.9 Hz, 1H), 3.23 (d, J = 5.2 Hz, 2H), 3.02-2.91 (m, 2H), 2.58 (t, J = 6.0 Hz, 2H), 1.91 (br. s., 2H), 1.80-1.68 (m, 2H) LCMS (ES): m/z 581.2 [M + H]$^+$. Human αVβ6 IC50 (nM) = 16. | Same method as for Example 19 |
| 155 | (S)-2-(((2-Chlorophenyl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.06 (s, 1H), 7.80 (s, 1H), 7.58-7.17 (m, 4H), 6.99 (d, J = 7.3 Hz, 1H), 6.19 (d, J = 7.3 Hz, 1H), 4.59-4.43 (m, 2H), 4.37 (t, J = 7.2 Hz, 2H), 3.51 (br. s., 2H), 3.24 (br. s., 2H), 2.94 (t, J = 7.0 Hz, 2H), 2.62-2.54 (m, 3H), 1.74 (d, J = 5.5 Hz, 2H) LCMS (ES): m/z 546.9 [M + H]$^+$. Human αVβ6 IC50 (nM) = 5.5. | Same method as for Example 19 |
| 156 | (S)-2-(((3-Bromophenyl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.05 (s, 1H), 7.78 (s, 1H), 7.62-7.46 (m, 2H), 7.38-7.18 (m, 2H), 7.00 (d, J = 7.3 Hz, 1H), 6.19 (d, J = 7.3 Hz, 1H), 4.45-4.25 (m, 3H), 3.56 (br. s., 4H), 3.24 (br. s., 2H), 3.00-2.89 (m, 2H), 2.58 (t, J = 6.1 Hz, 2H), 1.78-1.68 (m, 2H) LCMS (ES): m/z 591.1 [M + H]$^+$. Human αVβ6 IC50 (nM) = 21. | Same method as for Example 19 |
| 157 | (S)-2-(((3,5-Bis(trifluoromethyl)phenyl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.16-8.00 (m, 4H), 7.79 (s, 1H), 7.02 (d, J = 7.3 Hz, 1H), 6.20 (d, J = 7.3 Hz, 1H), 4.75-4.55 (m, 2H), 4.37 (t, J = 7.2 Hz, 2H), 4.18 (br. s., 1H), 3.63-3.41 (m, 1H), 3.29-3.13 (m, 3H), 2.95 (t, J = 7.2 Hz, 2H), 2.59 (t, J = 5.8 Hz, 2H), 1.74 (br. s., 2H) LCMS (ES): m/z 649.0 [M + H]$^+$. Human αVβ6 IC50 (nM) = 16. | Same method as for Example 19 |

TABLE A-continued

| Example No. | Structure | Data | Method |
|---|---|---|---|
| 158 | (S)-2-(((5-Methylisoxazol-3-yl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.07 (s, 1H), 7.80 (s, 1H), 7.02 (d, J = 7.0 Hz, 1H), 6.33 (s, 1H), 6.21 (d, J = 7.3 Hz, 1H), 4.44 (s, 2H), 4.38 (t, J = 7.3 Hz, 2H), 3.48 (br. s., 1H), 3.25 (br. s., 2H), 3.17 (s, 2H), 2.95 (t, J = 7.3 Hz, 2H), 2.60 (t, J = 6.0 Hz, 2H), 2.39 (s, 3H), 1.82-1.68 (m, 2H) LCMS (ES): m/z 518.0 [M + H]$^+$. Human αVβ6 IC50 (nM) = 29. | Same method as for Example 19 |
| 159 | (S)-2-((Cyclopropylmethyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 7.80 (s, 1H), 7.53 (s, 1H), 6.77 (d, J = 7.3 Hz, 1H), 5.97 (d, J = 7.3 Hz, 1H), 4.13 (t, J = 7.2 Hz, 2H), 3.56 (br. s., 1H), 3.27-3.11 (m, 2H), 3.00 (br. s., 2H), 2.80-2.60 (m, 4H), 2.35 (t, J = 6.0 Hz, 2H), 1.50 (br. s., 2H), 0.85-0.71 (m, 1H), 0.24 (d, J = 7.9 Hz, 2H), 0.02 (dd, J = 14.2, 4.1 Hz, 2H) LCMS (ES): m/z 477.3 [M + H]$^+$. Human αVβ6 IC50 (nM) = 2.7. | Same method as for Example 19 |
| 160 | (S)-2-(((Hexyloxy)carbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 8.25-7.79 (m, 2H), 7.33 (d, J = 6.6 Hz, 1H), 6.57-6.27 (m, 1H), 4.44 (br. s., 2H), 4.02 (t, J = 6.4 Hz, 2H), 3.79 (d, J = 14.2 Hz, 2H), 3.46 (d, J = 5.5 Hz, 2H), 3.11 (br. s., 2H), 2.82-2.71 (m, 2H), 1.99-1.84 (m, 2H), 1.68-1.52 (m, 2H), 1.44-1.14 (m, 7H), 0.90 (t, J = 6.4 Hz, 3H) LCMS (ES): m/z 487.1 [M + H]$^+$. Human αVβ6 IC50 (nM) = 0.7. | Same method as for Example 19 |
| 161 | (S)-3-(1-(2-(5,6,7,8-Tetrahydro-1,8-naphthyridin-2-yl)ethyl)-1H-pyrazole-4-carboxamido)-2-((p-tolylmethyl)sulfonamido)propanoic acid | $^1$H NMR (500 MHz, DMSO-d$_6$) δ 8.13 (s, 1H), 7.84 (s, 1H), 7.55 (d, J = 8.6 Hz, 1H), 7.38-6.99 (m, 4H), 6.34 (d, J = 7.0 Hz, 1H), 4.45 (t, J = 6.8 Hz, 2H), 4.27 (s, 2H), 4.13-4.00 (m, 3H), 3.48 (br. s., 2H), 3.10 (br. s., 2H), 2.65 (br. s., 2H), 2.29 (s, 3H), 1.78 (br. s., 2H). LCMS (ES): m/z 527.0 [M + H]$^+$. Human αVβ6 IC50 (nM) = 15. | Same method as for Example 19 |
| 162 | (S)-2-(((But-2-yn-1-yloxy)carbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.07 (s, 1H), 7.81 (s, 1H), 7.02 (d, J = 7.2 Hz, 1H), 6.21 (d, J = 7.2 Hz, 1H), 4.58 (br. s., 2H), 4.38 (t, J = 7.2 Hz, 2H), 3.24 (br. s., 2H), 3.17 (s, 2H), 2.95 (t, J = 7.2 Hz, 3H), 2.64-2.56 (m, 2H), 1.92-1.65 (m, 5H) LCMS (ES): m/z 455.2 [M + H]$^+$. Human αVβ6 IC50 (nM) = 2.2. | Same method as for Example 19 |

TABLE A-continued

| Example No. | Structure | Data | Method |
|---|---|---|---|
| 163 | (S)-2-(((3-Chlorophenyl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-$d_6$) δ 8.08 (s, 1H), 7.83 (s, 1H), 7.51-7.30 (m, 4H), 7.08-6.96 (m, 1H), 6.21 (d, J = 7.2 Hz, 1H), 4.43-4.30 (m, 4H), 4.20-4.04 (m, 1H), 3.33-3.12 (m, 3H), 3.03-2.92 (m, 3H), 2.60 (t, J = 5.8 Hz, 2H), 1.81-1.68 (m, 2H) LCMS (ES): m/z 547.2 [M + H]$^+$. Human αVβ6 IC50 (nM) = 6.2. | Same method as for Example 19 |
| 164 | (S)-2-((Cyclohexylmethyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-$d_6$) δ 8.09 (s, 1H), 7.83 (s, 1H), 7.03 (d, J = 7.2 Hz, 1H), 6.21 (d, J = 7.2 Hz, 1H), 4.38 (t, J = 7.3 Hz, 2H), 3.31-3.13 (m, 4H), 2.98-2.78 (m, 3H), 2.65-2.57 (m, 2H), 1.75 (d, J = 6.0 Hz, 5H), 1.55 (br. s., 3H), 1.29-1.00 (m, 4H), 0.98-0.86 (m, 2H) LCMS (ES): m/z 519.0 [M + H]$^+$. Human αVβ6 IC50 (nM) = 6.4. | Same method as for Example 19 |
| 165 | (S)-2-(((2,4-Dichlorophenyl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-$d_6$) δ 8.07 (s, 1H), 7.81 (s, 1H), 7.65 (s, 1H), 7.59-7.49 (m, 1H), 7.44-7.34 (m, 1H), 6.99 (s, 1H), 6.19 (d, J = 7.2 Hz, 1H), 4.49 (br. s., 2H), 4.38 (br. s., 2H), 3.28-3.11 (m, 4H), 2.94 (t, J = 7.2 Hz, 2H), 2.58 (d, J = 5.8 Hz, 2H), 1.73 (br. s., 2H) LCMS (ES): m/z 580.9 [M + H]$^+$. Human αVβ6 IC50 (nM) = 2.9. | Same method as for Example 19 |
| 166 | (S)-2-(((2-Fluorophenyl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-$d_6$) δ 8.04 (s, 1H), 7.79 (s, 1H), 7.48-7.10 (m, 4H), 6.99 (d, J = 7.3 Hz, 1H), 6.18 (d, J = 7.3 Hz, 1H), 4.37 (br. s., 3H), 3.63 (d, J = 9.5 Hz, 4H), 3.23 (d, J = 4.9 Hz, 2H), 2.94 (t, J = 7.2 Hz, 2H), 2.65-2.56 (m, 2H), 1.73 (br. s., 2H) LCMS (ES): m/z 531.3 [M + H]$^+$. Human αVβ6 IC50 (nM) = 10. | Same method as for Example 19 |

TABLE A-continued

| Example No. | Structure | Data | Method |
|---|---|---|---|
| 167 | (S)-2-((Pyridin-4-ylmethyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.51 (br. s., 2H), 8.08 (s, 1H), 7.82 (s, 1H), 7.39 (br. s., 2H), 7.01 (d, J = 7.2 Hz, 1H), 6.20 (d, J = 7.2 Hz, 1H), 4.52-4.34 (m, 5H), 3.24 (br. s., 3H), 3.00-2.93 (m, 3H), 2.59 (t, J = 6.0 Hz, 2H), 1.73 (br. s., 2H) LCMS (ES): m/z 513.9 [M + H]$^+$. Human αVβ6 IC50 (nM) = 9.5. | Same method as for Example 19 |
| 168 | (S)-2-(((2-Fluorophenyl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.13 (s, 1H), 7.84 (s, 1H), 7.61 (d, J = 8.4 Hz, 1H), 7.45-7.30 (m, 2H), 7.19-7.10 (m, 2H), 6.36 (d, J = 7.1 Hz, 1H), 4.45 (t, J = 6.8 Hz, 2H), 4.37-4.28 (m, 2H), 4.13-4.04 (m, 2H), 3.49 (br. s., 2H), 3.11 (br. s., 2H), 2.93 (d, J = 5.2 Hz, 1H), 2.65 (d, J = 5.6 Hz, 2H), 1.78 (br. s., 2H) LCMS (ES): m/z 531.3 [M + H]$^+$. Human αVβ6 IC50 (nM) = 17. | Same method as for Example 19 |
| 169 | (S)-2-(((3-Cyanophenyl)methyl)sulfonamido)-3-(1-(2-(5,6,7,8-tetrahydro-1,8-naphthyridin-2-yl)ethyl)-1H-pyrazole-4-carboxamido)propanoic acid | $^1$H NMR (500 MHz, DMSO-d$_6$) δ 8.05 (br. s., 1H), 7.90-7.63 (m, 4H), 7.53 (br. s., 1H), 7.00 (d, J = 7.2 Hz, 1H), 6.19 (d, J = 7.2 Hz, 1H), 4.57-4.29 (m, 4H), 3.64-3.37 (m, 3H), 3.29-3.09 (m, 2H), 2.94 (t, J = 6.9 Hz, 2H), 2.57 (d, J = 6.0 Hz, 2H), 1.77-1.67 (m, 2H) LCMS (ES): m/z 537.9 [M + H]$^+$. Human αVβ6 IC50 (nM) = 13. | Same method as for Example 19 |
| 170 | (S)-2-(((2-Fluoroethoxy)carbonyl)amino)-3-(1-(2-(5,6,7,8-tetrahydro-1,8-naphthyridin-2-yl)ethyl)-1H-pyrazole-4-carboxamido)propanoic acid | $^1$H NMR (500 MHz, METHANOL-d$_4$) δ 7.91 (s, 1H), 7.87 (s, 1H), 7.08 (d, J = 7.2 Hz, 1H), 6.21 (d, J = 7.3 Hz, 1H), 4.59 (dt, J = 4.0, 2.1 Hz, 1H), 4.52-4.41 (m, 4.33-4.17 (m, 3H), 3.78-3.57 (m, 2H), 3.44-3.37 (m, 2H), 3.05 (t, J = 6.9 Hz, 2H), 2.70 (t, J = 6.3 Hz, 2H), 1.91-1.83 (m, 2H) LCMS (ES): m/z 449.2 [M + H]$^+$. Human αVβ6 IC50 (nM) = 5.5. | Same method as for Example 19 |

TABLE A-continued

| Example No. | Structure | Data | Method |
|---|---|---|---|
| 171 | (S)-3-(1-(3-((4,5-dihydro-1H-imidazol-2-yl)amino)propyl)-1H-pyrazole-4-carboxamido)-2-((2,4,6-trimethylphenyl)sulfonamido)propanoic acid | $^1$H NMR (500 MHz, Methanol-d$_4$) δ 8.05 (s, 1H), 7.88 (s, 1H), 6.96 (s, 2H), 4.26 (t, J = 6.5 Hz, 2H), 3.68 (s, 4H), 3.64-3.50 (m, 3H) 3.18 (t, J = 6.7 Hz, 2H), 2.63 (s, 6H), 2.25 (s, 3H), 2.13 (p, J = 6.5 Hz, 2H).) LCMS (ES): m/z 506.4 [M + H]$^+$. Human αVβ6 IC50 (nM) = 14. | Same method as for Example 8 |
| 172 | (2S)-3-(1-(3-((5-Hydroxy-1,4,5,6-tetrahydropyrimidin-2-yl)amino)propyl)-1H-pyrazole-4-carboxamido)-2-((2,4,6-trimethylphenyl)sulfonamido)propanoic acidacid | $^1$H NMR (500 MHz, Methanol-d$_4$) δ 8.06 (s, 1H), 7.88 (s, 1H), 6.95 (s, 2H), 4.25 (t, J = 6.4 Hz, 2H), 4.17 (p, J = 3.3 Hz, 2H), 3.70-3.49 (m, 3H), 3.39 (dd, J = 12.5, 2.9 Hz, 2H), 3.29-3.21 (m, 2H), 3.11 (t, J = 6.6 Hz, 2H), 2.63 (s, 6H), 2.25 (s, 3H), 2.11 (p, J = 6.6 Hz, 2H). LCMS (ES): m/z 536.2 [M + H]$^+$. Human αVβ6 IC50 (nM) = 4.5 | Same method as for Example 8 |
| 173 | (2S)-3-(1-(3-((5-Fluoro-1,4,5,6-tetrahydropyrimidin-2-yl)amino)propyl)-1H-pyrazole-4-carboxamido)-2-((2,4,6-trimethylphenyl)sulfonamido)propanoic acid | $^1$H NMR (500 MHz, Methanol-d$_4$) δ 8.08 (s, 1H), 7.87 (s, 1H), 6.94 (s, 2H), 5.15 (dt, J = 46.6, 2.4 Hz, 1H), 4.24 (t, J = 6.5 Hz, 2H), 3.72-3.40 (m, 7H), 3.13 (t, J = 6.6 Hz, 2H), 2.62 (s, 6H), 2.24 (s, 3H), 2.11 (p, J = 6.6 Hz, 2H). LCMS (ES): m/z 538.3 [M + H]$^+$. Human αVβ6 IC50 (nM) = 2.1 | Same method as for Example 8 |

Example 174. (S)-2-(((Benzyloxy)carbonyl)amino)-3-(((1-(2-(5,6,7,8-tetrahydro-1,8-naphthyridin-2-yl)ethyl)-1H-pyrazol-4-yl)methyl)amino)propanoic acid

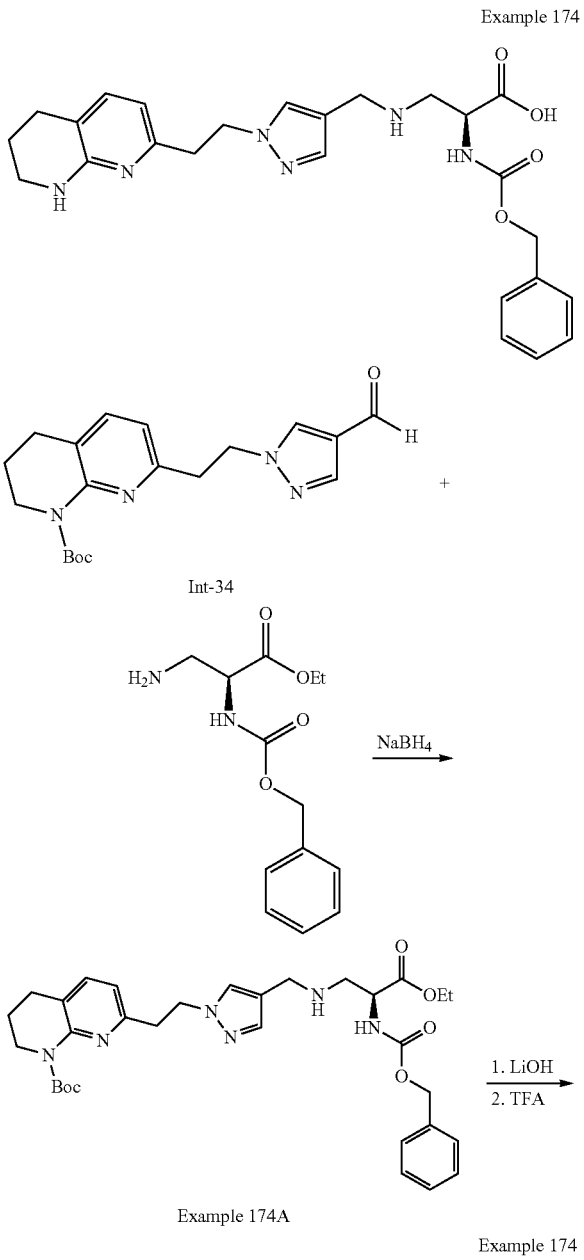 [SMILES: O=C(N[C@@H](CNCc1cnn(CCc2ccc3c(n2)NCCC3)c1)C(=O)O)OCc1ccccc1 ; CC(C)(C)OC(=O)N1CCCc2ccc(CCn3cc(C=O)cn3)nc21 ; CCOC(=O)[C@H](CN)NC(=O)OCc1ccccc1 ; "NaBH4" ; CCOC(=O)[C@H](CNCc1cnn(CCc2ccc3c(n2)N(C(=O)OC(C)(C)C)CCC3)c1)NC(=O)OCc1ccccc1]

Example 174 particles; Mobile Phase A: 5:95 acetonitrile: water with 0.1% TFA; Mobile Phase B: 95:5 acetonitrile: water with 0.1% TFA; Gradient: 15-100% B over 10 minutes, then a 5-minute hold at 100% B; Flow: 40 mL/min.) to afford Example E174A (20 mg, 42%) as a viscous oil: $^1$H NMR (400 MHz, Methanol-$d_4$)$^1$H NMR (500 MHz, Methanol-$d_4$) δ 8.06 (d, J=7.9 Hz, 1H), 7.83 (s, 1H), 7.63 (s, 1H), 7.43-7.27 (m, 5H), 7.19 (d, J=7.9 Hz, 1H), 5.16 (d, J=6.3 Hz, 1H), 5.14 (d, J=6.3 Hz, 1H), 4.61 (t, J=6.5 Hz, 2H), 4.57-4.47 (m, 1H), 4.30-4.11 (m, 4H), 4.02-3.96 (m, 2H), 3.55 (t, J=6.5 Hz, 2H), 3.54-3.44 (m, 2H), 2.93 (t, J=6.3 Hz, 2H), 2.05 (p, J=6.1 Hz, 2H), 1.67 (s, 9H), 1.26 (t, J=7.2 Hz, 3H). LCMS (ES): m/z 607.4 [M+H]$^+$.

Example 174: A mixture of Example 174A (20 mg, 0.033 mmol) and LiOH (2.76 mg, 0.115 mmol) in THF (1 mL) and H$_2$O (0.5 mL) was stirred at room temperature for 3 h. The volatiles were removed in vacuo. The residue was dissolved in TFA (1 mL) and CH$_2$Cl$_2$ (0.5 mL) and the mixture was stirred at RT for 16 h. The volatiles were removed in vacuo and the crude product was purified by preparative HPLC (Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min.) to afford Example 174 (14 mg, 89%): $^1$H NMR (500 MHz, Methanol-$d_4$) δ 7.81 (s, 1H), 7.57 (s, 1H), 7.43-7.28 (m, 6H), 6.40 (d, J=7.3 Hz, 1H), 5.13 (s, 2H), 4.56-4.39 (m, 2H), 4.18 (t, J=6.4 Hz), 4.16-4.10 (m, 2H), 3.42 (t, J=6.5 Hz, 2H), 3.34-3.22 (m, 2H), 3.17-3.06 (m, 2H), 2.75 (t, J=6.3 Hz, 2H), 1.94-1.85 (m, 2H). LCMS (ES): m/z 479.3 [M+H]$^+$. Human αVβ6 IC50 (nM)=6.2.

Example 175. 3-(((1-(2-(5,6,7,8-Tetrahydro-1,8-naphthyridin-2-yl)ethyl)-1H-pyrazol-4-yl)methyl)amino)propanoic acid

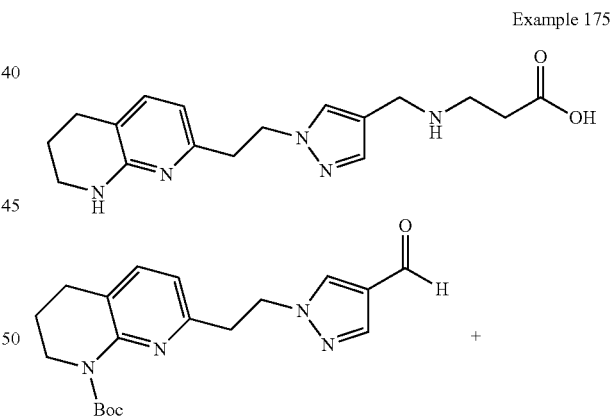

Example 175

Example 174A: A mixture of tert-butyl 7-(2-(4-formyl-1H-pyrazol-1-yl)ethyl)-3,4-dihydro-1,8-naphthyridine-1(2H)-carboxylate (20 mg, 0.079 mmol, Int-34) and (S)-ethyl 3-amino-2-(((benzyloxy)carbonyl)amino)propanoate (29.9 mg, 0.079 mmol) in MeOH (1 mL) was stirred at RT for 3 h. Sodium borohydride (5 mg, 0.132 mmol) was added and the reaction mixture was stirred at RT for 1 h. Aq. NH$_4$Cl solution (1 mL) was added and the organic solvent was evaporated. The crude product was diluted with H$_2$O (5 mL), extracted with EtOAc (3×7 mL). The organic layer was separated, dried over MgSO$_4$ and concentrated to give a crude product which was further purified by preparative HPLC (Column: Sunfire C18 OBD, 30×100 mm, 5-µm

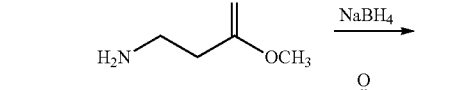

Example 175A

Example 175

Example 175A: A mixture of tert-butyl 7-(2-(4-formyl-1H-pyrazol-1-yl)ethyl)-3,4-dihydro-1,8-naphthyridine-1(2H)-carboxylate (18 mg, 0.051 mmol, Int-34), Et₃N (0.011 mL, 0.080 mmol) and methyl 3-aminopropanoate hydrochloride (7.75 mg, 0.056 mmol) in MeOH (1 mL) was stirred at RT for 3 h. Sodium borohydride (1.9 mg, 0.051 mmol) was added and the reaction mixture was stirred at RT for 1 h. Aq. NH₄Cl solution (1 mL) was added and the organic solvent was evaporated. The crude product was diluted with H₂O (3 mL), extracted with EtOAc (3×5 mL). The organic layer was separated, dried over MgSO₄ and concentrated to give a crude product which was further purified by preparative HPLC (Column: Sunfire C18 OBD, 30×100 mm, 5-μm particles; Mobile Phase A: 5:95 acetonitrile: water with 0.1% TFA; Mobile Phase B: 95:5 acetonitrile: water with 0.1% TFA; Gradient: 10-100% B over 10 minutes, then a 5-minute hold at 100% B; Flow: 40 mL/min.) to afford Example E175A (18 mg, 80%) as a viscous oil: ¹H NMR (500 MHz, Methanol-d₄) δ 8.09 (dd, J=7.9, 1.1 Hz, 1H), 7.85 (s, 1H), 7.64 (s, 1H), 7.23 (d, J=7.9 Hz, 1H), 4.63 (t, J=6.5 Hz, 2H), 4.16 (s, 2H), 4.05-3.96 (m, 2H), 3.75 (s, 3H), 3.57 (t, J=6.5 Hz, 2H), 3.27 (t, J=6.7 Hz, 2H), 2.95 (t, J=6.2 Hz, 2H), 2.80 (t, J=6.7 Hz, 2H), 2.16-2.03 (m, 2H), 1.67 (s, 9H).

Example 175: A mixture of Example 175A (6.6 mg, 0.015 mmol) and NaOH (100 μl, 1M aqueous) in THF (1 mL) was stirred at room temperature for 18 h. The volatiles were removed in vacuo. The residue was dissolved in TFA (1 mL) and CH₂Cl₂ (0.5 mL) and the mixture was stirred at RT for 2 h. The volatiles were removed in vacuo and the crude product was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-45% B over 20 minutes, then a 5-minute hold at 100% B; Flow: 20 mL/min.) to afford Example 175 (2.5 mg, 47%): ¹H NMR (500 MHz, Methanol-d₄) δ 7.63 (s, 1H), 7.60 (s, 1H), 7.07 (d, J=7.3 Hz, 1H), 6.19 (d, J=7.3 Hz, 1H), 4.46 (t, J=6.9 Hz, 2H), 4.06 (s, 2H), 3.41-3.38 (m, 2H), 3.12-2.96 (m, 4H), 2.78-2.65 (m, 2H), 2.46 (t, J=6.4 Hz, 2H), 1.91-1.82 (m, 2H). LCMS (ES): m/z 330.2 [M+H]⁺. Human αVβ6 IC50 (nM)=272.

Example 176. 3-(((Benzyloxy)carbonyl)((1-(2-(5,6,7,8-tetrahydro-1,8-naphthyridin-2-yl)ethyl)-1H-pyrazol-4-yl)methyl)amino)propanoic acid

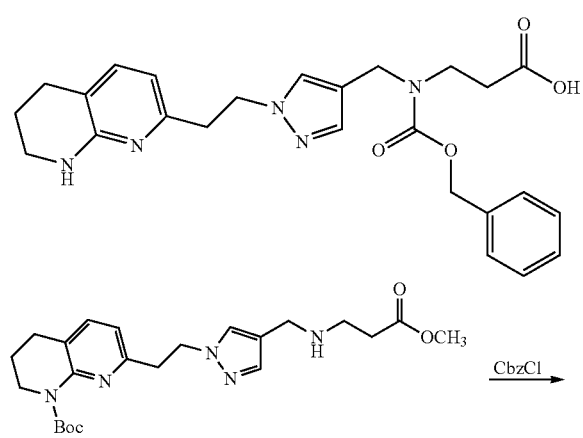

Example 176

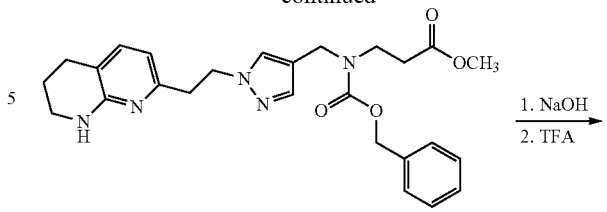

Example 176A

Example 176A: To a mixture of Example 175A (12 mg, 0.070 mmol), sodium bicarbonate (9.5 mg, 0.113 mmol) in THF (1 mL) and H₂O (0.5 mL) was added benzyl carbonochloridate (12 mg, 0.070 mmol). The reaction mixture was stirred at RT for 1 h. Organic solvent was evaporated. The crude product was diluted with H₂O (3 mL) and extracted with EtOAc (3×5 mL). The organic layer was separated, dried over MgSO₄ and concentrated to give a crude product which was used for next step without further purification. LCMS (ES): m/z 578.3 [M+H]⁺.

Example 176: A mixture of Example 176A (13 mg, 0.023 mmol) and NaOH (200 μl, 1M aqueous) in THF (1 mL) was stirred at room temperature for 6 h. The volatiles were removed in vacuo. The residue was dissolved in TFA (1 mL) and CH₂Cl₂ (0.5 mL) and the mixture was stirred at RT for 3 h. The volatiles were removed in vacuo and the crude product was purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min.) to afford Example 176 (4.9 mg, 48%): ¹H NMR (500 MHz, Methanol-d₄) δ 7.63-7.12 (m, 8H), 6.45-6.29 (m, 1H), 5.18 (s, 2H), 4.46-4.30 (m, 4H), 3.58-3.50 (m. 2H), 3.45 (t, J=5.7 Hz, 2H), 3.20-3.02 (m, 2H), 2.77 (t, J=6.3 Hz, 2H), 2.57-2.41 (m, 2H), 1.92 (p, J=6.0 Hz, 2H). LCMS (ES): m/z 464.3 [M+H]⁺. Human αVβ6 IC50 (nM)=249.

Biological Evaluation

All binding assays used the HTRF (homogeneous time resolved fluorescence) technology from Cisbio International, therefore all assays are described as HTRF binding assays. The assay results for the Examples are listed above together with the characterization data. The HTRF binding assays are established for the following integrins: human αVβ6, human αVβ1, human αVβ3, human αVβ5, and human αVβ8. All assays used the following assay buffer: 20 mM Tris, pH 7.4, 1 mM MgCl₂, 1 mM MnCl₂, 0.01% Tween 20, and 0.01% BSA. Alternatively, a SPA-based assay was used for evaluation of receptor binding.

The following describes the components and a representative procedure for the human αVβ6 HTRF binding assay: Recombinant human αVβ6 Integrin (R & D systems, 3817-AV) was biotinylated. Biotinylated human αVβ6 Integrin was added to assay vessel at a final concentration of 1.25 nM. FITC-conjugated fibronectin (Cytoskeleton, FNR02) was then added at the final concentration of 5 nM. The mixture was centrifuged at 600 rpm for three minutes using Thermo Fisher Heraeus Multifuge X3 centrifuge and then incubated at room temperature for an hour. Streptavidin Terbium (Cisbio international 610STLB) was then added at the final concentration of 0.625 nM. The resulting mixture was centrifuged at 600 rpm for three minutes using Thermo Fisher Heraeus Multifuge X3 centrifuge and then incubated at room temperature overnight in dark before reading HTRF signals.

The SPA-based assay was carried out according to the protocol and procedures similar to the ones described in the following reference with appropriate modifications to agents and ligands which are readily understood by one skilled in the art: Pachter J A, Zhang R, Mayer-Ezell R., "Scintillation proximity assay to measure binding of soluble fibronectin to antibody-captured αVβ1 integrin" Anal Biochem. 1995 Sep. 1; 230(1):101-7.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:
1. A compound of Formula (I):

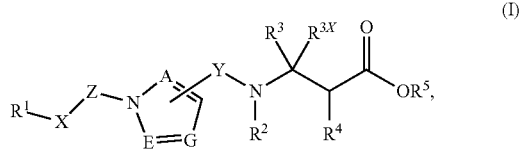

wherein:
A, E, and G are independently N or $CR^6$;
$L^1$ and $L^2$ are each independently $C_{1-4}$ alkylene;
X is a $C_{1-6}$ alkylene substituted with 0, 1, or 2 $R^{7b}$;
Y is C(O) or $CH_2$;
Z is a covalent bond, O, S, NH, —O—($C_{1-3}$ alkylene)-, —S—($C_{1-3}$ alkylene)-, or —NH—($C_{1-3}$ alkylene)-, wherein the $C_{1-3}$ alkylene is each independently substituted with 0, 1, or 2 $R^{7a}$;
g is an integer of 1 or 2;
n is an integer of 1 or 2;
r is an integer of 0, 1, 2, or 3;
t is an integer of 0, 1, 2, or 3;
$R^1$ is an Arginine mimetic moiety selected from the group consisting of

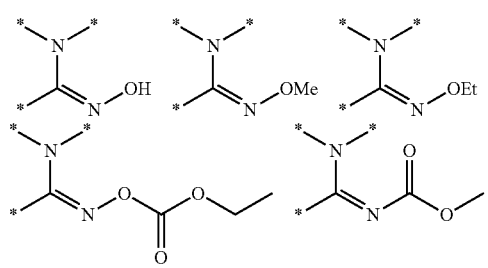

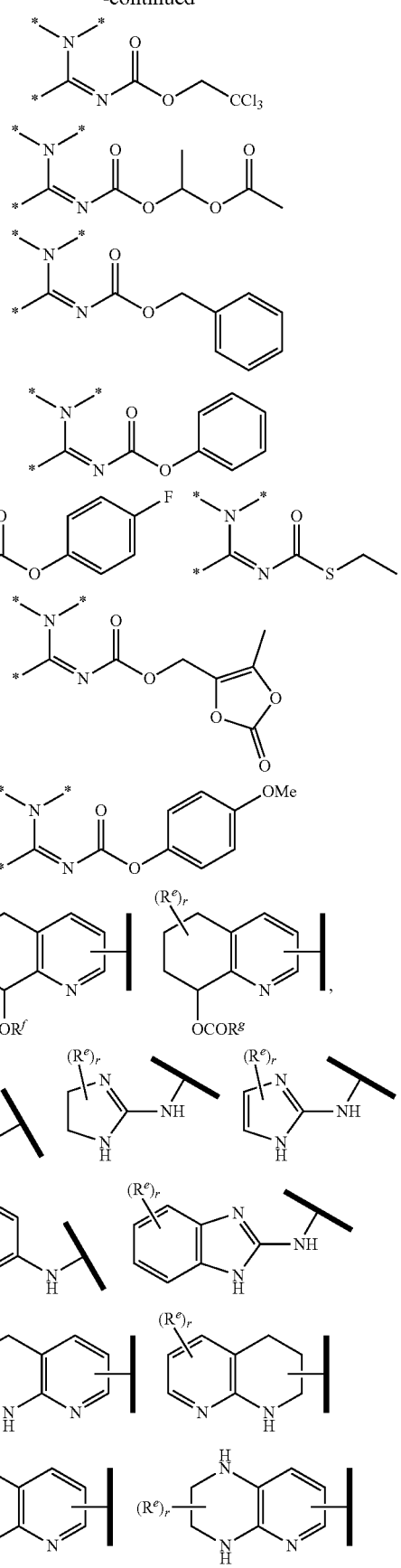

-continued

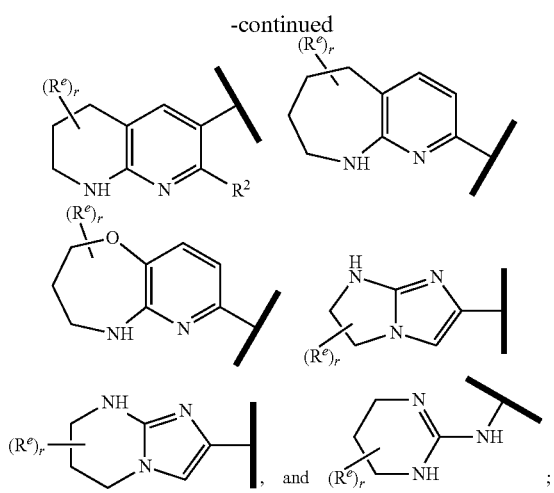

one of the asterisks in each of the arginine mimetics moiety is an attachment point to X, and the other two asterisks are hydrogen;

$R^2$ is hydrogen or $C_{1-6}$ alkyl;

$R^3$ is hydrogen, 3- to 10-membered carbocyclyl, carbocyclylalkyl, 6- to 10-membered aryl, arylalkyl, 3- to 14-membered heterocyclyl, heterocyclylalkyl, 5- to 14-membered heteroaryl, or heteroarylalkyl, wherein the alkyl, carbocyclyl, heterocyclyl, aryl, and heteroaryl, by themselves or as part of another group, are each independently substituted with 0, 1, 2, or 3 $R^8$;

$R^{3X}$ is hydrogen; or alternatively, $R^3$ and $R^{3X}$, together with the atom to which they are attached, form a carbocyclyl or a heterocyclyl, and the carbocyclyl and heterocyclyl are each independently substituted with 0, 1, 2, or 3 $R^{12}$;

$R^4$ is hydrogen, $C_{1-10}$ alkyl, 3- to 10-membered carbocyclyl, carbocyclylalkyl, 3- to 10-membered heterocyclyl, heterocyclylalkyl, 6- to 10-membered aryl, arylalkyl, 5- to 14-membered heteroaryl, heteroarylalkyl, $NR^aR^b$, OH, $OR^a$, $S(O)_nR^{10}$, $C(O)NR^aR^b$, $NHC(O)OR^a$, $NHC(O)NR^aR^b$, $NHC(O)R^{10}$, $OC(O)NR^aR^b$, $OC(O)R^{10}$, $NHS(O)_nNR^aR^b$, or $NHS(O)_nR^{10}$; wherein the alkyl, carbocyclyl, heterocyclyl, aryl, and heteroaryl, by themselves or as part of another group, are each independently substituted with 0, 1, 2, or 3 $R^{15}$;

$R^5$ is H, $R^{5a}$, or a structural moiety selected from

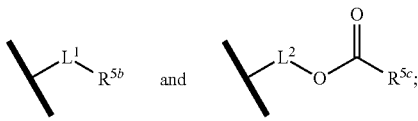

$R^{5a}$ and $R^{5b}$ are each independently $C_{1-6}$ alkyl, phenyl, or 5- to 7-membered heterocyclyl; wherein the alkyl, phenyl, and heterocyclyl are each independently substituted with 0 to 3 $R^{5d}$;

$R^{5c}$, is $C_{1-6}$ alkyl or 5- to 7-membered carbocyclyl; wherein the alkyl and carbocyclyl are each independently substituted with 0 to 3 $R^{5d}$;

$R^{5d}$, at each occurrence, is independently halo, OH, alkoxy, oxo, or alkyl; or alternatively, two adjacent $R^{5d}$ together with the atoms to which they are attached, form a carbocyclyl moiety;

$R^6$ is hydrogen, $C_{1-6}$ alkyl, $C_{3-5}$ cycloalkyl, heteroalkyl, cycloheteroalkyl, aryl, or heteroaryl, wherein the alkyl, cycloalkyl, heteroalkyl, cycloheteroalkyl, aryl, and heteroaryl are each independently substituted with 0, 1, 2, or 3 $R^9$;

$R^{7a}$ and $R^{7b}$ are each independently halo, cyano, hydroxyl, oxo, $NR^aR^b$, $C_{1-6}$ alkyl, haloalkyl, hydroxyalkyl, aminoalkyl, alkoxy, haloalkoxy, heteroalkyl, aryl, cycloalkyl, heteroaryl, cycloheteroalkyl, amido, carbamate, or sulfonamide; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the cycloalkyl and cycloheteroalkyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^8$ at each occurrence is independently halo, cyano, nitro, OH, $NR^aR^b$, $C_{1-6}$ alkyl, alkoxy, alkylamino, haloalkyl, haloalkoxy, haloalkylamino, hydroxyalkyl, aminoalkyl, alkylsulfonyl, sulfonamide, 3 to 6 membered carbocyclyl, 3 to 6 membered heterocyclyl, 6- to 10-membered aryl, or 5- to 10-membered heteroaryl; or alternatively, two $R^8$ at adjacent positions, together with the atoms to which they are attached, form a carbocyclyl or heterocyclyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^9$ at each occurrence is independently halo, cyano, nitro, OH, alkoxy, $NR^aR^b$, $C_{1-6}$ alkyl, heteroalkyl, aryl, cycloalkyl, heteroaryl, or cycloheteroalkyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the cycloalkyl and cycloheteroalkyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^{10}$ is $C_{1-6}$ alkyl, 3 to 10 membered carbocyclyl, or 3 to 10 membered heterocyclyl, wherein the alkyl, carbocyclyl, and heterocyclyl are each independently substituted with 0, 1, 2, or 3 $R^{11}$;

$R^{11}$ is halo, cyano, nitro, OH, alkoxy, $NR^aR^b$, alkyl, aryl, cycloalkyl, heteroaryl, cycloheteroalkyl, or $S(O)_g(aryl)$; wherein the aryl, alkyl, cycloalkyl, heteroaryl, and cycloheteroalkyl are each independently substituted with 0, 1, 2, or 3 $R^{13}$;

R$^{12}$ at each occurrence is independently halo, cyano, nitro, OH, alkoxy, NR$^a$R$^b$, alkyl, heteroalkyl, aryl, cycloalkyl, heteroaryl, or cycloheteroalkyl; or alternatively, two R$^{12}$ at adjacent positions, together with the atoms to which they are attached, form a carbocyclyl or heterocyclyl; wherein the aryl and heteroaryl, by themselves or as part of another group, are each independently substituted with one or more groups independently selected from halo, cyano, hydroxyl, amino, C$_{1-6}$ alkyl, haloalkyl, hydroxyalkyl, aminoalkyl, alkoxy, haloalkoxy, amido, carbamate, and sulfonamide; and the cycloalkyl and cycloheteroalkyl, by themselves or as part of another group, are each independently substituted with one or more groups independently selected from halo, cyano, hydroxyl, amino, oxo, C$_{1-6}$ alkyl, haloalkyl, hydroxyalkyl, aminoalkyl, alkoxy, haloalkoxy, amido, carbamate, and sulfonamide;

R$^{13}$ and R$^{14}$, at each occurrence, are independently halo, cyano, nitro, OH, alkoxy, NR$^a$R$^b$, alkyl, heteroalkyl, aryl, cycloalkyl, heteroaryl, or cycloheteroalkyl; wherein the aryl and heteroaryl, by themselves or as part of another group, are each independently substituted with one or more groups independently selected from halo, cyano, hydroxyl, amino, C$_{1-6}$ alkyl, haloalkyl, hydroxyalkyl, aminoalkyl, alkoxy, haloalkoxy, amido, carbamate, and sulfonamide; and the cycloalkyl and cycloheteroalkyl, by themselves or as part of another group, are each independently substituted with one or more groups independently selected from halo, cyano, hydroxyl, amino, oxo, C$_{1-6}$ alkyl, haloalkyl, hydroxyalkyl, aminoalkyl, alkoxy, haloalkoxy, amido, carbamate, and sulfonamide;

R$^{15}$ at each occurrence is independently halo, cyano, nitro, OH, NR$^a$R$^b$, C$_{1-6}$ alkyl, alkoxy, alkylamino, haloalkyl, haloalkoxy, haloalkylamino, hydroxyalkyl, aminoalkyl, alkylsulfonyl, sulfonamide, 3 to 6 membered carbocyclyl, 3 to 6 membered heterocyclyl, 6- to 10-membered aryl, or 5- to 10-membered heteroaryl; or alternatively, two R$^9$ at adjacent positions, together with the atoms to which they are attached, form a carbocyclyl or heterocyclyl; wherein the aryl and heteroaryl, by themselves or as part of another group, are each independently substituted with one or more groups independently selected from halo, cyano, hydroxyl, amino, C$_{1-6}$ alkyl, haloalkyl, hydroxyalkyl, aminoalkyl, alkoxy, haloalkoxy, amido, carbamate, and sulfonamide; and the carbocyclyl and heterocyclyl, by themselves or as part of another group, are each independently substituted with one or more groups independently selected from halo, cyano, hydroxyl, amino, oxo, C$_{1-6}$ alkyl, haloalkyl, hydroxyalkyl, aminoalkyl, alkoxy, haloalkoxy, amido, carbamate, and sulfonamide;

R$^a$ and R$^b$, at each occurrence, are independently hydrogen, C$_{1-10}$ alkyl, 3 to 10 membered carbocyclyl, or 3 to 10 membered heterocyclyl; wherein the alkyl, carbocyclyl, and heterocyclyl are each independently substituted with 0, 1, 2, or 3 R$^{14}$;

R$^e$ is OH, C$_{1-4}$ alkyl, halo, haloalkyl, or C$_{1-4}$ cycloalkyl;

R$^f$=H, CH$_3$, CH$_2$CH$_3$, or COOCH$_2$CH$_3$; and

R$^g$=CH$_3$, CH$_2$CH$_3$, CH$_2$CCl$_3$, phenyl, 4-fluorophenyl, 4-methoxyphenyl, benzyl,

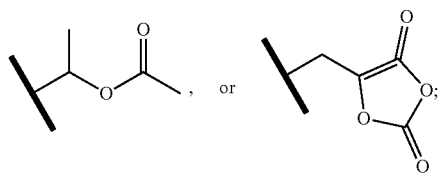

or a pharmaceutically acceptable salt thereof.

2. The compound of claim 1 or a pharmaceutically acceptable salt thereof, wherein A, E, and G, together with the nitrogen and carbon atoms, form a ring moiety selected from the following structural formula:

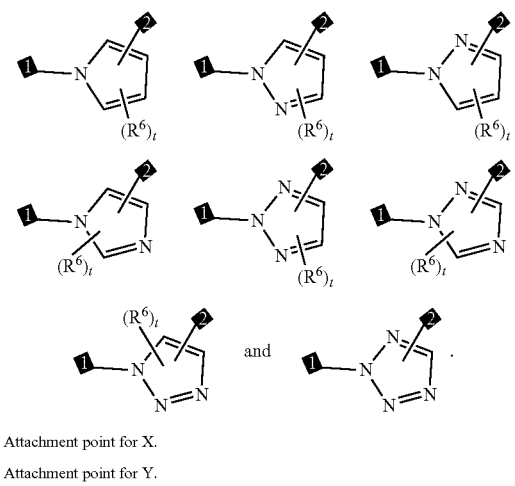

◆ Attachment point for X.
◇ Attachment point for Y.

3. The compound of claim 1 or a pharmaceutically acceptable salt thereof, wherein A, E, and G, together with the nitrogen and carbon atoms, form a ring moiety selected from the following structural formula:

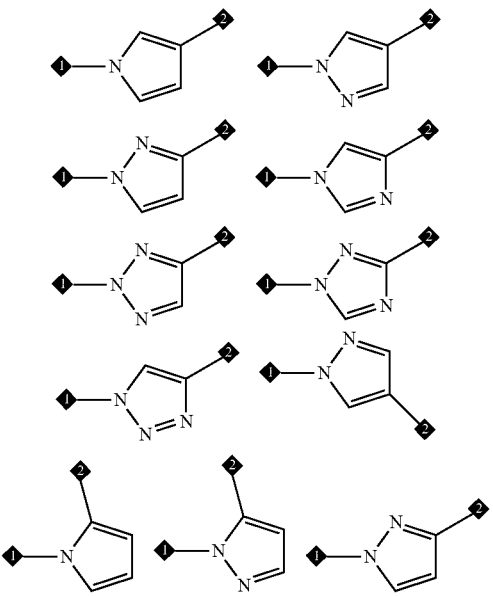

-continued

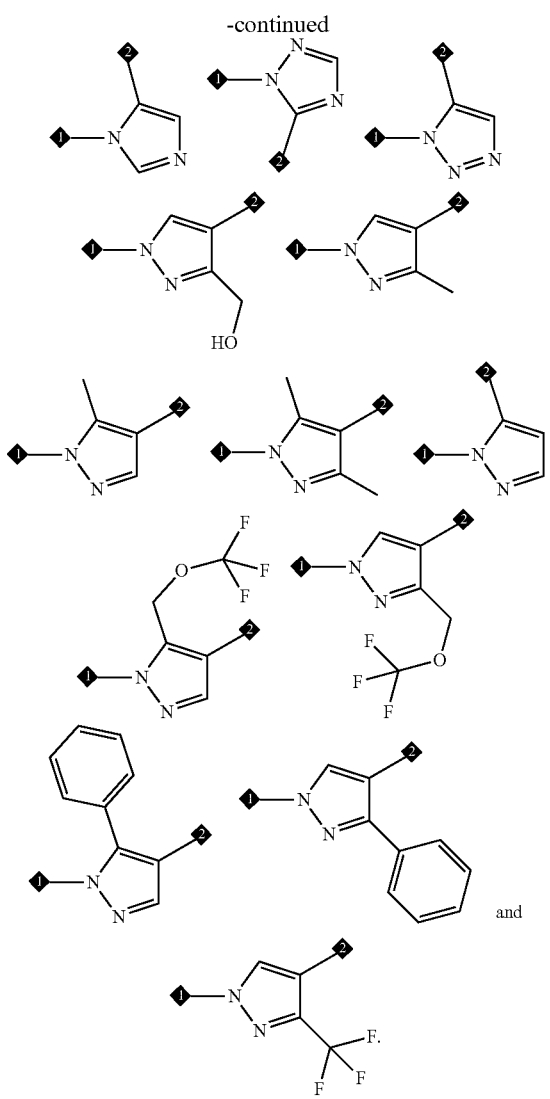

● Attachment point for X.
◆ Attachment point for Y.

4. The compound of claim 1 according to Formula (II) or a pharmaceutically acceptable salt thereof:

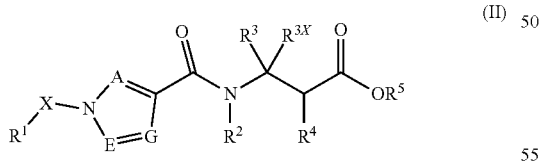

wherein:
R³ is hydrogen, C$_{1-10}$ alkyl, 3 to 10 membered carbocyclyl, or 3 to 10 membered heterocyclyl, wherein the alkyl, carbocyclyl, and heterocyclyl are each independently substituted with 0, 1, 2, or 3 R⁸;
R⁴ is hydrogen, C$_{1-10}$ alkyl, 3 to 10 membered carbocyclyl, 3 to 10 membered heterocyclyl, NR$^a$R$^b$, OH, OR$^a$, S(O)$_n$R¹⁰, C(O)NR$^a$R$^b$, NHC(O)OR$^a$, NHC(O)NR$^a$R$^b$, NHC(O)R¹⁰, OC(O)NR$^a$R$^b$, OC(O)R¹⁰, NHS(O)$_n$NR$^a$R$^b$, or NHS(O)$_n$R¹⁰;
t is an integer of 0, 1, or 2;

R$^{7b}$ is halo, cyano, nitro, OH, alkoxy, NR$^a$R$^b$, alkyl, heteroalkyl, aryl, cycloalkyl, heteroaryl, or cycloheteroalkyl;

R⁸ and R¹², at each occurrence, are independently halo, cyano, nitro, OH, alkoxy, NR$^a$R$^b$, alkyl, heteroalkyl, aryl, cycloalkyl, heteroaryl, or cycloheteroalkyl; or alternatively, two R⁸ at adjacent positions, together with the atoms to which they are attached, form a carbocyclyl or heterocyclyl; or two R¹² at adjacent positions, together with the atoms to which they are attached, form a carbocyclyl or heterocyclyl;

R⁹, at each occurrence, is independently halo, cyano, nitro, OH, alkoxy, NR$^a$R$^b$, alkyl, heteroalkyl, aryl, cycloalkyl, heteroaryl, or cycloheteroalkyl; and R¹³ and R¹⁴, at each occurrence, are independently halo, cyano, nitro, OH, alkoxy, NR$^a$R$^b$, alkyl, heteroalkyl, aryl, cycloalkyl, heteroaryl, or cycloheteroalkyl.

5. The compound of claim 1 or a pharmaceutically acceptable salt thereof, wherein R is selected from a structural formula selected from the group consisting of

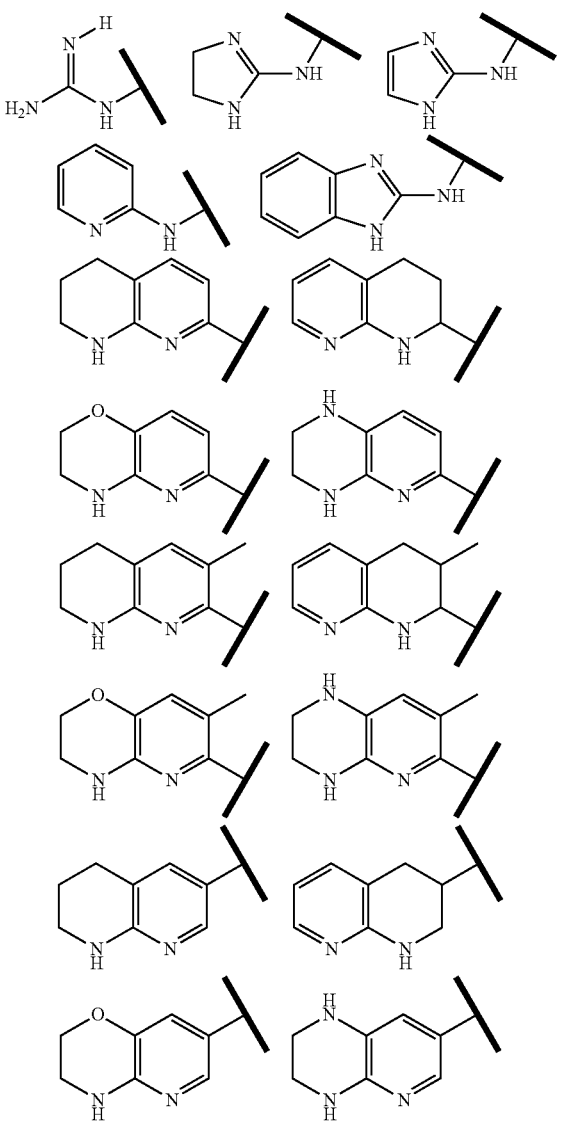

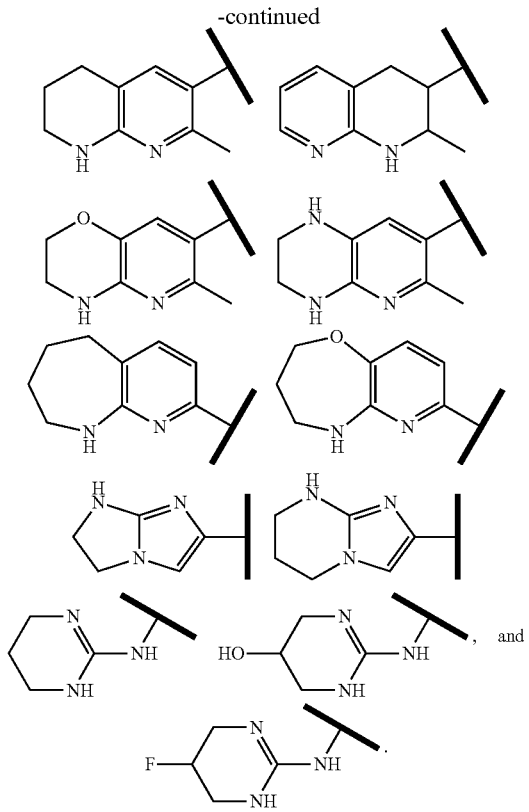

6. The compound of claim 1 or a pharmaceutically acceptable salt thereof, wherein $R^3$ is selected from hydrogen, $C_{1-6}$ alkyl, 6 to 10 membered aryl, and 5 to 10 membered heteroaryl, wherein each of the alkyl, aryl, and heteroaryl is independently substituted with 0, 1, 2, or 3 $R^8$; $R^{3X}$ is hydrogen; and $R^8$ is halo, cyano, nitro, OH, $NR^aR^b$, alkyl, hydroxyalkyl, alkoxy, alkoxyalkyl, aryl, aryloxy, cycloalkyl, haloalkyl, or haloalkoxy; or alternatively, two $R^8$ at adjacent positions, together with the atoms to which they are attached, form a carbocyclyl or heterocyclyl moiety.

7. The compound of claim 1 or a pharmaceutically acceptable salt thereof, wherein $R^3$ is selected from the group consisting of hydrogen, methyl,

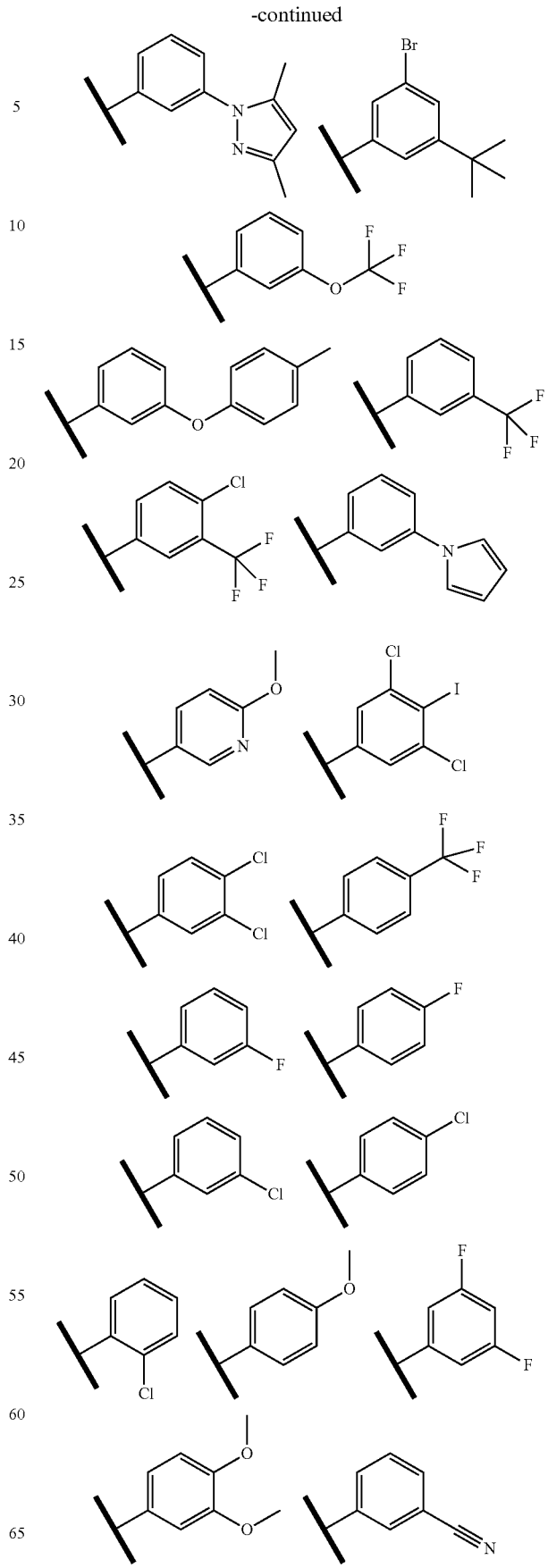

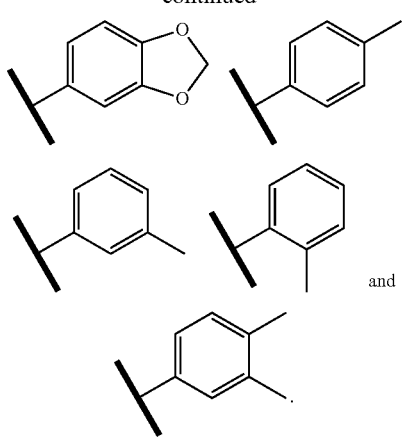

8. The compound of claim 1 or a pharmaceutically acceptable salt thereof, wherein $R^{10}$ is $C_{1-6}$ alkyl, phenyl, benzyl, or 3 to 10 membered heterocycloalkyl, wherein the alkyl, phenyl, benzyl, and heterocycloalkyl are each independently substituted with 0 to 3 $R^{13}$; and $R^{11}$ is halo, alkoxy, alkyl, aryl, cycloalkyl, heteroaryl, heterocycloalkyl, or $S(O)_g$(phenyl).

9. The compound of claim 1 or a pharmaceutically acceptable salt thereof, wherein $R^4$ is selected from hydrogen, $NH_2$, $NR^aR^b$ and the following structural moieties:

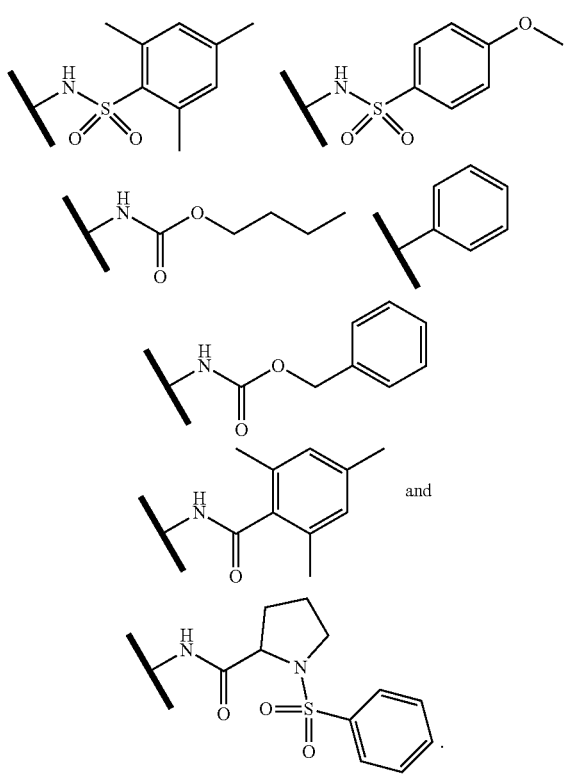

10. The compound of claim 1 or a pharmaceutically acceptable salt thereof, wherein $R^5$ is hydrogen or $R^{5a}$; and $R^{5a}$ is methyl, ethyl, isopropyl, n-butyl, isopentyl, or a structural moiety selected from

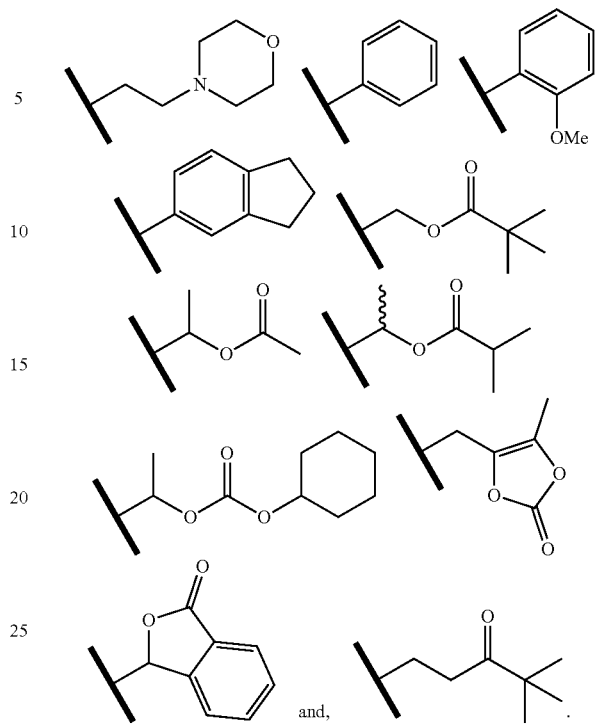

11. A pharmaceutical composition comprising a compound of claim 1, or a pharmaceutically acceptable salt thereof, and a pharmaceutically acceptable carrier.

12. The compound of claim 1 or a pharmaceutically acceptable salt thereof, wherein E, and G, together with the nitrogen and carbon atoms, form a ring moiety selected from:

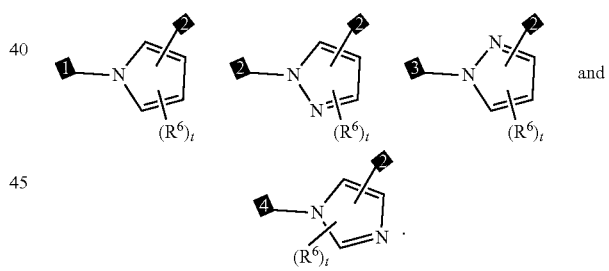

① Attachment point for X.
② Attachment point for Y.

13. The compound of claim 1 according to Formula (II):

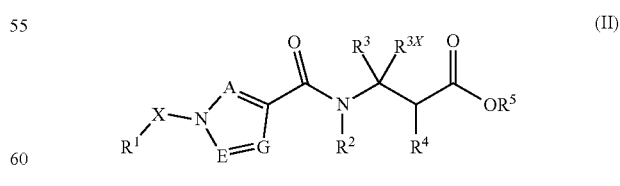

or a pharmaceutically acceptable salt thereof, wherein:
A and E are independently N or $CR^6$;
G is $CR^6$;
X is a $C_{1-3}$ alkylene;
Y is C(O);

$R^1$ is:

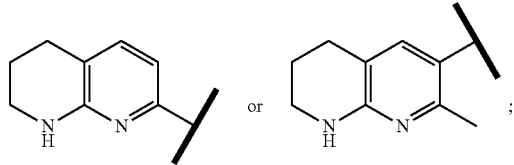

$R^3$ is:

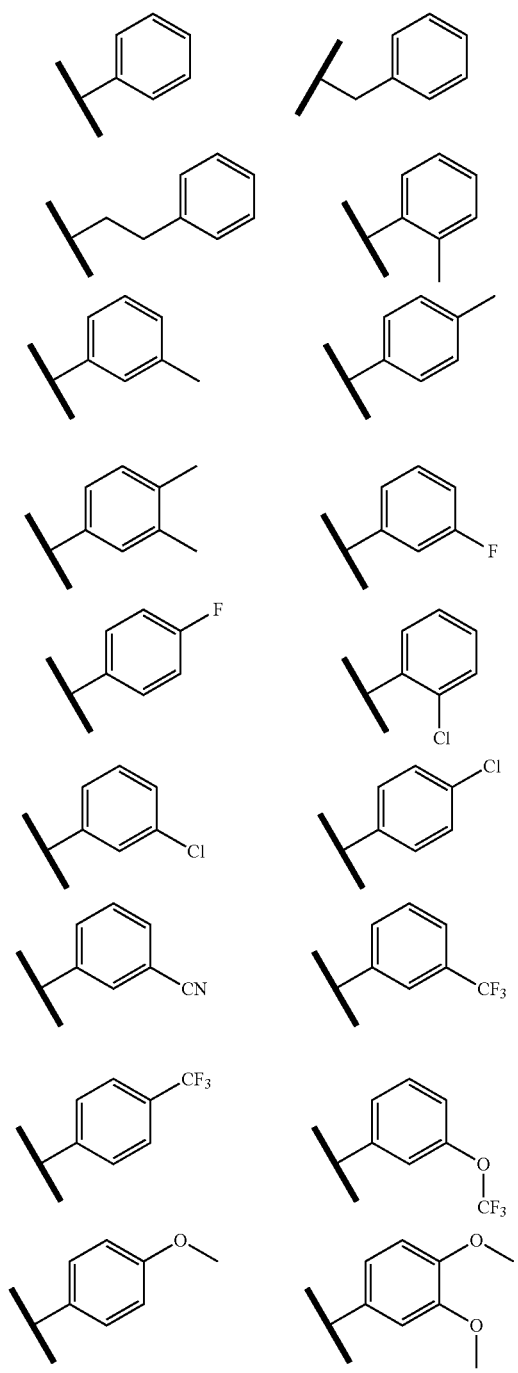

-continued

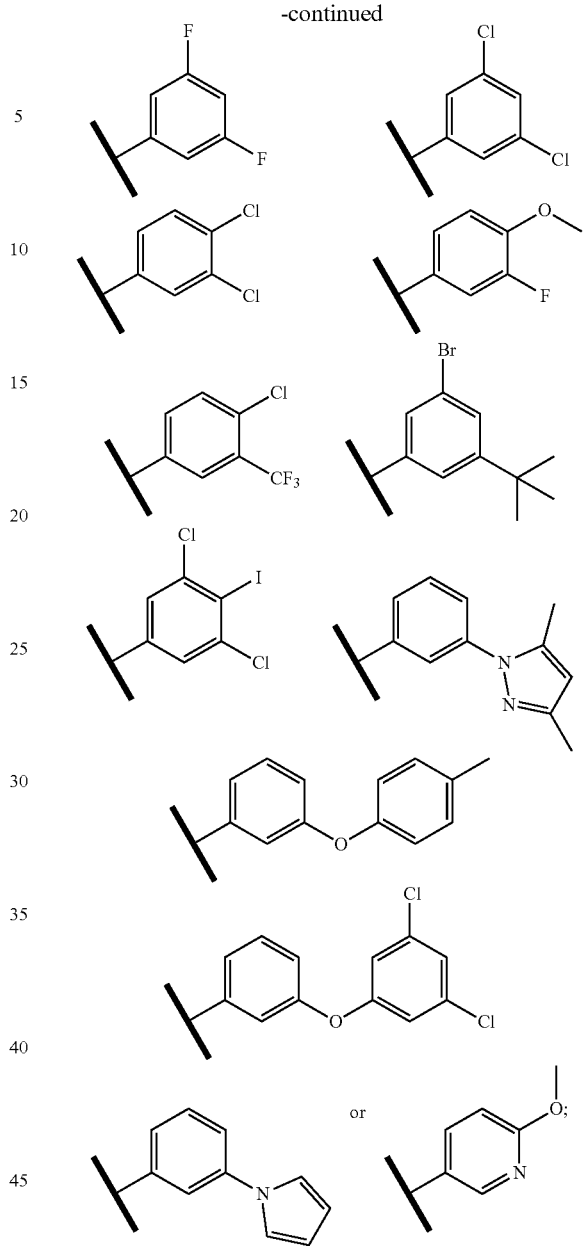

$R^4$ is hydrogen; and
$R^5$ is hydrogen or methyl.

14. The compound of claim 1 or a pharmaceutically acceptable salt thereof, wherein said compound is:

(S)-3-(3-(tert-Butoxymethyl)-1-(2-(5,6,7,8-tetrahydro-1, 8-naphthyridin-2-yl)ethyl)-1H-pyrazole-4-carboxamido)-3-(3-fluoro-4-methoxyphenyl)propanoic acid (1);

(S)-3-(3-Fluoro-4-methoxyphenyl)-3-(3-(hydroxymethyl)-1-(2-(5,6,7,8-tetrahydro-1,8-naphthyridin-2-yl)ethyl)-1H-pyrazole-4-carboxamido)propanoic acid (2);

(3-(3-(tert-Butoxymethyl)-1-(2-(5,6,7,8-tetrahydro-1,8-naphthyridin-2-yl)ethyl)-1H-pyrazole-4-carboxamido)-3-(3,5-dichlorophenyl)propanoic acid (3);

3-(3,5-Dichlorophenyl)-3-(3-(hydroxymethyl)-1-(2-(5,6, 7,8-tetrahydro-1,8-naphthyridin-2-yl)ethyl)-1H-pyrazole-4-carboxamido)propanoic acid (4);

3-(3-(tert-Butoxymethyl)-1-(3-(5,6,7,8-tetrahydro-1,8-naphthyridin-2-yl)propyl)-1H-pyrazole-4-carboxamido)-3-(3,5-dichlorophenyl)propanoic acid (5);

3-(3,5-Dichlorophenyl)-3-(3-(hydroxymethyl)-1-(3-(5,6,7,8-tetrahydro-1,8-naphthyridin-2-yl)propyl)-1H-pyrazole-4-carboxamido)propanoic acid (6);

(S)-3-(3,5-Dichlorophenyl)-3-(1-(3-(pyridin-2-ylamino)propyl)-1H-pyrazole-4-carboxamido)propanoic acid (7);

(S)-3-(3,5-Dichlorophenyl)-3-(1-(3-((4,5-dihydro-1H-imidazol-2-yl)amino)propyl)-1H-pyrazole-4-carboxamido)propanoic acid (8);

3-(3-Chlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid (9);

(S)-3-(3,5-Dichlorophenyl)-3-(2-(2-(5,6,7,8-tetrahydro-1,8-naphthyridin-2-yl)ethyl)-2H-1,2,3-triazole-4-carboxamido)propanoic acid (13);

(S)-3-(3,5-Dichlorophenyl)-3-(2-((2-methyl-5,6,7,8-tetrahydro-1,8-naphthyridin-3-yl)methyl)-2H-1,2,3-triazole-4-carboxamido)propanoic acid (14);

(S)-3-(3,5-Dichlorophenyl)-3-(1-(2-(5,6,7,8-tetrahydro-1,8-naphthyridin-2-yl)ethyl)-1H-pyrazole-4-carboxamido)propanoic acid (16);

3-(N-Ethyl-1-(2-(5,6,7,8-tetrahydro-1,8-naphthyridin-2-yl)ethyl)-1H-pyrazole-4-carboxamido)-3-(6-methoxypyridin-3-yl)propanoic acid (17);

(S)-3-(6-Methoxypyridin-3-yl)-3-(N-methyl-1-(2-(5,6,7,8-tetrahydro-1,8-naphthyridin-2-yl)ethyl)-1H-pyrazole-4-carboxamido)propanoic acid (18);

(S)-3-(3-bromo-5-(tert-butyl)phenyl)-3-(1-(2-(5,6,7,8-tetrahydro-1,8-naphthyridin-2-yl)ethyl)-1H-pyrazole-4-carboxamido)propanoic acid (22);

3-(5-(tert-Butoxymethyl)-1-(2-(5,6,7,8-tetrahydro-1,8-naphthyridin-2-yl)ethyl)-1H-pyrazole-4-carboxamido)-3-(3-(p-tolyloxy)phenyl)propanoic acid (23);

3-(4-Chloro-3-(trifluoromethyl)phenyl)-3-(1-(2-(5,6,7,8-tetrahydro-1,8-naphthyridin-2-yl)ethyl)-1H-pyrazole-4-carboxamido)propanoic acid (24);

(S)-3-(3,5-Dichlorophenyl)-3-(N-methyl-1-(2-(5,6,7,8-tetrahydro-1,8-naphthyridin-2-yl)ethyl)-1H-pyrazole-4-carboxamido)propanoic acid (25);

(S)-3-(3-Bromo-5-(tert-butyl)phenyl)-3-(5-(hydroxymethyl)-1-(2-(5,6,7,8-tetrahydro-1,8-naphthyridin-2-yl)ethyl)-1H-pyrazole-4-carboxamido)propanoic acid (26);

3-(5-(Hydroxymethyl)-1-(2-(5,6,7,8-tetrahydro-1,8-naphthyridin-2-yl)ethyl)-1H-pyrazole-4-carboxamido)-3-(3-(p-tolyloxy)phenyl)propanoic acid (27);

(S)-3-(3,5-dichlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid (29);

3-(3,5-Dichlorophenyl)-3-(1-(2-(5,6,7,8-tetrahydro-1,8-naphthyridin-2-yl)ethyl)-1H-pyrazole-4-carboxamido)propanoic acid (30);

3-(1-(2-(5,6,7,8-Tetrahydro-1,8-naphthyridin-2-yl)ethyl)-1H-pyrazole-4-carboxamido)-3-(3-(trifluoromethoxy)phenyl)propanoic acid (31);

3-(3,5-Dichlorophenyl)-3-(N-methyl-1-(2-(5,6,7,8-tetrahydro-1,8-naphthyridin-2-yl)ethyl)-1H-pyrazole-4-carboxamido)propanoic acid (32);

(S)-3-(3-Fluoro-4-methoxyphenyl)-3-(5-(hydroxymethyl)-1-(2-(5,6,7,8-tetrahydro-1,8-naphthyridin-2-yl)ethyl)-1H-pyrazole-4-carboxamido)propanoic acid (33);

3-(3-(1H-Pyrrol-1-yl)phenyl)-3-(5-(tert-butoxymethyl)-1-(2-(5,6,7,8-tetrahydro-1,8-naphthyridin-2-yl)ethyl)-1H-pyrazole-4-carboxamido)propanoic acid (34);

3-(4-Chloro-3-(trifluoromethyl)phenyl)-3-(5-(hydroxymethyl)-1-(2-(5,6,7,8-tetrahydro-1,8-naphthyridin-2-yl)ethyl)-1H-pyrazole-4-carboxamido)propanoic acid (35);

3-(5-(Hydroxymethyl)-1-(2-(5,6,7,8-tetrahydro-1,8-naphthyridin-2-yl)ethyl)-1H-pyrazole-4-carboxamido)-3-(3-(trifluoromethoxy)phenyl)propanoic acid (36);

3-(5-(tert-Butoxymethyl)-1-(2-(5,6,7,8-tetrahydro-1,8-naphthyridin-2-yl)ethyl)-1H-pyrazole-4-carboxamido)-3-(3-(3,5-dimethyl-1H-pyrazol-1-yl)phenyl)propanoic acid (37);

3-(3-(3,5-Dichlorophenoxy)phenyl)-3-(5-(hydroxymethyl)-1-(2-(5,6,7,8-tetrahydro-1,8-naphthyridin-2-yl)ethyl)-1H-pyrazole-4-carboxamido)propanoic acid (38);

(S)-3-(3-Fluoro-4-methoxyphenyl)-3-(1-(2-(5,6,7,8-tetrahydro-1,8-naphthyridin-2-yl)ethyl)-1H-pyrazole-4-carboxamido)propanoic acid (39);

3-(3,5-Dichlorophenyl)-3-(5-(hydroxymethyl)-N-methyl-1-(2-(5,6,7,8-tetrahydro-1,8-naphthyridin-2-yl)ethyl)-1H-pyrazole-4-carboxamido)propanoic acid (40);

3-(5-(tert-Butoxymethyl)-1-(2-(5,6,7,8-tetrahydro-1,8-naphthyridin-2-yl)ethyl)-1H-pyrazole-4-carboxamido)-3-(3,5-dichlorophenyl)propanoic acid (41);

3-(3-(3,5-Dimethyl-1H-pyrazol-1-yl)phenyl)-3-(5-(hydroxymethyl)-1-(2-(5,6,7,8-tetrahydro-1,8-naphthyridin-2-yl)ethyl)-1H-pyrazole-4-carboxamido)propanoic acid (42);

(S)-3-(5-(Hydroxymethyl)-1-(2-(5,6,7,8-tetrahydro-1,8-naphthyridin-2-yl)ethyl)-1H-pyrazole-4-carboxamido)-3-(6-methoxypyridin-3-yl)propanoic acid (42);

3-(5-(Hydroxymethyl)-1-(2-(5,6,7,8-tetrahydro-1,8-naphthyridin-2-yl)ethyl)-1H-pyrazole-4-carboxamido)-3-(3-(trifluoromethyl)phenyl)propanoic acid (44);

(S)-3-(3,5-Dichlorophenyl)-3-(N-methyl-1-(3-(5,6,7,8-tetrahydro-1,8-naphthyridin-2-yl)propyl)-1H-pyrazole-4-carboxamido)propanoic acid (45);

(S)-3-(6-Methoxypyridin-3-yl)-3-(1-(2-(5,6,7,8-tetrahydro-1,8-naphthyridin-2-yl)ethyl)-1H-pyrazole-4-carboxamido)propanoic acid (46);

3-(3,5-Dichlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid (47);

(S)-3-(3,5-Dichlorophenyl)-3-(N-methyl-1-(2-(5,6,7,8-tetrahydro-1,8-naphthyridin-2-yl)ethyl)-3-(trifluoromethyl)-1H-pyrazole-4-carboxamido)propanoic acid (48);

3-(3,5-Dichlorophenyl)-3-(5-methyl-1-(2-(5,6,7,8-tetrahydro-1,8-naphthyridin-2-yl)ethyl)-1H-pyrazole-4-carboxamido)propanoic acid (49);

(S)-3-(5-(tert-Butoxymethyl)-1-(2-(5,6,7,8-tetrahydro-1,8-naphthyridin-2-yl)ethyl)-1H-pyrazole-4-carboxamido)-3-(3-fluoro-4-methoxyphenyl)propanoic acid (50);

3-(5-(tert-Butoxymethyl)-1-(2-(5,6,7,8-tetrahydro-1,8-naphthyridin-2-yl)ethyl)-1H-pyrazole-4-carboxamido)-3-(3-(3,5-dichlorophenoxy)phenyl)propanoic acid (51);

3-(3,4-Dimethylphenyl)-3-(5-(hydroxymethyl)-1-(2-(5,6,7,8-tetrahydro-1,8-naphthyridin-2-yl)ethyl)-1H-pyrazole-4-carboxamido)propanoic acid (52);

3-(3-Cyanophenyl)-3-(5-(hydroxymethyl)-1-(2-(5,6,7,8-tetrahydro-1,8-naphthyridin-2-yl)ethyl)-1H-pyrazole-4-carboxamido)propanoic acid (53);

(S)-3-(3-Fluoro-4-methoxyphenyl)-3-(3-methyl-1-(2-(5,6,7,8-tetrahydro-1,8-naphthyridin-2-yl)ethyl)-1H-pyrazole-4-carboxamido)propanoic acid (54);

3-(5-(Hydroxymethyl)-1-(2-(5,6,7,8-tetrahydro-1,8-naphthyridin-2-yl)ethyl)-1H-pyrazole-4-carboxamido)-3-(m-tolyl)propanoic acid (55);

3-(Benzo[d][1,3]dioxol-5-yl)-3-(1-(2-(5,6,7,8-tetrahydro-1,8-naphthyridin-2-yl)ethyl)-1H-pyrazole-4-carboxamido)propanoic acid (56);

3-(3,4-Dichlorophenyl)-3-(3,5-dimethyl-1-(2-(5,6,7,8-tetrahydro-1,8-naphthyridin-2-yl)ethyl)-1H-pyrazole-4-carboxamido)propanoic acid (57);

3-(3,4-Dichlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid (58);

3-(5-(tert-Butoxymethyl)-1-(3-(5,6,7,8-tetrahydro-1,8-naphthyridin-2-yl)propyl)-1H-pyrazole-4-carboxamido)-3-(3,5-dichlorophenyl)propanoic acid (59);

(S)-3-(3,5-Dichlorophenyl)-3-(1-(3-(5,6,7,8-tetrahydro-1,8-naphthyridin-2-yl)propyl)-1H-pyrazole-4-carboxamido)propanoic acid (60);

(S)-3-(3-Bromo-5-(tert-butyl)phenyl)-3-(1-(3-(5,6,7,8-tetrahydro-1,8-naphthyridin-2-yl)propyl)-1H-pyrazole-4-carboxamido)propanoic acid (61);

3-(5-(Hydroxymethyl)-1-(2-(5,6,7,8-tetrahydro-1,8-naphthyridin-2-yl)ethyl)-1H-pyrazole-4-carboxamido)-3-(4-(trifluoromethyl)phenyl)propanoic acid (62);

(S)-3-(3-Bromo-5-(tert-butyl)phenyl)-3-(1-(2-(5,6,7,8-tetrahydro-1,8-naphthyridin-2-yl)ethyl)-3-(trifluoromethyl)-1H-pyrazole-4-carboxamido)propanoic acid (63);

3-(3-(1H-pyrrol-1-yl)phenyl)-3-(5-(hydroxymethyl)-1-(2-(5,6,7,8-tetrahydro-1,8-naphthyridin-2-yl)ethyl)-1H-pyrazole-4-carboxamido)propanoic acid (64);

3-(Benzo[d][1,3]dioxol-5-yl)-3-(5-(hydroxymethyl)-1-(2-(5,6,7,8-tetrahydro-1,8-naphthyridin-2-yl)ethyl)-1H-pyrazole-4-carboxamido)propanoic acid (65);

3-(5-(Hydroxymethyl)-1-(2-(5,6,7,8-tetrahydro-1,8-naphthyridin-2-yl)ethyl)-1H-pyrazole-4-carboxamido)-3-(p-tolyl)propanoic acid (66);

3-(4-Chlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid (67);

3-(3,5-Dichlorophenyl)-3-(5-(hydroxymethyl)-1-(3-(5,6,7,8-tetrahydro-1,8-naphthyridin-2-yl)propyl)-1H-pyrazole-4-carboxamido)propanoic acid (68);

3-(3,5-Dichlorophenyl)-3-(5-phenyl-1-(2-(5,6,7,8-tetrahydro-1,8-naphthyridin-2-yl)ethyl)-1H-pyrazole-4-carboxamido)propanoic acid (69);

3-(3,5-Dichlorophenyl)-3-(3-methyl-1-(2-(5,6,7,8-tetrahydro-1,8-naphthyridin-2-yl)ethyl)-1H-pyrazole-4-carboxamido)propanoic acid (70);

3-(4-Fluorophenyl)-3-(5-(hydroxymethyl)-1-(2-(5,6,7,8-tetrahydro-1,8-naphthyridin-2-yl)ethyl)-1H-pyrazole-4-carboxamido)propanoic acid (71);

3-(5-(Hydroxymethyl)-1-(2-(5,6,7,8-tetrahydro-1,8-naphthyridin-2-yl)ethyl)-1H-pyrazole-4-carboxamido)-3-phenylpropanoic acid (72);

3-(5-(Hydroxymethyl)-1-(2-(5,6,7,8-tetrahydro-1,8-naphthyridin-2-yl)ethyl)-1H-pyrazole-4-carboxamido)-3-(4-methoxyphenyl)propanoic acid (73);

(S)-3-(3-Fluoro-4-methoxyphenyl)-3-(1-(3-(5,6,7,8-tetrahydro-1,8-naphthyridin-2-yl)propyl)-1H-pyrazole-4-carboxamido)propanoic acid (74);

3-(3-Fluorophenyl)-3-(5-(hydroxymethyl)-1-(2-(5,6,7,8-tetrahydro-1,8-naphthyridin-2-yl)ethyl)-1H-pyrazole-4-carboxamido)propanoic acid (75);

3-(3,4-Dimethoxyphenyl)-3-(5-(hydroxymethyl)-1-(2-(5,6,7,8-tetrahydro-1,8-naphthyridin-2-yl)ethyl)-1H-pyrazole-4-carboxamido)propanoic acid (76);

3-(3,5-Dimethyl-1-(2-(5,6,7,8-tetrahydro-1,8-naphthyridin-2-yl)ethyl)-1H-pyrazole-4-carboxamido)-3-(4-(trifluoromethyl)phenyl)propanoic acid (77);

3-(3,4-Dichlorophenyl)-3-(3-phenyl-1-(2-(5,6,7,8-tetrahydro-1,8-naphthyridin-2-yl)ethyl)-1H-pyrazole-4-carboxamido)propanoic acid (78);

(S)-3-(3-Fluoro-4-methoxyphenyl)-3-(3-phenyl-1-(2-(5,6,7,8-tetrahydro-1,8-naphthyridin-2-yl)ethyl)-1H-pyrazole-4-carboxamido)propanoic acid (79);

3-(3,5-Difluorophenyl)-3-(5-(hydroxymethyl)-1-(2-(5,6,7,8-tetrahydro-1,8-naphthyridin-2-yl)ethyl)-1H-pyrazole-4-carboxamido)propanoic acid (80);

3-(3,5-Dichlorophenyl)-3-(3-phenyl-1-(2-(5,6,7,8-tetrahydro-1,8-naphthyridin-2-yl)ethyl)-1H-pyrazole-4-carboxamido)propanoic acid (82);

3-(3,5-Dichlorophenyl)-3-(3,5-dimethyl-1-(2-(5,6,7,8-tetrahydro-1,8-naphthyridin-2-yl)ethyl)-1H-pyrazole-4-carboxamido)propanoic acid (83);

3-(3-(tert-Butoxymethyl)-1-(2-(5,6,7,8-tetrahydro-1,8-naphthyridin-2-yl)ethyl)-1H-pyrazole-4-carboxamido)-3-(3,4-dichlorophenyl)propanoic acid (84);

(S)-3-(3,5-Dichlorophenyl)-3-(1-(2-(5,6,7,8-tetrahydro-1,8-naphthyridin-2-yl)ethyl)-3-(trifluoromethyl)-1H-pyrazole-4-carboxamido)propanoic acid (86);

(S)-3-(6-Methoxypyridin-3-yl)-3-(1-(3-(5,6,7,8-tetrahydro-1,8-naphthyridin-2-yl)propyl)-1H-pyrazole-4-carboxamido)propanoic acid (87);

(S)-3-(1-(3-((4,5-Dihydro-1H-imidazol-2-yl)amino)propyl)-1H-pyrazole-4-carboxamido)-3-(6-methoxypyridin-3-yl)propanoic acid (88);

5-Methyl-3-(1-(2-(5,6,7,8-tetrahydro-1,8-naphthyridin-2-yl)ethyl)-1H-pyrazole-4-carboxamido)hexanoic acid (89);

5-Phenyl-3-(1-(2-(5,6,7,8-tetrahydro-1,8-naphthyridin-2-yl)ethyl)-1H-pyrazole-4-carboxamido)pentanoic acid (90);

(S)-3-(3-Fluoro-4-methoxyphenyl)-3-(5-phenyl-1-(2-(5,6,7,8-tetrahydro-1,8-naphthyridin-2-yl)ethyl)-1H-pyrazole-4-carboxamido)propanoic acid (91);

(S)-3-(5-(Hydroxymethyl)-1-(2-(5,6,7,8-tetrahydro-1,8-naphthyridin-2-yl)ethyl)-1H-pyrazole-4-carboxamido)-3-(o-tolyl)propanoic acid (92);

(R)-3-(3,5-Dichlorophenyl)-3-(N-methyl-1-(2-(5,6,7,8-tetrahydro-1,8-naphthyridin-2-yl)ethyl)-1H-pyrazole-4-carboxamido)propanoic acid (93);

(S)-3-(6-Methoxypyridin-3-yl)-3-(1-(3-(pyridin-2-ylamino)propyl)-1H-pyrazole-4-carboxamido)propanoic acid (94);

3-(3-(tert-Butoxymethyl)-1-(2-(5,6,7,8-tetrahydro-1,8-naphthyridin-2-yl)ethyl)-1H-pyrazole-4-carboxamido)-3-(4-(trifluoromethyl)phenyl)propanoic acid (95);

Methyl (S)-3-(3-bromo-5-(tert-butyl)phenyl)-3-(1-(2-(5,6,7,8-tetrahydro-1,8-naphthyridin-2-yl)ethyl)-1H-pyrazole-4-carboxamido)propanoate (96);

(S)-3-(3,5-Dichlorophenyl)-3-(1-((5,6,7,8-tetrahydro-1,8-naphthyridin-2-yl)methyl)-1H-pyrazole-4-carboxamido)propanoic acid (97);

(S)-3-(3-Bromo-5-(tert-butyl)phenyl)-3-(1-((5,6,7,8-tetrahydro-1,8-naphthyridin-2-yl)methyl)-1H-pyrazole-4-carboxamido)propanoic acid (98);
4-Phenyl-3-(1-(2-(5,6,7,8-tetrahydro-1,8-naphthyridin-2-yl)ethyl)-1H-pyrazole-4-carboxamido)butanoic acid (99);
3-(3,5-Dichlorophenyl)-3-(3-methyl-1-((2-methyl-5,6,7,8-tetrahydro-1,8-naphthyridin-3-yl)methyl)-1H-pyrazole-4-carboxamido)propanoic acid (100);
Ethyl (S)-3-(3,5-dichlorophenyl)-3-(1-(2-(5,6,7,8-tetrahydro-1,8-naphthyridin-2-yl)ethyl)-1H-pyrazole-4-carboxamido)propanoate (101);
(S)-3-(6-Methoxypyridin-3-yl)-3-(1-((5,6,7,8-tetrahydro-1,8-naphthyridin-2-yl)methyl)-1H-pyrazole-4-carboxamido)propanoic acid (102);
3-(2-Chlorophenyl)-3-(5-(hydroxymethyl)-1-(2-(5,6,7,8-tetrahydro-1,8-naphthyridin-2-yl)ethyl)-1H-pyrazole-4-carboxamido)propanoic acid (103);
3-(3,5-Dichlorophenyl)-3-(N-ethyl-1-(2-(5,6,7,8-tetrahydro-1,8-naphthyridin-2-yl)ethyl)-1H-pyrazole-4-carboxamido)propanoic acid (104);
3-(3,5-Dichlorophenyl)-3-(3-(hydroxymethyl)-1-((2-methyl-5,6,7,8-tetrahydro-1,8-naphthyridin-3-yl)methyl)-1H-pyrazole-4-carboxamido)propanoic acid (105);
Ethyl (S)-3-(3-bromo-5-(tert-butyl)phenyl)-3-(1-(2-(5,6,7,8-tetrahydro-1,8-naphthyridin-2-yl)ethyl)-1H-pyrazole-4-carboxamido)propanoate (106);
3-(3,5-Dichlorophenyl)-3-(5-(hydroxymethyl)-1-(2-(2-methyl-5,6,7,8-tetrahydro-1,8-naphthyridin-3-yl)ethyl)-1H-pyrazole-4-carboxamido)propanoic acid (107);
3-(5-(tert-Butoxymethyl)-1-(2-(2-methyl-5,6,7,8-tetrahydro-1,8-naphthyridin-3-yl)ethyl)-1H-pyrazole-4-carboxamido)-3-(3,5-dichlorophenyl)propanoic acid (108);
2-(2-(1-(2-(5,6,7,8-Tetrahydro-1,8-naphthyridin-2-yl)ethyl)-1H-pyrazole-4-carboxamido)-2,3-dihydro-1H-inden-2-yl)acetic acid (109);
Methyl 3-(3,5-dichloro-4-iodophenyl)-3-(1-(2-(5,6,7,8-tetrahydro-1,8-naphthyridin-2-yl)ethyl)-1H-pyrazole-4-carboxamido)propanoate (110);
(S)-3-(3,5-Dichlorophenyl)-3-(1-(2-(5,6,7,8-tetrahydro-1,8-naphthyridin-2-yl)ethyl)-1H-imidazole-4-carboxamido)propanoic acid (116);
(S)-3-(3,5-Dichlorophenyl)-3-(1-(2-(5,6,7,8-tetrahydro-1,8-naphthyridin-2-yl)ethyl)-1H-1,2,4-triazole-3-carboxamido)propanoic acid (120);
S)-2-(((Benzyloxy)carbonyl)amino)-3-(((1-(2-(5,6,7,8-tetrahydro-1,8-naphthyridin-2-yl)ethyl)-1H-pyrazol-4-yl)methyl)amino)propanoic acid (174);
3-(((1-(2-(5,6,7,8-Tetrahydro-1,8-naphthyridin-2-yl)ethyl)-1H-pyrazol-4-yl)methyl)amino)propanoic acid (175); or
3-(((Benzyloxy)carbonyl)((1-(2-(5,6,7,8-tetrahydro-1,8-naphthyridin-2-yl)ethyl)-1H-pyrazol-4-yl)methyl)amino)propanoic acid (176).

15. The compound of claim 1 according to Formula (II):

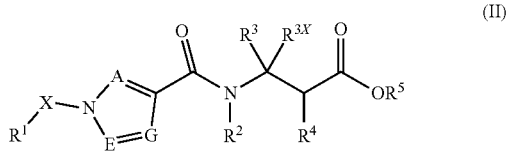

(II)

or a pharmaceutically acceptable salt thereof, wherein:
A and E are independently N or $CR^6$;
G is $CR^6$;
X is a $C_{1-3}$ alkylene;
Y is C(O);
$R^1$

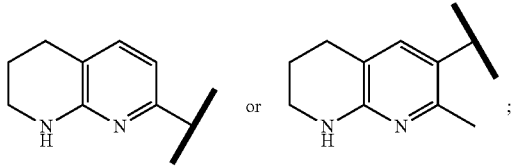

$R^2$ is hydrogen or methyl;
$R^3$ is hydrogen;
$R^4$ is $NH_2$, $NR^aR^b$,

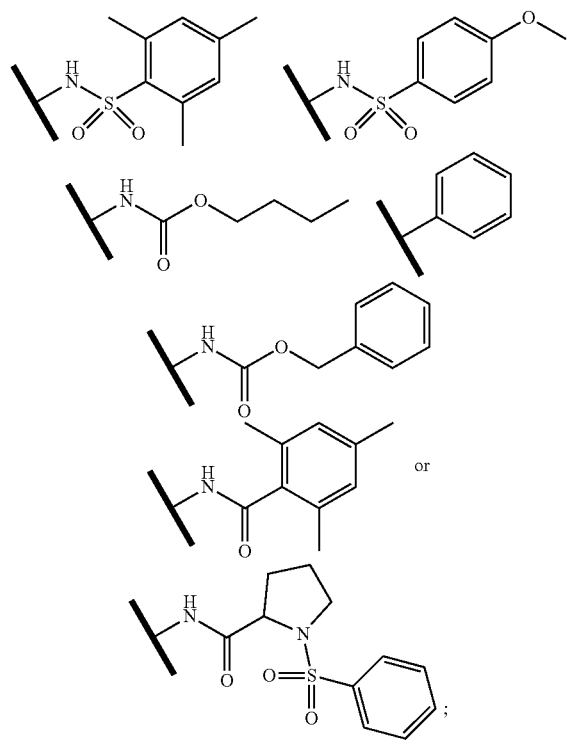

and
$R^5$ is hydrogen or methyl.

16. The compound of claim 1 or a pharmaceutically acceptable salt thereof, wherein said compound is:
(S)-3-(1-(2-(5,6,7,8-Tetrahydro-1,8-naphthyridin-2-yl)ethyl)-1H-pyrazole-4-carboxamido)-2-((2,4,6-trimethylphenyl)sulfonamido)propanoic acid (10);
(S)-2-Amino-3-(1-(2-(5,6,7,8-tetrahydro-1,8-naphthyridin-2-yl)ethyl)-1H-pyrazole-4-carboxamido)propanoic acid (11);
(S)-2-(((Benzyloxy)carbonyl)amino)-3-(1-(2-(5,6,7,8-tetrahydro-1,8-naphthyridin-2-yl)ethyl)-1H-pyrazole-4-carboxamido)propanoic acid (12);
(S)-3-(1-(2-(5,6,7,8-Tetrahydro-1,8-naphthyridin-2-yl)ethyl)-1H-pyrazole-4-carboxamido)-2-(2,4,6-trimethylbenzamido)propanoic acid (15);

(S)-2-((4-Methoxyphenyl)sulfonamido)-3-(1-(2-(5,6,7,8-tetrahydro-1,8-naphthyridin-2-yl)ethyl)-1H-pyrazole-4-carboxamido)propanoic acid (19);

(S)-2-((Butoxycarbonyl)amino)-3-(1-(2-(5,6,7,8-tetrahydro-1,8-naphthyridin-2-yl)ethyl)-1H-pyrazole-4-carboxamido)propanoic acid (20);

(S)-2-((S)-1-(phenylsulfonyl)pyrrolidine-2-carboxamido)-3-(1-(2-(5,6,7,8-tetrahydro-1,8-naphthyridin-2-yl)ethyl)-1H-pyrazole-4-carboxamido)propanoic acid (21);

(S)-3-(1-(3-(5,6,7,8-Tetrahydro-1,8-naphthyridin-2-yl)propyl)-1H-pyrazole-4-carboxamido)-2-((2,4,6-trimethylphenyl)sulfonamido)propanoic acid (28);

(S)-3-(1-(2-(2-Methyl-5,6,7,8-tetrahydro-1,8-naphthyridin-3-yl)ethyl)-1H-pyrazole-4-carboxamido)-2-((2,4,6-trimethylphenyl)sulfonamido)propanoic acid (81);

2-Phenyl-3-(1-(2-(5,6,7,8-tetrahydro-1,8-naphthyridin-2-yl)ethyl)-1H-pyrazole-4-carboxamido)propanoic acid (85);

(S)-3-(1-(2-(5,6,7,8-Tetrahydro-1,8-naphthyridin-2-yl)ethyl)-1H-1,2,3-triazole-4-carboxamido)-2-((2,4,6-trimethylphenyl)sulfonamido)propanoic acid (111);

(S)-3-(1-(2-(5,6,7,8-Tetrahydro-1,8-naphthyridin-2-yl)ethyl)-1H-pyrazole-3-carboxamido)-2-((2,4,6-trimethylphenyl)sulfonamido)propanoic acid (112);

(S)-3-(2-(2-(5,6,7,8-Tetrahydro-1,8-naphthyridin-2-yl)ethyl)-2H-1,2,3-triazole-4-carboxamido)-2-((2,4,6-trimethylphenyl)sulfonamido)propanoic acid (113);

(S)-3-(1-(2-(5,6,7,8-Tetrahydro-1,8-naphthyridin-2-yl)ethyl)-1H-imidazole-4-carboxamido)-2-((2,4,6-trimethylphenyl)sulfonamido)propanoic acid (114);

(S)-3-(1-(2-(5,6,7,8-Tetrahydro-1,8-naphthyridin-2-yl)ethyl)-1H-pyrazole-5-carboxamido)-2-((2,4,6-trimethylphenyl)sulfonamido)propanoic acid (115);

Ethyl (S)-3-(1-(2-(5,6,7,8-tetrahydro-1,8-naphthyridin-2-yl)ethyl)-1H-imidazole-4-carboxamido)-2-((2,4,6-trimethylphenyl)sulfonamido)propanoate (117);

(S)-3-(2-((2-Methyl-5,6,7,8-tetrahydro-1,8-naphthyridin-3-yl)methyl)-2H-1,2,3-triazole-4-carboxamido)-2-((2,4,6-trimethylphenyl)sulfonamido)propanoic acid (118);

(S)-3-(1-(2-(5,6,7,8-Tetrahydro-1,8-naphthyridin-2-yl)ethyl)-1H-pyrrole-3-carboxamido)-2-((2,4,6-trimethylphenyl)sulfonamido)propanoic acid (119);

(S)-2-(((Benzyloxy)carbonyl)amino)-3-(1-(2-(5,6,7,8-tetrahydro-1,8-naphthyridin-2-yl)ethyl)-1H-imidazole-4-carboxamido)propanoic acid (121);

(S)-3-(1-((2-Methyl-5,6,7,8-tetrahydro-1,8-naphthyridin-3-yl)methyl)-1H-pyrrole-3-carboxamido)-2-((2,4,6-trimethylphenyl)sulfonamido)propanoic acid (122);

(S)-3-(1-(2-(5,6,7,8-Tetrahydro-1,8-naphthyridin-2-yl)ethyl)-1H-1,2,4-triazole-3-carboxamido)-2-((2,4,6-trimethylphenyl)sulfonamido)propanoic acid (123);

(S)-2-(Butylsulfonamido)-3-(1-(2-(5,6,7,8-tetrahydro-1,8-naphthyridin-2-yl)ethyl)-1H-pyrazole-4-carboxamido)propanoic acid (124);

(S)-2-((Phenylmethyl)sulfonamido)-3-(1-(2-(5,6,7,8-tetrahydro-1,8-naphthyridin-2-yl)ethyl)-1H-pyrazole-4-carboxamido)propanoic acid (125);

(S)-2-(Ethylsulfonamido)-3-(1-(2-(5,6,7,8-tetrahydro-1,8-naphthyridin-2-yl)ethyl)-1H-pyrazole-4-carboxamido)propanoic acid (126);

(S)-2-((Propoxycarbonyl)amino)-3-(1-(2-(5,6,7,8-tetrahydro-1,8-naphthyridin-2-yl)ethyl)-1H-pyrazole-4-carboxamido)propanoic acid (127);

(S)-3-(1-(2-(5,6,7,8-Tetrahydro-1,8-naphthyridin-2-yl)ethyl)-1H-pyrazole-4-carboxamido)-2-(((2-(trifluoromethyl)phenyl)methyl)sulfonamido)propanoic acid (128);

(S)-3-(1-(2-(5,6,7,8-Tetrahydro-1,8-naphthyridin-2-yl)ethyl)-1H-pyrazole-4-carboxamido)-2-((3,3,3-trifluoropropyl)sulfonamido)propanoic acid (129);

(S)-2-((Methoxycarbonyl)amino)-3-(1-(2-(5,6,7,8-tetrahydro-1,8-naphthyridin-2-yl)ethyl)-1H-pyrazole-4-carboxamido)propanoic acid (130);

(S)-2-((Isobutoxycarbonyl)amino)-3-(1-(2-(5,6,7,8-tetrahydro-1,8-naphthyridin-2-yl)ethyl)-1H-pyrazole-4-carboxamido)propanoic acid (131);

(S)-2-((Ethoxycarbonyl)amino)-3-(1-(2-(5,6,7,8-tetrahydro-1,8-naphthyridin-2-yl)ethyl)-1H-pyrazole-4-carboxamido)propanoic acid (132);

(S)-2-(((Allyloxy)carbonyl)amino)-3-(1-(2-(5,6,7,8-tetrahydro-1,8-naphthyridin-2-yl)ethyl)-1H-pyrazole-4-carboxamido)propanoic acid (133);

(S)-2-(((Pentyloxy)carbonyl)amino)-3-(1-(2-(5,6,7,8-tetrahydro-1,8-naphthyridin-2-yl)ethyl)-1H-pyrazole-4-carboxamido)propanoic acid (134);

(S)-2-(((But-3-en-1-yloxy)carbonyl)amino)-3-(1-(2-(5,6,7,8-tetrahydro-1,8-naphthyridin-2-yl)ethyl)-1H-pyrazole-4-carboxamido)propanoic acid (135);

(S)-2-(((Prop-2-yn-1-yloxy)carbonyl)amino)-3-(1-(2-(5,6,7,8-tetrahydro-1,8-naphthyridin-2-yl)ethyl)-1H-pyrazole-4-carboxamido)propanoic acid (136);

(S)-2-(((Neopentyloxy)carbonyl)amino)-3-(1-(2-(5,6,7,8-tetrahydro-1,8-naphthyridin-2-yl)ethyl)-1H-pyrazole-4-carboxamido)propanoic acid (137);

(S)-2-(Propylsulfonamido)-3-(1-(2-(5,6,7,8-tetrahydro-1,8-naphthyridin-2-yl)ethyl)-1H-pyrazole-4-carboxamido)propanoic acid (138);

(S)-2-((2-(Naphthalen-1-yl)ethyl)sulfonamido)-3-(1-(2-(5,6,7,8-tetrahydro-1,8-naphthyridin-2-yl)ethyl)-1H-pyrazole-4-carboxamido)propanoic acid (139);

(S)-2-(((3,5-Dichlorophenyl)methyl)sulfonamido)-3-(1-(2-(5,6,7,8-tetrahydro-1,8-naphthyridin-2-yl)ethyl)-1H-pyrazole-4-carboxamido)propanoic acid (140);

(S)-2-(((3,4-Dichlorophenyl)methyl)sulfonamido)-3-(1-(2-(5,6,7,8-tetrahydro-1,8-naphthyridin-2-yl)ethyl)-1H-pyrazole-4-carboxamido)propanoic acid (141);

(S)-2-(((3-Fluorophenyl)methyl)sulfonamido)-3-(1-(2-(5,6,7,8-tetrahydro-1,8-naphthyridin-2-yl)ethyl)-1H-pyrazole-4-carboxamido)propanoic acid (142);

(S)-3-(1-(2-(5,6,7,8-Tetrahydro-1,8-naphthyridin-2-yl)ethyl)-1H-pyrazole-4-carboxamido)-2-((m-tolylmethyl)sulfonamido)propanoic acid (143);

(S)-2-(Pentylsulfonamido)-3-(1-(2-(5,6,7,8-tetrahydro-1,8-naphthyridin-2-yl)ethyl)-1H-pyrazole-4-carboxamido)propanoic acid (144);

(S)-2-((2-Methylpropyl)sulfonamido)-3-(1-(2-(5,6,7,8-tetrahydro-1,8-naphthyridin-2-yl)ethyl)-1H-pyrazole-4-carboxamido)propanoic acid (145);

(S)-3-(1-(2-(5,6,7,8-Tetrahydro-1,8-naphthyridin-2-yl)ethyl)-1H-pyrazole-4-carboxamido)-2-(((4-(trifluoromethoxy)phenyl)methyl)sulfonamido)propanoic acid (146);

(S)-2-((2-Methoxyethyl)sulfonamido)-3-(1-(2-(5,6,7,8-tetrahydro-1,8-naphthyridin-2-yl)ethyl)-1H-pyrazole-4-carboxamido)propanoic acid (147);

(S)-2-((2-Ethoxyethyl)sulfonamido)-3-(1-(2-(5,6,7,8-tetrahydro-1,8-naphthyridin-2-yl)ethyl)-1H-pyrazole-4-carboxamido)propanoic acid (148);

(S)-2-(((2-Methoxyethoxy)carbonyl)amino)-3-(1-(2-(5,6,7,8-tetrahydro-1,8-naphthyridin-2-yl)ethyl)-1H-pyrazole-4-carboxamido)propanoic acid (149);

(S)-3-(1-(2-(5,6,7,8-Tetrahydro-1,8-naphthyridin-2-yl)ethyl)-1H-pyrazole-4-carboxamido)-2-(((4-(trifluoromethyl)phenyl)methyl)sulfonamido)propanoic acid (150);

(S)-2-((2-(1,3-Dioxoisoindolin-2-yl)ethyl)sulfonamido)-3-(1-(2-(5,6,7,8-tetrahydro-1,8-naphthyridin-2-yl)ethyl)-1H-pyrazole-4-carboxamido)propanoic acid (151);

(2S)-2-((((2-Ethylhexyl)oxy)carbonyl)amino)-3-(1-(2-(5,6,7,8-tetrahydro-1,8-naphthyridin-2-yl)ethyl)-1H-pyrazole-4-carboxamido)propanoic acid (152);

(S)-3-(1-(2-(5,6,7,8-Tetrahydro-1,8-naphthyridin-2-yl)ethyl)-1H-pyrazole-4-carboxamido)-2-(((2,2,2-trifluoroethoxy)carbonyl)amino)propanoic acid (153);

(S)-3-(1-(2-(5,6,7,8-Tetrahydro-1,8-naphthyridin-2-yl)ethyl)-1H-pyrazole-4-carboxamido)-2-(((3-(trifluoromethyl)phenyl)methyl)sulfonamido)propanoic acid (154);

(S)-2-(((2-Chlorophenyl)methyl)sulfonamido)-3-(1-(2-(5,6,7,8-tetrahydro-1,8-naphthyridin-2-yl)ethyl)-1H-pyrazole-4-carboxamido)propanoic acid (155);

(S)-2-(((3-Bromophenyl)methyl)sulfonamido)-3-(1-(2-(5,6,7,8-tetrahydro-1,8-naphthyridin-2-yl)ethyl)-1H-pyrazole-4-carboxamido)propanoic acid (156);

(S)-2-(((3,5-Bis(trifluoromethyl)phenyl)methyl)sulfonamido)-3-(1-(2-(5,6,7,8-tetrahydro-1,8-naphthyridin-2-yl)ethyl)-1H-pyrazole-4-carboxamido)propanoic acid (157);

(S)-2-(((5-Methylisoxazol-3-yl)methyl)sulfonamido)-3-(1-(2-(5,6,7,8-tetrahydro-1,8-naphthyridin-2-yl)ethyl)-1H-pyrazole-4-carboxamido)propanoic acid (158);

(S)-2-((Cyclopropylmethyl)sulfonamido)-3-(1-(2-(5,6,7,8-tetrahydro-1,8-naphthyridin-2-yl)ethyl)-1H-pyrazole-4-carboxamido)propanoic acid (159);

(S)-2-(((Hexyloxy)carbonyl)amino)-3-(1-(2-(5,6,7,8-tetrahydro-1,8-naphthyridin-2-yl)ethyl)-1H-pyrazole-4-carboxamido)propanoic acid (160);

(S)-3-(1-(2-(5,6,7,8-Tetrahydro-1,8-naphthyridin-2-yl)ethyl)-1H-pyrazole-4-carboxamido)-2-((p-tolylmethyl)sulfonamido)propanoic acid (161);

(S)-2-(((But-2-yn-1-yloxy)carbonyl)amino)-3-(1-(2-(5,6,7,8-tetrahydro-1,8-naphthyridin-2-yl)ethyl)-1H-pyrazole-4-carboxamido)propanoic acid (162);

(S)-2-(((3-Chlorophenyl)methyl)sulfonamido)-3-(1-(2-(5,6,7,8-tetrahydro-1,8-naphthyridin-2-yl)ethyl)-1H-pyrazole-4-carboxamido)propanoic acid (163);

(S)-2-((Cyclohexylmethyl)sulfonamido)-3-(1-(2-(5,6,7,8-tetrahydro-1,8-naphthyridin-2-yl)ethyl)-1H-pyrazole-4-carboxamido)propanoic acid (164);

(S)-2-(((2,4-Dichlorophenyl)methyl)sulfonamido)-3-(1-(2-(5,6,7,8-tetrahydro-1,8-naphthyridin-2-yl)ethyl)-1H-pyrazole-4-carboxamido)propanoic acid (165);

(S)-2-(((2-Fluorophenyl)methyl)sulfonamido)-3-(1-(2-(5,6,7,8-tetrahydro-1,8-naphthyridin-2-yl)ethyl)-1H-pyrazole-4-carboxamido)propanoic acid (166);

(S)-2-((Pyridin-4-ylmethyl)sulfonamido)-3-(1-(2-(5,6,7,8-tetrahydro-1,8-naphthyridin-2-yl)ethyl)-1H-pyrazole-4-carboxamido)propanoic acid (167);

(S)-2-(((4-Fluorophenyl)methyl)sulfonamido)-3-(1-(2-(5,6,7,8-tetrahydro-1,8-naphthyridin-2-yl)ethyl)-1H-pyrazole-4-carboxamido)propanoic acid (168);

(S)-2-(((3-Cyanophenyl)methyl)sulfonamido)-3-(1-(2-(5,6,7,8-tetrahydro-1,8-naphthyridin-2-yl)ethyl)-1H-pyrazole-4-carboxamido)propanoic acid (169);

(S)-2-(((2-Fluoroethoxy)carbonyl)amino)-3-(1-(2-(5,6,7,8-tetrahydro-1,8-naphthyridin-2-yl)ethyl)-1H-pyrazole-4-carboxamido)propanoic acid (170);

(S)-3-(1-(3-((4,5-dihydro-1H-imidazol-2-yl)amino)propyl)-1H-pyrazole-4-carboxamido)-2-((2,4,6-trimethylphenyl)sulfonamido)propanoic acid (171);

(2S)-3-(1-(3-((5-Hydroxy-1,4,5,6-tetrahydropyrimidin-2-yl)amino)propyl)-1H-pyrazole-4-carboxamido)-2-((2,4,6-trimethylphenyl)sulfonamido)propanoic acid (172); or (2S)-3-(1-(3-((5-Fluoro-1,4,5,6-tetrahydropyrimidin-2-yl)amino)propyl)-1H-pyrazole-4-carboxamido)-2-((2,4,6-trimethylphenyl)sulfonamido)propanoic acid (173).

\* \* \* \* \*

UNITED STATES PATENT AND TRADEMARK OFFICE
CERTIFICATE OF CORRECTION

PATENT NO. : 10,851,098 B2
APPLICATION NO. : 16/347829
DATED : December 1, 2020
INVENTOR(S) : Devasthale et al.

Page 1 of 2

It is certified that error appears in the above-identified patent and that said Letters Patent is hereby corrected as shown below:

In the Claims

In Claim 1, Column 200, Line 39-44 (Approx.), delete " 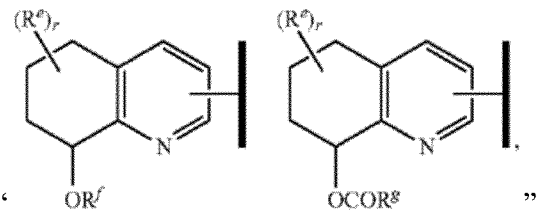 "

and insert -- 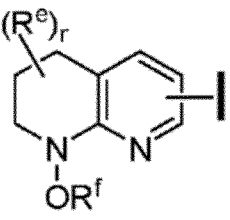 ' --, therefor.

In Claim 1, Column 201, Line 61, delete "$R^{5c}$," and insert -- $R^{5c}$ --, therefor.

In Claim 1, Column 201, Line 67, delete "forma" and insert -- form a --, therefor.

In Claim 1, Column 204, Line 1-9 (Approx.), delete " 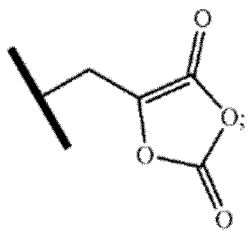 " and

Signed and Sealed this
Thirtieth Day of November, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,851,098 B2 insert -- 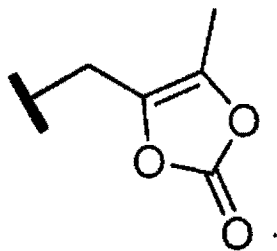 --, therefor.

In Claim 2, Column 204, Line 30-33 (Approx.), delete " 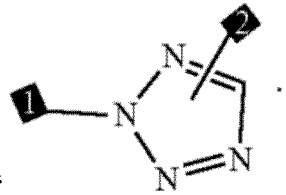 " and insert -- 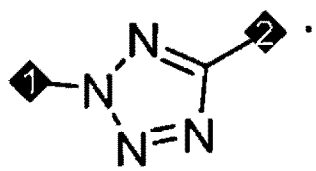 --, therefor.

In Claim 3, Column 205, Line 1-7 (Approx.), after " 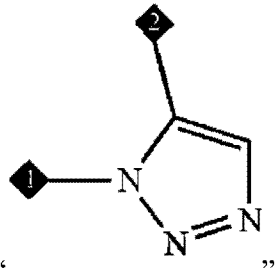 " insert -- 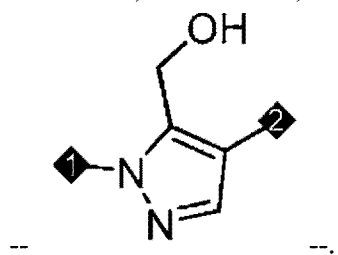 --.

In Claim 5, Column 206, Line 21, delete "R" and insert -- $R^1$ --, therefor.

In Claim 12, Column 210, Line 34 (Approx.), after "wherein" insert -- A, --.

In Claim 14, Column 217, Line 48 (Approx.), delete "S)" and insert -- (S) --, therefor.

In Claim 15, Column 218, Line 6, after "$R^1$" insert -- is --.